United States Patent
Bailey et al.

(10) Patent No.: US 6,821,972 B2
(45) Date of Patent: Nov. 23, 2004

(54) 3-HETEROCYCLYLPROPANOHYDROXAMIC ACID PCP INHIBITORS

(75) Inventors: Simon Bailey, Sandwich (GB); Paul Vincent Fish, Sandwich (GB); Kim James, Sandwich (GB); Gavin Alistar Whitlock, Sandwich (GB)

(73) Assignee: Pfizer Inc., New York, NY (US)

( * ) Notice: Subject to any disclaimer, the term of this patent is extended or adjusted under 35 U.S.C. 154(b) by 154 days.

(21) Appl. No.: 10/112,338

(22) Filed: Mar. 29, 2002

(65) Prior Publication Data

US 2003/0069291 A1 Apr. 10, 2003

Related U.S. Application Data

(60) Provisional application No. 60/293,379, filed on May 24, 2001.

(30) Foreign Application Priority Data

Mar. 30, 2001 (GB) ................................................ 0108102

(51) Int. Cl.[7] ..................... C07D 271/06; C07D 263/34; C07D 413/06; A61K 31/421; A61P 17/02
(52) U.S. Cl. .................... 514/236.2; 544/310; 544/238; 544/364; 544/131; 544/405; 514/274; 514/374; 514/252.05; 514/364; 514/340; 514/253.1; 514/255.05; 514/307; 548/131; 548/235; 546/269.4; 546/144; 546/271.4
(58) Field of Search ................................. 544/310, 238, 544/364, 131, 405; 514/274, 374, 252.05, 364, 340, 253.1, 236.2, 255.05, 307; 548/131, 235; 546/269.4, 144, 271.4

(56) References Cited

U.S. PATENT DOCUMENTS

| 6,448,278 B2 | 9/2002 | Bailey et al. |
| 6,452,041 B1 | 9/2002 | Derrick et al. |
| 6,645,993 B2 | 11/2003 | Fish et al. |

FOREIGN PATENT DOCUMENTS

| WO | WO 99 29667 A | 6/1999 |
| WO | WO 00 58278 A | 10/2000 |
| WO | WO 01 47901 A | 7/2001 |

OTHER PUBLICATIONS

Steward, Marimastat: Current status of development. Cancer Chemother. Pharmacol., 43:S56–S60.*

* cited by examiner

Primary Examiner—Richard L. Raymond
Assistant Examiner—Hong Liu
(74) Attorney, Agent, or Firm—J. Michael Dixon

(57) ABSTRACT

Compounds of formula (I):

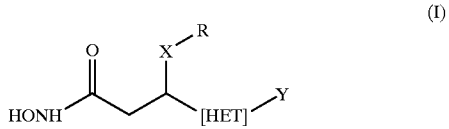

and their salts, solvates, hydrates and prodrugs are useful PCP inhibitors, processes for making the same, compositions comprising the same, and methods of treating a PCP-mediated condition or disease using the same.

14 Claims, No Drawings

3-HETEROCYCLYLPROPANOHYDROXAMIC ACID PCP INHIBITORS

CROSS-REFERENCE TO RELATED APPLICATIONS

This non-provisional patent application claims priority to United Kingdom Application No. GB 0108102.5, filed Mar. 30, 2001, and to U.S. Provisional Application No. 60/293,379, filed May 24, 2001, each of which is hereby incorporated by reference in its entirety.

FIELD OF THE INVENTION

This invention relates to a certain class of compounds, and the pharmaceutically acceptable salts, solvates and prodrugs thereof, which inhibit Procollagen C-proteinase ("PCP"). These compounds are useful in the treatment of mammals having conditions alleviable by inhibition of PCP. Especially of interest is an antiscarring treatment for wounds.

BACKGROUND OF THE INVENTION

Fibrotic tissues, including dermal scars, are characterised by excessive accumulation of extracellular matrix, mainly collagen type I. It is thought that inhibition of collagen deposition will reduce formation of scar tissue. Collagen is secreted as the precursor, procollagen, which is transformed into the insoluble collagen by cleavage of the C-terminal propeptide by PCP. PCP is a zinc-dependent metalloprotease which is secreted from TGF-β-activated fibroblasts belonging to the subfamily of astacin-like proteases and able to cleave the C-terminal peptide of types I, II and III procollagens. Furthermore, data suggest that PCP activates lysyl oxidase, an enzyme essential for the formation of covalent cross-links which stabilise the fibrous form of collagen. Therefore, inhibition of PCP may not only reduce collagen deposition but may also make collagen more accessible for degradation.

Collagen is integral to, among other things, the proper formation of connective tissue. Thus, the over- or underproduction of collagen or the production of abnormal collagen (including incorrectly processed collagen) has been linked with numerous connective tissue diseases and disorders. Mounting evidence suggests that PCP is an essential key enzyme for the proper maturation of collagen (see for example International Patent Application publication number WO 97/05865).

At present more than nineteen types of collagens have been identified. These collagens, including fibrillar collagen types I, II, III are synthesized as procollagen precursor molecules which contain amino- and carboxy-terminal peptide extensions. These peptide extensions, referred to as "pro-regions," are designated as N- and C-propeptides, respectively.

The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, Annu. Rev. Biochem. 47:129–162; Bornstein and Traub, 1979, in: The Proteins (eds. Neurath, H. and Hill, R. H.), Academic Press, New York, pp. 412–632; Kivirikko et al., 1984, in: Extracellur Matrix Biochemistry (eds. Piez, K. A. and Reddi. A. H.), Elsevier Science Publishing Co., Inc., New York, pp. 83–118; Prockop and Kivirikko, 1984, N. Engl. J. Med. 311:376–383; Kuhn, 1987, in: Structure and Function of Collagen Types (eds. Mayne, R. and Burgeson, R. E.), Academic Press, Inc., Orlando, Fla., pp. 1–42.

An array of conditions has been associated with the inappropriate or unregulated production of collagen, including pathological fibrosis or scarring, including endocardial sclerosis, idiopathic interstitial fibrosis, interstitial pulmonary fibrosis, perimuscular fibrosis, Symmers' fibrosis, pericentral fibrosis, hepatitis, dermatofibroma, cirrhosis such as binary cirrhosis and alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and Pyronie's disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis and restenosis. Other conditions where collagen plays a key role include burns. Fibrosis of lung tissue is also observed in patients suffering from chronic obstructive airways disease (COAD) and asthma. One strategy for the treatment of these diseases and conditions is to inhibit the overproduction and/or deposition and/or unregulation of collagen. Thus, identification and isolation of molecules which control, inhibit and/or modulate the production and deposition of collagen are of major medical interest.

Recent evidence suggests that PCP is the essential key enzyme that catalyzes the cleavage of the Procollagen C-propeptide. This has been demonstrated in fibrillar collagens, including type I, type II, and type III collagen.

PCP was first observed in the culture media of human and mouse fibroblasts (Goldberg et al., 1975, Cell 4:45–50; Kessler and Goldberg, 1978, Anal. Biochem. 86:463–469), and chick tendon fibroblasts (Duskin et al., 1978, Arch. Biochem. Biophys. 185:326–332; Leung et al., 1979, J. Biol. Chem. 254:224–232). An acidic proteinase which removes the C-terminal propeptides from type I procollagen has also been identified (Davidson et al., 1979, Eur. J. Biochem. 100:551).

A partially purified protein having PCP activity was obtained from chick calvaria in 1982. Njieha et al., 1982, Biochemistry 23:757–764. In 1985, chicken PCP was isolated, purified and characterized from conditioned media of chick embryo tendons. Hojima et al., 1985, J. Biol. Chem. 260:15996–16003. Murine PCP has been subsequently purified from media of cultured mouse fibroblasts. Kessler et al., 1986, Collagen Relat. Res. 6:249–266; Kessler and Adar, 1989, Eur. J. Biochem. 186:115–121. Finally, the cDNA encoding human PCP has been identified, as set forth in the above-referenced articles and references disclosed therein.

Experiments conducted with these purified forms of chick and mouse PCP have indicated that the enzyme is instrumental in the formation of functional collagen fibers. Fertala et al., 1994, J. Biol. Chem. 269:11584.

As a consequence of the enzyme's apparent importance to collagen production, scientists have identified a number of PCP inhibitors. See, e.g., Hojima et al., supra. For example, several metal chelators have demonstrated activity as PCP inhibitors. Likewise, chymostatin and pepstatin A were found to be relatively strong inhibitors of PCP. Additionally, $\alpha_2$-Macroglobulin, ovostatin, and fetal bovine serum appear to at least partially inhibit PCP activity.

Dithiothreitol, SDS, concanavalin A, $Zn^{2+}$, $Cu^{2+}$, and $Cd^{2+}$ are similarly reported to be inhibitory at low concentrations. Likewise, some reducing agents, several amino acids, phosphate, and ammonium sulfate were inhibitory at concentrations of 1–10 mM. Further, the enzyme was shown to be inhibited by the basic amino acids lysine and arginine (Leung et al., supra; Ryhänen et al., 1982, Arch. Biochem. Biophys. 215:230–235). Finally, high concentrations of NaCl or Tris-HCl buffer were found to inhibit PCP's activity. For example, it is reported that, with 0.2, 0.3, and 0.5M NaCl, the activity of PCP was reduced 66, 38, and 25%, respectively, of that observed with the standard assay concentration of 0.15M. Tris-HCl buffer in a concentration of 0.2–0.5M markedly inhibited activity (Hojima et al., supra). PCP activity and its inhibition have been determined using a wide array of assays. See e.g., Kessler and Goldberg, 1978, Anal. Biochem. 86:463; Njieha et al., 1982, Biochemistry 21:757–764. As articulated in numerous publications, the enzyme is difficult to isolate by conventional biochemical means and the identity of the cDNA sequence encoding such enzyme was not known until reported in the above referenced and related patent applications.

In view of its essential role in the formation and maturation of collagen, PCP appears to be an ideal target for the treatment of disorders associated with the inappropriate or unregulated production and maturation of collagen.

Matrix metalloproteases (MMPs) constitute a family of structurally similar zinc-containing metalloproteases, which are involved in the remodelling, repair and degradation of extracellular matrix proteins, both as part of normal physiological processes and in pathological conditions.

Another important function of certain MMPs is to activate other enzymes, including other MMPs, by cleaving the pro-domain from their protease domain. Thus, certain MMPs act to regulate the activities of other MMPs, so that over-production in one MMP may lead to excessive proteolysis of extracellular matrix by another, e.g. MMP-14 activates pro-MMP-2.

During the healing of normal and chronic wounds, MMP-1 is expressed by migrating keratinocytes at the wound edges (U. K. Saarialho-Kere, S. O. Kovacs, A. P. Pentland, J. Clin. Invest. 1993, 92, 2858–66). There is evidence which suggests MMP-1 is required for keratinocyte migration on a collagen type I matrix in vitro, and is completely inhibited by the presence of the non-selective MMP inhibitor SC44463 ((N-4-hydroxy)-N1-[(1S)-2-(4-methoxyphenyl)methyl-1-((1R)-methylamino)carbonyl)]-(2R)-2-(2-methylpropyl)butanediamide) (B. K. Pilcher, J. A. Dumin, B. D. Sudbeck, S. M. Krane, H. G. Welgus, W. C. Parks, J. Cell Biol., 1997, 137, 1–13). Keratinocyte migration in vivo is essential for effective wound healing to occur.

MMP-2 and MMP-9 appear to play important roles in wound healing during the extended remodelling phase and the onset of re-epithelialisation, respectively (M. S. Agren, Brit. J. Dermatology, 1994, 131, 634–40; T. Salo, M. Mäkänen, M. Kylmäniemi, Lab. Invest., 1994, 70, 176–82). The potent, non-selective MMP inhibitor BB94 ((2S,3R)-5-methyl-3-{[(1S)-1-(methylcarbamoyl)-2-phenylethyl]carbamoyl}-2-[(2-thienylthio)methyl]hexanohydroxamic acid, batimastat) inhibits endothelial cell invasion of basement membrane, thereby inhibiting angiogenesis (G. Tarboletti, A. Garofalo, D. Belotti, T. Drudis, P. Borsotti, E. Scanziani, P. D. Brown, R. Giavazzi, J. Natl. Cancer Inst., 1995, 87, 293–8). There is evidence that this process requires active MMP-2 and/or 9.

Thus PCP inhibitors which significantly inhibit MMPs 1 and/or 2 and/or 9 would be expected to impair wound healing. MMP-14 is responsible for the activation of MMP-2, and thus inhibition of MMP-14 might also result in impaired wound healing.

For recent reviews of MMPs, see Zask et al., Current Pharmaceutical Design, 1996, 2, 624–661; Beckett, Exp. Opin. Ther. Patents, 1996, 6, 1305–1315; and Beckett et al., Drug Discovery Today, vol. 1 (no.1), 1996, 16–26.

Alternative names for various MMPs and substrates acted on by these are shown in the table below (Zask et al., supra).

| Enzyme | Other names | Preferred substrates |
| --- | --- | --- |
| MMP-1 | Collagenase-1, interstitial collagenase | Collagens I, II, III, VII, X, gelatins |
| MMP-2 | Gelatinase A, 72 kDa gelatinase | Gelatins, collagens IV, V, VII, X, elastin, fibronectin; activates pro-MMP-13 |
| MMP-3 | Stromelysin-1 | Proteoglycans, laminin, fibronectin, gelatins. |
| MMP-7 | Pump, Matrilysin | Proteoglycans, laminin, fibronectin, gelatins, collagen IV, elastin, activates pro-MMP-1 and -2. |
| MMP-8 | Collagenase-2, neutrophil collagenase | Collagens I, II, III |
| MMP-9 | Gelatinase B, 92 kDa gelatinase | Gelatins, collagens IV, V, elastin |
| MMP-12 | Macrophage metalloelastase | Elastin, collagen IV, fibronectin, activates pro-MMP-2 & 3. |
| MMP-13 | Collagenase-3 | Collagens I, II, III, gelatins |
| MMP-14 | MT-MMP-1 | Activates pro-MMP-2 & 13, gelatins |
| MMP-15 | MT-MMP-2 | unknown |
| MMP-16 | MT-MMP-3 | Activates pro-MMP-2 |
| MMP-17 | MT-MMP-4 | unknown |

International Patent Applications PCT/IB00/01855 (published as WO 01/47901) and PCT/IB01/02360 (filed on $7^{th}$ Dec. 2001), and foreign equivalents thereof, describe various 3-heterocyclylpropanohydroxamic acid PCP inhibitors. The teachings of these documents are herein incorporated by reference in their entirety.

The identification of effective compounds which specifically inhibit the activity of PCP to regulate and modulate abnormal or inappropriate collagen production is therefore desirable and the object of this invention.

SUMMARY OF THE INVENTION

According to one aspect of the present invention, there are provided compounds of formula (I):

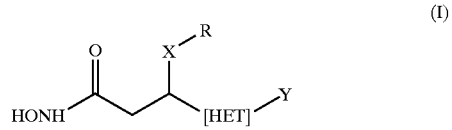

wherein [HET] is a divalent heterocyclic moiety selected from:

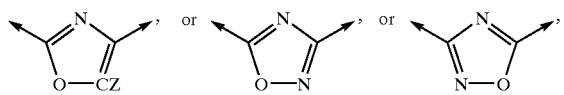

X is $C_{1-6}$ alkylene or $C_{2-6}$ alkenylene, each of which is optionally substituted by one or more fluorine atoms; R is aryl, $C_{5-8}$ cycloalkenyl or $C_{3-8}$ cycloalkyl optionally substituted by one or more fluorine atoms;

Z is H or $C_{1-4}$ alkyl;

Y is a mono- or bicyclic unsaturated ring system containing from 5 to 10 ring atoms, of which up to 4 which are hetero-atoms independently selected from N, O and S, and which ring system is optionally substituted by one or more substituents independently selected from =O, $C_{1-4}$ alkyl, $C_{1-4}$ alkoxy, $NR^1R^2$, $SO_2NR^1R^2$, $CO_2R^1$, $CONR^1R^2$, $CH_2CO_2R^1$, $NR^1CO_2R^2$, $NR^1SO_2R^2$ or $het^1$;

$R^1$ and $R^2$ are each independently selected from H and $C_{1-4}$ alkyl optionally substituted by $C_{1-4}$ alkoxy;

$het^1$ is a N-linked 4- to 6-membered mono- or bicyclic heterocycle optionally containing 1 or 2 further hetero ring atoms independently selected from N and O, which heterocycle is optionally substituted by one or more substituents independently selected from =O, $C_{1-4}$ alkyl, $C_{1-4}$ alkoxy, $NR^1R^2$, $SO_2NR^1R^2$, $CO_2R^1$, $CONR^1R^2$, $CH_2CO_2R^1$, $NR^1CO_2R^2$, $NR^1SO_2R^2$ or $het^2$, $het^2$ is a N-linked 4- to 6-membered mono- or bicyclic heterocycle optionally containing 1 or 2 further hetero ring atoms independently selected from N and O;

"aryl" is phenyl optionally substituted by one or more substituents independently selected from $R^1$, OH, $SO_2$ ($C_{1-4}$ alkyl) and/or $C(O)_p(C_{1-4}$ alkyl) groups;

and the pharmaceutically acceptable salts, solvates (including hydrates) and prodrugs thereof.

"Alkyl", "alkylene", "alkoxy", "alkanoyl", and "alkenylene" groups, including groups incorporating said moieties, may be straight chain or branched where the number of carbon atoms allows.

Halogen is taken to mean fluorine, chlorine, bromine or iodine.

Pharmaceutically-acceptable salts are well known to those skilled in the art, and for example include those mentioned in the art cited above, and by Berge et al, in J. Pharm. Sci., 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate, pamoate, carasylate, and p-toluenesulphonate salts.

Pharmaceutically acceptable base addition salts are well known to those skilled in the art, and for example include those mentioned in the art cited above, and can be formed from bases which form non-toxic salts and include the aluminium, calcium, lithium, magnesium, potassium, sodium and zinc salts, and salts of non-toxic amines such as diethanolamine.

Certain of the compounds of formula (I) may exist in one or more zwitterionic forms. Certain of the compounds of formula (I) may exist in one or more tautomeric forms. Certain of the compounds of formula (I), their salts, solvates, prodrugs, etc. may exist in one or more polymorphic forms. It is to be understood that the compounds of formula (I) include all such zwitterions, tautomers and polymorphs.

The compounds of formula (I), their salts, hydrates, prodrugs etc. can exhibit isotopic variation, e.g. forms with enriched $^2H$, $^{13}C$, $^{14}C$, $^{15}N$, $^{18}O$, etc. may be prepared, for example by suitable variation of the synthetic methods described herein using methods and reagents known in the art or routine modification thereof. All such isotopic variants are included in the scope of the invention.

Prodrug moieties are well-known to those skilled in the art (see for example the article by H Feres, in Drugs of Today, vol 19, no.9 (1983) pp.499–538, especially section Al), and for example include those specifically mentioned in A. A. Sinkula's article in Annual Reports in Medicinal Chemistry, vol 10, chapter 31, pp.306–326, herein incorporated by reference, and the references therein. Specific prodrug moieties which may be specifically mentioned are aliphatic-aromatic, carbonate, phosphate and carboxylic esters, carbamates, peptides, glycoside, acetals and ketals, tetrahydropyranyl and silyl ethers. Such prodrug moieties can be cleaved in situ, e.g. are hydrolysable in physiological conditions, to give compounds of formula (I).

Certain of the compounds of the formula (I) may exist as geometric isomers. The compounds of the formula (I) may possess one or more asymmetric centers, apart from the specified centers in formula (I), and so exist in two or more stereoisomeric forms. The present invention includes all the individual stereoisomers and geometric isomers of the compounds of formula (I) and mixtures thereof.

Preferably the compounds of formula (I) have the following stereochemistry (IA):

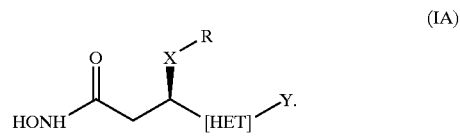

(IA)

Preferably X is a linear $C_{2-6}$ alkylene moiety optionally substituted by one or more fluorine atoms. More preferably X is propylene.

Preferably [HET] is

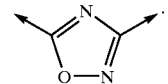

Preferably R is $C_{3-8}$ cycloalkyl optionally substituted by one or more fluorine atoms. More preferably R is cyclobutyl, cyclopentyl or cyclohexyl optionally substituted by one or more fluorine atoms. Most preferably R is cyclohexyl.

Preferably Y is a 5- or 6-membered unsaturated ring containing 0, 1 or 2 ring hetero-atoms independently selected from N and O, and which ring is optionally substituted by one or more substituents independently selected from =O, $C_{1-4}$ alkyl, $C_{1-4}$ alkoxy, $NR^1R^2$, $SO_2NR^1R^2$, $CO_2R^1$, $CONR^1R^2$, $CH_2CO_2R^1$, $NR^1CO_2R^2$, $NR^1SO_2R^2$ and $het^1$.

More preferably Y is a 5- or 6-membered unsaturated ring containing 0, 1 or 2 ring hetero-atoms independently selected from N and O, and which ring is optionally substituted by one or more substituents independently selected from =O, $CONH_2$, $CONHCH_3$, $CON(CH_3)_2$, $CH_3$, $NH_2$, $CO_2C_2H_5$, $CO_2H$, $CH_2CO_2CH_3$, $NHCH_3$, $NHC_2H_5$, $N(CH_3)_2$, morpholino, imidazol-1-yl, methoxy, ethoxy and $NHSO_2CH_3$.

Yet more preferably Y is 5-carbamoylpyridin-3-yl, uracil-5-yl, pyridin-4-yl, 6-methylpyridin-3-yl, 5-carboxypyridin-3-yl, 6-methoxycarbonylmethylpyridin-3-yl, 6-(4-methylpiperazino)pyridin-3-yl, 6-(3-dimethylaminoazetidino)pyridin-3-yl, 6-(3-morpholinoazetidino)pyridin-3-yl, 4-carboxypyridin-2-yl, 6-dimethylaminopyridin-3-yl, 6-(imidazol-1-yl)pyrazin-2-yl, 3-morpholinopyrazin-2-yl, 3-pyrrolidinopyrazin-2-yl, 3-dimethylaminopyrazin-2-yl, 3-methylaminopyrazin-2-yl, 3-methylsulphonamidophenyl, 3-carboxyphenyl or 6-ethoxypyrazin-2-yl. Most preferably Y is uracil-5-yl or 4-carboxypyridin-2-yl.

A preferred group of compound of formula (I) are those wherein each substituent is as specified in the Examples below.

Another preferred group are the compounds of the Examples below and the salts, solvates and prodrugs thereof. Especially preferred are the compounds of Examples 1 and 25 and the salts, solvates and prodrugs thereof.

A further aspect of the invention is a PCP inhibitor of formula (I) which is selective against MMP-1 and/or MMP-2 and/or MMP-9 and/or MMP-14.

A further aspect of the invention is the use of a PCP inhibitor of formula (I) which is selective against MMP-1 and/or MMP-2 and/or MMP-9 and/or MMP-14 in medicine.

Further related to this aspect of the invention is the use of a PCP inhibitor of formula (I) which is selective against MMP-1 and/or MMP-2 and/or MMP-9 and/or MMP-14 in the manufacture of an antiscarring medicament.

Further related to this aspect of the invention is a method of treating a condition mediated by PCP and in which MMP-1 and/or MMP-2 and/or MMP-9 and/or MMP-14 have a beneficial effect, with an effective amount of PCP inhibitor of formula (I) which is selective against MMP-1 and/or MMP-2 and/or MMP-9 and/or MMP-14, an example of such a condition being a wound.

Preferably the PCP inhibitor of formula (I) mentioned in this aspect of the invention is selective against at least MMP-1, MMP-2 and MMP-9. Most preferably the said PCP inhibitor of formula (I) is selective against MMP-1, MMP-2, MMP-9, and MMP-14.

Preferably the selective PCP inhibitor of formula (I) has an $IC_{50}$ vs. PCP of 0.5 $\mu$M or lower, and selectivities vs. MMP-2 and MMP-9 of at least 30-fold, in the tests described herein.

Preferably the selective PCP inhibitor of formula (I) has an $IC_{50}$ vs. PCP of 0.1M or lower, and selectivities vs. MMP-1, MMP-2, MMP-9 and MMP-14 of at least 300-fold, in the tests described herein.

Another aspect of the invention is a substance of formula (I) described herein, including the salts, solvates and prodrugs thereof, for use in medicine.

Another aspect of the invention is a substance of formula (I) described herein, including the salts, solvates and prodrugs thereof, for use in treating a PCP-mediated condition, such as in an antiscarring medicament.

Another aspect of the invention is the use of the substances of formula (I) described herein, including the salts, solvates and prodrugs thereof, in the manufacture of a medicament for treatment of a PCP-mediated condition (e.g. an antiscarring medicament).

Another aspect of the invention is a pharmaceutical composition comprising a compound of formula (I), salts thereof, solvates thereof and/or prodrugs thereof, and a pharmaceutically acceptable diluent, carrier or adjuvant.

Another aspect of the invention is the combination of a compound of formula (I), or a salt, solvate or prodrug thereof, with another material useful in treating wounds, such as:

(i) a growth factor such as TGF-β-3 (Renovo), IGF-1 (Genentech), IGF-1 complex (Celtrix), KGF-2 or FGF-10 (Sumitomo), DWP-401/EGF (Daewoong) or SNK-863 (Sanwa Kagaku Kenkyusho);

(ii) a growth factor agonist such as Noggin (Regeneron);

(iii) a growth factor antibody/antisense material, such as those to: TGF-β-1 or 2 (Renovo, CaT), PDGF (11 Yang) or CTGF (Fibrogen);

(iv) a hormone such as DHEAS (Pharmadigm), ConXn/Relaxin (Connetics);

(v) an antibody to adhesion compounds such as ICAM-1 (Boehringer);

(vi) a MMP beneficial to healing of wounds, such as Collagenase ABC (BioSpecifics);

(vii) a barrier such as ADCON (Gliatech);

(viii) skin products such as artificial skin systems such as those based on DermaGraft (Advanced Tissue Sciences Inc.), INTEGRA Artificial Skin (Integra Life Sciences Holding Corp.), cell cultures such as Apligraf/Graftskin (Novartis), those developed by Cell Genesys Inc., AlloDerm (LifeCell) or matrix formulation products such as Argidene gel (Telios Pharmaceuticals Inc.);

(ix) a uPA inhibitor such as those disclosed in WO 99/01451; and (x) a MMP-3 inhibitor such as those disclosed in WO99/35124, WO 99/29667 and WO 00/74681.

Yet another aspect of the invention is a method of treatment of a condition mediated by PCP comprising administration of a therapeutically-effective amount of a substance according to the above definitions.

It is to be appreciated that reference to treatment includes prophylaxis as well as the alleviation of established symptoms of PCP-mediated conditions and diseases.

The invention further provides Methods for the production of compounds of the invention, which are described below and in the Examples and Preparations. The skilled man will appreciate that the compounds of the invention could be made by methods other than those specifically described herein, by adaptation of the methods herein described in the sections below and/or adaptation thereof, for example by methods known in the art. Suitable guides to synthesis, functional group transformations, use of protecting groups, etc. are, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), and any updated versions of said standard works.

In the Methods below, unless otherwise specified, the substituents are as defined above with reference to the compounds of formula (I) above.

DETAILED DESCRIPTION OF THE INVENTION

The compounds of formula (I) may be made from the corresponding acids of formula (II) or the corresponding protected N-hydroxy acid species (E), where "P" is a suitable NHO-protecting group such as those mentioned in Greene and Wuts, supra. Of particular interest are compounds of formula (III) where "P" is a tri($C_{1-4}$ alkyl)silyl group such as trimethylsilyl (TMS).

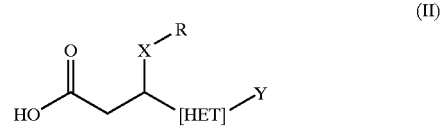

(II)

(III)

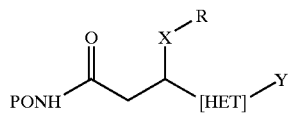

(V)

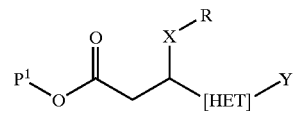

Deprotection of compounds of formula (III) to give compounds of formula (I) can be carried out using a suitable deprotection regime. For example, when P is TMS, an acidic hydrolysis can be used, such as reaction with methanolic hydrochloric acid or aqueous citric acid.

Transformation of acids (II) into compounds of formula (I) can be carried out using a number of methods, such as reaction with carbonyldiimdazole and a suitable base such as triethylamine, in a suitable solvent such as tetrahydrofuran (THF), followed by reaction with hydroxylamine (NH$_2$OH, suitably generated from a salt thereof, such as the hydrochloride, in the presence of a suitable base such as a tertiary amine, for example triethylamine).

Alternatively, acids (II) can be transformed into activated acid derivatives (IV), where L is a suitable leaving group such as OCO(C$_{1-4}$ alkyl) or imidazolyl, which can then be reacted with a protected hydroxylamine species "PONH$_2$", to give compounds of formula (III), above. Suitable examples of this transformation include reaction of the acid (II) with a suitable chloro-ester such as isobutyl chloroformate, with a suitable base, e.g. a tertiary amine such as triethylamine or N-methyhnorpholine to give an activated acid (IV), where L is OCO(isobutyl). Suitable examples of preparation of compounds of formula (IV) where L is imidazolyl include reaction of acid (II) with carbonyldiimidazole in a suitable solvent such as methylene chloride, or with carbonyldiimidazole with a suitable tertiary amine base such as triethylamine in a suitable ether solvent such as THF.

(IV)

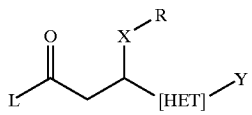

The compounds of formula (IV) can be transformed into compounds of formula (III) by reaction with compounds of formula PONH$_2$, where P is as described earlier.

Compounds of formula (I) may also be made directly from compounds of formula (IV) by reaction with hydroxylamine, suitably generated in situ from a salt thereof (e.g. hydrochloride salt) and a suitable base such as a tertiary amine (e.g. triethylamine).

Compounds of formula (III) can be transformed into compounds of formula (I) as described earlier.

Compounds of formula (II) can be made by deprotection of the compounds of formula (V) where P$^1$ is a suitable carboxylic acid protecting group such as t-butyl, with a suitable deprotecting regime. For example when P$^1$ is t-butyl, the deprotection can be carried by reaction with trifluoroacetic acid.

Certain compounds of formula (I) may be transformed into other compounds of formula (I) by suitable functional group interconversion (FGI) of a type well-known to those skilled in the art. For examples where the compound of formula (I) contains an ester or acid moiety, these can be interconverted readily by known hydrolysis or esterification methods respectively. Hydrolysis of an ethyl ester is exemplified in Example 11 below which mentions the use of lithium hydroxide as base. Another example of an interconversion of compounds of formula (I) is where one compound of formula (I) contains what could be regarded as a protecting group and the interconversion can be regarded as a deprotection—e.g. Example 33 below describes the conversion of a t-butoxycarbonylamino compound (of Example 32) into the corresponding free amine using trifluoroacetic acid (TFA). Many other FGIs of compounds of formula (I) into other compounds of formula (I) are possible using methods exemplified in the Examples and Preparations sections below, and standard FGI chemistry known in the art.

The compounds of formula (I), (II), (III) and (IV) may be made by methods outlined in Schemes 1–11 below, or by analogous methods.

Scheme 1

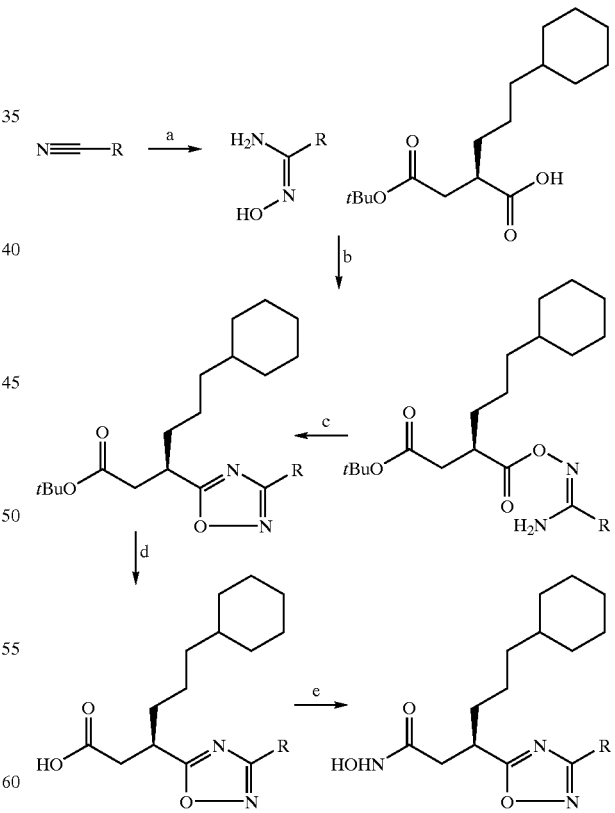

Examples 1–10,
18–24, 26, 44, 45,
48–56, 60, 62–68

$^a$(a), HONH$_2$; (b), CDI or WSCDI/HOBT or WSCDI/4-DMAP; (c), Xylene 130° C. or neat 130° C.; (d), TFA; (e), $t$BuOCOCl or CDI, then TMSONH$_2$, then MeOH or 2M HCl, or HONH$_2$.

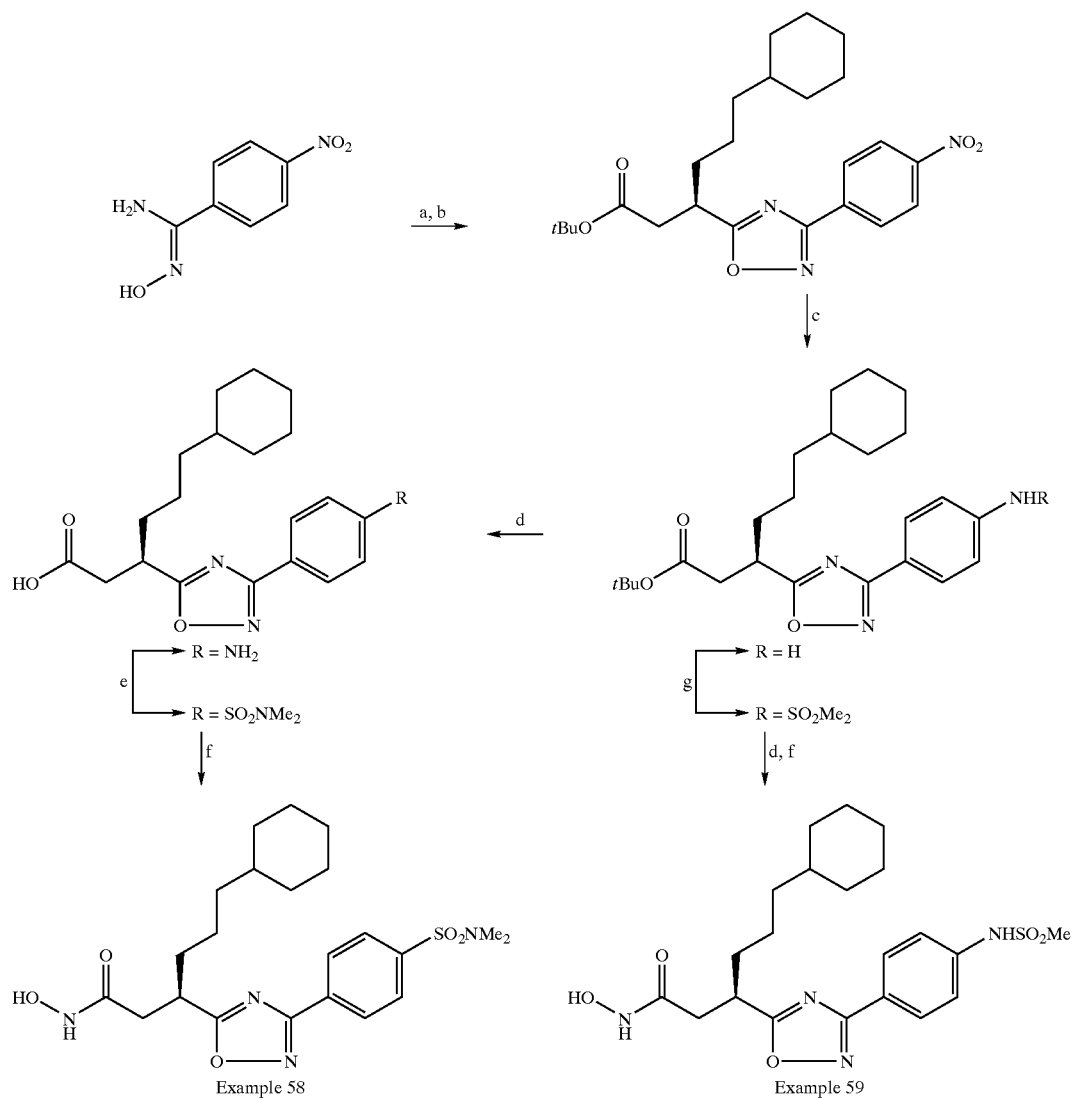
Scheme 2
(a), CDI or WSCDI/HOBT or WSCDI/4-DMAP; (b), Xylene 130° C. or neat 130° C.; (c), SnCl₂; (d), TFA; (e), i, cHCl, NaNO₂, ii, SO₂, CuCl₂, iii, NHMe₂; (f), iBuOCOCl or CDI, then TMSONH₂, , then MeOH, or HONH₂; (g), MeSO₂Cl.
Scheme 3
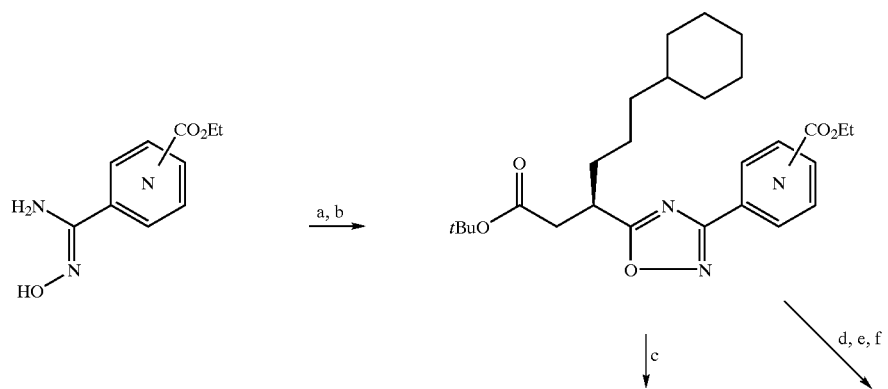

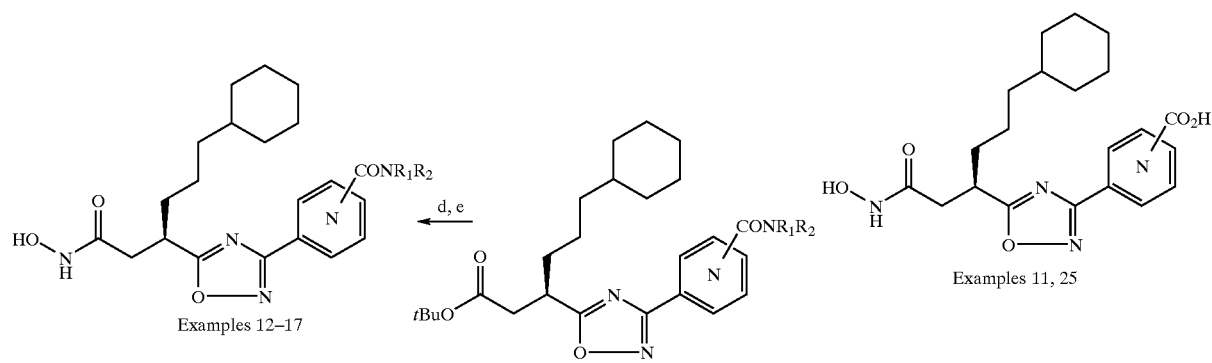
(a), CDI or WSCDI/HOBT or WSCDI/4-DMAP; (b), Xylene 130° C. or ne at 130° C.; (c),
NHR₁R₂; (d) TFA; (e), iBuOCOCl or CDI, then TMSONH₂, then MeOH, or HONH₂; (f) LiOH.
Scheme 4
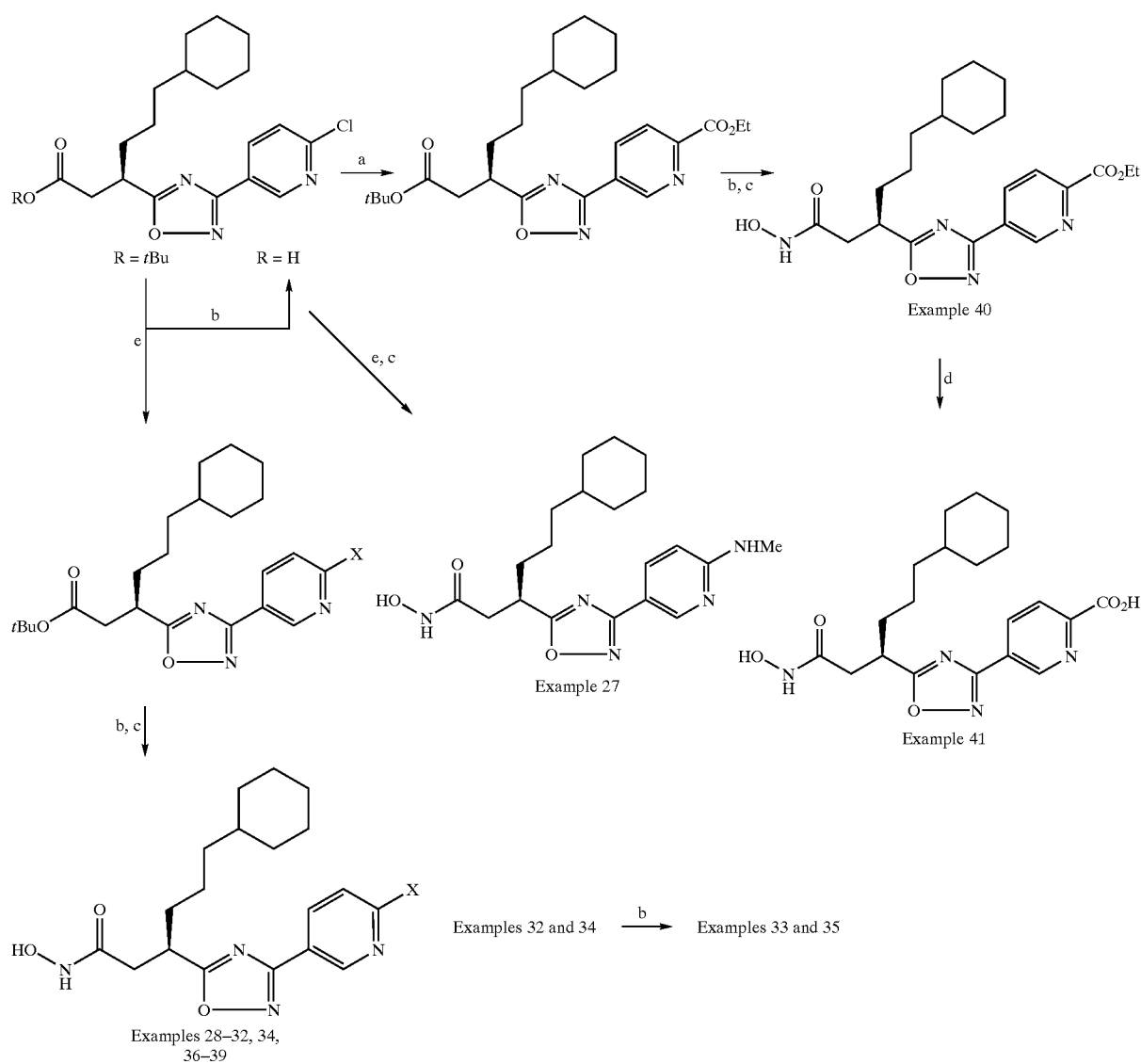
(a), Pd cat, CO, EtOH; (b), TFA; (c), iBuOCOCl or CDI, then TMSONH₂, then MeOH, or HONH₂;
(d), LiOH; (e), NHR₁R₂

Scheme 5
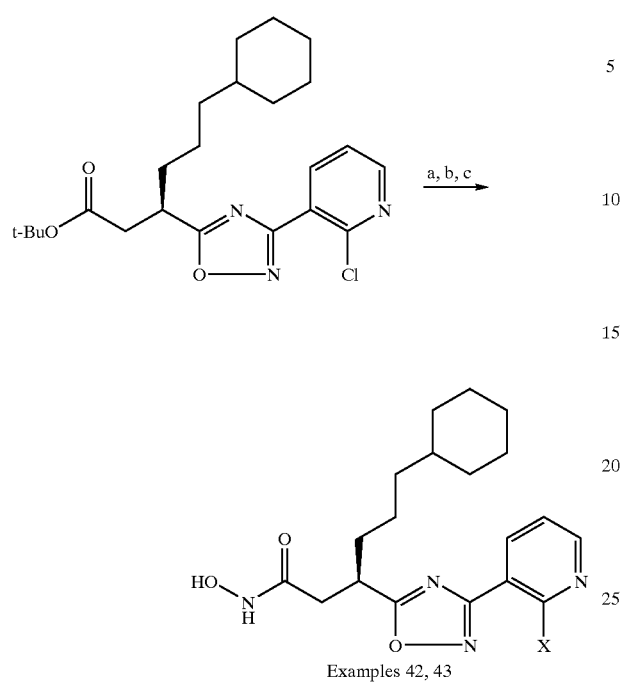
(a), TFA; (b), NHR₁R₂, (c) iBuOCOCl or CDI, then TMSONH₂, then MeOH, or HONH₂.
Scheme 7
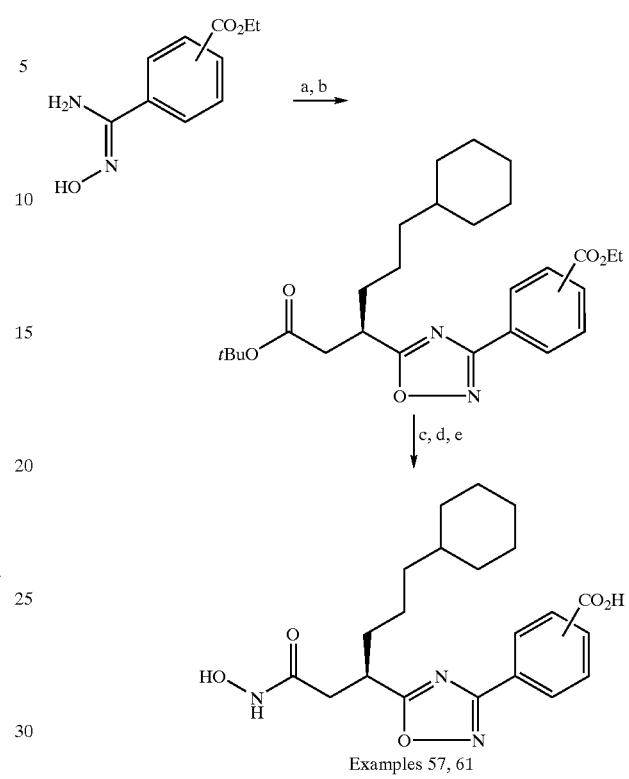
(a), CDI or WSCDI/HOBT or WSCDI/4-DMAP; (b), Xylene 130° C. or ne at 130° C.;
(c), TFA; (d), iBuOCOCl or CDI, then TMSONH₂, then MeOH, or HONH₂; (e) LiOH.
Scheme 6
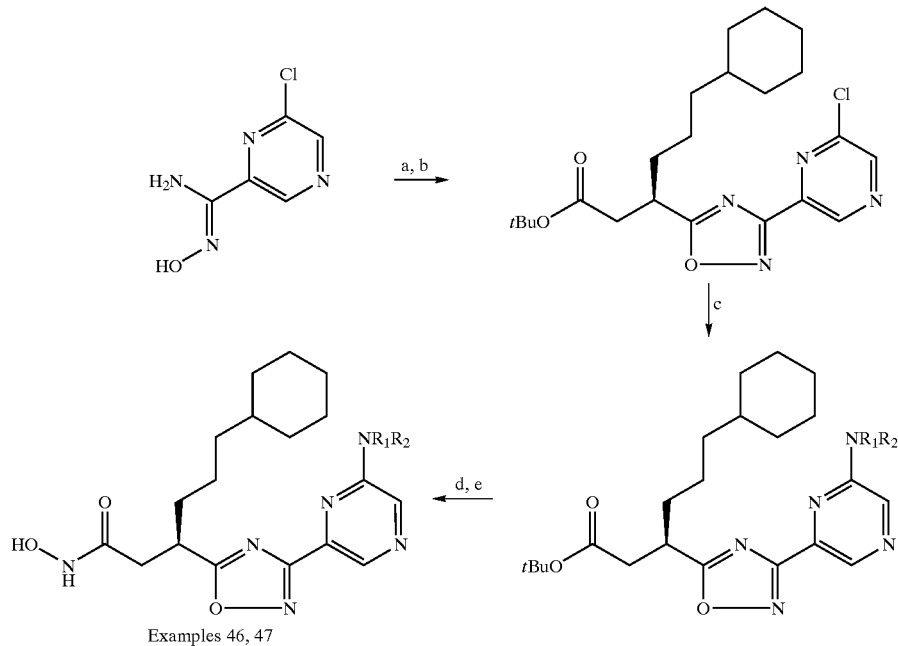
(a), CDI or WSCDI/HOBT or WSCDI/4-DMAP; (b), Xylene 130° C. or ne at 130° C.; (c),
TFA; (d), NHR₁R₂; (e), iBuOCOCl or CDI, then TMSONH₂, then MeOH, or HONH₂.

Scheme 8
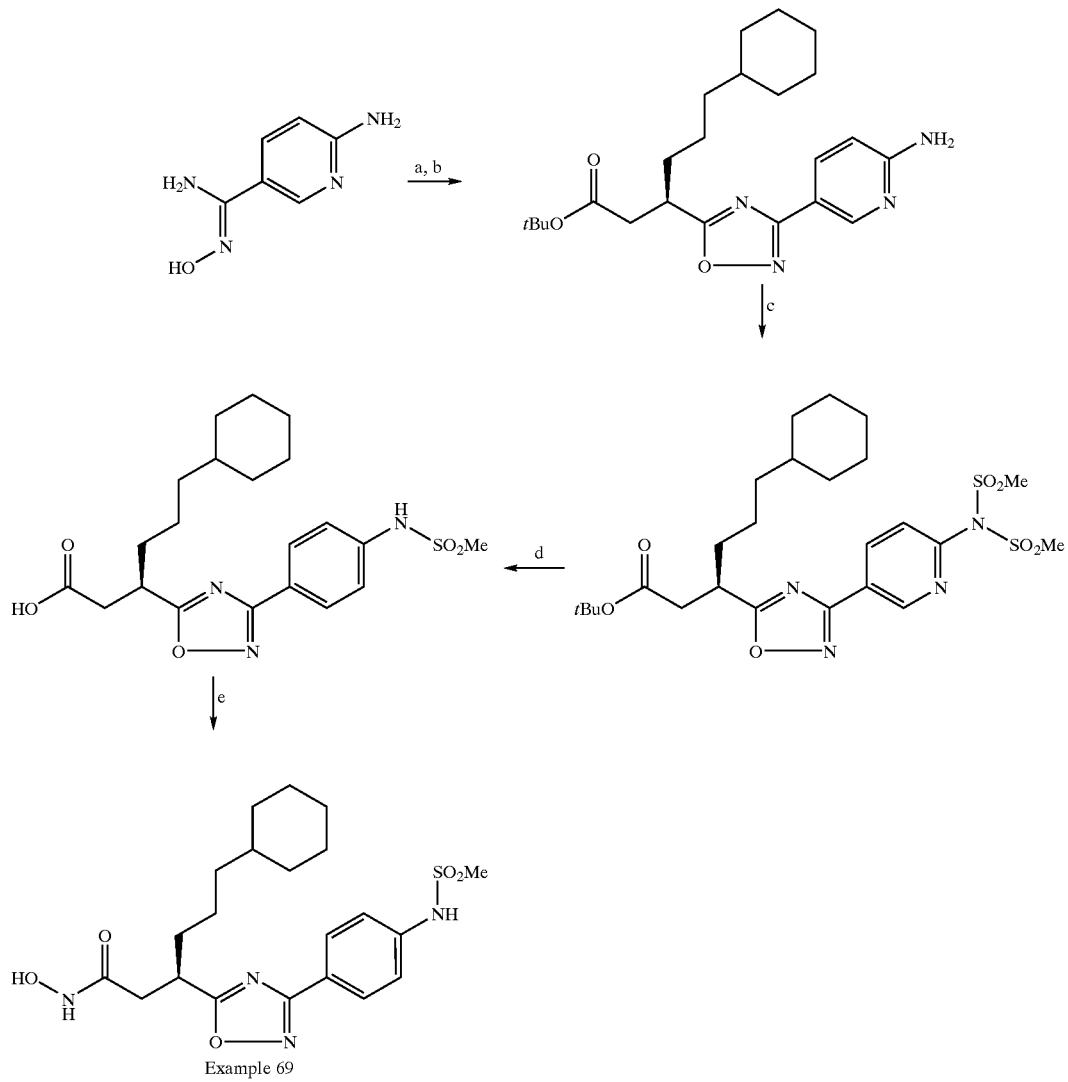
(a), CDI or WSCDI/HOBT or WSCDI/4-DMAP; (b), Xylene 130° C. or ne at 130° C.; (c), MeSO₂Cl.; (d), NaOH; (e), iBuOCOCl or CDI, then TMSONH₂, then MeOH, or HONH₂.
Scheme 9
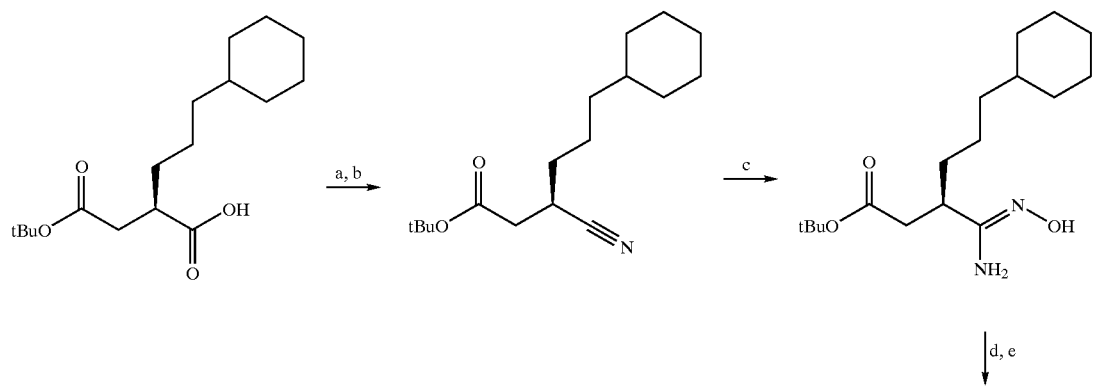

-continued
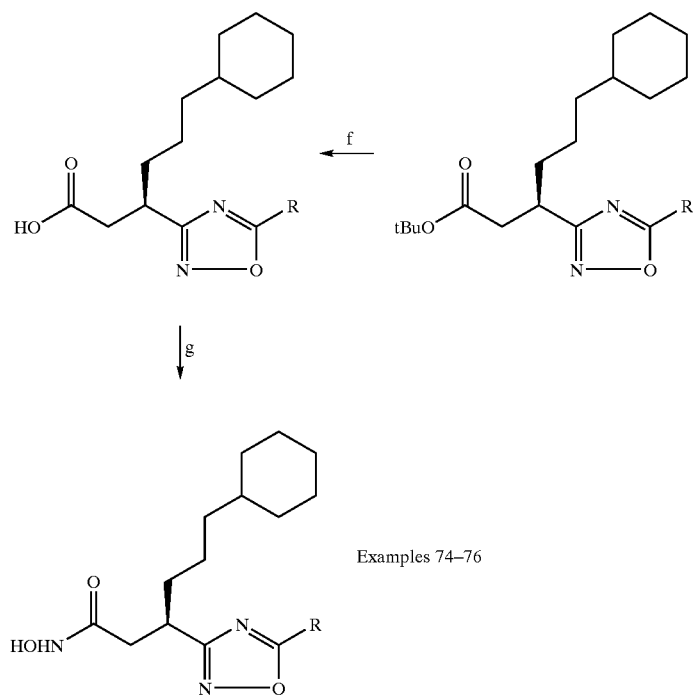
Examples 74–76
[a](a), iBuOCOCl then ammonia (b), TFAA, pyridine; (c), HONH$_2$.HCl, N-methylmorpholine, ethanol, reflux; (d), WSCDI, DMAP, RCO$_2$H; (e), 140° C., (f) TFA, (g) iBuOCOCl, N-methylmorpholine, HONH$_2$.HCl or HOBt, WSCDI, aqueous HONH$_2$.
Scheme 10
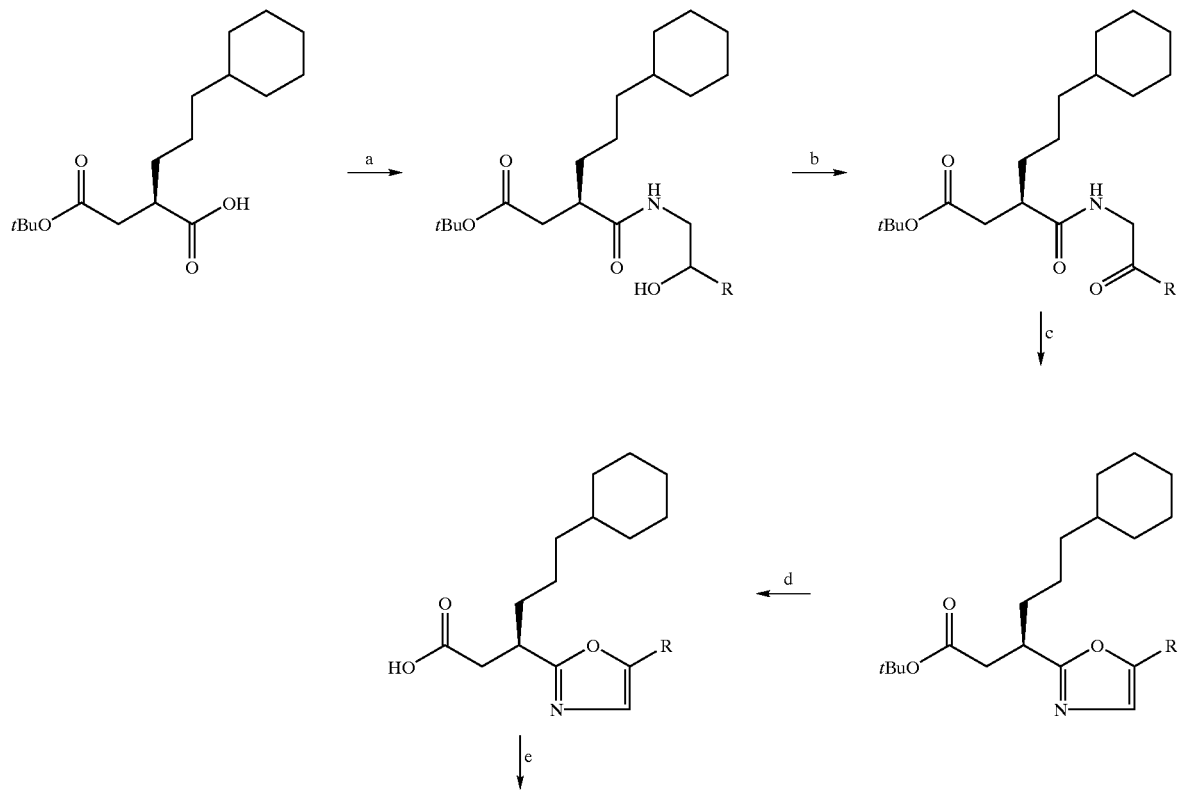

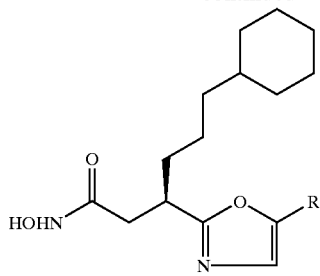

Examples 72, 73

(a), WSCDI/HOBT+ RCH(OH)CH$_2$NH$_2$; (b), Dess-Martin periodinane; (c), triflic anhydride, triphenylphosphine oxide, triethylamine; (d), TFA; (e), *i*BuOCOCl or CDI, then TMSONH$_2$.

Scheme 11

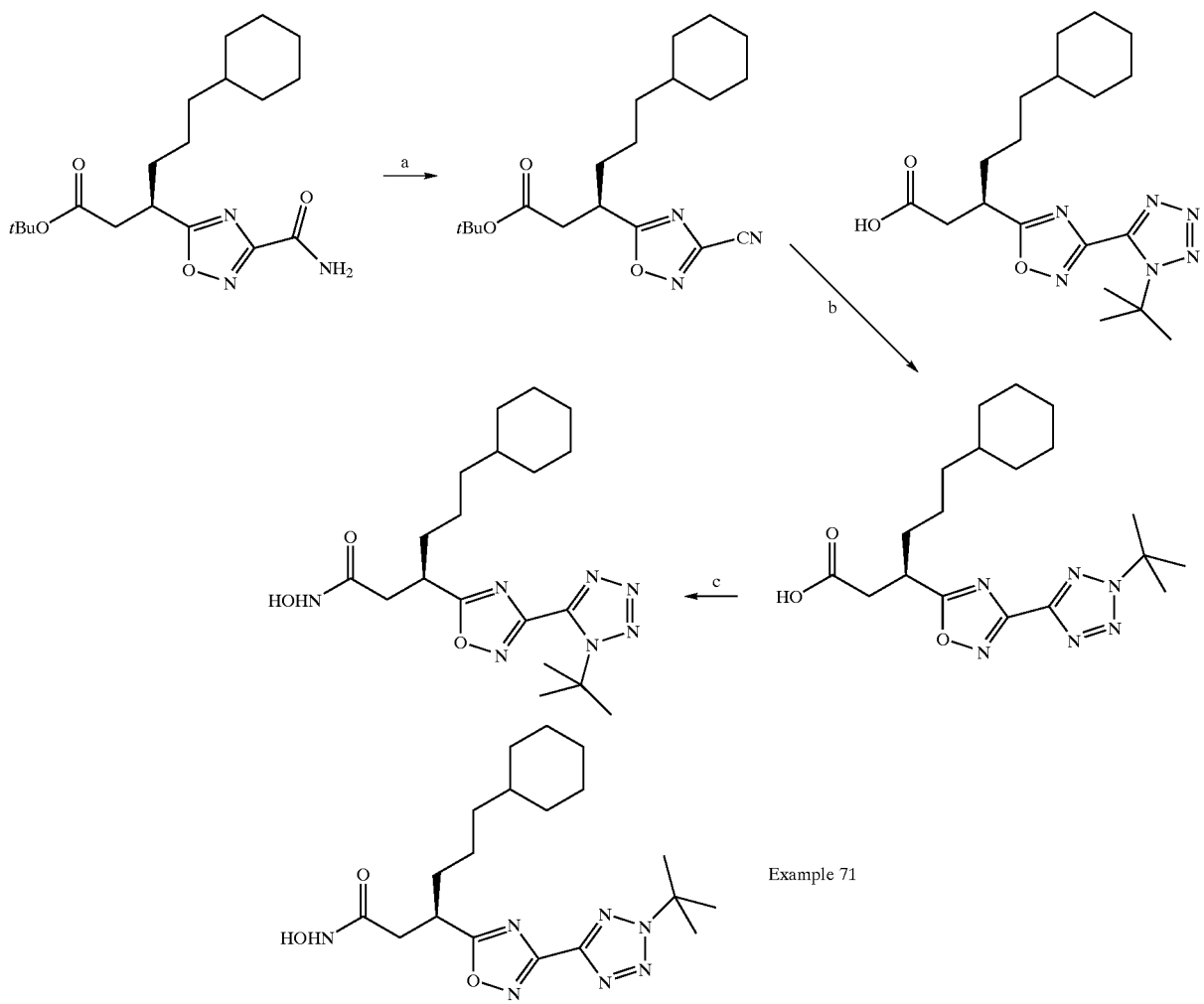

Example 71

(a), TFAA, pyridine; (b), TMS-azide; (c), HOAt, WSCDI, TMSONH$_2$.

It will be apparent to those skilled in the art that other protection and subsequent deprotection regimes during synthesis of a compound of the invention may be achieved by conventional techniques, for example as described in the volumes by Greene and Wuts, and Kocienski, supra, some of which are mentioned specifically herein.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Compounds of the invention are available by either the methods described herein in the methods, schemes, Examples and Preparations or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

The compounds, salts, solvates (including hydrates) and prodrugs of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base. In certain cases preferential crystallisation of one of the enantiomers can occur from a solution of a mixture of enantiomers, thus enriching the remaining solution in the other enantiomer.

For human use, the compounds of formula (I) or their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targeting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract. The compounds or salts can be injected parenterally, for example, intravenously, intramuscularly, intradermally or subcutaneously. For parenteral administration, they are best used in the form of a sterile aqueous solution or suspension which may contain other substances, for example, enough salt or glucose to make the solution isotonic with blood. They can be administered topically, or transdermally, in the form of creams, gels, suspensions, lotions, ointments, dusting powders, sprays, foams, mousses, drug-incorporated dressings, solutions, sponges, fibres, microemulsions, films, skin patches, ointments such as petrolatum or white soft paraffin based ointments or via a skin patch or other device. Penetration enhancers may be used, and the compound may be used in combination with cyclodextrins. In addition, the compound may be delivered using iontophoresis, electropration, phonophoresis or sonophoresis. They could be administered directly onto a wound site. They could be incorporated into a coated suture. For example they can be incorporated into a lotion or cream consisting of an aqueous or oily emulsion of mineral oils; sorbitan monostearate; polysorbate 60; cetyl esters wax; cetearyl alcohol; 2-octyldodecanol; benzyl alcohol; water; polyethylene glycols and/or liquid paraffin, or they can be incorporated into a suitable ointment consisting of one or more of the following—mineral oil; liquid petrolatum; white petrolatum; propylene glycol; polyoxyethylene polyoxypropylene compound; emulsifying wax and water, or as hydrogel with cellulose or polyacrylate derivatives or other viscosity modifiers, or as a dry powder or liquid spray or aerosol with butane/propane, HFA, CFC, $CO_2$ or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly for ophthalmic use e.g., via intraocular injection, or sustained release device or in a lens implant, via subconjunctival injection, or as an eye drop with appropriate buffers, viscosity modifiers (e.g. cellulose or polyacrylate derivatives), preservatives (e.g. benzalkonium chloride (BZK)) and agents to adjust tonicity (e.g. sodium chloride). Such formulation techniques are well-known in the art.

For certain uses, vaginal, rectal and nasal (e.g. by inhalation of a dry powder or aerosol) administration would be suitable.

All such formulations may also contain appropriate stabilisers and preservatives.

For oral and parenteral administration to human patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

Ocular Formulation

The compounds or their salts, solvates or prodrugs may be administered topically by the ocular route. They may be formulated as sterile, isotonic, pH adjusted, buffered suspensions or solutions. A polymer may be added such as crossed-linked polyacrylic acid, polyinylalcohol, hyaluronic acid, a cellulosic polymer (e.g. hydroxypropylmethylcellulose, hydroxyethylcellulose, methyl cellulose), or a heteropolysaccharide polymer (e.g. gelan gum). Alternatively, they may be formulated in an ointment such as petrolatum or mineral oil, incorporated into bio-degradable (e.g. absorbable gel sponges, collagen) or non-biodegradable (e.g. silicone) implants, lenses or delivered via particulate or vesicular systems such as niosomes or liposomes. Formulations may be optionally combined with a preservative, such as benzalkonium chloride. In addition, they may be delivered using iontophoresis. The compound may also be used in combination with cyclodextrins.

An example of preferred formulation excipients of a compound, salt, solvate or prodrug according to the invention comprises:

| Ingredients | % (w/w) composition |
| --- | --- |
| $NaH_2PO_4$ | 0.370 |
| $Na_2HPO_4$ | 0.567 |
| Glycine | 0.430 |
| Carbomer 940 | 1.000 |
| Water | to 100 |
| pH adjusted to ~7 | |

The preferred formulation will be a buffered solution (preferably using monobasic and dibasic sodium phosphate) containing 0.5 to 5.0% of a cross-linked polyacrylic acid, pH adjusted to around 7 with the addition of a stabiliser such as glycine.

For topical administration to human patients with acute/surgical wounds or scars, the daily dosage level of the compounds, in suspension or other formulation, could be from 0.01 to 50 mg/ml, preferably from 0.3 to 30 mg/ml.

The dosage will vary with the size of the wound, whether or not the wound is open or closed or partially closed, and whether or not the skin is intact.

The physician in any event will determine the actual dosage which will be most suitable for a an individual patient and it will vary with the age, weight and response of the particular patient, as well as the efficacy of the drug compound. The above dosages are exemplary of the average case; there can of course be individual instances where higher or lower dosage ranges are merited, and such are within the scope of this invention.

Biological Test Methods

PCP Inhibition

In order to determine potency of PCP inhibitors a fluorogenic PCP cleavage assay was used. This assay is based on the template of Beekman et al. (FEBS Letters (1996), 390: 221–225) using a fluorogenic substrate. The substrate (Dabcyl-Arg-Tyr-Tyr-Arg-Ala-Asp-Asp-Ala-Asn-Val-Glu (EDANS)-$NH_2$) contains the cleavage site of human PCP (Hojima et al., J Biol Chem (1985), 260: 15996–16003). Human PCP has been purified from supernatant of stable transfected CHO cells using hydrophobic interaction column followed by Superdex 200 gel filtration. 4 μg total protein of this enzyme preparation was incubated with various concentrations of the substance to be tested and $3 \times 10^{-6}$ M substrate in assay buffer (50 mM Tris-Base, pH 7.6 containing 150 mM NaCl, 5 mM $CaCl_2$, 1 μM $ZnCl_2$ and 0.01% Brij 35). The assay was performed in 96-well black fluorimeter plates and fluorescence was read continuously in a fluorimeter over 2.5 hours ($\lambda_{ex}$=340 nm, $\lambda_{em}$=485 nm) at a constant 37° C. with shaking. Release of the fluorogenic signal was in linear correlation to PCP activity. Reading of the mean velocity from 30 min after start of experiment until 2.5 hours was calculated by the Biolise software. $IC_{50}$ values were calculated by plotting % inhibition values against compound concentration using Tessela add in for Excel spreadsheet. Example compounds were tested and were found to have $IC_{50}$ values vs. PCP of 1 μM or less.

MMP Inhibition

The ability of compounds to inhibit the cleavage of fluorogenic peptides by MMPs 1, 2, 9, and 14 is described below. The assays for MMPs 2, 9, and 14 are based upon the original protocol described by Knight et al. (Fed.Euro.Biochem.Soc., 296 (3), 263–266; 1992), with the slight modifications given below.

Inhibition of MMP-1

(i) Enzyme Preparation

Catalytic domain MMP-1 was prepared at Pfizer Central Research. A stock solution of MMP-1 (1 μM) was activated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 μM $ZnSO_4$, 0.05% Brij 35) pH 7.5 to a concentration of 0 nM. The final concentration of enzyme used in the assay was 1 nM.

(ii) Substrate

The fluorogenic substrate used in this assay was Dnp-Pro-β-cyclohexyl-Ala-Gly-Cys(Me)-His-Ala-Lys(N-Me-Ala)-$NH_2$ as originally described by Bickett et al (Anal. Biochem, 212, 58–64, 1993). The final substrate concentration used in the assay was 10 μM.

(iii) Determination of Enzyme Inhibition

Test compounds were dissolved in dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG LabTechnologies, Aylesbury, UK) at an excitation wavelength of 355 nm and emission wavelength of 440 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-2 and MMP-9

(i) Enzyme Preparation

Catalytic domain MMP-2 and MMP-9 were prepared at Pfizer Central Research. A stock solution of MMP-2/MMP-9 (1M) was activated by the addition of aminophenylmercuric acetate (APMA). For MMP-2 and MMP-9, a final concentration of 1 mM APMA was added, followed by incubation for 1 hour at 37° C. The enzymes were then diluted in Tris-HCl assay buffer (100 mM Tris, 100 mM NaCl, 10 mM $CaCl_2$ and 0.16% Brij 35, pH 7.5), to a concentration of 10 nM. The final concentration of enzyme used in the assays was 1 nM.

(ii) Substrate

The fluorogenic substrate used in this screen was Mca-Arg-Pro-Lys-Pro-Tyr-Ala-Nva-Trp-Met-Lys(Dnp)-$NH_2$ (Bachem Ltd, Essex, UK) as originally described by Nagase et al (J.Biol.Chem., 269(33), 20952–20957, 1994). This substrate was selected because it has a balanced hydrolysis rate against MMPs 2 and 9 ($k_{cat}/k_m$ of 54,000, 59,400 and 55,300 $s^{-1}$ $M^{-1}$ respectively). The final substrate concentration used in the assay was 5 μM.

(iii) Determination of Enzyme Inhibition

Test compounds were dissolved in dimethyl sulphoxide and diluted with test buffer solution (as above) so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence using a fluorimeter (Fluostar; BMG LabTechnologies, Aylesbury, UK) at an excitation wavelength of 328 nm and emission wavelength of 393 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-14

(i) Enzyme Preparation

Catalytic domain MMP-14 was purchased from Prof. Tschesche, Department of Biochemistry, Faculty of Chemistry, University of Bielefeld, Germany. A 10 μM enzyme stock solution was activated for 20 minutes at 25° C. following the addition of 5 μg/ml of trypsin (Sigma, Dorset, UK). The trypsin activity was then neutralised by the addition of 50 μg/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$ and 0.16% Brij 35, pH 7.5) to a concentration of 10 nM. The final concentration of enzyme used in the assay was 1 nM.

(ii) Substrate

The fluorogenic substrate used in this screen was Mca-Pro-Leu-Gly-Leu-Dpa-Ala-Arg-$NH_2$ (Bachem Ltd, Essex, UK) as described by Will et al (J. Biol. Chem., 271(29), 17119–17123, 1996). The final substrate concentration used in the assay was 10 μM. Examples tested all had PCP IC50's of 0.3 μM or less.

Determination of enzyme inhibition by test compounds was performed in the same manner as described for MMPs-2 and -9 above.

All references mentioned herein in this text are incorporated by reference in their entirety.

The compounds of the invention are illustrated by the Examples below.

EXAMPLES AND PREPARATIONS

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (1R) spectra were measured using a Nicolet Magna 550 Fourier transform infra-red spectrometer. Flash chromatography refers to column chromatography on silica gel (Kieselgel 60, 230–400 mesh, from E. Merck, Darm stadt. Kieselgel 60 $F_{254}$ plates from E. Merck were used for TLC, and compounds were visualised using UV light, 5% aqueous potassium permanganate or Dragendorff's reagent (oversprayed with aqueous sodium nitrite). Thermal analyses by Differential Scanning Calorimetry (DSC) and ThermoGravimetric Analysis (TGA) were obtained using Perkin Elmer DSC7 and TGA7. Moisture sorption characteristics were recorded using Surface Measurement Systems Ltd. Automated Water Sorption Analyser DVS 1. Water content was determined on a Mitsubishi CA100 (Coulometric Karl Fisher Titrator). Powder X-ray diffraction (PXRD) pattern was determined using a Siemens D5000 powder X-ray diffractometer fitted with an automatic sample changer, a theta-theta goniometer, automatic beam divergence slits, a secondary monochromator and a scintillation counter. Other measurements were taken using standard equipment. Hexane refers to a mixture of hexanes (HPLC grade) b.p. 65–70° C. "Ether" and "$Et_2O$" refers to diethyl ether. Acetic acid refers to glacial acetic acid. 1-Hydroxy-7-aza-1H-1,2,3-benzotriazole (HOAt). "HOBT" is 1-hydroxy-1H-1,2,3-benzotriazole. N-[(dimethylamino)-1H-1,2,3-triazolo[4,5-b]pyridin-1-ylmethylene]-N-methylmethaninium hexafluorophosphate N-oxide (HATU) and 7-azabenzotriazol-1-yloxytris(pyrrolidino)phosphonium hexafluorophosphate (PYAOP) were purchased from PerSeptive Biosystems U.K. Ltd. "DIPE" refers to diisopropyl ether. Reverse-phase silica gel for flash chromatography was obtained from Fluka (Fluka 100, $C_{18}$, 40–63 μ). "DCM" is dichloromethane. "THF" is tetrahydrofuran. "WSCDI" is 1-(3-dimethylaminopropyl)-3-ethylcarbodiimide hydrochloride. "EtOAc" is ethyl acetate. "MeOH" is methanol. "DMSO" is dimethylsulphoxide. "ACE-Cl" is 1-chloroethyl chloroformate. "NMM" is N-methylmorpholine. "Pentane" refers to High Performance Liquid Chromatography (HPLC) grade n-pentane (b.pt.35–37° C.). Nomenclature has been allocated using the commercially available ACD program. Standard abbreviations are used throughout, e.g. "Me" is methyl, "Et" is ethyl, "Pr" is propyl, "Ph" is phenyl, etc.

[a]HPLC autopurification was performed using 2 columns—Phenomenex LUNA C8 150×21.2 mm, 10 μm and Phenomenex MAGELLEN C18 150×21.2 mm, 5 μm, eluting with a gradient system of organic solvent [ammonium acetate (aq) 100 mM: acetonitrile (1:9)]: aqueous solvent [ammonium acetate (ag) 100 mM: acetonitrile (9:1)].

[b]HPLC autopurification was performed using 2 columns—Phenomenex LUNA C8 150×21.2 mm, 10 μm and Phenomenex MAGELLEN C18 150×21.2 mm, 5 μm, eluting with a gradient system of organic solvent (acetonitrile): aqueous solvent (0.1% aqueous trifluoroacetic acid).

Example 1
(3R)-6-CYCLOHEXYL-3-[3-(2,4-DIOXO-1,2,3,4-TETRAHYDRO-5-PYRIMIDINVYL)-1,2,4-OXADIAZOL-5-YL]-N-HYDROXYHEXANAMIDE

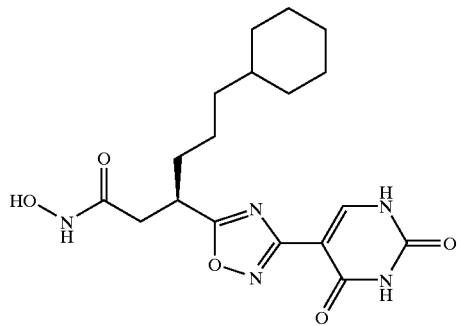

To a solution of the title compound from Preparation 3 (0.30 g, 0.8 mmol) in tetrahydrofuran (10 mL) was added triethylamine (0.225 mL, 1.6 mmol). The reaction was cooled to 0° C. in an ice bath, then iso-butylchloroformate (0.11 mL, 0.9 mmol) was added and a precipitate began to form immediately. The mixture was stirred for 1 hour, then O-trimethylsilyl hydroxylamine (0.32 ML, 2.6 mmol) was added and the reaction was warmed to room temperature and stirred for 2 hours. Methanol (10 mL) was added, stirring was continued for 1 hour and then the solvent was removed in vacuo. The residue was partitioned between 2M aqueous hydrochloric acid (20 mL) and ethyl acetate (100 mL). The layers were separated and the aqueous layer was extracted with ethyl acetate (2×100 mL). The combined organic extracts were dried ($MgSO_4$), the solvent was removed in vacuo and the residue was purified by flash chromatography on silica gel (dichloromethane/methanol/acetic acid 90:10:0.5 as eluant) to give the title compound as a white solid (0.19 g).

Mpt 210° C.
$^1$H NMR (400 MHz, $D_6$-DMSO) δ 0.74–0.89 (m, 2H), 1.06–1.24 (m, 8H), 1.53–1.69 (m, 7H), 2.66–2.81 (m, 2H), 3.39–3.47 (m, 1H), 8.05 (s, 1H), 10.9–11.4 (br s, 2H).
LRMS (ES) 414 (M+Na).
Anal. Calcd. For $C_{18}H_{24}N_5O_5$+1.0$H_2O$, 0.1 $CH_2Cl_2$, 0.1 AcOH: C, 51.85; H, 6.56; N, 16.52. Found C, 51.79; H, 6.50; N, 16.13.

Example 2
(3R)-6-CYCLOHEXYL-N-HYDROXY-3-[3-(6-METHYL-3-PYRIDAZINYL)-1,2,4-OXADMZOL-5-YL] HEXANAMIDE

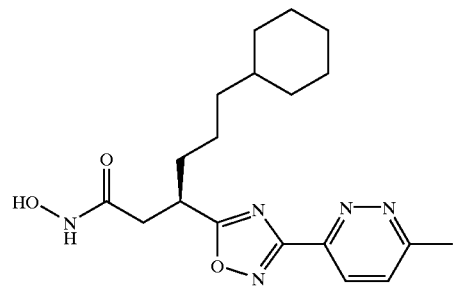

29

To a solution of the title compound from Preparation 6 (0.30 g, 0.9 mmol) in tetrahydrofuran (10 mL) was added triethylamine (0.225 mL, 1.6 mmol). The reaction was cooled to 0° C. in an ice bath, then iso-butylchloroformate (0.13 mL, 1.0 mmol) was added and a precipitate began to form immediately. The mixture was stirred for 1 hour, then O-trimethylsilyl hydroxylamine (0.32 mL, 2.6 mmol) was added and the reaction was warmed to room temperature and stirred overnight. Methanol (10 mL) was added, stirring was continued for 1 hour and then the solvent was removed in vacuo. The residue was purified by flash chromatography on silica gel (dichloromethane/methanol/aqueous ammonia solution 90:10:0.5 as eluant) to give the title compound as a glassy solid (0.28 g).

Mpt 48–55° C.
$^1$H NMR (400 MHz, D$_6$-DMSO) δ 60.75–0.88 (m, 2H), 1.06–1.30 (m, 8H), 1.53–1.77 (m, 7H), 2.42–2.60 (m, 2H), 2.48 (s, 3H), 3.50–3.59 (m, 1H), 8.64 (s, 1H), 8.71 (s, 1H), 9.06 (s, 1H), 10.41 (s, 1H).
LRMS (ES) 769 (2M+Na), 396 (M+Na), 374 (M+H).
Anal. Calcd. For C$_{19}$H$_{27}$N$_5$O$_3$+0.4H$_2$O: C, 59.95; H, 7.36; N, 18.40. Found C, 59.94; H, 7.64; N, 18.12.

Example 3
(3R)-6-CYCLOHEXYL-N-HYDROXY-3-[3-(1-METHYL-1H-IMIDAZOL-2-YL)-1,2,4-OXADIAZOL-5-YL]HEXANAMIDE

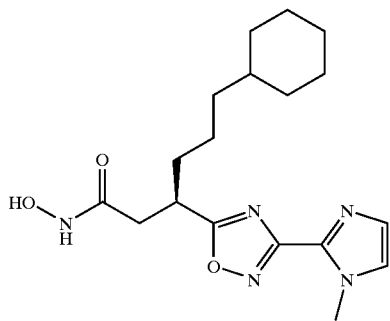

To a solution of the title compound from Preparation 9 (0.60 g, 1.5 mmol) in tetrahydrofuran (20 mL) was added triethylamine (0.42 mL, 3.0 mmol). The reaction was cooled to 0° C. in an ice bath, then iso-butylchloroformate (0.21 mL, 1.65 mmol) was added and a precipitate began to form immediately. The mixture was stirred for 2 hours, then O-trimethylsilyl hydroxylamine (0.6 mL, 5.0 mmol) was added and the reaction was warmed to room temperature and stirred overnight. Methanol (10 mL) was added, stirring was continued for 2 hours and then the solvent was removed in vacuo. The residue was partitioned between water (50 mL) and ethyl acetate (50 mL). The layers were separated and the aqueous layer was extracted with ethyl acetate (50 mL). The combined organic extracts were dried (MgSO$_4$), the solvent was removed in vacuo and the residue was purified by flash chromatography on silica gel (dichloromethane/methanol/ acetic acid 90:10:1.0 as eluant) to give the title compound as a white foam (0.35 g).

Mpt 55–60° C.
$^1$H NMR (400 MHz, D$_6$-DMSO) δ 0.77–0.92 (m, 2H), 1.06–1.30 (m, 8H), 1.53–1.77 (m, 7H), 2.40–2.60 (m, 2H), 3.46–3.54 (m, 1H), 3.91 (s, 3H), 7.10 (s, 1H), 7.42 (s, 1H), 8.72 (s, 1H), 10.45 (s, 1H).
LRMS (ES) 745 (2M+Na), 723 (2M+H), 384 (M+Na), 362 (M+H).
Anal. Calcd. For C$_{18}$H$_{27}$N$_5$O$_3$+0.75H$_2$O: C, 57.66; H, 7.36; N, 18.68. Found C, 57.76; H, 7.59; N, 18.83.

30

Example 4
(3R)-6-CYCLOHEXYL-N-HYDROXY-3-[3-(6-METHYL-2-OXO-1,2-DIHYDRO-3-PYRIDINYL)-1,2,4-OXADLAZOL-5-YL]HEXANAMIDE

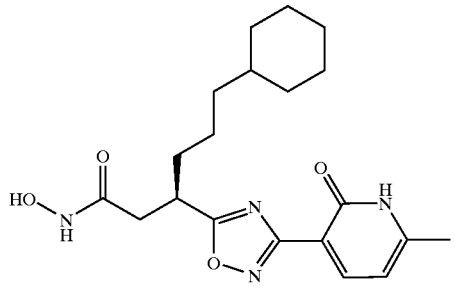

To a solution of the title compound from Preparation 12 (0.45 g, 1.2 mmol) in tetrahydrofuran (20 mL) was added triethylamine (0.34 mL, 2.4 mmol). The reaction was cooled to 0° C. in an ice bath, then iso-butylchloroformate (0.17 mL, 1.3 mmol) was added and a precipitate began to form immediately. The mixture was stirred for 2 hours, then O-trimethylsilyl hydroxylamine (0.48 mL, 4.0 mmol) was added and the reaction was warmed to room temperature and stirred for 4 hours. Methanol (10 mL) was added, stirring was continued for 1 hour and then the solvent was removed in vacuo. The residue was partitioned between water (50 mL) and dichloromethane (50 mL). The layers were separated and the aqueous layer was extracted with dichloromethane (2×100 mL). The combined organic extracts were dried (Na$_2$SO$_4$), the residue was triturated with hot diisopropyl ether to give the title compound as a white solid (0.42 g).

Mpt 145–148° C.
$^1$H NMR (400 MHz, CDCl$_3$) δ 0.73–0.86 (m, 2H), 1.25–1.46 (m, 8H), 1.53–1.69 (m, 7H), 2.24 (s, 3H), 2.37–3.55 (m, 2H), 3.40–3.47 (m, 1H), 6.15 (d, 1H), 8.02 (d, 1H), 8.66 (s, 1H), 10.38 (s, 1H), 12.0 (br s, 1H).
LRMS (ES) 411 (M+Na), 389 (M+H).
Anal. Calcd. For C$_{20}$H$_{28}$N$_4$O$_4$+0.9H$_2$O: C, 59.36; H, 7.42; N, 13.84. Found C, 59.47; H, 7.43; N, 13.73.

Example 5
(3R)-6-CYCLOHEXYL-N-HYDROXY-3-[3-(6-OXO-1,6-DIHYDRO-3-PYRIDAZINYL)-1,2,4-OXADIAZOL-5-YL]HEXANAMIDE

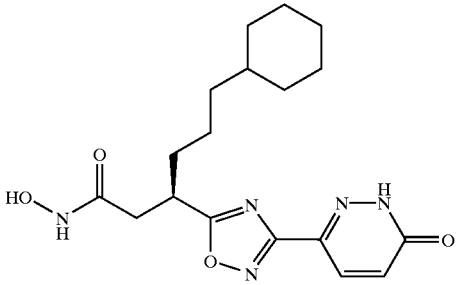

The title compound was obtained as a white solid from the title compound from Preparation 16, using a similar method to that described in Example 3.

Mpt 174–177° C.
$^1$H NMR (400 MHz, CDCl$_3$) δ 0.76–0.88 (m, 2H), 1.07–1.30 (m, 8H), 1.54–1.75 (m, 7H), 2.41–2.60 (m, 2H), 3.44–3.52 (m, 1H), 7.01 (d, 1H), 7.83 (d, 1H), 8.62 (s, 1H), 10.38 (s, 1H), 13.43 (br s, 1H).
LRMS (ES) 398 (M+Na), 376 (M+H).

Example 6
(3R)-6-CYCLOHEXYL-N-HYDROXY-3-[3-(2-PYRIMIDINYL)-1,2,4-OXADIAZOL-5-YL]HEXANAMIDE

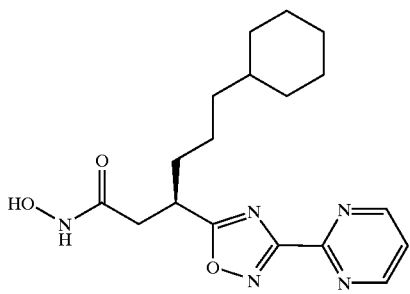

The title compound was obtained as a white solid from the title compound of Preparation 19, using a similar method to that described in Example 3. The residue was crystallised from toluene/dichloromethane and then washed with water to remove traces of triethylamine hydrochloride.

Mpt 159–161° C.

$^1$H NMR (400 MHz, D$_6$-DMSO) δ 0.75–0.86 (m, 2H), 1.06–1.26 (m, 8H), 1.52–1.65 (m, 5H), 1.52–1.76 (m, 2H), 2.42–2.61 (m, 2H), 3.54–3.60 (m, 1H), 7.67 (dd, 1H), 8.63 (s, 1H), 8.99 (d, 2H), 10.40 (s, 1H).

LRMS (ES) 382 (M+Na), 360 (M+H).

Anal. Calcd. For C$_{18}$H$_{25}$N$_5$O$_3$+0.2H$_2$O: C, 59.55; H, 7.05; N, 19.29. Found C, 59.70; H, 7.01; N, 18.91.

Example 7
(3R)-6-CYCLOHEXYL-N-HYDROXY-3-[3-(5-PYRIMIDINYL)-1,2,4-OXADIAZOL-5-YL]HEXANAMIDE

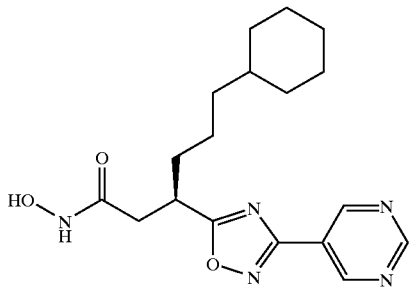

The title compound was obtained as a white low melting foam from the title compound of Preparation 22, using a similar method to that described in Example 3. The residue was purified by flash chromatography on silica gel (first column—graded elution of pentane to pentane/ethyl acetate 2:1 to 1:1; second column graded elution dichloromethane to dichloromethane/methanol 98:2 to 95:5; third column ethyl acetate as eluant).

$^1$H NMR (400 MHz, D$_6$-DMSO) δ 0.72–0.84 (m, 2H), 1.05–1.28 (m, 8H), 1.53–1.72 (m, 7H), 2.44–2.60 (m, 2H), 3.50–3.58 (m, 1H), 8.82 (s, 1H), 9.31 (s, 2H), 9.39 (s, 1H), 10.54 (s, 1H).

LRMS (ES) 382 (M+Na), 360 (M+11).

Anal. Calcd. For C$_{18}$H$_{25}$N$_5$O$_3$+0.2 EtOAc: C, 59.89; 11, 7.11; N, 18.57. Found C, 60.09; H, 7.13; N, 18.31.

Example 8
(3R)-6-CYCLOHEXYL-N-HYDROXY-3-[3-(3-METHOXY-5-ISOXAZOLYL)-1,2,4-OXADIAZOL-5-YL]HEXANAMIDE

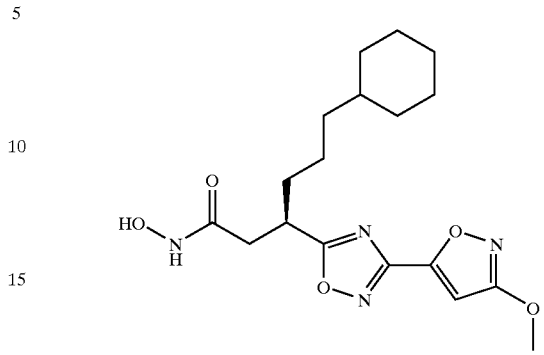

The title compound was obtained as a clear oil from the title compound of Preparation 26, using a similar method to that described in Example 3. The residue was purified by flash chromatography on silica gel (first column—graded elution of dichloromethane to dichloromethane/methanol 98:2 to 95:5; second column—graded elution of pentane/ethyl acetate 2:1 to 1:1 to 100% ethyl acetate).

$^1$H NMR (400 MHz, D$_6$-DMSO) δ 0.74–0.85 (m, 2H), 1.05–1.27 (m, 8H), 1.55–1.63 (m, 5H), 1.63–1.72 (m, 2H), 2.44–2.59 (m, 2H), 3.47–3.56 (m, 1H), 3.98 (s, 3H), 7.00 (s, 1H), 8.66 (s, 1H), 10.40 (s, 1H).

LRMS (ES) 401 (M+Na), 379 (M+H).

Anal. Calcd. For C$_{18}$H$_{26}$N$_4$O$_5$+0.1 EtOAc: C, 57.07; H, 6.98; N, 14.47. Found C, 56.87; H, 7.03; N, 14.16.

Example 9
(3R)-3-[3-(4-AMINO-1,2,5-OXADIAZOL-3-YL)-1,2,4-OXADIAZOL-5-YL]-6-CYCLOHEXYL-N-HYDROXY-HEXANAMIDE

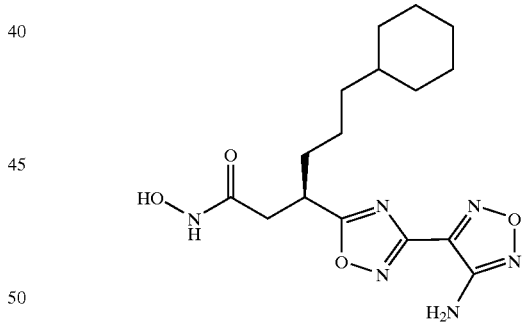

To a solution of the title compound from Preparation 28 (0.19 g, 0.5 mmol) in dichloromethane (10 mL) was added 1,1-carbonyldiimidazole (0.08 g, 0.5 mmol). The reaction was stirred at room temperature for 1 hour then O-trimethylsilyl hydroxylamine (0.2 mL, 1.5 mmol) was added and the reaction was stirred at room temperature overnight. Methanol (5 mL) was added and stirring was continued for 2 hours. The solvent was removed in vacuo, then the residue was dissolved in ethyl acetate (20 mL) and washed with water (20 mL) and brine (20 mL). The organic layer was dried (MgSO$_4$) and the solvent was removed in vacuo. The residue was purified by flash chromatography on silica gel (dichloromethane/methanol 90:10) to give the title compound as a white solid (0.11 g).

Mpt 149–152° C.

¹H NMR (400 MHz, D₆-DMSO) δ 0.77–0.88 (m, 2H), 1.03–1.31 (m, 8H), 1.53–1.67 (m, 5H), 1.67–1.78 (m, 2H), 2.42–2.63 (m, 2H), 3.51–3.60 (m, 1H), 6.34 (s, 2H), 8.67 (s, 1H), 10.42 (s, 1H).

LRMS (ES) 401 (M+Na), 379 (M+H).

HRMS Calcd for $C_{16}H_{24}N_6O_4$ 364.1859. Found 387.1749 (M+Na), 365.1931 (M+H).

Example 10
ETHYL 5-(5-{(1R)-4-CYCLOHEXYL-1-[2-(HYDROXYAMINO)-2-OXOETHYL]BUTYL}-1,2,4-OXADIAZOL-3-YL)NICOTINATE

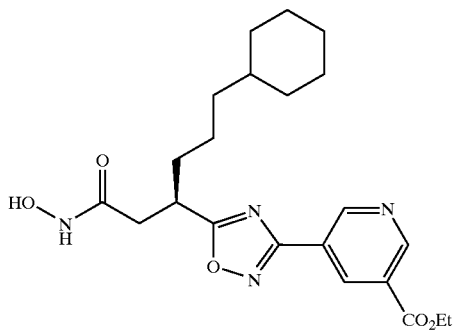

The title compound was obtained as a pale yellow foam from the title compound of Preparation 31, using a similar method to that described in Example 9. The residue was purified by flash chromatography on silica gel (graded elution of $CH_2Cl_2/MeOH/NH_3$ 97.5:2.5:0.25 to 95:5:0.5).

¹H NMR (400 MHz, D₆-DMSO) δ 0.75–0.86 (m, 2H), 1.06–1.32 (m, 8H), 1.35 (t, 3H), 1.53–1.66 (m, 5H), 1.66–1.75 (m, 2H), 2.42–2.60 (m, 2H), 3.50–3.58 (m, 1H), 4.40 (q, 2H), 8.65 (s, 1H), 8.70 (s, 1H), 9.22 (s, 2H), 9.35 (s, 1H), 10.40 (s, 1H).

LRMS (ES) 453 (M+Na), 431 (M+H).

Anal. Calcd. For $C_{22}H_{30}N_4O_5+0.2H_2O$: C, 60.87; H, 7.06; N, 12.91. Found C, 60.94; H, 7.06; N, 12.98.

Example 11
5-(5-{(1R)-4-CYCLOHEXYL-1-[2-(HYDROXYAMINO)-2-OXOETHYL]BUTYL}-1,2,4-OXADIAZOL-3-YL) NICOTINIC ACID

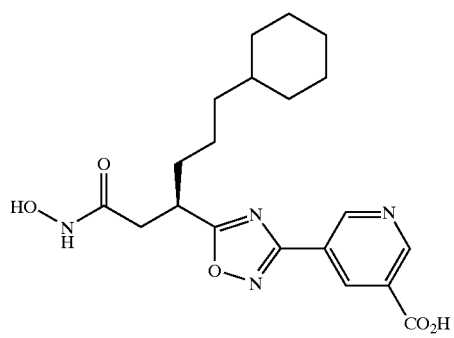

To a solution of the title compound of Example 10 (0.41 g, 0.95 mmol) in tetrahydrofuran (5 mL) was added a solution of lithium hydroxide (0.08 g, 1.9 mmol) in water (3 mL) and the reaction was stirred at room temperature overnight. The solvent was removed in vacuo, and the residue was diluted with water (5 mL), acidified to pH 1 with 2M aqueous hydrochloric acid and then extracted with ethyl acetate (2×20 mL). The organic layers were dried (Na₂SO4) and the solvent was removed in vacuo to give a pale orange solid. This was triturated with diisopropylether, the solid was collected by filtration and dried to give the title compound as a white solid (0.22 g).

Mpt 94–96° C.

¹H NMR (400 MHz, D₆-DMSO) δ 0.75–0.86 (m, 2H), 1.03–1.30 (m, 8H), 1.53–1.64 (m, 5H), 1.64–1.76 (m, 2H), 2.38–2.63 (m, 2H), 3.50–3.60 (m, 1H), 8.65 (br s, 1H), 8.68 (s, 1H), 9.19 (s, 2H), 9.31 (s, 1H), 10.40 (s, 1H).

LRMS (ES) 401 (M–H).

Anal. Calcd. For $C_{18}H_{26}N_4O_5$: C, 59.03; H, 6.56; N, 13.77. Found C, 58.96; H, 6.64; N, 13.45.

Example 12
5-(5-{(1R)-4-CYCLOHEXYL-1-[2-(HYDROXYAMINO)-2-OXOETHYL]BUTYL}-1,2,4-OXADIAZOLE-3-YL) NICOTINAMIDE

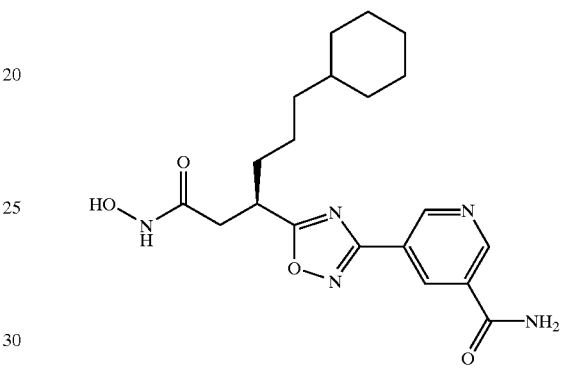

The title compound was obtained as a white solid from the title compound of Preparation 34, using a similar method to that described in Example 9. The residue was purified by flash chromatography on silica gel (graded elution of dichloromethane/methanol/aqueous ammonia solution 95:5:0.5 to 85:15:1.5).

Mpt 187–189° C.

¹H NMR (400 MHz, D₆-DMSO) δ 0.70–0.83 (m, 2H), 1.00–1.27 (m, 8H), 1.51–1.62 (m, 5H), 1.62–1.74 (m, 2H), 2.41–2.62 (m, 2H), 3.48–3.57 (m, 1H), 7.78 (s, 1H), 8.40 (s, 1H), 8.71 (s, 1H), 8.82 (s, 1H), 9.18 (s, 1H), 9.25 (s, 1H), 10.55 (s, 1H).

LRMS (ES) 400 (M–H).

Anal. Calcd. For $C_{20}H_{27}N_5O_4+0.2H_2O$: C, 59.30; H, 6.82; N, 17.29. Found C, 59.21; H, 6.80; N, 17.28.

Example 13
5-(5-{(R)-4-CYCLOHEXYL-1-[2-(HYDROXYAMINO)-2-OXOETHYL]BUTYL}-1,2,4-OXADIAZOL-3-YL)-N,N-DIMETHYLNICOTINAMIDE

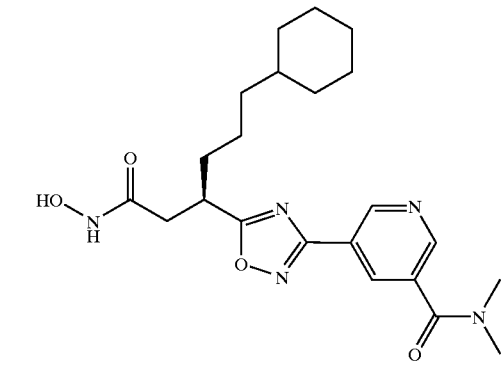

The title compound was obtained as a white foam from the title compound of Preparation 36, using a similar method to that described in Example 9. The residue was purified by flash chromatography on silica gel (dichloromethane/methanol/aqueous ammonia solution 95:5:0.5 as eluant).

$^1$NMR (400 MHz, D$_6$-DMSO) δ 0.75–0.85 (m, 2H), 1.02–1.30 (m, 8H), 1.54–1.64 (m, 5H), 1.64–1.75 (m, 2H), 2.40–2.60 (m, 2H), 2.98 (br d, 6H), 3.49–3.57 (m, 1H), 8.30 (s, 1H), 8.65 (s, 1H), 8.79 (s, 1H), 9.17 (s, 1H), 10.40 (s, 1H).

LRMS (ES) 428 (M−H).

Anal. Calcd. For C$_{22}$H$_{31}$N$_5$O$_4$+0.35 H$_2$O: C, 60.63; H, 7.33; N, 16.07. Found C, 60.34; H, 7.34; N, 16.37.

Example 14
5-(5-{(1R)-4-CYCLOHEXYL-1-[2-(HYDROXYAMINO)-2-OXOETHYL]BUTYL}-1,2,4-OXADIAZOL-3-YL)-N-METHYLNICOTINAMIDE

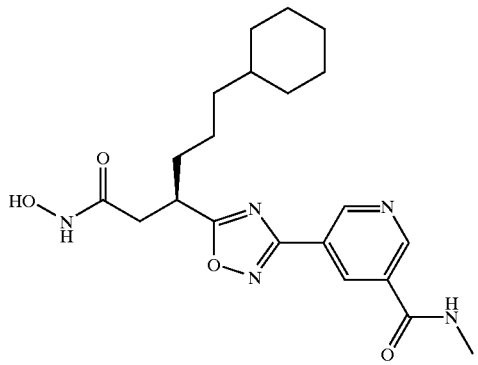

The title compound was obtained as a white foam from the title compound of Preparation 38, using a similar method to that described in Example 9. The residue was purified by flash chromatography on silica gel (dichloromethane/methanol/aqueous ammonia solution 95:5:0.5 as eluant) followed by washing with water.

$^1$H NMR (400 MHz, D$_6$-DMSO) δ 0.75–0.86 (m, 2H), 1.04–1.29 (m, 8H), 1.53–1.65 (m, 5H), 1.65–1.77 (m, 2H), 2.42–2.64 (m, 2H), 2.82 (d, 3H), 3.50–3.57 (m, 1H), 8.65 (s, 2H), 8.73 (s, 1H), 9.14 (s, 1H), 9.20 (s, 1H), 10.40 (s, 1H).

LRMS (ES) 414 (M−H).

Anal. Calcd. For C$_{21}$H$_{29}$N$_5$O$_4$+0.25H$_2$O: C, 60.06; H, 7.08 N, 16.67. Found C, 60.00; H, 7.10; N, 16.70.

Example 15
2-(5-{(1R)-4-CYCLOHEXYL-1-[2-(HYDROXYAMINO)-2-OXOETHYL]BUTYL}-1,2,4-OXADIAZOL-3-YL)ISONICOTINAMIDE

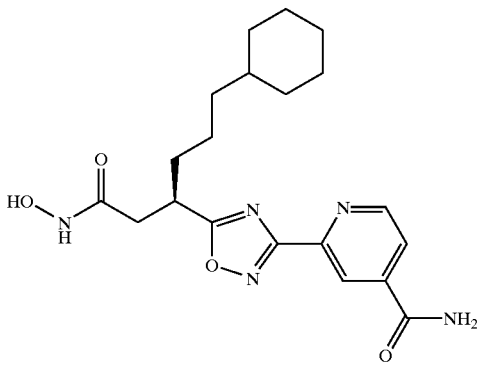

The title compound was obtained as a white foam from the title compound of Preparation 42, using a similar method to that described in Example 9. The residue was purified by flash chromatography on silica gel (graded elution of dichloromethane/methanol/aqueous ammonia solution 95:5:0.5 to 85:15:1.5).

Mpt 165–167° C.

$^1$H NMR (400 MHz, D$_6$-DMSO) δ 0.74–0.85 (m, 2H), 1.04–1.29 (m, 8H), 1.52–1.64 (m, 5H), 1.64–1.77 (m, 2H), 2.41–2.62 (m, 2H), 3.48–3.57 (m, 1H), 7.73 (s, 1H), 7.95 (d, 1H), 8.35 (s, 1H), 8.40 (s, 1H), 8.69 (s, 1H), 8.87 (d, 1H), 10.43 (s, 1H).

LRMS (ES) 424 (M+Na), 402 (M+H).

Anal. Calcd. For C$_{20}$H$_{27}$N$_5$O$_4$+0.5H$_2$O: C, 58.52; H, 6.88; N, 17.06. Found C, 58.52; H, 6.80; N, 17.02.

Example 16
2-(5-{(1R)-4-CYCLOHEXYL-1-[2-(HYDROXYAMINO)-2-OXOETHYL]BUTYL}-1,2,4-OXADIAZOL-3-YL)-N-METHYLISONICOTINAMIDE

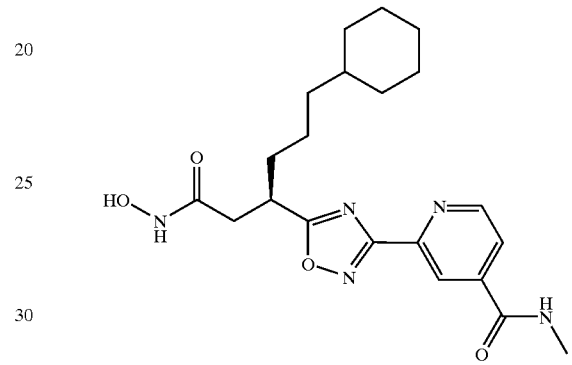

The title compound was obtained as a white foam from the title compound of Preparation 44, using a similar method to that described in Example 9. The residue was purified by flash chromatography on silica gel (graded elution of dichloromethane/methanol/aqueous ammonia solution 95:5:0.5 to 85:15:1.5).

Mpt 114–116° C.

$^1$H NMR (400 MHz, D$_6$-DMSO) δ 0.74–0.85 (m, 2H), 1.02–1.29 (m, 8H), 1.51–1.64 (m, 5H), 1.64–1.76 (m, 2H), 2.40–2.63 (m, 2H), 2.81 (s, 3H), 3.49–3.57 (m, 1H), 7.90 (d, 1H), 8.37 (s, 1H), 8.65 (s, 1H), 8.80 (s, 1H), 8.87 (d, 1H), 10.41 (s, 1H).

LRMS (ES) 438 (M+Na), 416 (M+H).

Anal. Calcd. For C$_{21}$H$_{29}$N$_5$O$_4$+0.3H$_2$O: C, 59.93; H, 7.09; N, 16.64. Found C, 59.96; H, 7.07; N, 16.65.

Example 17
2-(5-{(1R)-4-CYCLOHEXYL-1-[2-(HYDROXYAMINO)-2-OXOETHYL]BUTYL}-1,2,4-OXADIAZOL-3-YL)-N,N-DIMETHYLISONICOTINAMIDE

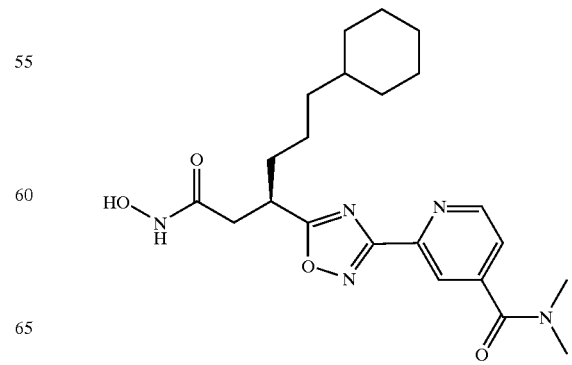

The title compound was obtained as a white foam from the title compound of Preparation 46, using a similar method to that described in Example 9. The residue was purified by flash chromatography on silica gel (graded elution of dichloromethane/methanol/aqueous ammonia solution 95:5:0.5 to 90:10:1).

Mpt 58–62° C.

$^1$H NMR (400 MHz, D$_6$-DMSO) δ 0.74–0.86 (m, 2H), 1.03–1.29 (m, 8H), 1.53–1.64 (m, 5H), 1.64–1.76 (m, 2H), 2.40–2.63 (m, 2H), 2.90 (s, 3H), 2.99 (s, 3H), 3.49–3.57 (m, 1H), 7.58 (d, 1H), 7.96 (s, 1H), 8.66 (s, 1H), 8.80 (d, 1H), 10.40 (s, 1H).

LRMS (ES) 452 (M+Na), 430 (M+H).

Anal. Calcd. For C$_{22}$H$_{31}$N$_5$O$_4$+0.4H$_2$O: C, 60.51; H, 7.34; N, 16.04. Found C, 60.49; H, 7.28; N, 15.99.

Example 18
(3R)-6-CYCLOHEXYL-N-HYDROXY-3-[3-(2-PYRIDINYL)-1,2,4-OXADIAZOL-5-YL]HEXANAMIDE

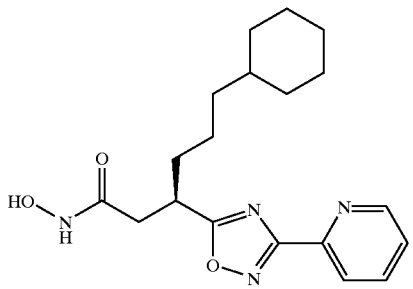

The title compound was obtained as a colorlesscolorless oil from the title compound of Preparation 48, using a similar method to that described in Example 9. The residue was purified by flash chromatography on silica gel (dichloromethane/methanol/aqueous ammonia solution 95:5:0.5 as eluant).

$^1$H NMR (300 MHz, CDCl$_3$) δ 0.74–0.89 (m, 2H), 1.03–1.39 (m, 8H), 1.50–1.93 (m, 7H), 2.53–2.92 (m, 2H), 3.67–3.79 (m, 1H), 0.7.40–7.50 (m, 1H), 7.80–7.88 (m, 1H), 8.10 (d, 1H), 8.77 (d, 1H).

LRMS (ES) 381 (M+Na), 359 (M+H).

Example 19
(3R)-6-CYCLOHEXYL-N-HYDROXY-3-[3-(3-PYRIDINYL)-1,2,4-OXADIAZOL-5-YL]HEXANAMIDE

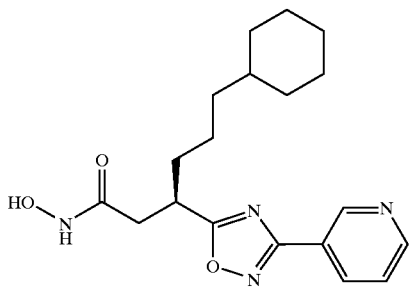

The title compound was obtained as a colorlesscolorless oil from the title compound of Preparation 50, using a similar method to that described in Example 9. The residue was purified by flash chromatography on silica gel (dichloromethane/methanol/aqueous ammonia solution 90:10:1 as eluant).

$^1$H NMR (300 MHz, D$_6$-DMSO) δ 0.72–0.85 (m, 2H), 1.01–1.28 (m, 8H), 1.56–1.74 (m, 7H), 2.46–2.62 (m, 2H), 3.48–3.59 (m, 1H), 7.59 (dd, 1H), 8.32 (d, 1H), 8.74–8.81 (m, 2H), 9.16 (d, 1H), 10.52 (s, 1H).

LRMS (ES) 381 (M+Na), 359 (M+H).

Example 20
(3R)-6-CYCLOHEXYL-N-HYDROXY-3-[3-(4-PYRIDINYL)-1,2,4-OXADIAZOLE-5-YL]HEXANAMIDE

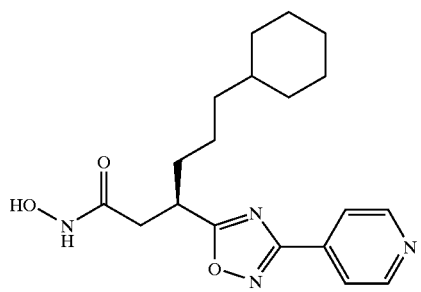

The title compound was obtained as a white solid from the title compound of Preparation 52, using a similar method to that described in Example 9. The residue was purified by flash chromatography on silica gel (dichloromethane/methanol/aqueous ammonia solution 95:5:0.5 as eluant).

$^1$H NMR (400 MHz, D$_6$-DMSO) δ 0.74–0.84 (m, 2H), 1.02–1.28 (m, 8H), 1.55–1.66 (m, 5H), 1.66–1.74 (m, 2H), 2.43–2.61 (m, 2H), 3.48–3.58 (m, 1H), 7.90 (d, 2H), 8.76–8.82 (m, 3H), 10.52 (s, 1H).

LRMS (ES) 381 (M+Na), 359 (M+H).

Example 21
(3R)-6-CYCLOHEXYL-N-HYDROXY-3-[3-(6-METHYL-3-PYRIDINYL)-1,2,4-OXADIAZOL-5-YL]HEXANAMIDE

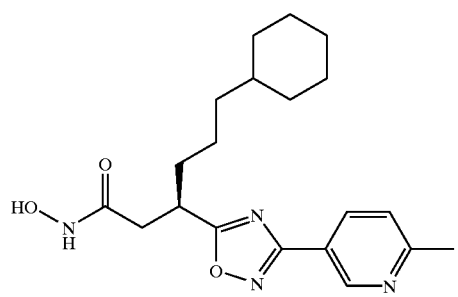

The title compound was obtained as a white solid from the title compound of Preparation 55, using a similar method to that described in Example 9. The residue was purified by preparative HPLC.

$^1$H NMR (400 MHz, CD$_3$OD) δ 0.80–0.91 (m, 2H), 1.10–1.40 (m, 8H), 1.58–1.74 (m, 5H), 1.74–1.88 (m, 2H), 2.59 (dd, 1H), 2.62 (s, 3H), 2.70 (dd, 1H), 3.59–3.66 (m, 1H), 7.46 (d, 1H), 8.31 (d, 1H), 9.05 (s, 1H).

LRMS (ES) 395 (M+Na), 373 (M+H).

Example 22
(3R)-3-[3-(6-AMINO-3-PYRIDINYL)-1,2,4-OXADIAZOL-5-YL]-6-CYCLOHEXYL-N-HYDROXYHEXANAMIDE

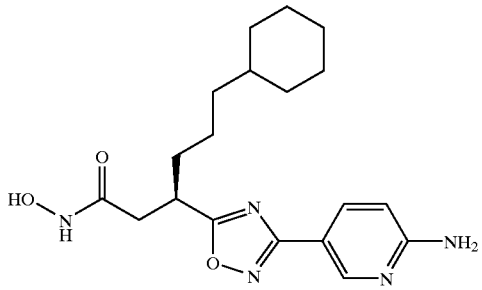

To a solution of the title compound from Preparation 59 (0.21 g, 0.6 mmol) in dichloromethane (20 mL) was added N-methylmorpholine (0.07 mL, 0.66 mmol). The reaction was cooled to 0° C. in an ice bath, then iso-butylchloroformate (0.09 mL, 0.66 mmol) was added. The mixture was stirred for 1 hour, then O-trimethylsilyl hydroxylamine (0.48 mL, 4.0 mmol) was added and the reaction was warmed to room temperature and stirred for 1 hour. Methanol (10 mL) was added, stirring was continued for 20 minutes and then the solvent was removed in vacuo. The residue was partitioned between water (50 mL) and ethyl acetate (50 mL). The organic layer was dried (MgSO$_4$), the solvent was removed in vacuo and the residue was purified by preparative HPLC to give the title compound as a white solid (0.06 g).
Mpt 168–170° C.
$^1$H NMR (400 MHz, CD$_3$OD) δ 0.80–0.92 (m, 2H), 1.11–1.37 (m, 8H), 1.60–1.74 (m, 5H), 1.74–1.84 (m, 2H), 2.57 (dd, 1H), 2.68 (dd, 1H), 3.56–3.62 (m, 1H), 6.65 (d, 1H), 8.00 (d, 1H), 8.57 (s, 1H).
LRMS (ES) 396 (M+Na), 374 (M+H).

Example 23
(3R)-6-CYCLOHEXYL-3-{3-[2-(DIMETHYLAMINO)-4-PYRIDINYL]-1,2,4-OXADIAZOL-5-YL}-N-HYDROXYHEXANAMIDE

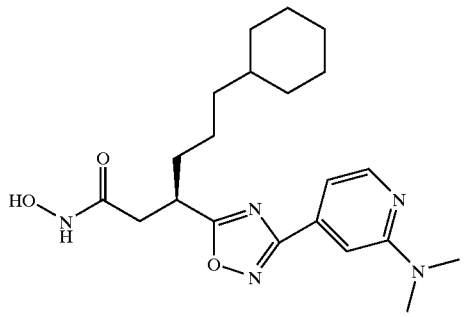

To a solution of the title compound from Preparation 62 (0.32 g, 0.64 mmol) in tetrahydrofuran (10 mL) was added triethylamine (0. 9 mL, 0. 64 mmol) followed by 1,1-carbonyldiimidazole (0.10 g, 0.64 mmol). The mixture was stirred at room temperature for 2 hours, then hydroxylamine hydrochloride (0.04 g, 0.64 mmol) was added and the reaction was stirred at room temperature overnight. The solvent was removed in vacuo, and the residue was partitioned between water (50 mL) and ethyl acetate (50 mL). The organic layer was washed with brine, then dried (MgSO$_4$) and the solvent was removed in vacuo. The residue was purified by flash chromatography on silica gel (graded elution of dichloromethane/methanol/aqueous ammonia solution 95:5:0.5 to 80:20:3) to give the title compound as a yellow oil (0.05 g).
$^1$H NMR (400 MHz, CD$_3$OD) δ 0.80–0.92 (m, 2H), 1.11–1.40 (m, 8H), 1.59–1.72 (m, 5H), 1.76–1.85 (m, 2H), 2.58 (dd, 1H), 2.69 (dd, 1H), 3.15 (s, 3H), 3.60–3.6.66 (m, 1H), 7.16 (d, 1H), 7.25 (s, 1H), 8.19 (6, 1H).
LRMS (TSP) 401 (M+H).

Example 24
ETHYL 2-(5-{(1R)-4-CYCLOHEXYL-1-[2-(HYDROXYAMINO)-2-OXOETHYL]BUTYL}-1,2,4-OXADIAZOL-3-YL)ISONICOTINATE

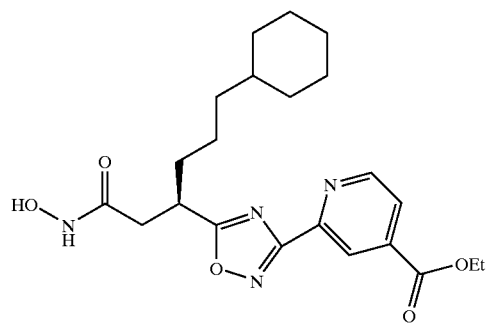

The title compound was obtained as a colorlesscolorless oil from the title compound of Preparation 63, using a similar method to that described in Example 22.
$^1$H NMR (300 MHz, CDCl$_3$) δ 60.75–0.89 (m, 2H), 1.11–1.40 (m, 8H), 1.45 (t, 3H), 1.53–1.97 (m, 7H), 2.68 (dd, 1H), 2.84 (dd, 1H), 3.67–3.79 (m, 1H), 4.48 (q, 2H), 7.98 (d, 1H), 8.61 (s, 1H), 8.90 (d, 1H).
LRMS (ES) 453 (M+Na), 431 (M+H).

Example 25
2-(5-{(1R)-4-CYCLOHEXYL-1-[2-(HYDROXYAMINO)-2-OXOETHYL]BUTYL}-1,2,4-OXADIAZOL-3-YL)ISONICOTINIC ACID

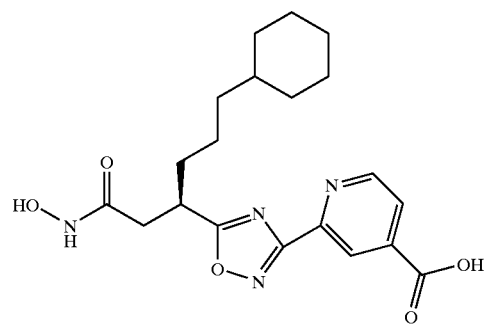

To a solution of the title compound of Example 24 (0.44 g, 1.0 mmol) in methanol (20 mL) was added a solution of lithium hydroxide (0.09 g, 2.0 mmol) in water (7 mL) and the reaction was stirred at room temperature for 2 hours. The solvent was removed in vacuo, and the residue was diluted with water (20 mL) and dichloromethane (20 mL). The layers were separated, the organic layer was discarded and the aqueous layer was acidified to pH 4 with 2M aqueous hydrochloric acid and then extracted with dichloromethane (2×20 mL). The combined organic layers were dried (MgSO$_4$) and the solvent was removed in vacuo to give the title compound as a white solid (0.04 g).

Mpt 117–122° C.

¹H NMR (300 MHz, CD₃OD) δ 0.80–0.93 (m, 2H), 1.06–1.47 (m, 8H), 1.53–1.75 (m, 5H), 1.75–1.93 (m, 2H), 2.62 (dd, 1H), 2.74 (dd, 1H), 3.62–3.73 (m, 1H), 8.07 (d, 1H), 8.62 (s, 1H), 8.89 (d, 1H).

LRMS (TSP) 403 (M).

Example 26
METHYL [5-(5-{(1R)-4-CYCLOHEXYL-1-[2-(HYDROXYAMINO)-2-OXOETHYL]BUTYL}-1,2,4-OXADIAZOL-3-YL)-2-PYRIDINYL]ACETATE

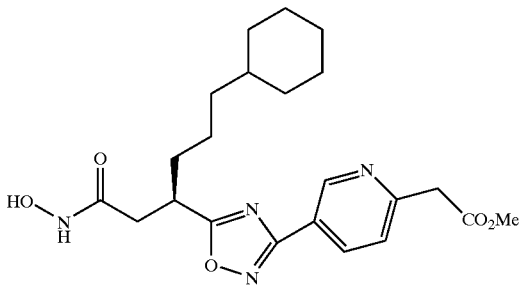

The title compound was obtained as a pale yellow solid from the title compound of Preparation 67, using a similar method to that described in Example 22.

¹H NMR (300 MHz, CD₃OD) δ 0.80–0.94 (m, 2H), 1.08–1.42 (m, 8H), 1.55–1.75 (m, 5H), 1.75–1.88 (m, 2H), 2.60 (dd, 1H), 2.72 (dd, 1H), 3.59–3.69 (m, 1H), 3.73 (s, 3H), 3.97 (s, 2H), 7.58 (d, 1H), 8.40 (d, 1H), 9.12 (s, 1H).

LRMS (ES) 453 (M+Na), 431 (M+H).

Example 27
(3R)-6-CYCLOHEXYL-N-HYDROXY-3-{3-[6-(METHYLAMINO)-3-PYRIDINYL]-1,2,4-OXADIAZOL-5-YL}HEXANAMIDE

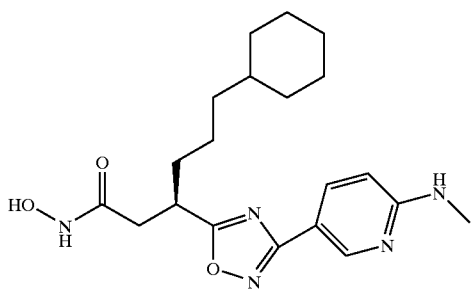

To a solution of the title compound from Preparation 71 (0.24 g, 0.65 mmol) in tetrahydrofuran (7 mL) was added 1,1-carbonyldiimidazole (0.12 g, 0.72 mmol). The reaction was stirred at room temperature for 1 hour then O-trimethylsilyl hydroxylamine (0.24 mL, 2.0 mmol) was added and the reaction was stirred at room temperature for 48 hours. 10% aqueous citric acid solution (10 mL) was added and stirring was continued for 1.5 hours. The mixture was diluted with ethyl acetate (20 mL) and water (20 mL), the layers were separated and the aqueous layer was extracted with ethyl acetate (2×20 mL). The combined organic extracts were washed with saturated aqueous sodium bicarbonate solution (20 mL), saturated aqueous sodium dihydrogen citrate solution (20 mL). The organic layer was dried (MgSO₄) and the solvent was removed in vacuo. The residue was purified by preparative HPLC, with the title compound being isolate as a white solid (0.07 g) after freeze-drying.

Mpt 127–129° C.

¹H NMR (400 MHz, CD₃OD) δ 0.78–0.90 (m, 2H), 1.09–1.37 (m, 8H), 1.58–1.72 (m, 5H), 1.72–1.82 (m, 2H), 2.56 (dd, 1H), 2.67 (dd, 1H), 2.90 (s, 3H), 3.54–3.61 (m, 1H), 6.58 (d, 1H), 7.95 (dd, 1H), 8.61 (d, 1H).

LRMS (ES) 388 (M+H).

Example 28
(3R)-6-CYCLOHEXYL-3-{3-[6-(ETHYLAMINO)-3-PYRIDINYL]-1,2,4-OXADIAZOL-5-YL}-N-HYDROXYHEXANAMIDE

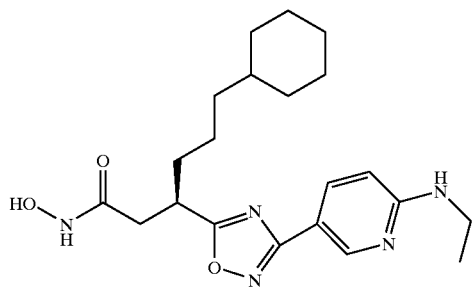

The title compound was obtained as a white solid from the title compound of Preparation 72, using a similar method to that described in Example 27.

Mpt 146–148° C.

¹H NMR (300 MHz, CD₃OD) δ 0.79–0.93 (m, 2H), 1.08–1.40 (m, 1H), 1.59–1.82 (m, 7H), 2.56 (dd, 1H), 2.67 (dd, 1H), 3.37 (q, 2H), 3.52–3.62 (m, 1H), 6.59 (d, 1H), 7.94 (dd, 1H), 8.60 (d, 1H).

LRMS (ES) 402 (M+H).

Example 29
(3R)-6-CYCLOHEXYL-N-HYDROXY-3-{3-[6-(ISOPROPYLAMINO)-3-PYRIDINYL]-1,2,4-OXADIAZOL-5-YL}HEXANAMIDE

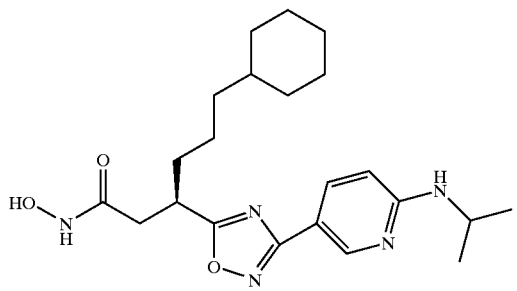

The title compound was obtained as a colorlesscolorless oil from the title compound of Preparation 73, using a similar method to that described in Example 22.

¹H NMR (300 MHz, CD₃OD) δ 0.80–0.94 (m, 2H), 1.08–1.38 (m, 14H), 1.60–1.82 (m, 7H), 2.55 (dd, 1H), 2.68 (dd, 1H), 3.53–3.63 (m, 1H), 4.02–4.12 (m, 1H), 6.58 (d, 1H), 7.93 (dd, 1H), 8.60 (d, 1H).

LRMS (ES) 416 (M+H).

Example 30
(3R)-6-CYCLOHEXYL-N-HYDROXY-3-(3-{6-[(2-METHOXYETHYL)AMINO]-3-PYRIDINYL}-1,2,4-OXADIAZOL-5-YL)HEXANAMIDE

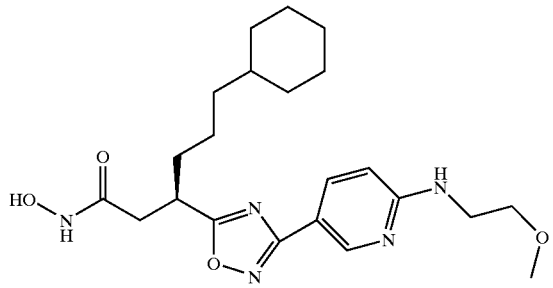

To a solution of the title compound from Preparation 74 (0.08 g, 0.2 mmol) in tetrahydrofuran (3 mL) was added 1-(3-dimethylaminopropyl)-3-ethylcarbodiimide hydrochloride (0.04 g, 0.22 mmol), triethylamine (0.03 mL, 0.22 mmol) and O-trimethylsilyl hydroxylamine (0.03 mL, 0.22 mmol) and the reaction was stirred at room temperature for 5 hours. Further amounts of 1-(3-dimethylaminopropyl)-3-ethylcarbodiimide hydrochloride (0.02 g, 0.11 mmol) and O-trimethylsilyl hydroxylamine (0.015 mL, 0.11 mmol) were added and the reaction was continued at room temperature for 24 hours. 1M aqueous citric acid solution (10 mL) was added and the mixture was extracted with ethyl acetate (2×20 mL). The combined organic extracts were dried ($Na_2SO_4$), the solvent was removed in vacuo and the residue was purified by reverse phase HPLC (acetonitrile/0.1 M aqueous ammonium acetate solution as eluant) to give the title compound as a white solid (0.02 g) after freeze drying.

$^1$H NMR (300 MHz, $CD_3OD$) δ 0.77–0.91 (m, 2H), 1.06–1.40 (m, 8H), 1.55–1.76 (m, 7H), 2.61–2.71 (m, 2H), 3.28–3.46 (m, 5H), 3.55–3.70 (m, 3H), 6.15 (br s, 1H), 6.33 (d, 1H), 7.81 (d, 1H), 8.35 (s, 1H).

LRMS (ES) 432 (M+H).

Example 31
(3R)-6-CYCLOHEXYL-N-HYDROXY-3-{3-[6-(1-PYRROLIDINYL)-3-PYRIDINYL]-1,2,4-OXADIAZOL-5-YL}HEXANAMIDE

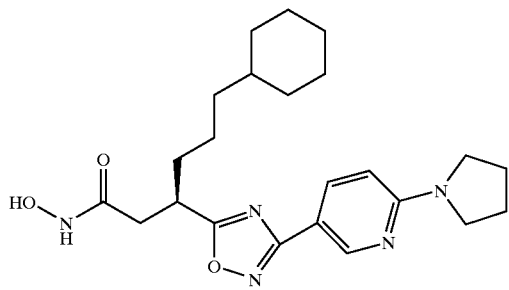

The title compound was obtained as a white solid from the title compound of Preparation 75, using a similar method to that described in Example 27.

Mpt 137–145° C.

$^1$H NMR (300 MHz, $CD_3OD$) δ 0.80–0.91 (m, 2H), 1.09–1.36 (m, 8H), 1.59–1.72 (m, 5H), 1.72–1.81 (m, 2H), 1.99–2.08 (m, 4H), 2.56 (dd, 1H), 2.67 (dd, 1H), 3.44–3.54 (m, 4H), 3.54–3.65 (m, 1H), 6.60 (d, 1H), 8.06 (dd, 1H), 8.68 (d, 1H).

LRMS (ES) 428 (M+H).

Example 32
TERT-BUTYL 4-[5-(5-{(1R)-4-CYCLOHEXYL-1-[2-(HYDROXYAMINO)-2-OXOETHYL]BUTYL}-1,2,4-OXADIAZOL-3-YL)-2-PYRIDINYL]-1-PIPERAZINE-CARBOXYLATE

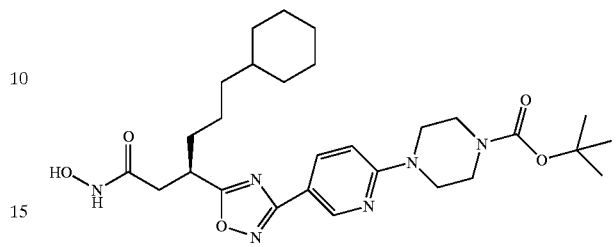

The title compound was obtained as a colorless oil from the title compound of Preparation 76, using a similar method to that described in Example 22.

$^1$H NMR (300 MHz, $CD_3OD$) δ 0.75–0.93 (m, 2H), 1.00–1.35 (m, 8H), 1.45 (s, 9H), 1.50–1.66 (m, 5H), 1.66–1.82 (m, 2H), 2.50–2.60 (m, 1H), 2.60–2.78 (m, 1H), 3.44–3.66 (m, 9H), 6.59 (d, 1H), 7.98 (d, 1H), 8.74 (s, 1H).

LRMS (ES) 543 (M+H).

Example 33
(3R)-6-CYCLOHEXYL-N-HYDROXY-3-{3-[6-(1-PIPERAZINYL)-3-PYRIDINYL]-1,2,4-OXADIAZOL-5-YL}HEXANAMIDE

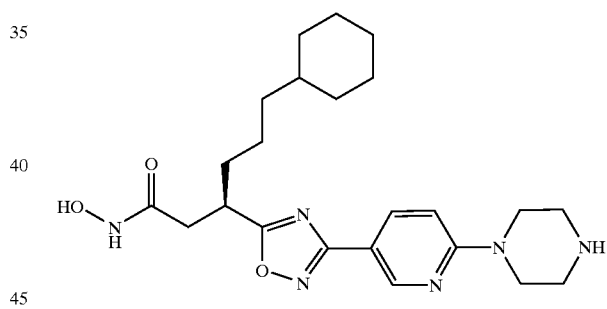

To a solution of the title compound from Example 32 (0.37 g, 0.7 mmol) in dichloromethane (5 mL) was added trifluoroacetic acid (5 mL) and the reaction was stirred at room temperature for 1.5 hours. The solvent was removed in vacuo and the residue was azeotroped with toluene. The residue was then dissolved in ethyl acetate (30 mL) and washed with saturated aqueous sodium bicarbonate solution (30 mL) followed by 10% aqueous citric acid solution (30 mL). The acidic aqueous layer was basified to pH 7 with saturated aqueous sodium bicarbonate solution and then extracted with ethyl acetate (3×30 mL). The combined organic extracts were washed with water (30 mL), dried ($MgSO_4$) and the solvent was removed in vacuo to give the title compound as a viscous oil (0.03 g).

$^1$NMR (300 MHz, $CD_3OD$) δ 0.80–0.91 (m, 2H), 1.05–1.40 (m, 8H), 1.53–1.70 (m, 5H), 1.70–1.84 (m, 2H), 2.54 (dd, 1H), 2.66 (dd, 1H), 2.88–2.96 (m, 4H), 3.50–3.62 (m, 5H), 6.87 (d, 1H), 8.06 (d, 1H), 8.70 (s, 1H).

LRMS (ES) 443 (M+H).

Example 34
TERT-BUTYL 3-[5-(5-{(1R)-4-CYCLOHEXYL-1-[2-(HYDROXYAMINO)-2-OXOETHYL]BUTYL}-1,2,4-OXADIAZOL-3-YL)-2-PYRIDINYL]-3-AZABICYCLO[3.1.0]HEX-6-YLCARBAMATE

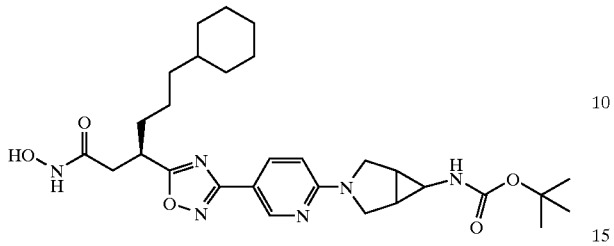

The title compound was obtained as a yellow oil from the title compound of Preparation 77, using a similar method to that described in Example 22.

$^1$H NMR (400 MHz, CDCl$_3$) δ 0.78–0.95 (m, 2H), 1.07–1.70 (m, 24H), 1.70–1.90 (m, 2H), 2.60 (dd, 1H), 2.88–3.01 (m, 1H), 3.50–3.61 (m, 3H), 3.79–3.88 (m, 2H), 4.74 (s, 1H), 6.33 (d, 1H), 7.97 (d, 1H), 8.75 (s, 1H).

LRMS (ES) 555 (M+H).

Example 35
(3R)-3-{3-[6-(6-AMINO-3-AZABICYCLO[3.1.0]HEX-3-YL)-3-PYRIDINYL]-1,2,4-OXADIAZOL-5-YL}-6-CYCLOHEXYL-N-HYDROXYHEXANAMIDE

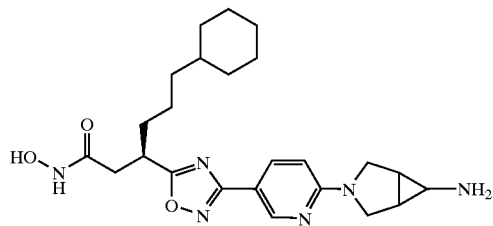

The title compound was obtained as a yellow oil from the title compound of Example 34, using a similar method to that described in Example 33.

$^1$H NMR (400 MHz, CD$_3$OD) δ 0.78–1.00 (m, 2H), 1.07–1.70 (m, 9H), 1.54–1.87 (m, 8H), 2.54 (dd, 1H), 2.66 (dd, 1H), 3.45–3.63 (m, 3H), 3.67–3.76 (m, 2H), 6.54 (d, 1H), 8.05 (d, 1H), 8.66 (s, 1H).

LRMS (ES) 455 (M+H).

Example 36
(3R)-6-CYCLOHEXYL-N-HYDROXY-3-{3-[6-(4-METHYL-1-PIPERAZINYL)-3-PYRIDINYL]-1,2,4-OXADIAZOL-5-YL}HEXANAMIDE

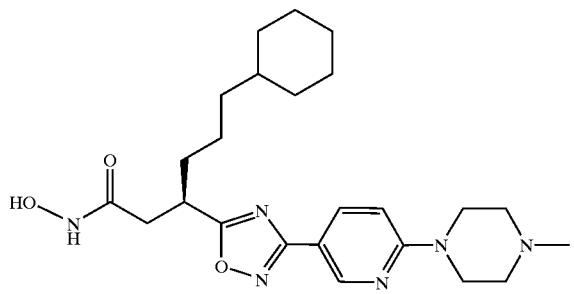

The title compound was obtained as a brown oil from the title compound of Preparation 79, using a similar method to that described in Example 22.

$^1$H NMR (300 MHz, CDCl$_3$) δ 0.80–0.91 (m, 2H), 1.08–1.39 (m, 8H), 1.56–1.72 (m, 5H), 1.72–1.83 (m, 2H), 2.39 (s, 3H), 2.52–2.63 (m, 5H), 2.67 (dd, 1H), 3.55–3.62 (m, 1H), 3.68–3.74 (m, 4H), 6.90 (d, 1H), 8.09 (dd, 1H), 8.74 (d, 1H).

LRMS (TSP) 455 (M).

Example 37
(3R)-6-CYCLOHEXYL-3-(3-{6-[3-(DIMETHYLAMINO)-1-AZETIDINYL]-3-PYRIDINYL}-1,2,4-OXADIAZOL-5-YL)-N-HYDROXYHEXANAMIDE

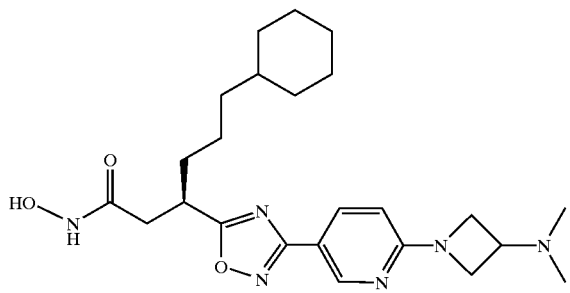

The title compound was obtained as a white solid from the title compound of Preparation 81, using a similar method to that described in Example 22.

Mpt 136–137° C.

$^1$H NMR (400 MHz, CD$_3$OD) δ 0.79–0.92 (m, 2H), 1.11–1.39 (m, 8H), 1.57–1.72 (m, 5H), 1.72–1.86 (m, 2H), 2.25 (s, 6H), 2.54 (dd, 1H), 2.67 (dd, 1H), 3.28–3.36 (m, 1H), 3.54–3.61 (m, 1H), 3.89–3.97 (m, 2H), 4.15–4.20 (m, 2H), 6.50 (d, 1H), 8.07 (dd, 1H), 8.67 (d, 1H).

LRMS (ES) 457 (M+H).

Example 38
(3R)-6-CYCLOHEXYL-N-HYDROXY-3-(3-{6-[3-(4-MORPHOLINYL)-1-AZETIDINYL]-3-PYRIDINYL}-1,2,4-OXADIAZOL-5-YL)HEXANAMIDE

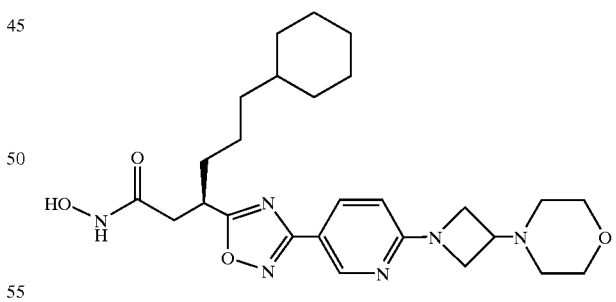

The title compound was obtained as a white solid from the title compound of Preparation 83, using a similar method to that described in Example 22.

Mpt 151–153° C.

$^1$NMR (300 MHz, D$_6$-DMSO) δ 0.70–0.88 (m, 2H), 1.00–1.36 (m, 8H), 1.47–1.79 (m, 7H), 2.25–2.43 (m, 4H), 2.43–2.62 (m, 2H), 3.20–3.63 (m, 2H), 3.51–3.63 (m, 4H), 3.80–3.91 (m, 2H), 3.98–4.11 (m, 2H), 6.49 (d, 1H), 7.98 (dd, 1H), 8.62 (d, 1H), 8.80 (s, 1H), 10.50 (s, 11).

LRMS (ES) 499 (M+H).

Example 39
(3R)-6-CYCLOHEXYL-3-{3-[6-(DIMETHYLAMINO)-3-PYRIDINYL]-1,2,4-OXADIAZOL-5-YL}-N-HYDROXYHEXANAMIDE

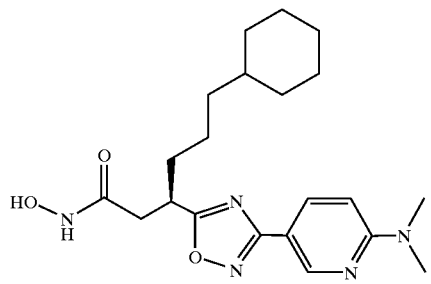

The title compound was obtained as a colorless glass from the title compound of Preparation 85, using a similar method to that described in Example 22, apart from the use of dimethylformamide as the reaction solvent.

$^1$H NMR (300 MHz, CDCl$_3$) δ 60.72–0.88 (m, 2H), 1.03–1.36 (m, 8H), 1.45–1.82 (m, 7H), 2.58 (dd, 1H), 2.72 (dd, 1H), 3.13 (s, 6H), 3.54–3.64 (m, 1H), 6.49 (d, 1H), 7.92 (d, 1H), 8.71 (s, 1H).

LRMS (ES) 402 (M+H).

Example 40
ETHYL 5-(5-{(1R)-4-CYCLOHEXYL-1-[2-(HYDROXYAMINO)-2-OXOETHYL]BUTYL}-1,2,4-OXADIAZOL-3-YL)-2-PYRIDINECARBOXYLATE

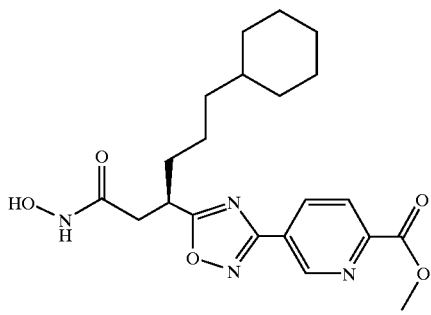

The title compound was obtained as a white foam from the title compound of Preparation 87, using a similar method to that described in Example 9. The compound was purified by preparative HPLC.

$^1$H NMR (300 MHz, CDCl$_3$) δ 0.72–0.90 (m, 2H), 1.02–1.35 (m, 8H), 1.46 (t, 3H), 1.54–1.70 (m, 5H), 1.70–1.87 (m, 2H), 2.64 (dd, 1H), 2.78 (dd, 1H), 3.61–3.72 (m, 1H), 4.49 (q, 2H), 8.18 (d, 1H), 8.40 (d, 1H), 9.29 (s, 1H).

LRMS (ES) 883 (2M+Na), 453 (M+Na), 431 (M+H).

Example 41
5-(5-{(1R)-4-CYCLOHEXYL-1-[2-(HYDROXYAMINO)-2-OXOETHYL]BUTYL}-1,2,4-OXADIAZOL-3-YL)-2-PYRIDINECARBOXYLIC ACID

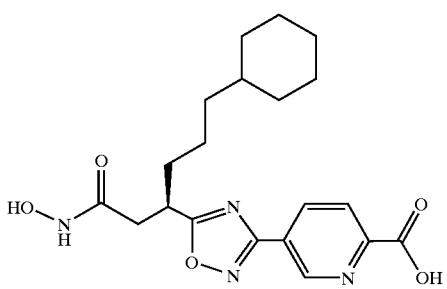

The title compound was obtained as a white solid from the title compound of Preparation 41, using a similar method to that described in Example 25. The compound was purified by preparative HPLC.

Mpt 168–170° C.

$^1$H NMR (300 MHz, CD$_3$OD) δ 0.78–0.96 (m, 2H), 1.08–1.42 (m, 8H), 1.57–1.88 (m, 7H), 2.51–2.80 (m, 2H), 3.57–3.72 (m, 1H), 8.29 (d, 1H), 8.60 (d, 1H), 9.30 (s, 1H).

LRMS (TSP) 403 (M+H).

Example 42
(3R)-6-CYCLOHEXYL-N-HYDROXY-3-{3-[2-(4-METHYL-1-PIPERAZINYL)-3-PYRIDINYL]-1,2,4-OXADIAZOL-5-YL}HEXANAMIDE

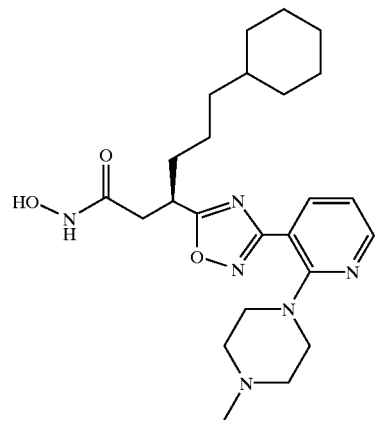

The title compound was obtained as a colorless oil from the title compound of Preparation 90, using a similar method to that described in Example 22.

$^1$H NMR (300 MHz, CDCl$_3$) δ 0.74–0.92 (m, 2H), 1.01–1.42 (m, 8H), 1.52–1.90 (m, 7H), 2.40 (s, 3H), 2.56–2.80 (m, 6H), 3.14–3.27 (m, 2H), 3.45–3.72 (m, 3H), 6.83 (dd, 1H), 7.00–7.80 (br, 2H), 7.88 (d, 1H), 8.29 (d, 1H).

LRMS (ES) 457 (M+H).

Example 43
(3R)-6-CYCLOHEXYL-N-HYDROXY-3-{3-[2-(METHYLAMINO)-3-PYRIDINYL]-1,2,4-OXADIAZOL-5-YL}HEXANAMIDE

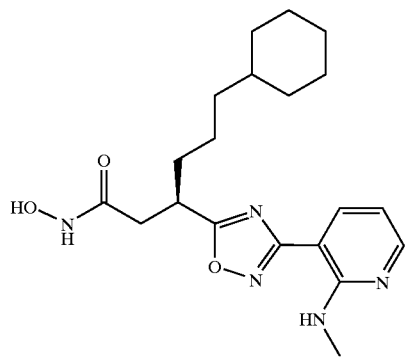

The title compound was obtained as a pale yellow oil from the title compound of Preparation 91, using a similar method to that described in Example 22.

¹H NMR (300 MHz, CD₃OD) δ 0.80–0.94 (m, 2H), 1.08–1.39 (m, 8H), 1.60–1.75 (m, 5H), 1.75–1.86 (m, 2H), 2.60 (dd, 1H), 2.71 (dd, 1H), 3.58–3.68 (m, 1H), 6.72 (dd, 1H), 8.21 (d, 1H), 8.33 (d, 1H).

LRMS (ES) 371 (M).

Example 44

(3R)-6-CYCLOHEXYL-N-HYDROXY-3-[3-(2-PYRAZINYL)-1,2,4-OXADLAZOL-5-YL]HEXANAMIDE

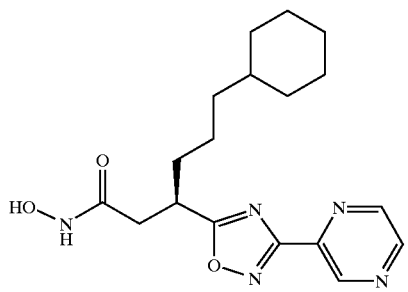

The title compound was obtained as a white solid from the title compound of Preparation 93, using a similar method to that described in Example 23.

Mpt 124–125° C.

¹H NMR (400 MHz, CD₃OD) δ 0.80–0.93 (m, 2H), 1.10–1.43 (m, 8H), 1.58–1.75 (m, 5H), 1.75–1.92 (m, 2H), 2.61 (dd, 1H), 2.73 (dd, 1H), 3.53–3.62 (m, 1H), 8.75–8.80 (m, 2H), 9.32 (s, 1H).

LRMS (TSP) 360 (M+H).

Example 45

(3R)-6-CYCLOHEXYL-N-HYDROXY-3-{3-[6-(1-PYRROLIDINYL)-2-PYRAZINYL]-1,2,4-OXADIAZOL-5-YL}HEXANAMIDE

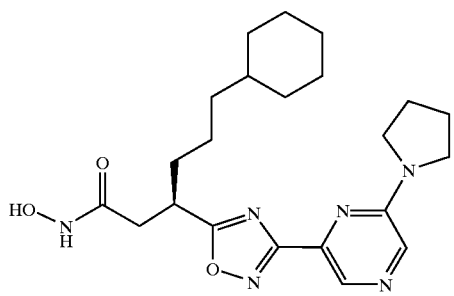

The title compound was obtained as a white solid from the title compound of Preparation 95, using a similar method to that described in Example 23.

Mpt 124–125° C.

¹H NMR (400 MHz, D₆-DMSO) δ 0.75–0.96 (m, 2H), 1.03–1.30 (m, 8H), 1.50–1.74 (m, 7H), 1.93–2.00 (m, 4H), 2.58–2.80 (m, 2H), 3.43–3.56 (m, 5H), 8.13 (s, 1H), 8.30 (s, 1H), 8.78 (s, 1H), 10.50 (s, 1H).

LRMS (ES) 451 (M+Na), 429 (M+H).

Example 46

(3R)-6-CYCLOHEXYL-N-HYDROXY-3-{3-[6-(4-METHYL-1-PIPERAZINYL)-2-PYRAZINYL]-1,2,4-OXADIAZOL-5-YL}HEXANAMIDE

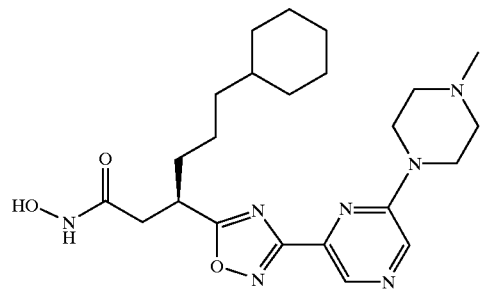

The title compound was obtained as a white foam from the title compound of Preparation 98, using a similar method to that described in Example 9. The compound was purified by preparative HPLC.

¹H NMR (400 MHz, CD₃OD) δ 0.80–0.93 (m, 2H), 1.08–1.40 (m, 8H), 1.50–1.74 (m, 5H), 1.75–1.85 (m, 2H), 2.40 (s, 3H), 2.56–2.77 (m, 6H), 3.60–3.67 (m, 1H), 3.76–3.82 (m, 4H), 8.38 (s, 1H), 8.47 (s, 1H).

LRMS (ES) 480 (M+Na), 458 (M+H).

Example 47

(3R)-6-CYCLOHEXYL-N-HYDROXY-3-{3-[6-(1H-IMIDAZOL-1-YL)-2-PYRAZINYL]-1,2,4-OXADIAZOL-5-YL}HEXANAMIDE

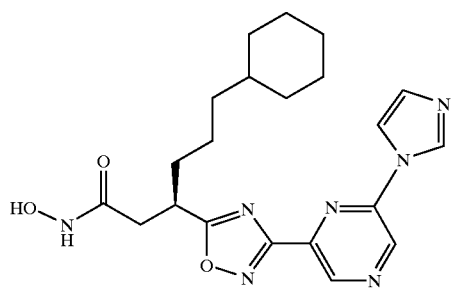

The title compound was obtained as a white solid from the title compound of Preparation 100, using a similar method to that described in Example 9. The product was recrystallised from methanol.

Mpt 165° C.

¹H NMR (400 MHz, CD₃OD) δ 0.80–0.92 (m, 2H), 1.08–1.40 (m, 8H), 1.60–1.73 (m, 5H), 1.77–1.90 (m, 2H), 2.64 (dd, 1H), 2.75 (dd, 1H), 3.63–3.73 (m, 1H), 7.23 (s, 1H), 8.12 (s, 1H), 8.78 (s, 1H), 9.24 (s, 1H), 9.26 (s, 1H).

LRMS (ES) 448 (M+Na), 426 (M+H).

Example 48

(3R)-6-CYCLOHEXYL-N-HYDROXY-3-{3-[3-(4-METHYL-1-PIPERAZINYL)-2PYRAZINYL]-1,2,4-OXADIAZOL-5-YL}HEXANAMIDE

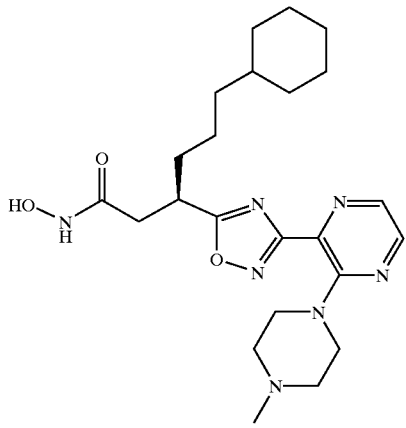

The title compound was obtained as a white foam from the title compound of Preparation 104, using a similar method to that described in Example 9. The product was purified by preparative HPLC.

$^1$H NMR (400 MHz, CD$_3$OD) δ 0.80–0.92 (m, 2H), 1.08–1.40 (m, 8H), 1.60–1.73 (m, 5H), 1.77–1.90 (m, 2H), 2.45 (s, 3H), 2.64 (dd, 1H), 2.70–2.80 (m, 5H), 3.30–3.50 (m, 4H), 3.63–3.73 (m, 1H), 8.12 (s, 1H), 8.40 (s, 1H).

LRMS (ES) 458 (M+H).

Example 49

(3R)-6-CYCLOHEXYL-N-HYDROXY-3-{3-[3-(4-MORPHOLINYL)-2-PYRAZINYL]-1,2,4-OXADIAZOL-5-YL}HEXANAMIDE

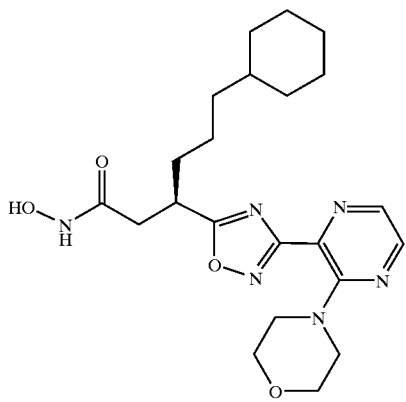

The title compound was obtained as a yellow foam from the title compound of Preparation 108, using a similar method to that described in Example 23. The product was purified by preparative HPLC.

$^1$H NMR (300 MHz, CD$_3$OD) δ 0.81–0.93 (m, 2H), 1.13–1.38 (m, 8H), 1.58–1.74 (m, 5H), 1.74–1.86 (m, 2H), 2.61 (dd, 1H), 2.70 (dd, 1H), 3.26–3.35 (m, 4H), 3.58–3.68 (m, 1H), 3.68–3.79 (m, 4H), 8.14 (s, 1H), 8.32 (s, 1H).

LRMS (ES) 467 (M+Na), 445 (M+H).

Example 50

(3R)-6-CYCLOHEXYL-N-HYDROXY-3-{3-[3-(1-PYRROLIDINYL)-2-PYRAZINYL]-1,2,4-OXADIAZOL-5-YL}HEXANAMIDE

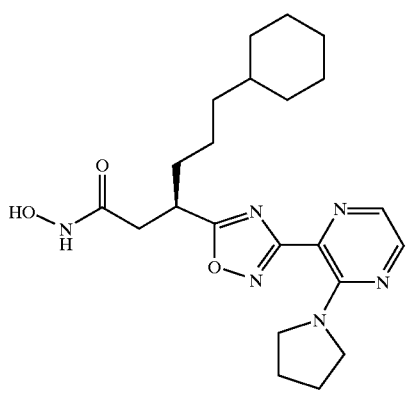

The title compound was obtained as a white foam from the title compound of Preparation 112, using a similar method to that described in Example 23. The product was purified by preparative HPLC.

$^1$H NMR (400 MHz, CD$_3$OD) δ 0.80–0.93 (m, 2H), 1.08–1.38 (m, 8H), 1.58–1.74 (m, 5H), 1.74–1.85 (m, 2H), 1.85–1.94 (m, 4H), 2.58 (dd, 1H), 2.67 (dd, 1H), 3.25–3.34 (m, 4H), 3.61–3.68 (m, 1H), 7.90 (d, 1H), 8.20 (d, 1H).

LRMS (ES) 451 (M+Na), 428 (M+H).

Example 51

(3R)-6-CYCLOHEXYL-3-{3-[3-(DIMETHYLAMINO)-2-PYRAZINYL]-1,2,4-OXADIAZOL-5-YL}-N-HYDROXYHEXANAMIDE

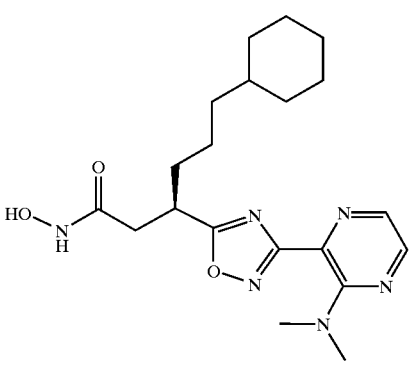

The title compound was obtained as a white foam from the title compound of Preparation 116, using a similar method to that described in Example 23. The product was purified by preparative HPLC.

$^1$H NMR (400 MHz, CD$_3$OD). δ 0.80–0.93 (m, 2H), 1.10–1.38 (m, 8H), 1.58–1.74 (m, 5H), 1.74–1.85 (m, 2H), 2.58 (dd, 1H), 2.70 (dd, 1H), 2.93 (s, 6H), 3.59–3.67 (m, 1H), 7.98 (d, 1H), 8.21 (d, 1H).

LRMS (ES) 425 (M+Na), 403 (M+H).

Example 52

(3R)-6-CYCLOHEXYL-N-HYDROXY-3-{3-[3-(METHYLAMINO)-2-PYRAZINYL]-1,2,4-OXADIAZOL-5-YL}HEXANAMIDE

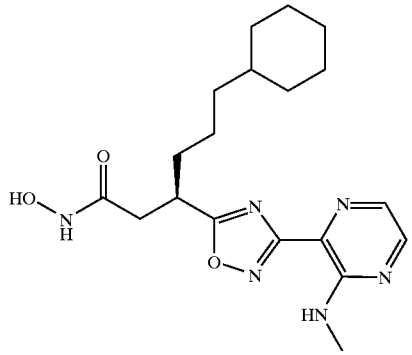

The title compound was obtained as a white solid from the title compound of Preparation 119, using a similar method to that described in Example 23. The product was purified by preparative HPLC.

Mpt 115–120° C.

$^1$H NMR (400 MHz, CD$_3$OD) δ 0.80–0.92 (m, 2H), 1.10–1.42 (m, 8H), 1.57–1.74 (m, 5H), 1.74–1.87 (m, 2H), 2.60 (dd, 1H), 2.72 (dd, 1H), 3.11 (d, 3H), 3.61–3.70 (m, 1H), 7.41 (br s, 1H), 7.92 (d, 1H), 8.25 (d, 1H).

LRMS (ES) 411 (M+Na), 389 (M+H).

Anal. Calcd. For C$_{19}$H$_{28}$N$_6$O$_3$: C, 58.75; H, 7.27; N, 21.63. Found C, 58.68; H, 7.30; N, 21.49.

Example 53

(3R)-6-CYCLOHEXYL-N-HYDROXY-3-(3-PHENYL-1,2,4-OXADIAZOL-5-YL)HEXANAMIDE

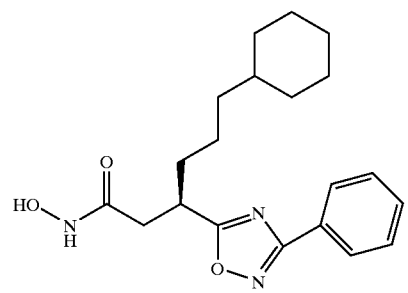

The title compound was obtained as a colorless oil from the title compound of Preparation 121, using a similar method to that described in Example 23.

$^1$H NMR (400 MHz, CDCl$_3$) δ 0.78–0.90 (m, 2H), 1.06–1.38 (m, 8H), 1.58–1.84 (m, 7H), 2.50–2.62 (m, 1H), 2.62–2.77 (m, 1H), 3.55–3.63 (m, 1H), 7.40–7.51 (m, 3H), 7.97–8.06 (m, 2H).

LRMS (TSP) 380 (M+Na), 358 (M+H).

Example 54

(3R)-6-CYCLOHEXYL-N-HYDROXY-3-[3-(4-METHOXYPHENYL)-1,2,4-OXADIAZOLE-5-YL]HEXANAMIDE

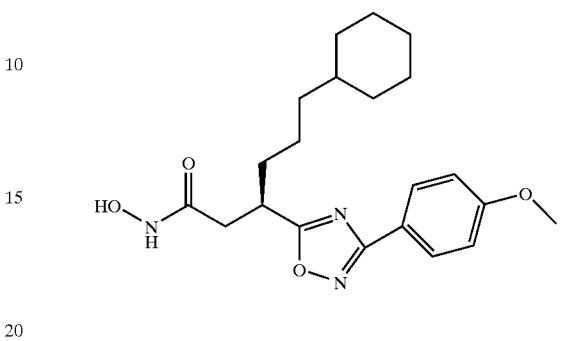

The title compound was obtained as a colorless oil from the title compound of Preparation 123, using a similar method to that described in Example 22.

$^1$H NMR (400 MHz, CDCl$_3$) δ 0.79–0.92 (m, 2H), 1.10–1.38 (m, 8H), 1.59–1.72 (m, 5H), 1.72–1.84 (m, 2H), 2.56 (dd, 1H), 2.70 (dd, 1H), 3.56–3.63 (m, 1H), 3.86 (s, 3H), 7.03 (d, 2H), 7.97 (d, 2H).

LRMS (TSP) 388 (M+H).

Example 55

(3R)-3-[3-(1,3-BENZODIOXOL-5-YL)-1,2,4-OXADIAZOL-5-YL]-6-CYCLOHEXYL-N-HYDROXYHEXANAMIDE

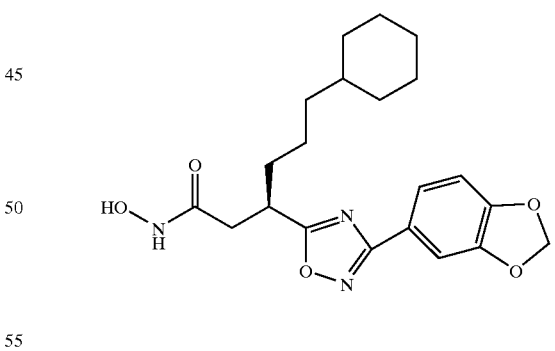

The title compound was obtained as a colorless oil from the title compound of Preparation 125, using a similar method to that described in Example 23.

$^1$H NMR (300 MHz, CDCl$_3$) δ 60.75–0.90 (m, 2H), 1.05–1.37 (m, 8H), 1.58–1.83 (m, 7H), 2.49–2.61 (m, 1H), 2.61–2.74 (m, 1H), 3.53–3.63 (m, 1H), 6.01 (s, 2H), 6.87 (d, 1H), 7.45 (s, 1H), 7.57 (d, 1H).

LRMS (TSP) 402 (M+H).

Example 56

ETHYL 4-(5-{(1R)-4-CYCLOHEXYL-1-[2-(HYDROXYAMINO)-2-OXOETHYL]BUTYL}-1,2,4-OXADIAZOL-3-YL)BENZOATE

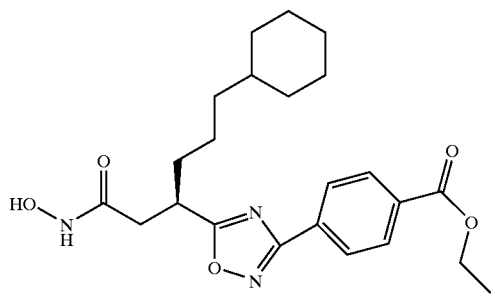

The title compound was obtained as a colorless foam from the title compound of Preparation 127, using a similar method to that described in Example 22.

$^1$H NMR (400 MHz, CD$_3$OD) δ 0.80–0.94 (m, 2H), 1.10–1.48 (m, 1H), 1.57–1.74 (m, 5H), 1.74–1.88 (m, 2H), 2.59 (dd, 1H), 2.70 (dd, 1H), 3.59–3.68 (m, 1H), 4.40 (q, 2H), 8.17 (s, 4H).

LRMS (TSP) 429 (M).

Example 57

4-(5-{(1R)-4-CYCLOHEXYL-1-[2-(HYDROXYAMINO)-2-OXOETHYL]BUTYL}-1,2,4-OXADIAZOL-3-YL)BENZOIC ACID

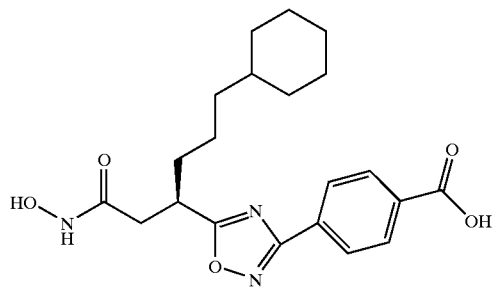

The title compound was obtained as a white solid from the title compound of Example 56, using a similar method to that described in Example 25. The compound was purified by preparative HPLC.

Mpt 142–146° C.

$^1$H NMR (400 MHz, CD$_3$OD) δ 0.78–0.92 (m, 2H), 1.10–1.38 (m, 8H), 1.58–1.72 (m, 5H), 1.72–1.88 (m, 2H), 2.54–2.62 (m, 1H), 2.62–2.76 (m, 1H), 3.57–3.67 (m, 1H), 8.10–8.17 (m, 4H).

LRMS (TSP) 429 (M).

Example 58

(3R)-6-CYCLOHEXYL-3-(3-{4-[(DIMETHYLAMINO)SULFONYL]PHENYL}-1,2,4-OXADIAZOL-5-YL)-N-HYDROXYHEXANAMIDE

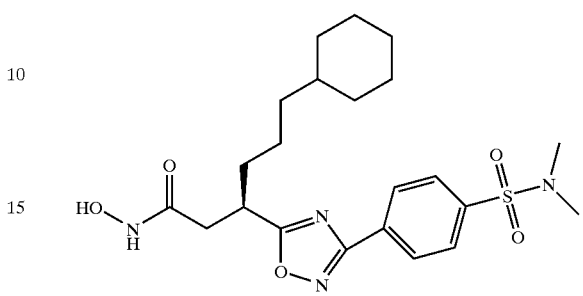

The title compound was obtained as a white solid from the title compound of Preparation 131, using a similar method to that described in Example 22.

Mpt 52–60° C.

$^1$H NMR (300 MHz, CD$_3$OD) δ 0.78–0.93 (m, 2H), 1.08–1.40 (m, 8H), 1.58–1.73 (m, 5H), 1.73–1.88 (m, 2H), 2.59 (dd, 1H), 2.65–2.77 (m, 7H), 3.59–3.70 (m, 1H), 7.94 (d, 2H), 8.29 (d, 2H).

LRMS (TSP) 464 (M).

Example 59

(3R)-6-CYCLOHEXYL-N-HYDROXY-3-(3-{4-[(METHYLSULFONYL)AMINO]PHENYL}-1,2,4-OXADIAZOL-5-YL)HEXANAMIDE

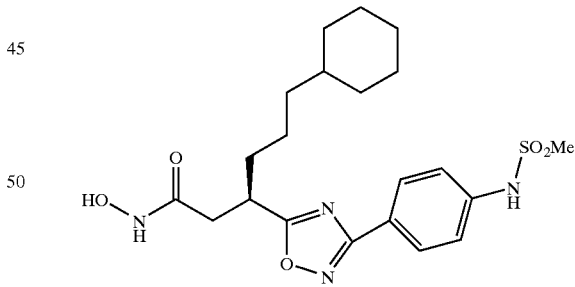

The title compound was obtained as a white foam from the title compound of Preparation 133, using a similar method to that described in Example 22.

$^1$H NMR (300 MHz, CDCl$_3$) δ 0.77–0.92 (m, 2H), 1.00–1.40 (m, 8H), 1.58–1.92 (m, 7H), 2.64 (dd, 1H), 2.79 (dd, 1H), 3.01 (s, 3H), 3.55–3.66 (m, 1H), 7.20 (d, 2H), 7.67 (br s, 1H), 7.87 (d, 2H), 8.94 (br s, 1H).

LRMS (ES) 473 (M+Na), 451 (M+H).

Example 60

ETHYL 3-(5-{(1R)-4-CYCLOHEXYL-1-[2-(HYDROXYAMINO)-2-OXOETHYL]BUTYL-1,2,4-OXADIAZOL-3-YL}BENZOATE

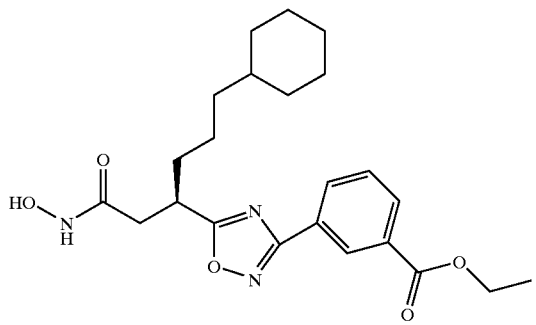

The title compound was obtained as a brown foam from the title compound of Preparation 136, using a similar method to that described in Example 22.

$^1$H NMR (300 MHz, CDCl$_3$) δ 0.77–0.91 (m, 2H), 1.03–1.48 (m, 1H), 1.54–1.92 (m, 7H), 2.63 (dd, 1H), 2.80 (dd, 1H), 3.61–3.22 (m, 1H), 4.42 (q, 2H), 7.55 (dd, 1H), 8.17 (d, 1H), 8.21 (d, 1H), 8.66 (s, 1H).

LRMS (TSP) 430 (M+H).

Example 61

3-(5-{(1R)-4-CYCLOHEXYL-1-[2-(HYDROXYAMINO)-2-OXOETHYL]BUTYL}-1,2,4-OXADIAZOL-3-YL)BENZOIC ACID

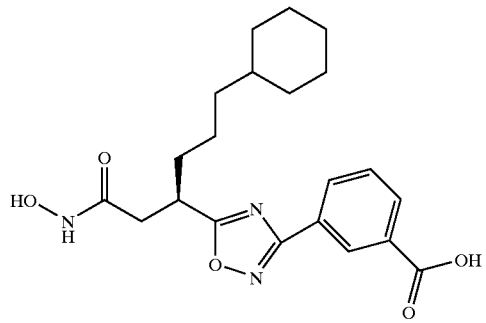

The title compound was obtained as a white solid from the title compound of Example 60, using a similar method to that described in Example 25. The reaction was carried out at 70° C. and the product was purified by preparative HPLC.

$^1$H NMR (300 MHz, D$_6$-DMSO) δ 0.72–0.87 (m, 2H), 1.00–1.36 (m, 8H), 1.47–1.90 (m, 7H), 2.43–2.63 (m, 2H), 3.45–3.58 (m, 1H), 7.70 (dd, 1H), 8.14 (d, 1H), 8.21 (d, 1H), 8.54 (s, 1H), 8.79 (br s, 1H), 10.50 (s, 1H), 13.30 (br s, 1H).

LRMS (ES) 402 (M+H).

Example 62

(3R)-6-CYCLOHEXYL-3-[3-(3,5-DIMETHOXYPHEN-YL)-1,2,4-OXADIAZOL-5-YL]-N-HYDROXYHEXANA-MIDE

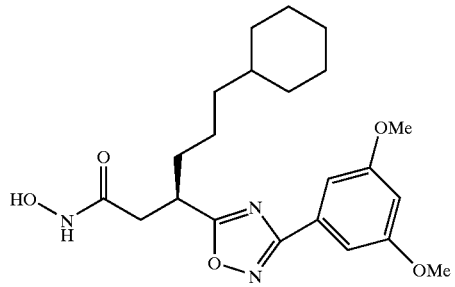

The title compound was obtained as a white solid from the title compound of Preparation 138, using a similar method to that described in Example 23.

$^1$H NMR (400 MHz, CD$_3$OD) δ 0.80–0.92 (m, 2H), 1.10–1.38 (m, 8H), 1.60–1.72 (m, 5H), 1.72–1.84 (m, 2H), 2.57 (dd, 1H), 2.70 (dd, 1H), 3.58–3.67 (m, 1H), 3.85 (s, 6H), 6.65 (s, 1H), 7.19 (s, 2H).

LRMS (TSP) 417 (M).

Example 63

(3R)-6-CYCLOHEXYL-N-HYDROXY-3-[3-(1H-PYRAZOL-4-YL)-1,2,4-OXADIAZOL-5-YL]HEXANA-MIDE

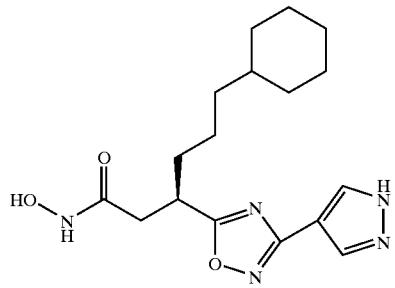

The title compound was obtained as a white solid from the title compound of Preparation 141, using a similar method to that described in Example 23.

$^1$H NMR (400 MHz, D$_6$-DMSO) δ 0.72–0.83 (m, 2H), 1.02–1.28 (m, 8H), 1.50–1.70 (m, 7H), 2.40–2.57 (m, 2H), 3.40–3.49 (m, 1H), 8.13 (br s, 2H), 8.78 (br s, 1H).

LRMS (TSP) 348 (M+H).

Example 64

(3R)-6-CYCLOHEXYL-N-HYDROXY-3-[3-(1H-PYRAZOL-3-YL)-1,2,4-OXADIAZOL-5-YL]HEXANA-MIDE

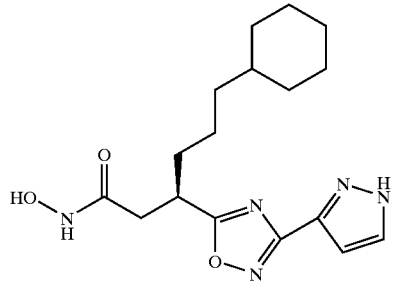

The title compound was obtained as a white solid from the title compound of Preparation 143, using a similar method to that described in Example 23.

¹H NMR (400 MHz, D₆-DMSO) δ 0.73–0.94 (m, 2H), 1.00–1.38 (m, 8H), 1.54–1.82 (m, 7H), 2.57–2.79 (m, 2H), 3.56–3.69 (m, 1H), 6.64 (s, 1H), 7.47 (s, 1H), 7.65 (s, 1H),

LRMS (TSP) 348 (M+H).

Example 65

(3R)-6-CYCLOHEXYL-3-[3-(2-FURYL)-1,2,4-OXADIAZOL-5-YL]-N-HYDROXYHEXANAMIDE

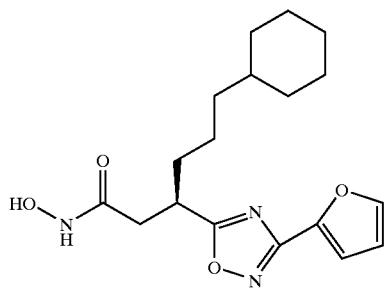

The title compound was obtained as a colorless oil from the title compound of Preparation 145, using a similar method to that described in Example 23.

¹H NMR (300 MHz, CDCl₃) δ 0.74–0.92 (m, 2H), 1.05–1.39 (m, 8H), 1.58–1.89 (m, 7H), 2.50–2.80 (m, 2H), 3.56–3.68 (m, 1H), 6.56 (d, 1H), 7.11 (d, 1H), 7.60 (s, 1H).

LRMS (TSP) 348 (M+H).

Example 66

3R)-6-CYCLOHEXYL-N-HYDROXY-3-[3-(3-QUINOLINYL)-1,2,4-OXADIAZOL-5-YL]HEXANAMIDE

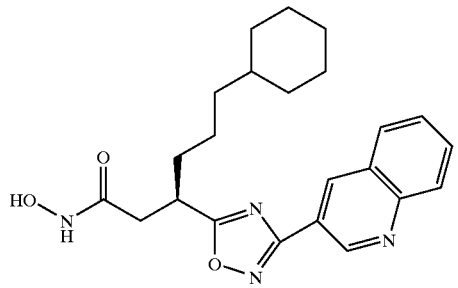

The title compound was obtained as a white solid from the title compound of Preparation 148, using a similar method to that described in Example 23.

¹H NMR (300 MHz, D₆-DMSO) δ 0.74–0.90 (m, 2H), 1.00–1.38 (m, 8H), 1.50–1.69 (m, 5H), 1.69–1.80 (m, 2H), 2.50–2.70 (m, 2H), 3.51–3.62 (m, 1H), 7.72 (dd, 1H), 7.90 (dd, 1H), 8.11 (d, 1H), 8.22 (d, 1H), 8.80 (s, 1H), 9.00 (s, 1H), 9.42 (s, 1H), 10.53 (s, 1H).

Example 67

(3R)-6-CYCLOHEXYL-N-HYDROXY-3-[3-(1-ISOQUINOLINYL)-1,2,4-OXADIAZOL-5-YL]HEXANAMIDE

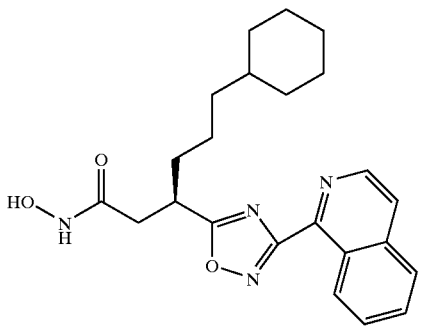

The title compound was obtained as a white solid from the title compound of Preparation 151, using a similar method to that described in Example 23.

¹H NMR (300 MHz, D₆-DMSO) δ 0.74–0.92 (m, 2H), 1.00–1.40 (m, 8H), 1.50–1.69 (m, 5H), 1.69–1.82 (m, 2H), 2.52–2.70 (m, 2H), 3.57–3.66 (m, 1H), 7.76 (dd, 1H), 7.88 (dd, 1H), 8.05–8.17 (m, 2H), 8.51 (d, 1H), 8.70 (d, 1H), 8.82 (s, 1H), 10.57 (s, 1H).

LRMS (ES) 431 (M+Na), 409 (M+H).

Example 68

(3R)-6-CYCLOHEXYL-N-HYDROXY-3-[3-(3-ISOQUINOLINYL)-1,2,4-OXADIAZOL-5-YL]HEXANAMIDE

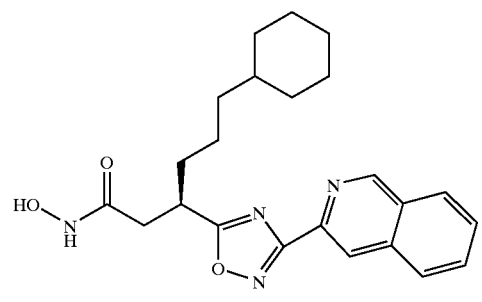

The title compound was obtained as a white solid from the title compound of Preparation 154, using a similar method to that described in Example 23.

¹H NMR (300 MHz, D₆-DMSO) δ 0.73–0.89 (m, 2H), 1.00–1.34 (m, 8H), 1.50–1.67 (m, 5H), 1.67–1.82 (m, 2H), 2.51–2.66 (m, 2H), 3.50–3.60 (m, 1H), 7.82 (dd, 1H), 7.90 (dd, 1H), 8.20 (d, 1H), 8.24 (d, 1H), 8.60 (s, 1H), 8.80 (br s, 1H), 9.46 (s, 1H), 10.55 (s, 1H).

LRMS (ES) 431 (M+Na), 409 (M+H).

Example 69
(3R)-6-CYCLOHEXYL-N-HYDROXY-3-(3-{6-[(METHYLSULFONYL)AMINO]-3-PYRIDINYL}-1,2,4-OXADIAZOL-5-YL)HEXANAMIDE

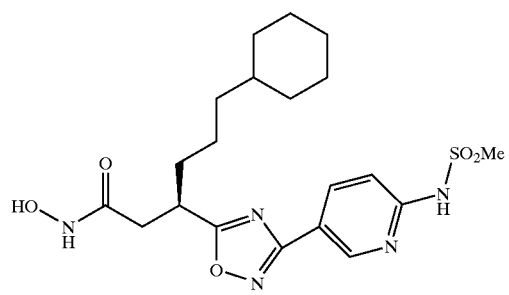

The title compound was obtained as a white solid from the title compound of Preparation 156, using a similar method to that described in Example 22. The residue was purified by trituration with diisopropyl ether.

Mpt 143–146° C.

$^1$H NMR (400 MHz, CD$_3$OD) δ 0.80–0.90 (m, 2H), 1.08–1.38 (m, 8H), 1.57–1.70 (m, 5H), 1.74–1.85 (m, 2H), 2.56 (dd, 1H), 2.68 (dd, 1H), 3.29 (s, 3H), 3.55–3.64 (m, 1H), 7.14 (d, 1H), 8.28 (d, 1H), 8.85 (s, 1H).

LRMS (ES) 474 (M+Na), 452 (M+H).

Example 70
(3R)-6-CYCLOHEXYL-3-[3-(6-ETHOXY-2-PYRAZINYL)-1,2,4-OXADIAZOL-5-YL]-N-HYDROXYHEXANAMIDE

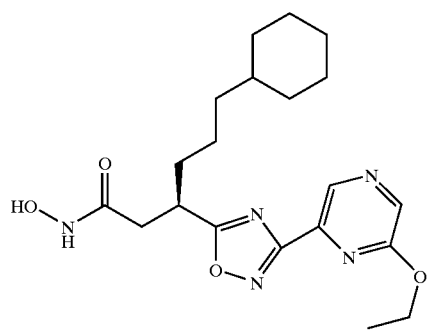

The title compound was obtained as a white solid from the title compound of Preparation 158, using a similar method to that described in Example 23. The reaction was performed without triethylamine and purified by preparative HPLC.

$^1$NMR (400 MHz, D$_6$-DMSO) δ 0.74–0.89 (m, 2H), 1.02–1.30 (m, 8H), 1.39 (t, 3H), 1.52–1.65 (m, 5H), 1.65–1.80 (m, 2H), 2.45–2.60 (m, 2H), 3.55 (m, 1H), 4.42 (q, 2H), 8.50 (s, 1H), 8.78–8.20 (m, 2H).

LRMS (ES) 426 (M+Na).

Example 71
(3R)-3-[3-(2-TERT-BUTYL-1H-TETRAAZOL-5-YL)-1,2,4-OXADIAZOL-5-YL]-6-CYCLOHEXYL-N-HYDROXYHEXANAMIDE AND (3R)-3-[3-(1-TERT-BUTYL-2H-TETRAAZOL-5-YL)-1,2,4-OXADIAZOL-5-YL]-6-CYCLOHEXYL-N-HYDROXYHEXANAMIDE

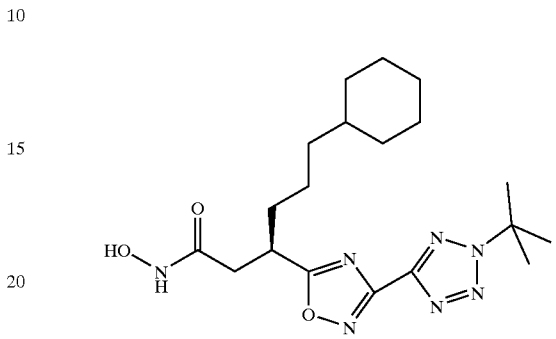

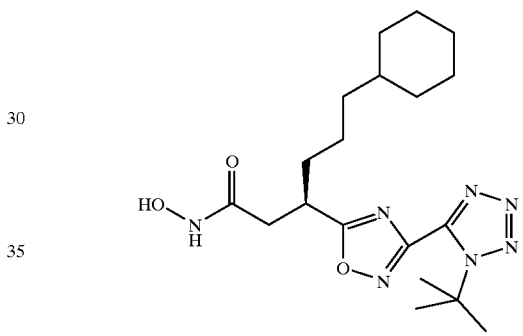

To a solution of the title compound from Preparation 160 (0.20 g, 0.52 mmol) in dried dichloromethane (3 mL) and pyridine (0.98 mL) was added 1-hydroxy-7-azabenzotriazole (0.070 g, 0.52 mmol) followed by 1-(3-dimethylaminopropyl)-3-ethylcarbodiimide hydrochloride (0.120 g, 0.62 mmol). The mixture was stirred at room temperature for 1 hour, then hydroxylamine hydrochloride (0.108 g, 1.56 mmol) was added and then stirred at room temperature overnight. The reaction mixture was partitioned between pH 7 buffer (50 mL) and ethyl acetate (50 mL). The organic layer was separated, dried (MgSO$_4$) and the solvent was removed in vacuo. The residue was purified by flash chromatography on silica gel (graded elution of dichloromethane/methanol/aqueous ammonia solution 98:2:0.2 to 95:5:0.5) to give the title compounds, a 1:1 mixture of isomers, as a brown oil (0.085 g).

LRMS (ES) 406 (M+H).

$^1$H NMR (400 MHz, D$_6$-DMSO) δ 0.75–0.89 (m, 4H), 1.02–1.34 (m, 18H), 1.52–1.68 (m, 22H), 1.68–1.80 (m, 8H), 2.54–2.66 (m, 2H), 2.84 (m, 2H), 3.08 (m, 2H), 3.52–3.62 (m, 2H), 8.64 (br s, 1H), 10.42 (br s, 1H).

Example 72

(3R)-6-CYCLOHEXYL-N-HYDROXY-3-(5-PHENYL-1,3-OXAZOL-2-YL)HEXANAMIDE

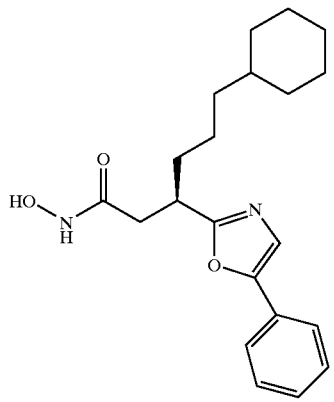

The title compound was obtained as a white solid from the title compound of Preparation 164, using a similar method to that described in Example 3. N-Methylmorpholine was used instead of triethylamine. Dimethylformamide was used as solvent and the residue was purified by column chromatography eluting with ethyl acetate.

$^1$H NMR (300 MHz, CDCl$_3$) δ 0.75–0.96 (m, 2H), 1.00–1.40 (m, 9H), 1.50–1.90 (m, 7H), 2.44–2.60 (m, 1H), 2.64–2.80 (m, 1H), 3.40–60 (m, 1H), 7.16 (s, 1H), 7.24–7.44 (m, 3H), 7.50–7.62 (m, 1H), 8.30–8.57 (br s, 1H), 9.60–9.10 (br s, 1H).

LRMS (TSP) 357 (M+H).

Example 73

(3R)-6-CYCLOHEXYL-N-HYDROXY-3-[5-(4-PYRIDINYL)-1,3-OXAZOL-2-YL]HEXANAMIDE

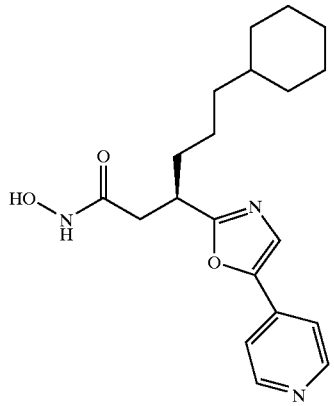

The title compound was obtained as a white solid from the title compound of Preparation 168, using a similar method to that described in Example 27.

$^1$H NMR (300 MHz, CH$_3$OD) δ 0.75–0.96 (m, 2H), 1.04–1.40 (m, 9H), 1.52–1.90 (m, 8H), 2.44–2.64 (m, 2H), 3.50 (m, 1H), 7.65 (m, 3H), 8.58 (m, 2H).

LRMS (ES) 358 (M+H).

Example 74

(3R)-6-CYCLOHEXYL-N-HYDROXY-3-[5-(3-PYRIDINYL)-1,2,4-OXADIAZOL-3-YL]HEXANAMIDE

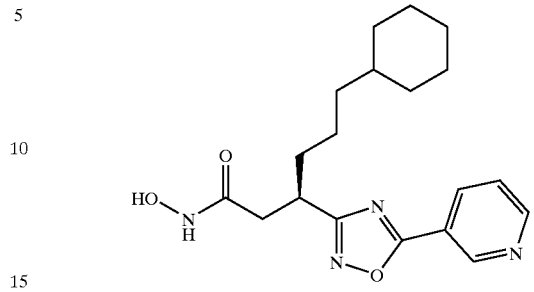

To a solution of the title compound from Preparation 172 (0.24 g, 0.6 mmol) in dichloromethane (10 mL) was added was added trifluoroacetic acid (5 mL) and the resulting solution was stirred at room temperature for 3 hours. The solvent and excess trifluoroacetic acid were removed in vacuo. The residue was dissolved in ethyl acetate (20 mL) and washed with aqueous sodium citrate solution (10 mL), brine (10 mL), then dried (Na$_2$SO$_4$) and concentrated under reduced pressure. The crude acid (0.2 g) was taken on to the next step without further purification.

To a solution of the above crude acid (0.2 g, 0.58 mmol) in dimethylformamide (10 mL) was added N-methylmorpholine (0.064 mL, 0.18 mmol). The reaction was cooled to 0° C. in an ice bath, then iso-butylchloroformate (0.083 mL, 0.64 mmol) was added. Further N-methylmorpholine (0.192 mL, 1.74 mmol) was added followed by hydroxylamine hydrochloride (0.120 g, 1.74 mmol) and the reaction was warmed to room temperature and stirred overnight. The solvent was removed in vacuo. The residue was partitioned between water (50 mL) and ethyl acetate (50 mL). The layers were separated and the aqueous layer was extracted with ethyl acetate (50 mL). The combined organic extracts were washed with brine (25 mL) and dried (Na$_2$SO$_4$). The residue was purified by flash chromatography on silica gel (graded elution of dichloromethane/methanol 99:1:1.0 to 80:20) to give the title compound as a white foam (0.056 g).

$^1$H NMR (400 MHz, CD$_3$OD) δ 0.77–0.92 (m, 2H), 1.04–1.40 (m, 9H), 1.58–1.88 (m, 8H), 2.46–2.68 (m, 2H), 3.50 (m, 1H), 7.64 (m, 1H), 8.54 (d, 1H), 8.80 (d, 1H), 9.28 (s, 1H).

LRMS (ES) 359 (M+H), 381 (M+Na).

Example 75

(3R)-6-CYCLOHEXYL-N-HYDROXY-3-[5-(2-PYRAZINYL)-1,2,4-OXADIAZOL-3-YL]HEXANAMIDE

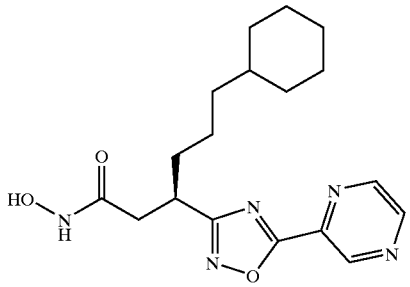

To a solution of the title compound from Preparation 173 (0.18 g, 0.45 mmol) in dichloromethane (8 mL) was added was added trifluoroacetic acid (4 mL) and the resulting solution was stirred at room temperature for 3 hours. The solvent and excess trifluoroacetic acid were removed in vacuo. The residue was dissolved in ethyl acetate (20 mL) and washed with aqueous sodium citrate solution (2×10 mL), brine (10 mL), then dried ($Na_2SO_4$) and concentrated under reduced pressure. The crude acid (0.17 g) was taken on to the next step without further purification.

To a solution of the above crude acid (0.170 g, 0.45 mmol), hydroxybenzotriazole (0.069 g, 0.45 mmol) in 1,4-dioxane (5 mL) was added 1,3-dicyclohexylcarbodiimide (0.093 mL, 0.45 mmol). The mixture was stirred for 1.5 hours. A precipitate began to form, then 50% aqueous hydroxylamine (0.030 mL, 4.5 mmol) was added and stirring was continued overnight. The reaction mixture was filtered and the solvent removed in vacuo. The residue was dissolved in ethyl acetate (50 mL) and washed with saturated aqueous sodium bicarbonate (2×30 mL). The combined washings were extracted with ethyl acetate and the combined organic layers were washed with brine and dried ($Na_2SO_4$). The residue was purified by preparative HPLC then triturated with ice-cold water to give the title compound as a white solid (0.064 g).

Mpt 126–127° C.
$^1$H NMR (300 MHz, $CDCl_3$) δ 0.72–0.90 (m, 2H), 1.00–1.40 (m, 8H), 1.54–2.00 (m, 7H), 2.56–2.80 (m, 2H), 3.58 (m, 1H), 8.80 (s, 2H), 9.40 (s, 1H).
LRMS (ES) 382 (M+Na), 360 (M+H).
Anal. Calcd. For $C_{18}H_{25}N_5O_3$: C, 60.15; H, 7.01; N, 19.48. Found C, 60.34; H, 7.32; N, 17.12.

Example 76
(3R)-6-CYCLOHEXYL-N-HYDROXY-3-[5-(5-PYRIMIDINYL)-1,2,4-OXADIAZOL-3-YL]HEXANAMIDE

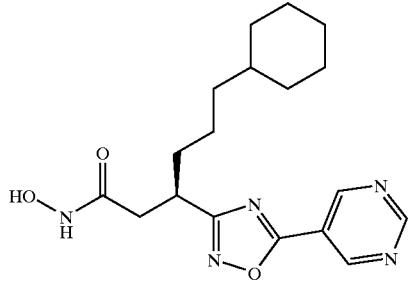

To a solution of the title compound from Preparation 174 (0.304 g, 0.76 mmol) in dichloromethane (8 mL) was added was added trifluoroacetic acid (4 mL) and the resulting solution was stirred at room temperature for 2.5 hours. The solvent and excess trifluoroacetic acid were removed in vacuo. The residue was dissolved in ethyl acetate (20 mL) and washed with aqueous sodium citrate solution (2×110 mL), brine (10 mL), then dried ($MgSO_4$) and concentrated under reduced pressure. The crude acid (0.276 g) was taken on to the next step without further purification.

The title compound was obtained as a white solid (0.124 g) from the above crude acid (0.276 g), using a similar method to that described in Example 3. N-Methylmorpholine was used instead of triethylamine. The reaction mixture was acidified with 1N citric acid solution (15 mL) and stirred for 4 hours. The reaction mixture was extracted with ethyl acetate (3×50 mL) dried ($MgSO_4$), the solvent was removed in vacuo and the residue was recystallised from hexane:ethyl acetate.

Mpt 138–139° C.
$^1$H NMR (300 MHz, $CDCl_3$) δ 0.76–0.92 (m, 2H), 1.02–1.40 (m, 8H), 1.50–1.90 (m, 7H), 2.52–2.80 (m, 2H), 3.55 (m, 1H), 9.40 (s, 3H).
LRMS (ES) 382 (M+Na), 360 (M+H).
Anal. Calcd. For $C_{18}H_{25}N_5O_3$: C, 60.15; H, 7.01; N, 19.48. Found C, 60.15; H, 7.14; N, 19.30.

Examples 77–81

In addition to the above Examples, the following further Examples 77–81 were made using analogous methods to those mentioned above, and they exhibit PCP-inhibiting properties:

77

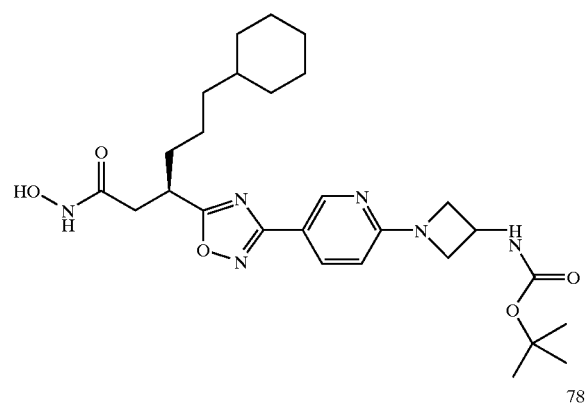

78

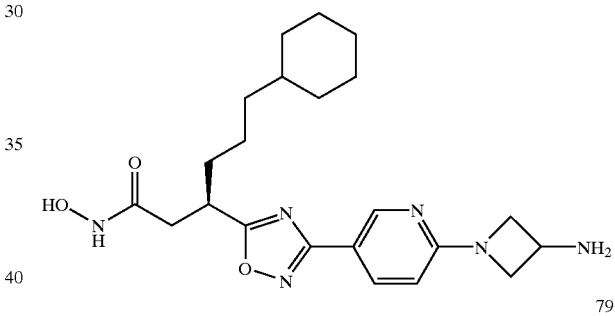

79

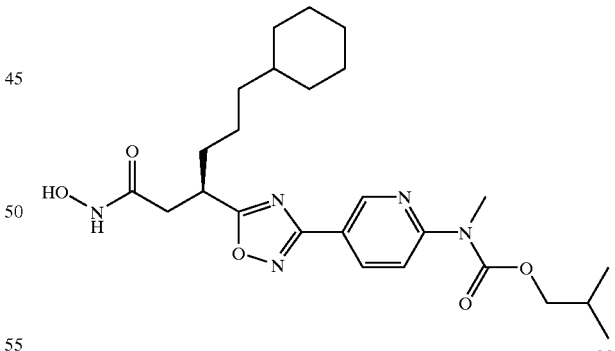

80

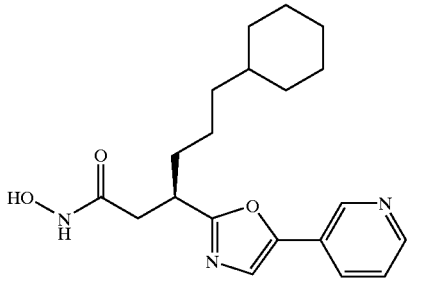

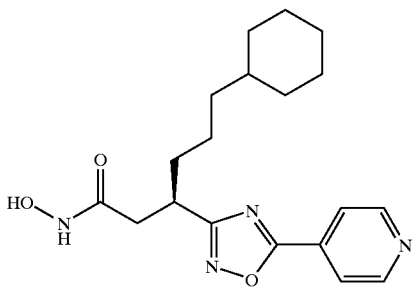

Preparation 1
N'-Hydroxy-2,4-dioxo-1,2,3,4-tetrahydro-5-pyrimidinecarboximidamide

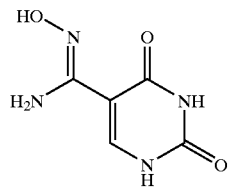

5-Cyano uracil (2.0 g, 14.6 mmol) was suspended in methanol (50 mL), then hydroxylamine hydrochloride (1.4 g, 20.0 mmol) and triethylamine (2.8 mL, 20.0 mmol) were added and the mixture was heated to reflux overnight. The mixture was cooled to room temperature, the solid was collected by filtration, washed with methanol and dried to give the title compound as a pale yellow solid (1.8 g).
$^1$H NMR (400 MHz, D$_6$-DMSO) δ 5.71 (br s, 2H), 7.62 s, 1H), 11.0–11.4 (br s, 1H).
LRMS (ES) 363 (2M+Na), 193 (M+Na), 171 (M+H).

Preparation 2
tert-Butyl (3R)-6-cyclohexyl-3-[3-(2,4-dioxo-1,2,3,4-tetrahydro-5-pyrimidinyl)-1,2,4-oxadiazol-5-yl]hexanoate

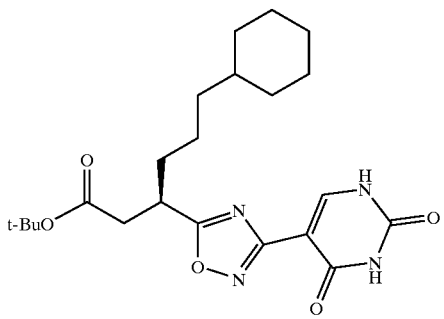

To a solution of the title compound from Preparation 175 (0.45 g, 1.5 mmol) in dichloromethane (20 mL) was added 1-hydroxybenzotriazole (0.245 g, 1.8 mmol), 1-(3-dimethylaminopropyl)-3-ethylcarbodiimide hydrochloride (0.34 g, 1.8 mmol) followed by the title compound from Preparation 1 (0.305 g, 1.8 mmol). After 1 hour the reaction was still heterogeneous and therefore dimethylformamide (10 mL) was added to aid solubility. The reaction was stirred at room temperature overnight, then the dichloromethane was removed in vacuo and the remaining solution was dissolved in water (100 mL) and extracted with ethyl acetate (2×100 mL). The combined organic extracts were dried (MgSO$_4$) and the solvent was removed in vacuo. The residue was suspended in xylene (20 mL) and then heated to reflux for 4 hours. The reaction mixture was cooled to room temperature, the solvent was removed in vacuo and the residue was purified by flash chromatography on silica gel (dichloromethane/methanol 95:5 as eluant) to afford the title compound as a pale yellow solid (0.60 g).
$^1$H NMR (400 MHz, D$_6$-DMSO) δ 0.73–0.95 (m, 2H), 1.03–1.20 (m, 17H), 1.52–1.73 (m, 7H), 2.64–2.74 (m, 2H), 8.00 (s, 1H), 11.0–11.7 (br s, 2H).
LRMS (ES) 887 (2M+Na), 455 (M+Na).

Preparation 3
(3R)-6-Cyclohexyl-3-[3-(2,4-dioxo-1,2,3,4-tetrahydro-5-pyrimidinyl)-1,2,4-oxadiazol-5-yl]hexanoic acid

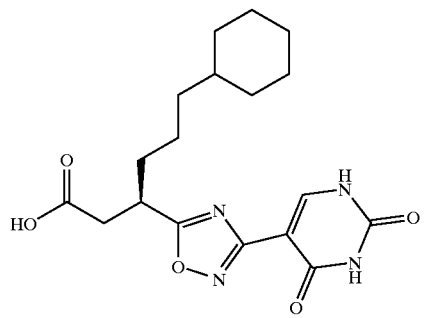

To a solution of the title compound from Preparation 2 (0.58 g, 1.34 mmol) in dichloromethane (20 mL) was added trifluoroacetic acid (10 mL) and the resulting green solution was stirred at room temperature for 2 hours. The solvent and excess trifluoroacetic acid were removed in vacuo, the residue was azeotroped with toluene to give a brown solid which was triturated with diisopropyl ether. The solid was collected by filtration and dried under high vacuum to give the title compound as a white solid (0.40 g).
Mpt 240–244° C.
$^1$H NMR (400 MHz, D$_6$-DMSO) δ 0.72–0.89 (m, 2H), 1.03–1.17 (m, 8H), 1.53–1.72 (m, 7H), 2.66–2.81 (m, 2H), 3.36–3.47 (m, 1H), 8.01 (s, 1H), 11.32 (br s, 1H), 11.38 (br s, 1H), 12.05–12.30 (br s, 1H).
LRMS (ES) 375 (M−H).

Preparation 4
N'-Hydroxy-6-methyl-3-pyridazinecarboximidamide

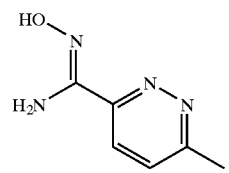

3-Cyano-6-methyl pyridazine (U.S. Pat. No. 5,914,319) (0.77 g, 6.4 mmol) was dissolved in methanol (20 mL), then hydroxylamine hydrochloride (0.66 g, 9.6 mmol) and triethylamine (1.3 mL, 9.6 mmol) were added and the mixture was stirred at room temperature overnight. The mixture was chilled in an ice-bath, then the solid was collected by filtration, washed with methanol and dried to give the title compound as a pale yellow solid (0.84 g).
$^1$H NMR (400 MHz, D$_6$-DMSO) δ 2.48 (s, 3H), 5.76 (s, 2H), 8.47 (s, 1H), 8.90 (s, 1H), 9.95 (s, 1H).
LRMS (ES) 153 (M+H).

Preparation 5
tert-Butyl (3R)-6-Cyclohexyl-3-[3-(6-methyl-3-pyridazinyl)-1,2,4-oxadiazol-5-yl]hexanoate

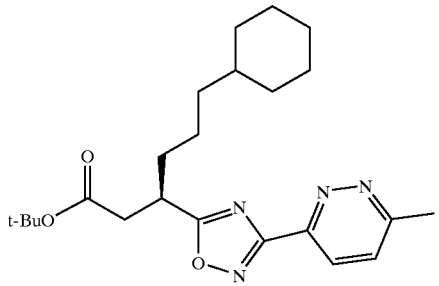

To a solution of the title compound from Preparation 175 (0.45 g, 1.5 mmol) in CH$_2$Cl$_2$ (20 mL) was added 1-hydroxybenzotriazole (0.245 g, 1.8 mmol), 1-(3-dimethylaminopropyl)-3-ethylcarbodiimide hydrochloride (0.34 g, 1.8 mmol) followed by the title compound from Preparation 4 (0.28 g, 1.8 mmol). After 1 hour the reaction was still heterogeneous and therefore dimethylformamide (5 mL) was added to aid solubility. The reaction was stirred at room temperature overnight, then the dichloromethane was removed in vacuo and the remaining solution was dissolved in water (100 mL) and extracted with ethyl acetate (3×50 mL). The combined organic extracts were dried (MgSO$_4$) and the solvent was removed in vacuo. The residue was dissolved in xylene (15 mL) and then heated to reflux for overnight. The reaction mixture was cooled to room temperature, the solvent was removed in vacuo and the residue was purified by flash chromatography on silica gel (dichloromethane/methanol 99:1 as eluant) to afford the title compound as a viscous yellow oil (0.40 g).

$^1$H NMR (400 MHz, CDCl$_3$) δ 0.75–0.88 (m, 2H), 1.07–1.22 (m, 6H), 1.23–1.34 (m, 2H), 1.37 (s, 9H), 1.58–1.70 (m, 5H), 1.71–1.92 (m, 2H), 2.66 (s, 3H), 2.72 (dd, 1H), 2.93 (dd, 1H), 3.54–3.62 (m, 1H), 8.62 (s, 1H), 9.22 (s, 1H).

LRMS (ES) 851 (2M+Na), 437 (M+Na).

Preparation 6
(3R)-6-Cyclohexyl-3-[3-(6-methyl-3-pyridazinyl)-1,2,4-oxadiazol-5-yl]hexanoic acid

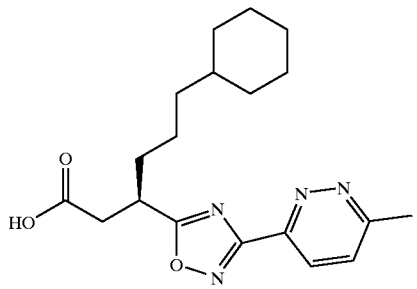

To a solution of the title compound from Preparation 5 (0.38 g, 0.92 mmol) in dichloromethane (10 mL) was added trifluoroacetic acid (10 mL) and the resulting solution was stiffed at room temperature for 1 hour. The solvent was removed in vacuo, and the residue was azeotroped with toluene to give the title compound as a yellow oil (0.33 g).

$^1$H NMR (400 MHz, CDCl$_3$) δ 0.75–0.88 (m, 2H), 1.03–1.38 (m, 8H), 1.58–1.70 (m, 5H), 1.71–1.92 (m, 2H), 2.69 (s, 3H), 2.87 (dd, 1H), 3.09 (dd, 1H), 2.54–2.62 (m, 1H), 8.68 (s, 1H), 9.24 (s, 1H).

LRMS (ES) 357 (M–H).

Preparation 7
N'-Hydroxy-1-methyl-1H-imidazole-2-carboximidamide

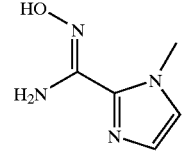

1-Methyl-2-cyanoimidazole (0.85 g, 8.0 mmol) (J. Chem. Soc. Perkin Trans. I 1994, 239) was dissolved in methanol (20 mL), then hydroxylamine hydrochloride (0.66 g, 9.6 mmol) and triethylamine (1.3 mL, 9.6 mmol) were added and the mixture was stirred at room temperature for 1 hour. The mixture was chilled in an ice-bath, then the solid was collected by filtration, washed with methanol and dried to give the title compound as a white crystalline solid which was contaminated with triethylamine hydrochloride (0.90 g).

$^1$H NMR (400 MHz, D$_6$-DMSO) δ 3.78 (s, 3H), 5.52 (br s, 2H), 6.88 (s, 1H), 7.14 (s, 1H), 9.68 (s, 1H).

Preparation 8
tert-Butyl (3R)-6-Cyclohexyl-N-hydroxy-3-[3-(1-methyl-1H-imidazol-2-yl)-1,2,4-oxadiazol-5-yl]hexanoate

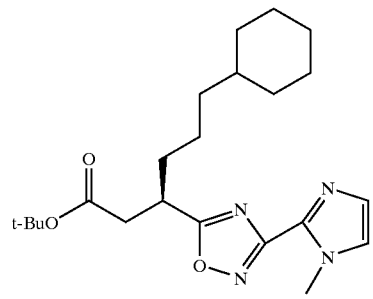

To a solution of the title compound from Preparation 175 (0.60 g, 2.0 mmol) in CH$_2$Cl$_2$ (20 ml) was added 1-hydroxybenzotriazole (0.32 g, 2.4 mmol), 1-(3-dimethylaminopropyl)-3-ethylcarbodiimide hydrochloride (0.45 g, 2.4 mmol) followed by the title compound from Preparation 7' (0.40 g, 2.2 mmol) and triethylamine (0.32 mL, 2.4 mmol). The reaction was stirred at room temperature overnight, then the solution was diluted with dichloromethane (30 mL) and washed with water (50 mL) and brine (50 mL). The organic layer was dried (Na$_2$SO$_4$) and the solvent was removed in vacuo. The residue was dissolved in xylene (10 mL) and then heated to reflux for 48 hours. The reaction mixture was cooled to room temperature, the solvent was removed in vacuo and the residue was purified by flash chromatography on silica gel (pentane/ethyl acetate 2:1 as eluant) to afford the title compound as a viscous yellow oil (0.62 g).

$^1$H NMR (400 MHz, CDCl$_3$) δ 0.77–0.92 (m, 2H), 1.08–1.34 (m, 8H), 1.39 (s, 9H), 1.56–1.92 (m, 7H), 2.66 (dd, 1H), 2.91 (dd, 1H), 3.48–3.56 (m, 1H), 4.00 (s, 3H), 7.01 (s, 1H), 7.20 (s, 1H).

LRMS (ES) 827 (2M+Na), 425 (M+Na).

Preparation 9
(3R)-6-Cyclohexyl-N-hydroxy-3-[3-(1-methyl-1H-imidazol-2-yl)-1,2,4-oxadiazol-5-yl]hexanoic acid

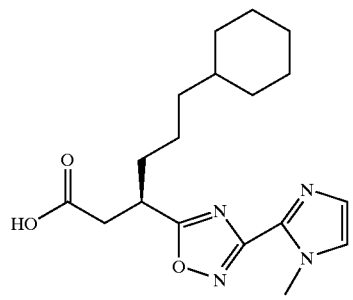

To a solution of the title compound from Preparation 8 (0.59 g, 1.5 mmol) in dichloromethane (110 mL) was added trifluoroacetic acid (5 mL) and the resulting solution was stirred at room temperature for 1 hour. The solvent was removed in vacuo, and the residue was azeotroped with toluene to give the title compound as a yellow gum (0.52 g).

$^1$H NMR (400 MHz, CDCl$_3$) δ 0.77–0.92 (m, 2H), 1.06–1.26 (m, 6H), 1.27–1.40 (m, 2H), 1.56–1.95 (m, 7H), 2.81 (dd, 1H), 2.97 (dd, 1H), 3.51–3.60 (m, 1H), 4.15 (s, 3H), 7.25 (s, 1H), 7.54 (s, 1H).

LRMS (ES) 345 (M–H).

Preparation 10
N'-Hydroxy-6-methyl-2-OXO-1,2-dihydro-3-pyridinecarboximidamide

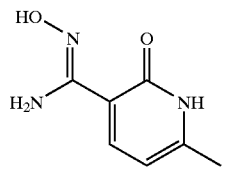

The title compound was obtained as a pale yellow solid from 2-hydroxy-3-cyano-6-methylpyridine, using a similar method to that described in Preparation 1.

$^1$H NMR (400 MHz, D$_6$-DMSO) δ 2.19 (s, 3H), 6.07 (d, 1H), 6.19 (s, 2H), 7.81 (d, 1H),

LRMS (ES) 190 (M+Na), 168 (M+H).

Preparation 11
tert-Butyl (3R)-6-Cyclohexyl-N-hydroxy-3-[3-(6-methyl-2-oxo-1,2-dihydro-3-pyridinyl)-1,2,4-oxadiazol-5-yl]hexanoate

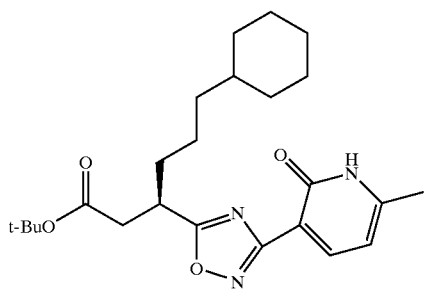

The title compound was obtained as a white foam from the title compound from Preparation 175 and the title compound from Preparation 10, using a similar method to that described in Preparation 2.

$^1$H NMR (400 MHz, CDCl$_3$) δ 0.77–0.90 (m, 2H), 1.13–1.21 (m, 6H), 1.23–1.34 (m, 2H), 1.39 (s, 9H), 1.63–1.82 (m, 7H), 2.44 (s, 3H), 2.63 (dd, 1H), 2.82 (dd, 1H), 3.47–3.54 (m, 1H), 6.20 (d, 1H), 8.25 (d, 1H).

LRMS (ES) 881 (2M+Na), 452 (M+Na).

Preparation 12
(3R)-6-Cyclohexyl-N-hydroxy-3-[3-(6-methyl-2-oxo-1,2-dihydro-3-pyridinyl)-1,2,4-oxadiazol-5-yl]hexanoic acid

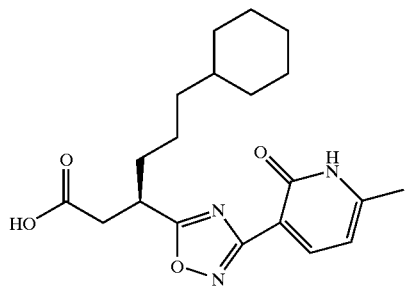

The title compound was obtained as a white solid from the title compound from Preparation 11, using a similar method to that described in Preparation 3.

Mpt 189–192° C.

$^1$H NMR (400 MHz, CDCl$_3$) δ 0.77–0.90 (m, 2H), 1.11–1.27 (m, 6H), 1.27–1.41 (m, 2H), 1.56–1.87 (m, 7H), 2.33 (s, 3H), 2.79 (dd, 1H), 2.97 (dd, 1H), 3.51–3.60 (m, 1H), 6.19 (d, 1H), 8.23 (d, 1H).

LRMS (ES) 372 (M–H).

Preparation 13
6-Oxo-1,6-dihydro-3-pyridazinecarbonitrile

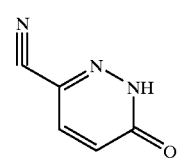

6-Oxo-1,6-dihydropyridazine-3-carboxamide (J. Chem. Soc. 1948, 2195) (1.1 g, 8.0 mmol) was suspended in dichloromethane (20 mL), cooled to 0° C. then pyridine (1.3 mL, 16 mmol) and trifluoroacetic anhydride (1.2 mL, 8.4 mmol) were added and the reaction was stirred at room temperature for 1 hour. A further 5 mL of pyridine was added to aid solubility and then the reaction was warmed to room temperature and stirred overnight. The mixture was diluted with water (100 mL) and then extracted with dichloromethane (3×100 mL). The combined organic extracts were dried (Na2SO4), the solvent was removed in vacuo, with residual pyridine removed by azeotroping with toluene. The residue was purified by flash chromatography on silica gel (dichloromethane/methanol 95:5 as eluant) to give the title compound as an off-white solid (0.8 g).

$^1$H NMR (400 MHz, CDCl$_3$) δ 7.03 (d, 1H), 7.40 (d, 1H), 11.23 (br s, 1H).

Preparation 14
N'-Hydroxy-6-oxo-1,6-dihydro-3-pyridazinecarboximidamide

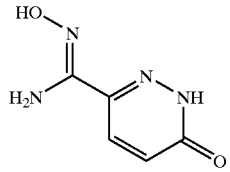

The title compound was obtained as a pale yellow solid from the title compound from Preparation 13, using a method similar to that described in Preparation 4.

$^1$H NMR (400 MHz, D$_6$-DMSO) δ 5.52 (s, 2H), 6.82 (d, 1H), 7.70 (d, 1H), 10.04 (s, 1H), 12.95 (br s, 1H).

LRMS (ES) 177 (M+Na), 155 (M+H).

Preparation 15
tert-Butyl (3R)-6-Cyclohexyl-N-hydroxy-3-[3-(6-oxo-1,6-dihydro-3-pyridazinyl)-1,2,4-oxadiazol-5-yl]hexanoate

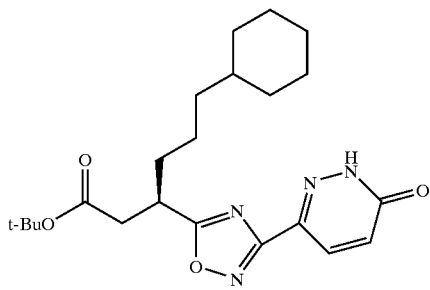

The title compound was obtained as a yellow oil from the title compound from Preparation 175 and the title compound from Preparation 14, using a method similar to that described in Preparation 2.

$^1$H NMR (400 MHz, CDCl$_3$) δ 0.80–0.92 (m, 2H), 1.12–1.57 (m, 17H), 1.58–1.92 (m, 7H), 2.69 (dd, 1H), 2.88 (dd, 1H), 3.50–3.57 (m, 1H), 7.04 (d, 1H), 7.94 (s, 1H).

LRMS (ES) 855 (2M+Na), 439 (M+Na), 417 (M+H).

Preparation 16
(3R)-6-Cyclohexyl-N-hydroxy-3-[3-(6-oxo-1,6-dihydro-3-pyridazinyl)-1,2,4-oxadiazol-5-yl]hexanoic acid

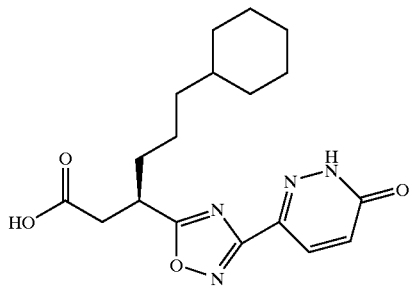

The title compound was isolated as a white solid from the title compound from Preparation 15, using a method similar to that described in Preparation 3.

Mpt 170–172° C.

$^1$H NMR (400 MHz, CDCl$_3$) δ 0.80–0.93 (m, 2H), 1.12–1.40 (m, 8H), 1.58–1.73 (m, 5H), 1.73–1.91 (m, 2H), 2.84 (dd, 1H), 3.09 (dd, 1H), 3.56–3.67 (m, 1H), 7.06 (d, 1H), 7.96 (d, 1H).

LRMS (ES) 359 (M−H).

Preparation 17
N'-Hydroxy-2-pyrimidinecarboximidamide

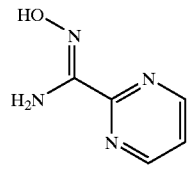

The title compound was obtained as a pale yellow solid from 2-cyanopyrimidine, using a similar method to that described in Preparation 7.

$^1$H NMR (400 MHz, D$_6$-DMSO) δ 5.71 (s, 2H), 7.46 (d, 1H), 8.80 (d, 2H), 10.03 (s, 1H),

LRMS (ES) 161 (M+Na), 139 (M+H).

Preparation 18
tert-Butyl (3R)-6-Cyclohexyl-N-hydroxy-3-[3-(2-pyrimidinyl)-1,2,4-oxadiazol-5-yl]hexanoate

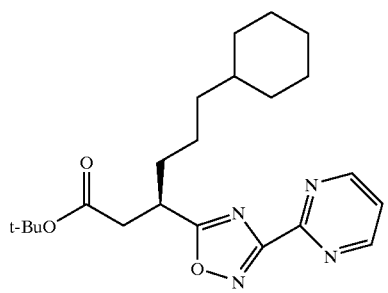

The title compound was obtained as a yellow oil from the title compound from Preparation 175 and the title compound from Preparation 17, using a similar method to that described in Preparation 5.

$^1$H NMR (400 MHz, CDCl$_3$) δ 0.76–0.91 (m, 2H), 1.05–1.44 (m, 17H), 1.55–1.69 (m, 5H), 1.70–1.81 (m, 1H), 1.81–1.97 (m, 1H), 2.70 (dd, 1H), 2.94 (dd, 1H), 3.55–3.63 (m, 1H), 7.40 (dd, 1H), 8.93 (d, 2H).

LRMS (ES) 823 (2M+Na), 423 (M+Na), 401 (M+H).

Anal. Calcd. For C$_{22}$H$_{32}$N$_4$O$_3$+0.2 CH$_2$Cl$_2$: C, 63.87; H, 7.82; N, 13.42. Found C, 64.02; H, 7.89; N, 13.30.

Preparation 19
(3R)-6-Cyclohexyl-N-hydroxy-3-[3-(2-pyrimidinyl)-1,2,4-oxadiazol-5-yl]hexanoic acid

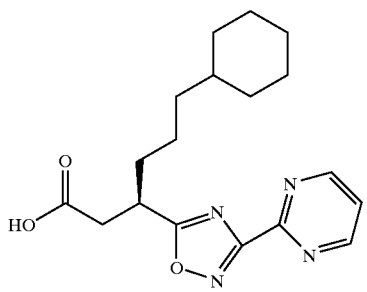

To a solution of the title compound from Preparation 18 (0.78 g, 1.95 mmol) in dichloromethane (10 mL) was added trifluoroacetic acid (2 mL) and the resulting solution was stirred at room temperature overnight. The solvent was removed in vacuo, and the residue was azeotroped with toluene give the title compound as a yellow oil (0.67 g).

¹H NMR (400 MHz, CDCl₃) δ 0.76–0.92 (m, 2H), 1.07–1.26 (m, 6H), 1.26–1.40 (m, 2H), 1.55–1.69 (m, 5H), 1.72–1.96 (m, 2H), 2.86 (dd, 1H), 3.13 (dd, 1H), 3.60–3.69 (m, 1H), 7.43 (dd, 1H), 8.97 (d, 2H).

LRMS (ES) 343 (M–H).

Preparation 20
N'-Hydroxy-5-pyrimidinecarboximidamide

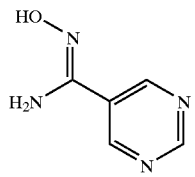

5-Cyanopyrimidine (J. Org. Chem. 1962, 27, 2264) (0.64 g, 6.1 mmol) was dissolved in methanol (20 mL), the solution was cooled to 0° C. then hydroxylamine hydrochloride (0.42 g, 6.1 mmol) and triethylamine (0.84 mL, 6.1 mmol) were added and the mixture was heated to reflux overnight. The mixture was cooled to room temperature, and the solvent was removed in vacuo. The residue was pre-absorbed onto silica gel, and purified by flash chromatography on silica gel (dichloromethane/methanol/aqueous ammonia—95:5:0.5 as eluant) to give a yellow solid which was contaminated with triethylamine hydrochloride. Recrystallisation from ethanol gave the title compound as a white solid (0.44 g).

Mpt 172–175° C.

¹H NMR (400 MHz, D₆-DMSO) δ 6.01 (s, 2H), 8.99 (s, 2H), 9.14 (s, 1H), 9.95 (s, 1H).

Anal. Calcd. For C₅H₆N₄O: C, 43.48; H, 4.38; N, 40.56. Found C, 43.46; H, 4.36; N, 40.27.

Preparation 21
tert-Butyl(3R)-6-Cyclohexyl-N-hydroxy-3-[3-(5-pyrimidinyl)-1,2,4-oxadiazol-5-yl]hexanoate

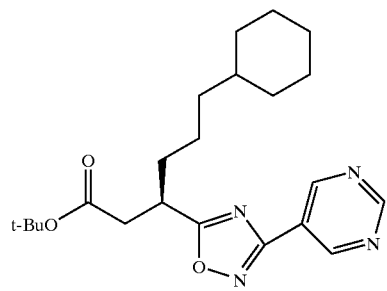

The title compound was obtained as a yellow oil from the title compound from Preparation 175 and the title compound from Preparation 20, using a similar method to that described in Preparation 5.

¹H NMR (400 MHz, CDCl₃) δ 0.78–0.91 (m, 2H), 1.10–1.46 (m, 8H), 1.39 (s, 9H), 1.58–1.88 (m, 7H), 2.70 (dd, 1H), 2.96 (dd, 1H), 3.50–3.60 (m, 1H), 9.32 (s, 1H), 9.37 (s, 2H).

LRMS (ES) 423 (M+Na), 401 (M+H).

Anal. Calcd. For C₂₂H₃₂N₄O₃: C, 65.97; H, 8.05; N, 13.99. Found C, 65.93; H, 8.11; N, 13.65.

Preparation 22
(3R)-6-Cyclohexyl-N-hydroxy-3-[3-(5-pyrimidinyl)-1,2,4-oxadiazol-5-yl]hexanoic acid

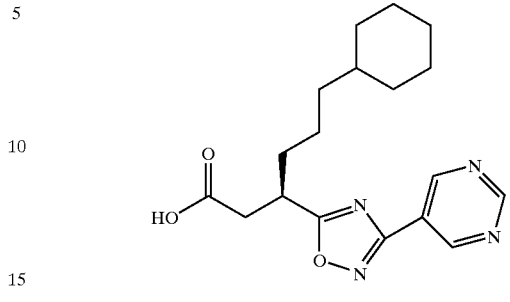

The title compound was obtained as a yellow oil from the title compound of Preparation 21, using a similar method to that described in Preparation 19. ¹H NMR (400 MHz, CDCl₃) δ 0.80–0.93 (m, 2H), 1.12–1.28 (m, 6H), 1.28–1.40 (m, 2H), 1.58–1.73 (m, 5H), 1.74–1.91 (m, 2H), 2.83 (dd, 1H), 3.04 (dd, 1H), 3.56–3.63 (m, 1H), 9.35 (s, 1H), 9.40 (s, 2H).

LRMS (ES) 343 (M–H).

Preparation 23
3-Methoxy-5-isoxazolecarbonitrile

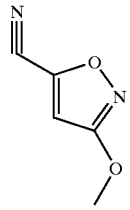

3-Methoxy-5-isoxazolecarboxamide (J. Chem Soc. 1968, 172) (1.0 g, 7.0 mmol) was dissolved in dichloromethane (20 mL), cooled to 0° C. then pyridine (1.1 mL, 14 mmol) and trifluoroacetic anhydride (1.0 mL, 7.4 mmol) were added and the reaction was stirred at 0° C. for 40 minutes. The mixture was diluted with dichloromethane (10 mL) and then washed with 5% aqueous citric acid solution (3×20 mL). The combined organic extracts were dried (Na₂SO₄), and the solvent was removed in vacuo to give the title compound as a yellow oil (0.69 g).

¹H NMR (400 MHz, CDCl₃) δ 4.04 (s, 3H), 6.51 (s, 1H).

Preparation 24
N'-Hydroxy-3-methoxy-5-isoxazolecarboximidamide

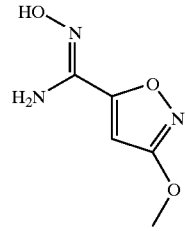

The title compound was obtained as a white solid from the title compound from Preparation 23, using a similar method to that described in Preparation 20.

Mpt 173–174° C.

¹H NMR (400 MHz, D₆-DMSO) δ 3.89 (s, 3H), 5.86 (s, 2H), 6.43 (s, 1H), 10.06 (s, 1H),

Anal. Calcd. For $C_5H_7N_3O_3$: C, 38.22; H, 4.49; N, 26.74. Found C, 38.25; H, 4.43; N, 26.41.

Preparation 25 tert-Butyl (3R)-6-Cyclohexyl-N-hydroxy-3-[3-(3-methoxy-5-isoxazolyl)-1,2,4-oxadiazol-5-yl]hexanoate

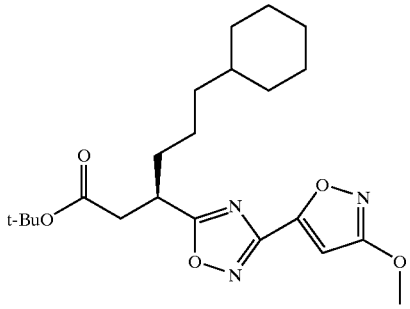

The title compound was obtained as a yellow oil from the title compound from Preparation 175 and the title compound from Preparation 24, using a similar method to that described in Preparation 5.

$^1$H NMR (400 MHz, $D_6$-DMSO) 0.73–0.86 (m, 2H), 1.04–1.28 (m, 8H), 1.29 (s, 9H), 1.50–1.65 (m, 5H), 1.65–1.76 (m, 2H), 2.76 (m, 2H), 3.44–3.63 (m, 1H), 3.97 (s, 3H), 7.02 (s, 1H).

LRMS (ES) 861 (2M+Na), 442 (M+Na).

Anal. Calcd. For $C_{22}H_{33}N_3O_5$+0.5 PhMe+0.1 $CH_2Cl_2$: C, 64.86; H, 7.91; N, 8.86. Found C, 64.73; H, 7.94; N, 8.63.

Preparation 26

(3R)-6-Cyclohexyl-N-hydroxy-3-[3-(3-methoxy-5-isoxazolyl)-1,2,4-oxadiazol-5-yl]hexanoic acid

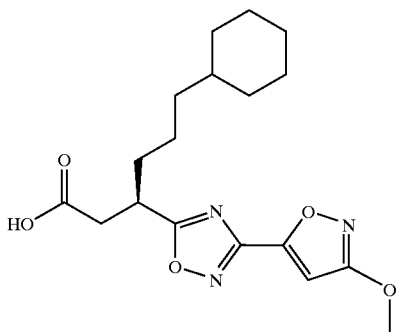

The title compound was obtained as a yellow oil from the title compound of Preparation 25, using a similar method to that described in Preparation 19.

$^1$H NMR (400 MHz, $CDCl_3$) δ 0.79–0.90 (m, 2H), 1.11–1.34 (m, 8H), 1.58–1.72 (m, 5H), 1.72–1.86 (m, 2H), 2.80 (dd, 1H), 3.01 (dd 1H), 3.52–3.61 (m, 1H), 4.04 (s, 3H), 6.55 (s, 1H).

LRMS (ES) 362 (M–H).

Anal. Calcd. For $C_{18}H_{25}N_3O_5$: C, 59.49; H, 6.93; N, 11.56. Found C, 59.08; H, 7.00; N, 11.32.

Preparation 27 tert-Butyl (3R)-3-[3-(4-Amino-1,2,5-oxadiazol-3-yl)-1,2,4-oxadiazol-5-yl]-6-cyclohexyl-N-hydroxyhexanoate

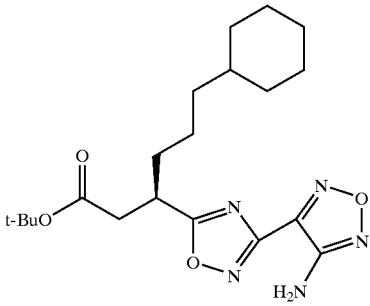

To a solution of the title compound from Preparation 175 (0.50 g, 1.7 mmol) in dichloromethane (20 mL) was added 1-hydroxybenzotriazole (0.23 g, 1.7 mmol), 1-(3-dimethylaminopropyl)-3-ethylcarbodiimide hydrochloride (0.35 g, 1.85 mmol), N-methylmorpholine (0.20 mL, 1.85 mmol) and 4-amino-N'-hydroxy-1,2,5-oxadiazole-3-carboximidamide (0.24 g, 1.7 mmol) and the reaction was stirred at room temperature for 48 hours. Water (20 mL) was added, stirring was continued for 20 minutes and then the layers were separated using a Whatman 5 micron cartridge. The organic layer was concentrated in vacuo, the residue was then dissolved in xylene (15 mL) and heated to reflux for 24 hours. The reaction was cooled and the solution was purified by flash chromatography on silica gel (graded elution of ethyl acetate/pentane 0:100 to 20:80) to give the title compound as a brown oil (0.13 g).

$^1$H NMR (400 MHz, $CDCl_3$) δ 0.79–0.93 (m, 2H), 1.11–1.37 (m, 8H), 1.40 (s, 9H), 1.58–1.91 (m, 7H), 2.71 (dd, 1H), 2.90 (dd, 1H), 3.54–3.62 (m, 1H), 5.00 (s, 2H).

LRMS (ES) 428 (M+Na), 405 (M+H).

Preparation 28

(3R)-3-[3-(4-Amino-1,2,5-oxadiazol-3-yl)-1,2,4-oxadiazol-5-yl]-6-cyclohexyl-N-hydroxyhexanoic acid

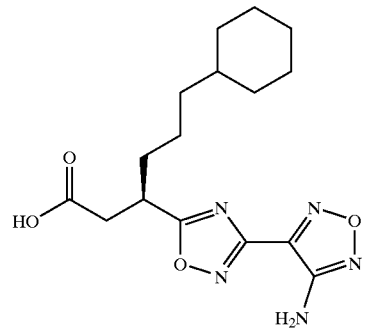

To the title compound of Preparation 27 (0.21 g, 0.5 mmol) was added hydrogen chloride in dioxane (3 mL of 4M solution) and the reaction was stirred at room temperature for 72 hours. The solvent was removed in vacuo and a further portion of hydrogen chloride in dioxane was added (3 mL of 4M solution) and stirring was continued at room temperature for 6 hours. The solvent was then removed in vacuo and the residue was dried under high vacuum to give the title compound as a yellow oil (0.19 g).

$^1$H NMR (400 MHz, $D_6$-DMSO) δ 0.75–0.87 (m, 2H), 1.02–1.31 (m, 8H), 1.51–1.66 (m, 5H), 1.66–1.89 (m, 2H), 2.79 (dd, 1H), 2.87 (dd, 1H), 3.45–3.56 (m, 1H), 6.37 (s, 2H).

LRMS (ES) 348 (M–H).

Preparation 29

Ethyl 5-[amino(hydroxyimino)methyl]nicotinate

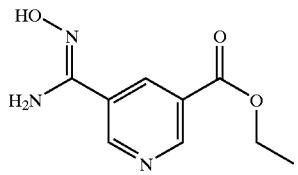

Ethyl-(5-cyano-3-pyridyl)carboxylate) (WO 96/30372) (1.8 g, 10.2 mmol) was dissolved in methanol (50 mL), the solution was cooled to 0° C. then hydroxylamine hydrochloride (0.71 g, 10.2 mmol) and triethylamine (1.4 mL, 10.2 mmol) were added and the mixture was stirred at room temperature for 72 hours. The solvent was removed in vacuo, and the residue was purified by flash chromatography on silica gel (graded elution of dichloromethane/methanol 95:5 to 93:7) to give the title compound as a white solid which contained 0.3 equivalents of triethylamine hydrochloride (2.5 g).

$^1$H NMR (400 MHz, CD$_3$OD) δ 1.40 (t, 3H), 4.42 (q, 2H), 8.59 (s, 1H), 9.00 (s, 1H), 9.10 (s, 1H).

LRMS (ES) 210 (M+H).

Preparation 30

Ethyl5-{5-[(1R)-1-(2-tert-butoxy-2-oxoethyl)-4-cyclohexylbutyl]-1,2,4-oxadiazol-3-yl}nicotinate

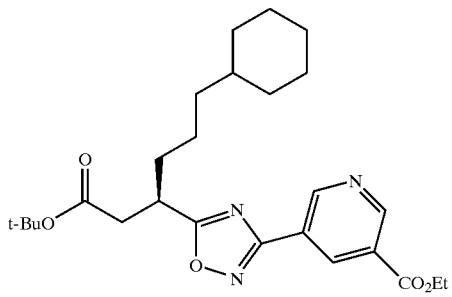

To a solution of the title compound from Preparation 175 (3.05 g, 10.2 mmol) in CH$_2$Cl$_2$ (100 mL) was added 1,1-carbonyldiimidazole (1.66 g, 10.2 mmol), and the reaction was stirred at room temperature overnight. The title compound from Preparation 29 (2.52 g, 10.2 mmol) was added and the mixture was stirred at room temperature for 72 hours. The solvent was removed in vacuo, the residue was dissolved in ethyl acetate (100 mL) and washed with water (3×100 mL). The organic layer was dried (Na2SO4) and the solvent was evaporated. The pale yellow residue was dissolved in xylene (200 mL) and the reaction was heated to reflux for 48 hours. The solvent was removed in vacuo and the residue was purified by flash chromatography on silica gel (graded elution with ethyl acetate/pentane 20:80 to 25:75) to give the title compound as a colorless oil (3.14 g).

$^1$H NMR (400 MHz, CDCl$_3$) δ 0.79–0.92 (m, 2H), 1.09–1.48 (m, 20H), 1.58–1.71 (m, 5H), 1.71–1.90 (m, 2H), 2.69 (dd, 1H), 2.87 (dd, 1H), 3.50–3.59 (m, 1H), 4.45 (q, 2H), 8.92 (s, 1H), 9.34 (s, 1H), 9.42 (s, 1H).

LRMS (ES) 494 (M+Na), 472 (M+H).

Anal. Calcd. For C$_{26}$H$_{37}$N$_3$O$_5$: C, 66.22; H, 7.91; N, 8.91. Found C, 66.17; H, 7.90; N, 8.74.

Preparation 31

(3R)-6-Cyclohexyl-3-{3-[5-(ethoxycarbonyl)-3-pyridinyl]-1,2,4-oxadiazol-5-yl}hexanoic acid

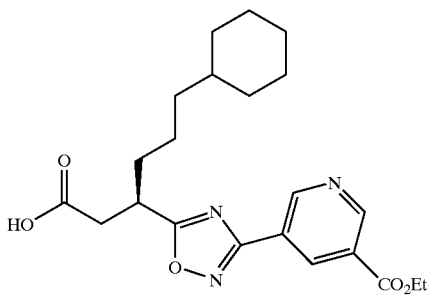

The title compound of Preparation 30 (0.70 g, 1.5 mmol) was dissolved in trifluoroacetic acid (5 mL) and the reaction was stirred at room temperature for 1.5 hours. The solvent was removed in vacuo, and the residue was azeotroped with toluene and then dichloromethane to give the title compound as a colorless oil (0.73 g).

$^1$H NMR (400 MHz, CDCl$_3$) δ 0.79–0.91 (m, 2H), 1.08–1.40 (m, 8H), 1.43 (t, 3H), 1.57–1.72 (m, 5H), 1.72–1.94 (m, 2H), 2.83 (dd, 1H), 3.07 (dd, 1H), 3.56–3.64 (m, 1H), 4.47 (q, 2H) 9.09 (s, 1H), 9.33 (s, 1H), 9.45 (s, 1H), 10.80 (br s, 1H).

LRMS (ES) 438 (M+Na), 416 (M+H).

Anal. Calcd. For C$_{22}$H$_{29}$N$_3$O$_5$+1.2 TFA: C, 53.06; H, 5.51; N, 7.61. Found C, 53.00; H, 5.61; N, 7.59.

Preparation 32 tert-Butyl (3R)-3-{3-[5-(aminocarbonyl)-3-pyridinyl]-1,2,4-oxadiazol-5-yl}-6-cyclohexylhexanoate

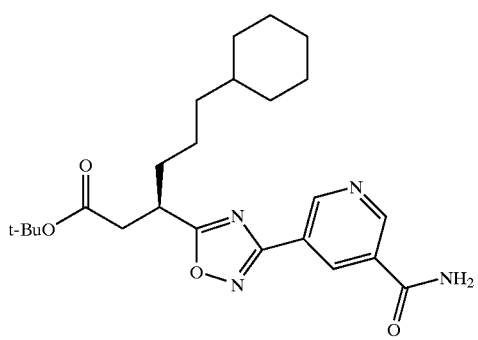

To a solution of the title compound from Preparation 30 (0.62 g, 1.3 mmol) in ethanol (2 mL) and tetrahydrofuran (2 mL) was added concentrated aqueous ammonia solution (1.5 mL) and the reaction was sealed then heated to 50° C. overnight. The solvent was removed in vacuo and the residue was purified by flash chromatography on silica gel (graded elution with ethyl acetate/hexane 50:50 to 75:25) to give the title compound as a colorless oil (0.12 g).

$^1$H NMR (400 MHz, CDCl$_3$) δ 0.80–0.90 (m, 2H), 1.08–1.44 (m, 17H), 1.57–1.71 (m, 5H), 1.71–1.89 (m, 2H), 2.68 (dd, 1H), 2.87 (dd, 1H), 3.50–3.58 (m, 1H), 6.00 (br s, 2H), 8.85 (s, 1H), 9.36 (s, 1H), 9.42 (s, 1H).

LRMS (ES) 465 (M+Na), 443 (M+H).

Anal. Calcd. For C$_{24}$H$_{134}$N$_4$O$_4$: C, 65.14; H, 7.74; N, 12.66. Found C, 65.14; H, 7.77; N, 12.61.

Preparation 33

(3R)-3-{3-[5-(Aminocarbonyl)-3-pyridinyl]-1,2,4-oxadiazol-5-yl}-6-cyclohexylhexanoic acid

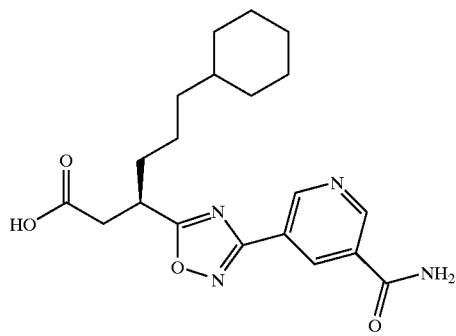

The title compound was obtained as a white foam from the title compound of Preparation 32, using a similar method to that described in Preparation 31.

$^1$H NMR (400 MHz, CDCl$_3$) δ 0.80–0.91 (m, 2H), 1.08–1.40 (m, 8H), 1.56–1.72 (m, 5H), 1.72–1.92 (m, 2H), 2.83 (dd, 1H), 3.01 (dd, 1H), 3.53–3.62 (m, 1H), 6.74 (br s, 2H), 8.84 (s, 1H), 9.16 (s, 1H), 9.35 (s, 1H).

LRMS (ES) 385 (M−H).

Anal. Calcd. For C$_{20}$H$_{26}$N$_4$O$_4$+0.8 TFA: C, 54.31; H, 5.66; N, 11.73. Found C, 54.29; H, 5.85; N, 11.50.

Preparation 34

5-{5-[(1R)-1-(2-tert-butoxy-2-oxoethyl)-4-cyclohexylbutyl]-1,2,4-oxadiazol-3-yl}nicotinic acid

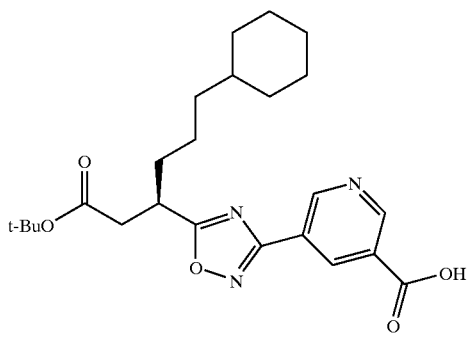

To a solution of the title compound from Preparation 30 (1.0 g, 2.1 mmol) in tetrahydrofuran (7 mL) was added lithium hydroxide (0.18 g, 0.2 mmol)) and the reaction was stirred vigorously at room temperature for 1.5 hours. The mixture was diluted with water (10 mL), acidified to pH1 with 2M aqueous hydrochloric acid and then extracted with ethyl acetate (2×100 mL). The combined organic extracts were dried (Na$_2$SO$_4$), and the solvent was removed in vacuo to give the title compound as a colorless oil which solidified on standing (0.95 g).

$^1$H NMR (400 MHz, CDCl$_3$) δ 0.80–0.92 (m, 2H), 1.08–1.44 (m, 17H), 1.57–1.73 (m, 5H), 1.73–1.91 (m, 2H), 2.71 (dd, 1H), 2.90 (dd, 1H), 3.52–3.60 (m, 1H), 9.00 (s, 1H), 9.39 (s, 1H), 9.51 (s, 1H).

LRMS (ES) 442 (M−H).

Anal. Calcd. For C$_{24}$H$_{33}$N$_3$O$_5$: C, 64.99; H, 7.50; N, 9.47. Found C, 65.00; H, 7.48; N, 9.38.

Preparation 35 tert-Butyl (3R)-6-Cyclohexyl-3-(3-{5-[(dimethylamino)carbonyl]-3-pyridinyl)-1,2,4-oxadiazol-5-yl}hexanoate

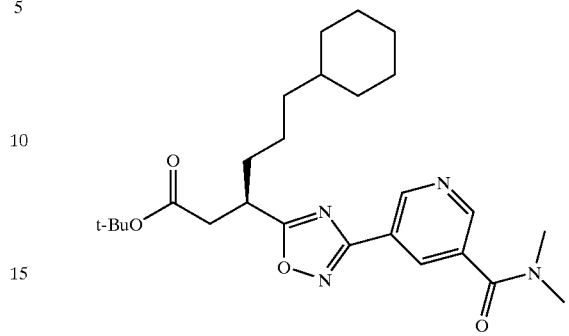

To a solution of the title compound from Preparation 34 (0.48 g, 1.1 mmol) in tetrahydrofuran (7 mL) was added 1,1-carbonyldiimidazole (0.19 g, 1.2 mmol) and the reaction was stirred at room temperature for 1 5 hours. Dimethylamine (1.9 mL of 5.6M solution in ethanol, 10.7 mmol) was added and the reaction was stirred at room temperature overnight. The solvent was removed in vacuo and the residue was purified by flash chromatography on silica gel (graded elution with ethyl acetate/pentane 50:50 to 75:25) to give the title compound as a viscous oil (0.43 g).

$^1$H NMR (400 MHz, CDCl$_3$) δ 0.78–0.87 (m, 2H), 1.08–1.42 (m, 17H), 1.57–1.83 (m, 7H), 2.68 (dd, 1H), 2.87 (dd, 1H), 3.04 (s, 3H), 3.15 (s, 3H), 3.48–3.56 (m, 1H), 8.41 (s, 1H), 8.78 (s, 1H), 9.32 (s, 1H).

LRMS (ES) 493 (M+Na), 471 (M+H).

Anal. Calcd. For C$_{26}$H$_{38}$N$_4$O$_4$+0.15 EtOAc: C, 65.94; H, 8.16; N, 11.70. Found C, 65.96; H, 8.12; N, 11.66.

Preparation 36

(3R)-6-Cyclohexyl-3-(3-{5-[(dimethylamino)carbonyl/]-3-pyridinyl}-1,2,4-oxadiazol-5-yl)hexanoic acid

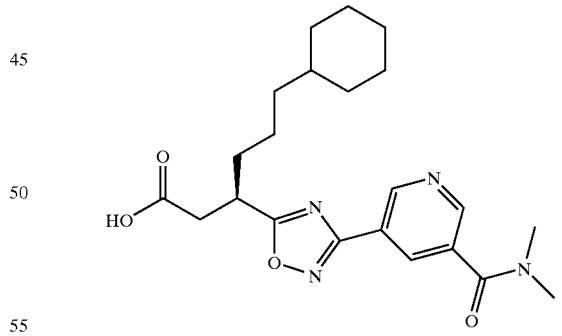

The title compound was obtained as a white foam from the title compound of Preparation 3 5, using a similar method to that described in Preparation 31.

$^1$H NMR (400 MHz, CDCl$_3$) δ 0.78–0.88 (m, 2H), 1.06–1.35 (m, 8H), 1.60–1.70 (m, 5H), 1.70–1.86 (m, 2H), 2.83 (dd, 1H), 3.05 (dd, 1H), 3.07 (s, 3H), 3.18 (s, 3H), 3.53–3.61 (m, 1H), 8.65 (s, 1H), 8.87 (s, 1H), 9.36 (s, 1H).

LRMS (ES) 413 (M−H).

Anal. Calcd. For C$_{22}$H$_{30}$N$_4$O$_4$+1.35 TFA: C, 52.19; H, 5.56; N, 9.86. Found C, 52.28; H, 5.68; N, 9.72.

Preparation 37 tert-Butyl (3R)-6-Cyclohexyl-3-(3-{5-[(methylamino)carbonyl]-3-pyridinyl}-1,2,4-oxadiazol-5-yl)hexanoate

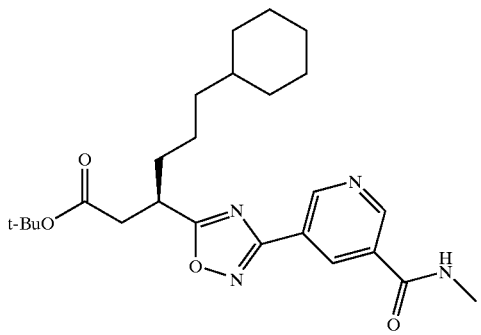

The title compound was obtained as a viscous oil from the title compound from Preparation 34 and methylamine in THF (2M solution), using a similar method to that described in Preparation 35.

$^1$H NMR (400 MHz, CDCl$_3$) δ 0.78–0.85 (m, 2H), 1.04–1.41 (m, 17H), 1.58–1.84 (m, 7H), 2.69 (dd, 1H), 2.88 (dd, 1H), 3.05 (s, 3H), 3.48–3.56 (m, 1H), 6.36 (br s, 1H), 8.67 (s, 1H), 9.11 (s, 1H), 9.38 (s, 1H).

LRMS (ES) 479 (M+Na), 457 (M+H).

Anal. Calcd. For C$_{25}$H$_{36}$N$_4$O$_4$+0.25 EtOAc: C, 65.25; H, 8.00; N, 11.71. Found C, 65.11; H, 8.02; N, 11.79.

Preparation 38

(3R)-6-Cyclohexyl-3-(3-{5-[(methylamino)carbonyl]-3-pyridinyl}-1,2,4-oxadiazol-5-yl)hexanoic acid

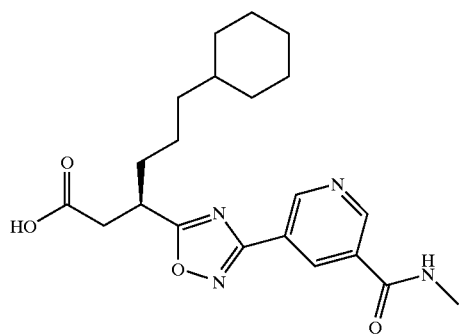

The title compound was obtained as a sticky gum from the title compound of Preparation 37, using a similar method to that described in Preparation 31.

$^1$H NMR (400 MHz, CDCl$_3$) δ 0.78–0.88 (m, 2H), 1.09–1.35 (m, 8H), 1.58–1.70 (m, 5H), 1.70–1.84 (m, 2H), 2.84 (dd, 1H), 3.02 (dd, 1H), 3.08 (d, 3H), 3.50–3.60 (m, 1H), 9.00 (s, 1H), 9.23 (s, 1H), 9.31 (s, 1H).

LRMS (ES) 399 (M−H).

Anal. Calcd. For C$_{21}$H$_{28}$N$_4$O$_4$+1.4 TFA+0.4 PhMe: C, 53.52; H, 5.5650 N, 9.39. Found C, 53.65; H, 5.66; N, 9.74.

Preparation 39

Ethyl 2-[Amino(hydroxyimino)methyl]isonicotinate

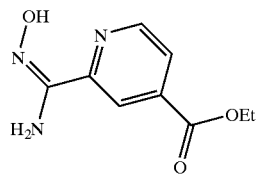

The title compound was obtained as a pale yellow solid from ethyl-2-cyanoisonicotinate (Heterocycles 1987, 26, 731) using a similar method to that described in Preparation 4.

$^1$H NMR (400 MHz, D$_6$-DMSO) δ 1.28 (t, 3H), 4.34 (q, 2H), 5.87 (s, 2H), 7.78 (d, 1H), 8.25 (s, 1H), 8.70 (d, 1H), 10.03 (s, 1H).

LRMS (ES) 210 (M+H).

Preparation 40

Ethyl 2-{5-[(1R)-1-(2-tert-butoxy-2-oxoethyl)-4-cyclohexylbutyl]-1,2,4-oxadiazol-3-yl}isonicotinate

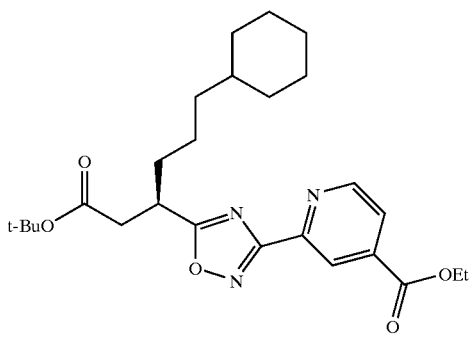

The title compound was obtained as a colorless oil from the title compound from Preparation 175 and the amidoxime from Preparation 39; using a similar method to that described in Preparation 30.

$^1$H NMR (400 MHz, CDCl$_3$) δ 0.80–0.92 (m, 2H), 1.08–1.48 (m, 20H), 1.57–1.71 (m, 5H), 1.71–1.94 (m, 2H), 2.69 (dd, 1H), 2.92 (dd, 1H), 3.53–3.61 (m, 1H), 4.46 (q, 2H), 7.95 (d, 1H), 8.64 (s, 1H), 9.92 (d, 1H).

LRMS (ES) 494 (M+Na), 472 (M+H).

Anal. Calcd. For C$_{26}$H$_{37}$N$_3$O$_5$+0.2 EtOAc: C, 65.80; H, 7.95; N, 8.59. Found C, 65.81; H, 7.89; N, 8.68.

Preparation 41 tert-Butyl (3R)-3-{3-[4-(aminocarbonyl)-2-pyridinyl]-1,2,4-oxadiazol-5-yl}-6-cyclohexylhexanoate

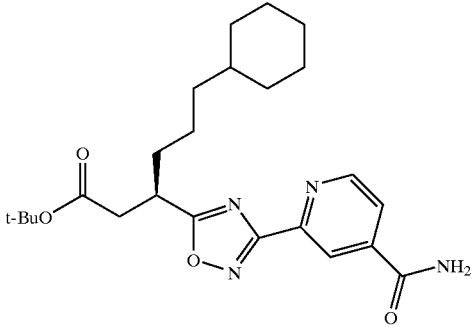

To a solution of the title compound from Preparation 40 (0.60 g, 1.3 mmol) in ethanol (3 mL) was added a saturated solution of ammonia in ethanol (15 mL) and the reaction was stirred at room temperature for 1.5 hours. Ammonia gas was bubbled through the reaction mixture for 30 minutes and then the reaction was stirred at room temperature for 48 hours. More ammonia gas was bubbled through the reaction mixture and the reaction was stirred at room temperature for 24 hours. The reaction mixture at this stage contained predominantly starting material. Concentrated aqueous ammonia solution (1 mL) was added, the reaction system was sealed and stirred at room temperature for 72 hours. The solvent was removed in vacuo and the residue was purified by flash chromatography on silica gel (graded elution with ethyl acetate/hexane 50:50 to 75:25) to give the title compound as a colorless oil (0.10 g).

$^1$H NMR (400 MHz, CDCl$_3$) δ 0.79–0.92 (m, 2H), 1.10–1.50 (m, 17H), 1.57–1.70 (m, 5H), 1.70–1.92 (m, 2H), 2.71 (dd, 1H), 2.92 (dd, 1H), 3.51–3.60 (m, 1H), 7.80 (d, 1H), 8.39 (s, 1H), 8.92 (d, 1H).

LRMS (ES) 465 (M+Na).

Anal. Calcd. For C$_{24}$H$_{34}$N$_4$O$_4$+0.15 EtOAc: C, 64.83; H, 7.78; N, 12.29. Found C, 64.68; H, 7.83; N, 12.44.

Preparation 42
(3R)-3-{3-[4-(Aminocarbonyl)-2-pyridinyl]-1,2,4-oxadiazol-5-yl}-6-cyclohexylhexanoic acid

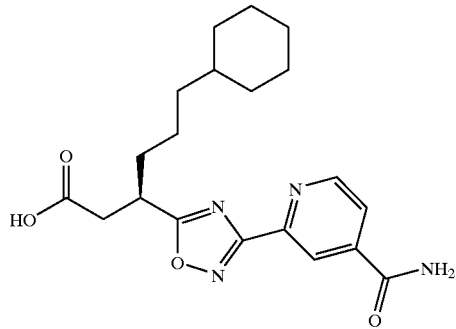

The title compound was obtained as a white solid from the title compound of Preparation 41, using a similar method to that described in Preparation 31.

$^1$H NMR (400 MHz, CD$_3$OD) δ 0.79–0.91 (m, 2H), 1.08–1.40 (m, 8H), 1.58–1.70 (m, 5H), 1.76–1.86 (m, 2H), 2.82 (dd, 1H), 2.97 (dd, 1H), 3.55–3.62 (m, 1H), 7.91 (d, 1H), 8.53 (s, 1H), 8.82 (d, 1H).

LRMS (ES) 385 (M–H).

Anal. Calcd. For C$_{20}$H$_{26}$N$_4$O$_4$+0.1 TFA: C, 60.98; H, 6.61; N, 14.08. Found C, 60.94; H, 6.67; N, 14.09.

Preparation 43
tert-Butyl (3R)-6-Cyclohexyl-3-(3-{4-[(methylamino)carbonyl]-2-pyridinyl}-1,2,4-oxadiazol-5-yl)hexanoate

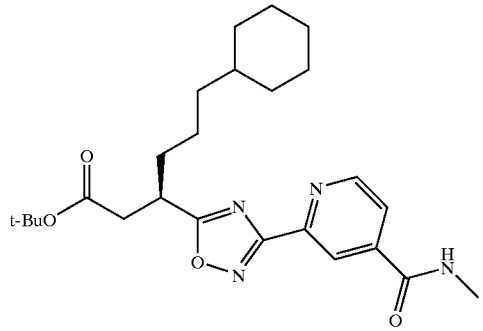

To a solution of the title compound from Preparation 40 (0.50 g, 1.1 mmol) in ethanol (10 mL) was added methylamine (2.7 mL of 2M in tetrahydrofuran, 5.4 mmol)) and the reaction was stirred at room temperature for 72 hours. The reaction was then heated to 45° C. for 24 hours. The solvent was removed in vacuo and the residue was purified by flash chromatography on silica gel (graded elution with ethyl acetate/hexane 50:50 to 75:25) to give the title compound as a colorless oil (0.18 g).

$^1$H NMR (400 MHz, CDCl$_3$) δ 0.80–0.92 (m, 2H), 1.12–1.46 (m, 17H), 1.58–1.71 (m, 5H), 1.71–1.92 (m, 2H), 2.70 (dd, 1H), 2.91 (dd, 1H), 3.07 (d, 3H), 3.52–3.60 (m, 1H), 6.23 (br s, 1H), 7.78 (d, 1H), 8.34 (s, 1H), 8.90 (d, 1H).

LRMS (ES) 479 (M+Na), 457 (M+H).

Anal. Calcd. For C$_{25}$H$_{36}$N$_4$O$_4$+0.15 EtOAc: C, 65.45; H, 7.98; N, 11.93. Found C, 65.24; H, 8.01; N, 12.13.

Preparation 44
(3R)-6-Cyclohexyl-3-(3-{4-[(methylamino)carbonyl]-2-pyridinyl}-1,2,4-oxadiazol-5-yl)hexanoic acid

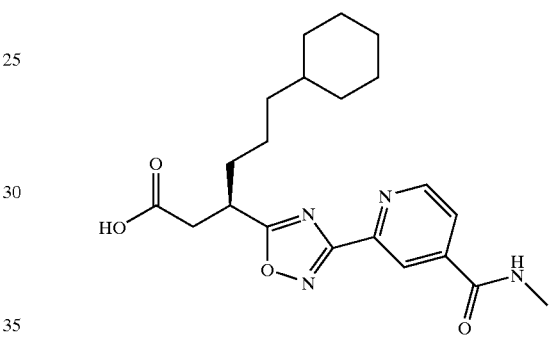

The title compound was obtained as a colorless gum from the title compound of Preparation 43, using a similar method to that described in Preparation 31.

$^1$HNMR (400 MHz, CDCl$_3$) δ 60.78–0.90 (m, 2H), 1.09–1.38 (m, 8H), 1.55–1.70 (m, 5H), 1.70–1.91 (m, 2H), 2.84 (dd, 1H), 3.00–3.11 (m, 4H), 3.53–3.63 (m, 1H), 6.64 (br s, 1H), 7.82 (s, 1H), 8.35 (s, 1H), 8.88 (d, 1H).

LRMS (ES) 399 (M–H).

Anal. Calcd. For C$_{21}$H$_{28}$N$_4$O$_4$+0.95 TFA +0.1H$_2$O: C, 53.87; H, 5.75; N, 10.97. Found C, 54.18; H, 5.83; N, 10.58.

Preparation 45
tert-Butyl (3R)-6-Cyclohexyl-3-(3-{4-[(dimethylamino)carbonyl]-2-pyridinyl}-1,2,4-oxadiazol-5-yl)hexanoate

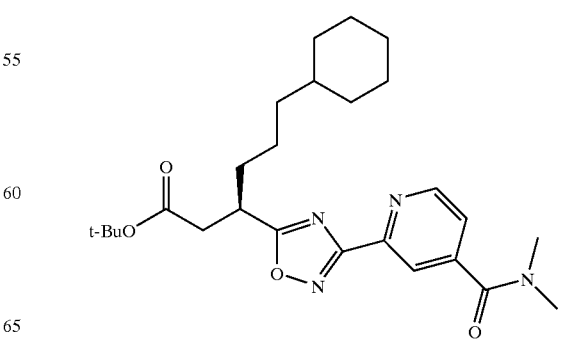

To a solution of the title compound from Preparation 40 (0.50 g, 1.1 mmol) in tetrahydrofuran (4 mL) was added dimethylamine (2.0 mL of 5.6M in ethanol, 10.6 mmol)). The reaction flask was sealed and the reaction was stirred at 60° C. for 48 hours. The solvent was removed in vacuo and the residue was purified by flash chromatography on silica gel (graded elution with ethyl acetate/hexane 50:50 to 75:25 to 100% ethyl acetate) to give the title compound as a colorless oil (0.14 g).

¹H NMR (400 MHz, CDCl₃) δ 0.79–0.90 (m, 2H), 1.08–1.40 (m, 17H), 1.48–1.92 (m, 7H), 2.68 (dd, 1H), 2.89 (dd, 1H), 2.95 (s, 3H), 3.12 (s, 3H), 3.52–3.60 (m, 1H), 7.38 (s, 1H), 8.10 (s, 1H), 8.84 (s, 1H).

LRMS (ES) 493 (M+Na), 471 (M+H).

Anal. Calcd. For C₂₆H₃₈N₄O₄+0.15H₂O: C, 65.98; H, 8.16; N, 11.84. Found C, 65.89; H, 8.14; N, 11.75.

Preparation 46
(3R)-6-Cyclohexyl-3-(3-{4-[(dimethylamino)carbonyl]-2-pyridinyl}-1,2,4-oxadiazol-5-yl)hexanoic acid

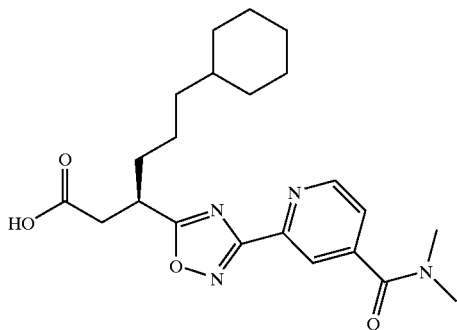

The title compound was obtained as a pale yellow oil from the title compound of Preparation 45, using a similar method to that described in Preparation 31.

¹H NMR (400 MHz, CDCl₃) δ 0.79–0.90 (m, 2H), 1.09–1.38 (m, 8H), 1.56–1.72 (m, 1H), 1.72–1.91 (m, 2H), 2.82 (dd, 1H), 2.94–3.17 (m, 7H), 3.55–3.64 (m, 1H), 7.45 (s, 1H), 8.14 (s, 1H), 8.87 (d, 1H).

LRMS (ES) 413 (M–H).

nal. Calcd. For C₂₂H₃₀N₄O₄+1.0 TFA: C, 54.54; 11, 5.9 1; N, 10.60. Found C, 54.62; H, 6.23; N, 10.45.

Preparation 47
tert-Butyl (3R)-6-Cyclohexyl-3-[3-(2-pyridinyl)-1,2,4-oxadiazol-5-yl]hexanoate

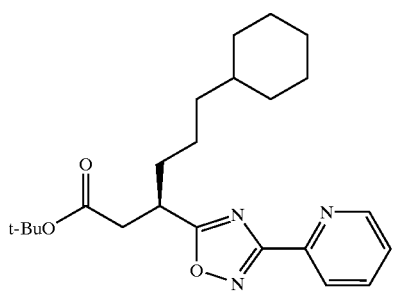

To a solution of the title compound from Preparation 175 (0.30 g, 1.0 mmol) in dichloromethane (15 mL) was added 1,1-carbonyldiimidazole (0.16 g, 1.0 mmol)). The reaction was stirred at room temperature for 2 hours then N-hydroxy-2-pyridinecarboximidamide (0.14 g, 1.0 mmol) was added and the reaction was stirred at room temperature overnight. The solvent was removed in vacuo and the residue was heated at 120° C. for 2 hours. The residue was then purified by flash chromatography on silica gel (dichloromethane/methanol/aqueous ammonia solution 99:1:0.1 as eluant) to give the title compound as a colorless oil (0.25 g).

¹H NMR (400 MHz, CDCl₃) δ 0.78–0.90 (m, 2H), 1.07–1.40 (m, 17H), 1.60–1.70(m, 5H), 1.70–1.94 (m, 2H), 2.70 (dd, 1H), 2.94 (dd, 1H), 3.50–3.60 (m, 1H), 7.38–7.44 (m, 1H), 7.80–7.86 (m, 1H), 8.14 (d, 1H), 8.80 (d, 1H).

LRMS (ES) 422 (M+Na), 400 (M+H).

Preparation 48
(3R)-6-Cyclohexyl-3-[3-(2-pyridinyl)-1,2,4-oxadiazol-5-yl] hexanoic acid

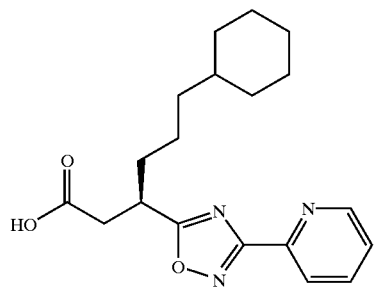

The title compound was obtained as a pale brown oil from the title compound of Preparation 45, using a similar method to that described in Preparation 31.

¹H NMR (400 MHz, CDCl₃) δ 0.76–0.93 (m, 2H), 1.06–1.37 (m, 8H), 1.56–1.71 (m, 5H), 1.71–1.94 (m, 2H), 2.93 (dd, 1H), 3.12 (dd, 1H), 3.55–3.65 (m, 1H), 7.46–7.55 (m, 1H), 7.90–7.96 (m, 1H), 8.18 (d, 1H), 8.83 (d, 1H).

LRMS (TSP) 366 (M+Na), 344 (M+H).

Preparation 49
tert-Butyl (3R)-6-cyclohexyl-3-[3-(3-pyridinyl)-1,2,4-oxadiazol-5-yl]hexanoate

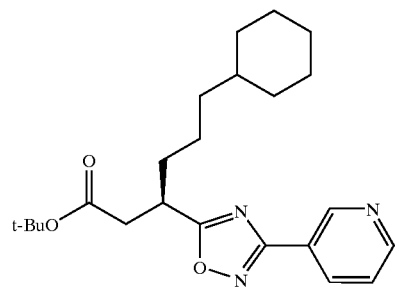

To a solution of the title compound from Preparation 175 (1.0 g, 3.3 mmol) in dichloromethane (30 mL) was added 1-(3-dimethylaminopropyl)-3-ethylcarbodiimide hydrochloride (0.65 g, 3.3 mmol), 4-dimethylamino pyridine (0.07 g, 0.6 mmol), and N'-hydroxy-3-pyridinecarboximidamide (0.45 g, 1.0 mmol) and the reaction was stirred at room temperature overnight. The solvent was removed in vacuo and the residue was heated at 120° C. for 8 hours. The residue was then purified by flash chromatography on silica gel (dichloromethane/methanol 95:5 as eluant) to give the title compound as a colorless oil (1.07 g).

¹H NMR (300 MHz, CDCl₃) δ 0.77–0.93 (m, 2H), 1.08–1.44 (m, 17H), 1.57–1.88 (m, 7H), 2.70 (dd, 1H), 2.87 (dd, 1H), 3.48–3.59 (m, 1H), 7.41 (dd, 1H), 8.30–8.38 (m, 1H), 8.69–8.75 (m, 1H), 9.30 (s, 1H).

LRMS (TSP) 422 (M+Na), 400 (M+H).

Preparation 50

(3R)-6-Cyclohexyl-3-[3-(3-pyridinyl)-1,2,4-oxadiazol-5-yl]hexanoic acid

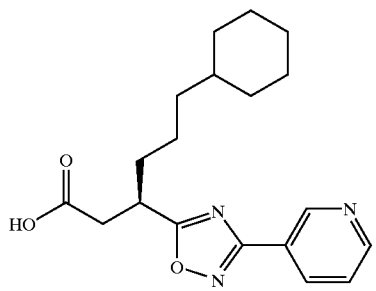

The title compound was obtained as an off-white solid from the title compound of Preparation 49, using a similar method to that described in Preparation 31.

$^1$H NMR (300 MHz, CDCl$_3$) δ 0.79–0.93 (m, 2H), 1.06–1.40 (m, 8H), 1.59–1.74 (m, 5H), 1.74–1.89 (m, 2H), 2.84 (dd, 1H), 3.07 (dd, 1H), 3.55–3.65 (m, 1H), 7.79 (dd, 1H), 8.75 (d, 1H), 8.91 (d, 1H), 9.40 (s, 1H).

LRMS (TSP) 366 (M+Na), 344 (M+H).

Preparation 51 tert-Butyl (3R)-6-Cyclohexyl-3-[3-(4-pyridinyl)-1,2,4-oxadiazol-5-yl]hexanoate

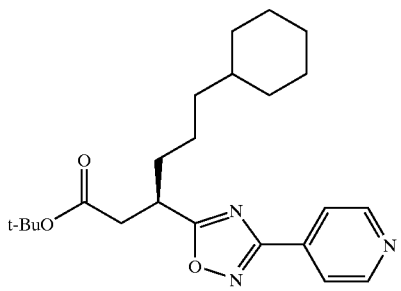

The title compound was obtained as a colorless oil from the title compound of Preparation 175 and N'-hydroxy-4-pyridinecarboximidamide, using a similar method to that described in Preparation 47.

$^1$H NMR (400 MHz, CDCl$_3$) δ 0.79–0.90 (m, 2H), 1.08–1.41 (m, 17H), 1.56–1.87 (m, 7H), 2.70 (dd, 1H), 2.87 (dd, 1H), 3.50–3.58 (m, 1H), 7.94 (d, 2H), 8.79 (d, 2H).

LRMS (TSP) 422 (M+Na), 400 (M+H).

Preparation 52

(3R)-6-Cyclohexyl-3-[3-(4-pyridinyl)-1,2,4-oxadiazol-5-yl]hexanoic acid

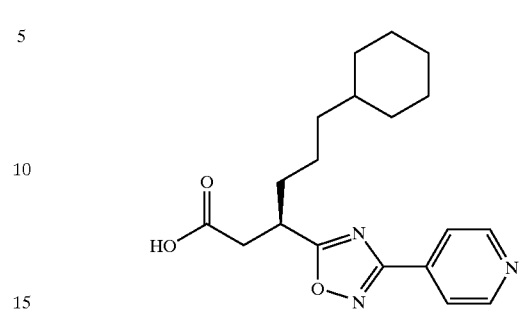

The title compound was obtained as a white solid from the title compound of Preparation 51, using a similar method to that described in Preparation 68.

$^1$H NMR (300 MHz, CDCl$_3$) δ 0.78–0.93 (m, 2H), 1.06–1.40 (m, 8H), 1.60–1.75 (m, 5H), 1.75–1.90 (m, 2H), 2.87 (dd, 1H), 3.06 (dd, 1H), 3.55–3.65 (m, 1H), 8.30 (d, 2H), 8.91 (d, 2H).

LRMS (TSP) 366 (M+Na), 344 (M+H).

Preparation 53

N'-Hydroxy-6-methyl-3-pyridinecarboximidamide

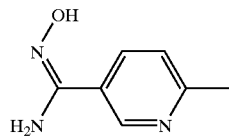

The title compound was obtained as a white solid from 2-methyl-4-cyanopyridine, using a similar method to that described in Preparation 31.

$^1$H NMR (300 MHz, CD$_3$OD) δ 2.55 (s, 3H), 4.85 (s, 2H), 7.32 (d, 1H), 7.95 (d, 1H), 8.66 (s, 1H).

Preparation 54 tert-Butyl (3R)-6-Cyclohexyl-3-[3-(6-methyl-3-pyridinyl)-1,2,4-oxadiazol-5-yl]hexanoate

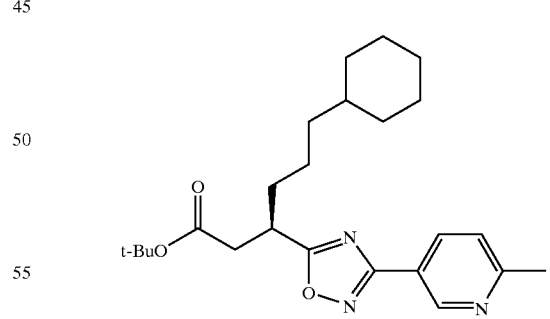

The title compound was obtained as a colorless oil from the title compound of Preparation 175 and the amidoxime from Preparation 53, using a similar method to that described in Preparation 47.

$^1$H NMR (400 MHz, CDCl$_3$) δ 0.75–0.90 (m, 2H), 1.03–1.41 (m, 17H), 1.58–1.84 (m, 7H), 2.61 (s, 3H), 2.67 (dd, 1H), 2.88 (dd, 1H), 3.47–3.57 (m, 1H), 7.23 (s, 1H), 8.21 (d, 1H), 9.17 (s, 1H).

LRMS (ES) 436 (M+Na), 414 (M+H).

Preparation 55
(3R)-6-Cyclohexyl-3-[3-(6-methyl-3-pyridinyl)-1,2,4-oxadiazo/-5-yl]hexanoic acid

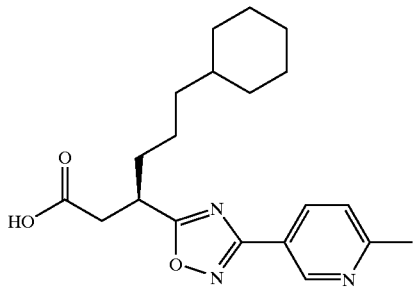

The title compound was obtained as a colorless oil from the title compound of Preparation 55, using a similar method to that described in Preparation 31. The residue was purified by flash chromatography on silica gel (graded elution of dichloromethane/methanol 98:2 to 95:5).

$^1$H NMR (300 MHz, CDCl$_3$) δ 0.78–0.92 (m, 2H), 1.08–1.39 (m, 8H), 1.59–1.74 (m, 5H), 1.74–1.90 (m, 2H), 2.70 (s, 3H), 2.81 (dd, 1H), 3.05 (dd, 1H), 3.52–3.62 (m, 1H), 7.42 (d, 1H), 8.43 (s, 1H), 9.21 (s, 1H).

LRMS (ES) 358 (M+H).

Preparation 56
N-(5-Cyano-2-pyridinyl)-2,2,2-trifluoroacetamide

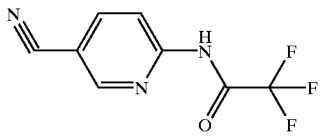

To a solution of 6-aminonicotinonitrile (2.0 g, 15 mmol) and pyridine (4.7 mL, 58 mmol) in tetrahydrofuran (80 mL) at 0° C. was added trifluoroacetic anhydride (4.5 mL, 32 mmol) slowly, ensuring internal temperature did not exceed 5° C. Once addition was complete the reaction was warmed to room temperature and stirred overnight. The solvent was removed in vacuo, the residue was then dissolved in ethyl acetate (100 mL) and washed with water (50 mL) then dried (MgSO$_4$). The solvent was removed in vacuo and the residue was purified by flash chromatography on silica gel (ethyl acetate/hexane 1:1 as eluant) to give the title compound as a white solid (2.7 g).

$^1$H NMR (400 MHz, CDCl$_3$) δ 8.02 (d, 1H), 8.30 (d, 1H), 8.53–8.75 (m, 2H).

Preparation 57
6-Amino-N'-hydroxy-3-pyridinecarboximidamide

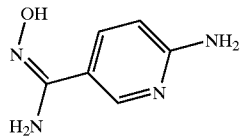

The title compound was obtained as a white solid from the title compound of Preparation 56, using a similar method to that described in Preparation 4.

$^1$H NMR (400 MHz, CD$_3$OD) δ 6.55 (d, 1H), 7.67 (dd, 1H), 8.18 (d, 1H).

LRMS (ES) 153 (M+M).

Preparation 58
tert-Butyl (3R)-3-[3-(6-Amino-3-pyridinyl)-1,2,4-oxadiazol-5-yl]-6-cyclohexyl hexanoate

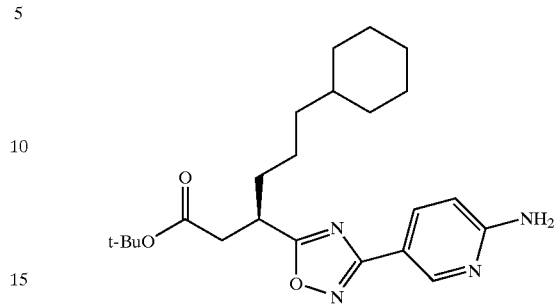

The title compound was obtained as a yellow oil from the title compound of Preparation 175 and the amidoxime from Preparation 57, using a similar method to that described in Preparation 47.

$^1$H NMR (400 MHz, CDCl$_3$) δ 0.80–0.91 (m, 2H), 1.10–1.45 (m, 17H), 1.55–1.87 (m, 7H), 2.64 (dd, 1H), 2.83 (dd, 1H), 3.45–3.52 (m, 1H), 4.71 (s, 2H), 6.52 (d, 1H), 8.07 (d, 1H), 8.86 (s, 1H).

LRMS (ES) 415 (M+H).

Preparation 59
(3R)-3-[3-(6-Amino-3-pyridinyl)-1,2,4-oxadiazol-5-yl]-6-cyclohexylhexanoic acid

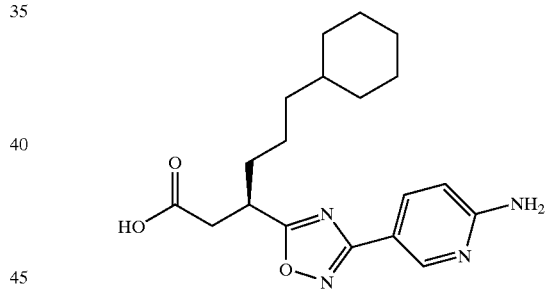

The title compound from Preparation 58 was dissolved in trifluoroacetic acid (5 mL) and the reaction was stirred at room temperature for 2 hours. The solution was evaporated to dryness and then the residue was azeotroped with toluene. The residue was dissolved in ethyl acetate (20 mL) and extracted with saturated sodium bicarbonate solution (20 mL). The organic layer was discarded and the aqueous layer was acidified to pH 5 with 10% citric acid solution and then extracted with ethyl acetate (2×50 mL). The combined organic extracts were washed with 10% citric acid solution (20 mL), water (20 mL) and then dried (MgSO$_4$). The solvent was removed in vacuo to give the title compound as a white solid (0.22 g).

$^1$H NMR (300 MHz, CD$_3$OD) δ 0.81–0.90 (m, 2H), 1.10–1.38 (m, 8H), 1.59–1.72 (m, 5H), 1.72–1.81 (m, 2H), 2.77 (dd, 1H), 2.90 (dd, 1H), 3.46–3.56 (m, 1H), 4.50 (br s, 2H), 6.64 (d, 1H), 8.00 (d, 1H), 8.55 (s, 1H).

LRMS (ES) 359 (M+H).

Preparation 60
2-(Dimethylamino)-N'-hydroxy-4-pyridinecarboximidamide

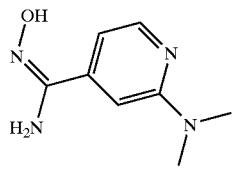

To a solution of hydroxylamine hydrochloride (0.47 g, 7.0 mmol) in methanol (10 mL) was added sodium metal (0.16 g, 7.0 mmol) portionwise. After all the sodium metal had dissolved 4-cyano-2-dimethylaminopyridine (1.0 g, 7.0 mmol) was added and the reaction was heated to reflux for 4 hours. The reaction was cooled to room temperature, filtered to remove precipitated sodium chloride and the filtrate was evaporated to dryness. The residue was dissolved in ethanol in order to crystallise the product but this was unsuccessful, so the solvent was removed in vacuo to give the title compound as a white solid (1.7 g), which was contaminated with ethanol.

$^1$H NMR (300 MHz, CDCl$_3$) δ 3.10 (s, 6H), 4.50–5.00 (br s, 3H), 6.65–6.73 (m, 2H), 8.16 (s, 1H).
LRMS (ES) 181 (M+H).

Preparation 61
tert-Butyl (3R)-6-Cyclohexyl-3-{3-[2-(dimethylamino)-4-pyridinyl]-1,2,4-oxadiazol-5-yl}hexanoate

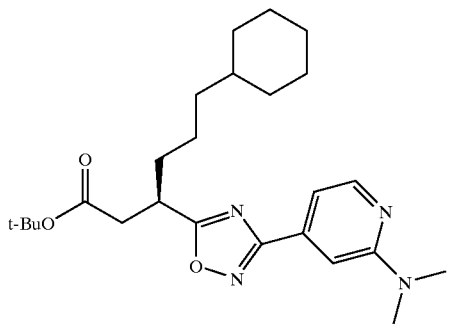

To a solution of the title compound from Preparation 175 (1.0 g, 3.3 mmol) in dichloromethane (30 mL) was added 1-(3-dimethylaminopropyl)-3-ethylcarbodiimide hydrochloride (0.65 g, 3.3 mmol), 4-dimethylamino pyridine (0.04 g, 0.3 mmol), and the amidoxime from Preparation 60' (0.61 g, 3.3 mmol. Dimethylfoirmamide (1 mL) was added to aid solubility and the reaction was stirred at room temperature overnight. The solution was washed with water (2×25 mL), saturated sodium bicarbonate solution (25 mL) and brine (30 mL). The organic layer was dried (MgSO4), the solvent was removed in vacuo and the residue was heated at 120° C. for 2 hours. The residue was cooled to room temperature and then purified by flash chromatography on silica gel (dichloromethane/methanol/aqueous ammonia solution 98:2:0.2 as eluant) to give the title compound as a brown oil (0.50 g).

$^1$H NMR (300 MHz, CDCl$_3$) δ 0.72–0.86 (m, 2H), 1.00–1.43 (m, 17H), 1.52–1.88 (m, 7H), 2.65 (dd, 1H), 2.83 (dd, 1H), 3.12 (s, 6H), 3.43–3.55 (m, 1H), 7.10–7.14 (m, 2H), 8.22 (d, 1H).
LRMS (TSP) 443 (M+H).

Preparation 62
(3R)-6-Cyclohexyl-3-{3-[2-(dimethylamino)-4-pyridinyl]-1,2,4-oxadiazol-5-yl}hexanoic acid

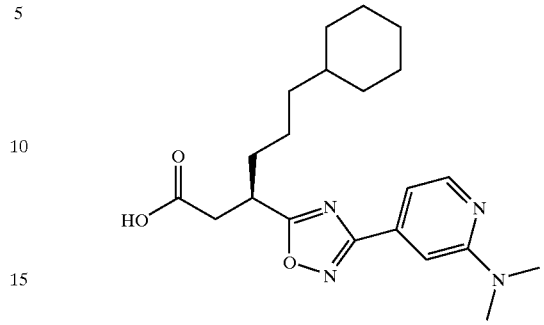

The title compound was obtained as a colorless oil from the title compound of Preparation 6 1, using a similar method to that described in Preparation 31.

$^1$H NMR (300 MHz, CDCl$_3$) δ 0.77–0.86 (m, 2H), 1.02–1.46 (m, 8H), 1.53–1.91 (m, 7H), 2.82 (dd, 1H), 3.01 (dd, 1H), 3.38 (s, 6H), 3.50–3.60 (m, 1H), 7.47 (d, 1H), 7.58 (s, 1H), 8.10 (d, 1H).

Preparation 63
(3R)-6-Cyclohexyl-3-{3-[4-(ethoxycarbonyl)-2-pyridinyl]-1,2,4-oxadiazol-5-yl}hexanoic acid

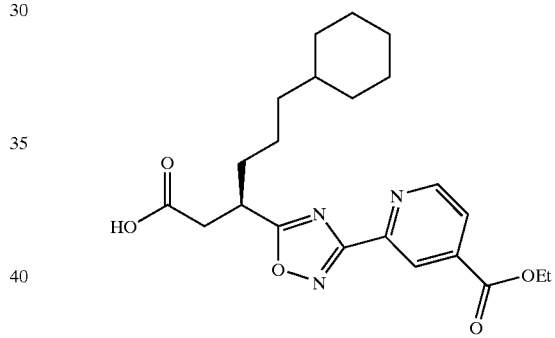

The title compound was obtained as a pale yellow oil from the title compound of Preparation 40, using a similar method to that described in Preparation 31.

$^1$H NMR (400 MHz, CDCl$_3$) δ 0.74–0.87 (m, 2H), 1.04–1.38 (m, 8H), 1.41 (t, 3H), 1.55–1.70 (m, 5H), 1.70–1.91 (m, 2H), 2.83 (dd, 1H), 3.06 (dd, 1H), 3.53–3.62 (m, 1H), 4.43 (q, 2H), 8.04 (d, 1H), 8.67 (s, 1H), 8.90 (d, 1H).
LRMS (TSP) 416 (M+H).

Preparation 64
Dimethyl 2-(5-Cyano-2-pyridinyl)malonate

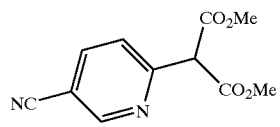

Dimethylmalonate (1.4 mL, 11.9 mmol) was added to a suspension of sodium hydride (0.48 g of a 60% dispersion in mineral oil, 11.9 mmol) in dimethylformamide (50 mL) at 0° C. The reaction was stirred at 0° C. for 1.5 hours, then 2-chloro-5-cyanopyridine (1.5 g, 10.8 mmol) was added and the reaction was stirred at room temperature for 1 hour and then heated to 100° C. for 3 hours. The reaction was cooled to room temperature, the solvent was removed in vacuo and the residue was purified by flash chromatography on silica gel (diethyl ether as eluant) to give the title compound as a colorless oil (1.1 g).

¹H NMR (300 MHz, CDCl₃) δ 3.78 (s, 6H), 5.02 (s, 1H), 7.67 (d, 1H), 7.98(dd, 1H), 8.82 (d, 1H).

LRMS (ES)491 (2M+Na), 257 (M+Na), 235 (M+H).

Preparation 65

Diethyl 2-{5-[Amino(hydroxyimino)methyl]-2-pyridinyl}malonate

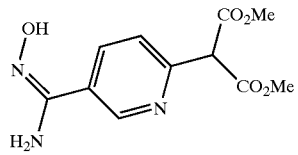

The title compound was obtained crude as a pale yellow solid from the title compound of Preparation 64, using a similar method to that described in Preparation 31.

The title compound was used in the next reaction without purification or characterisation.

Preparation 66 tert-Butyl (3R)-6-Cyclohexyl-3-{3-[6-(2-methoxy-2-oxoethyl)-3-pyridinyl]-1,2,4-oxadiazol-5-yl}hexanoate

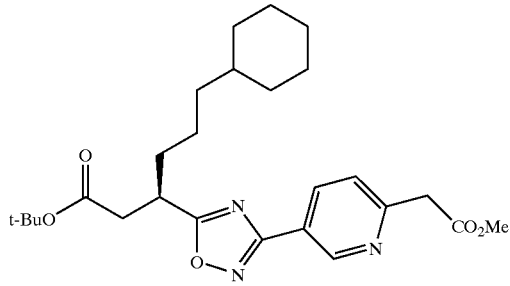

The title compound was obtained as a brown oil from the title compound of Preparation 175 and the amidoxime from Preparation 65, using a similar method to that described in Preparation 47.

¹H NMR (300 MHz, CDCl₃) δ 0.78–0.92 (m, 2H), 1.02–1.47 (m, 17H), 1.54–1.90 (m, 7H), 2.68 (dd, 1H), 2.87 (dd, 1H), 3.49–3.58 (m, 1H), 3.74 (s, 3H), 3.93 (s, 2H), 7.42 (d, 1H), 8.32 (d, 1H), 9.23 (s, 1H).

LRMS (ES) 494 (M+Na), 472 (M+H).

Preparation 67

(3R)-6-Cyclohexyl-3-{3-[6-(2-methoxy-2-oxoethyl)-3-pyridinyl]-1,2,4-oxadiazol-5-yl}hexanoic acid

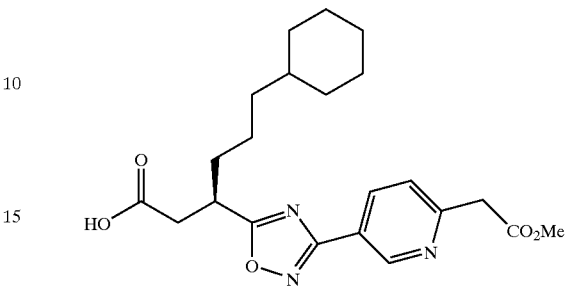

The title compound was obtained as a pale yellow oil from the title compound of Preparation 66, using a similar method to that described in Preparation 31.

¹H NMR (300 MHz, CDCl₃) δ 0.77–0.90 (m, 2H), 1.02–1.40 (m, 8H), 1.54–1.71 (m, 5H), 1.71–1.91 (m, 2H), 2.80 (dd, 1H), 3.03 (dd, 1H), 3.52–3.62 (m, 1H), 3.71 (s, 3H), 3.93 (s, 2H), 7.42 (d, 1H), 8.33 (d, 1H), 9.21 (s, 1H).

LRMS (TSP) 415 (M).

Preparation 68

6-Chloro-N'-hydroxy-3-pyridinecarboximidamide

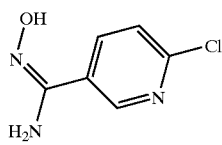

To a solution of sodium methoxide (15.6 g of 25–30% in methanol, 72 mmol) in methanol (70 mL) at 0° C. was added hydoxylamine hydrochloride (5.02 g, 72 mmol) and the mixture was then stirred at room temperature for 30 minutes. 5-cyano-2-chloropyridine (10 g, 72 mmol) was added and the reaction was heated to reflux for 3 hours. The reaction was cooled to room temperature, filtered to remove precipitated sodium chloride and the filtrate was evaporated to dryness. The residue was dissolved in ethanol in order to crystallise the product but this was unsuccessful, so the solvent was removed in vacuo to give the title compound as a white solid (12 g).

¹H NMR (300 MHz, CD₃OD) δ 7.49 (d, 1H), 8.06 (dd, 1H), 8.65 (d, 1H).

LRMS (ES) 172 (M+H).

Preparation 69 tert-Butyl (3R)-3-[3-(6-chloro-3-pyridinyl)-1,2,4-oxadiazol-5-yl]-6-cyclohexyl hexanoate

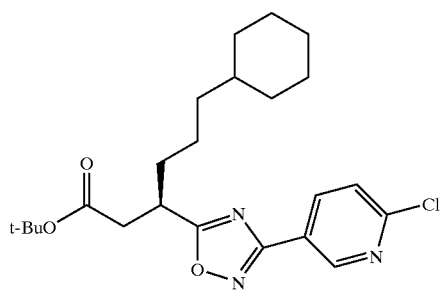

The title compound was obtained as an orange oil from the title compound of Preparation 175 and the amidoxime from Preparation 68, using a similar method to that described in Preparation 47.

$^1$H NMR (400 MHz, CDCl$_3$) δ 0.76–0.88 (m, 2H), 1.04–1.40 (m, 17H), 1.55–1.86 (m, 7H), 2.67 (dd, 1H), 2.85 (dd, 1H), 3.47–3.55 (m, 1H), 7.42 (d, 1H), 8.28 (dd, 1H), 9.06 (d, 1H).

LRMS (TSP) 433 (M).

Preparation 70

(3R)-3-[3-(6-Chloro-3-pyridinyl)-1,2,4-oxadiazol-5-yl]-6-cyclohexylhexanoic acid

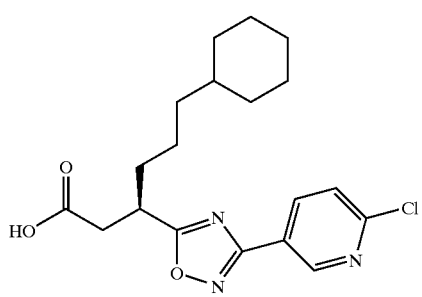

The title compound of Preparation 69 (3.0 g, 6.9 mmol) was dissolved in trifluoroacetic acid (101 mL) and the reaction was stirred at room temperature for 3 hours. The solvent was removed in vacuo, and the residue was azeotroped with toluene and then dichloromethane. The residue was dissolved in ethyl acetate (100 mL) and then washed with saturated aqueous sodium dihydrogen citrate solution (100 mL) and water (100 ml). The organic layer was dried (MgSO$_4$) and the solvent was removed in vacuo to give the title compound as a yellow oil (2.7 g).

$^1$H NMR (300 MHz, CDCl$_3$) δ 0.77–0.92 (m, 2H), 1.06–1.42 (m, 8H), 1.56–1.89 (m, 7H), 2.82 (dd, 1H), 3.05 (dd, 1H), 3.51–3.61 (m, 1H), 7.46 (d, 1H), 8.31 (dd, 1H), 9.08 (d, 1H).

LRMS (TSP) 378 (M+H).

Preparation 71

(3R)-6-Cyclohexyl-3-{3-[6-(methylamino)-3-pyridinyl}-1,2,4-oxadiazol-5-yl]hexanoic acid

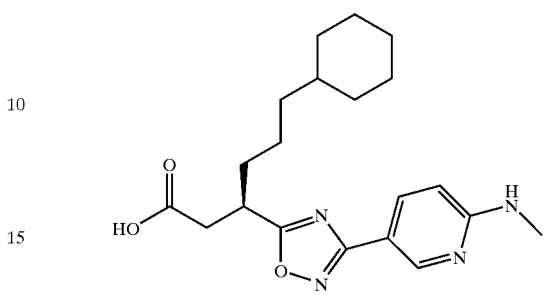

The title compound from Preparation 70 (0.8 g, 2.1 mmol) and methylamine (2.0 mL of a 33% solution in ethanol, 21 mmol) were heated in a sealed reaction vessel at 90° C. for 10 hours. The reaction mixture was cooled to room temperature and the residue was purified by flash chromatography on silica gel (graded elution of ethyl acetate/hexane 50:50 to ethyl acetate/acetic acid 99:1) to give the title compound as a colorless oil (0.24 g).

$^1$H NMR (300 MHz, CDCl$_3$) δ 0.77–0.90 (m, 2H), 1.02–1.41 (m, 8H), 1.53–1.70 (m, 5H), 1.70–1.86 (m, 2H), 2.75 (dd, 1H), 2.89 (s, 3H), 2.97 (dd, 1H), 3.51–3.61 (m, 1h), 6.48 (d, 1H), 8.14 (dd, 1H), 8.58 (d, 1H).

LRMS (TSP) 373 (M+H).

Preparation 72

(3R)-6-Cyclohexyl-3-{3-[6-(ethylamino)-3-pyridinyl]-1,2,4-oxadiazol-5-yl}hexanoic acid

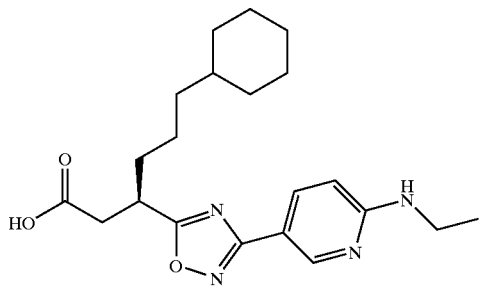

The title compound was obtained as a colorless oil from the title compound of Preparation 70 and ethylamine, using a similar method to that described in Preparation 71.

$^1$H NMR (300 MHz, CDCl$_3$) δ 60.84–0.92 (m, 2H), 1.06–1.45 (m, 1H), 1.53–1.88 (m, 7H), 2.76 (dd, 1H), 2.98 (dd, 1H), 3.15 (q, 2H), 3.55–3.63 (m, 1H), 6.48 (d, 1H), 8.12 (dd, 1H), 8.58 (d, 1H).

LRMS (TSP) 387 (M+H, 100%).

Preparation 73

(3R)-6-Cyclohexyl-3-{3-[6-(isopropylamino)-3-pyridinyl]-1,2,4-oxadiazol-5-yl}hexanoic acid

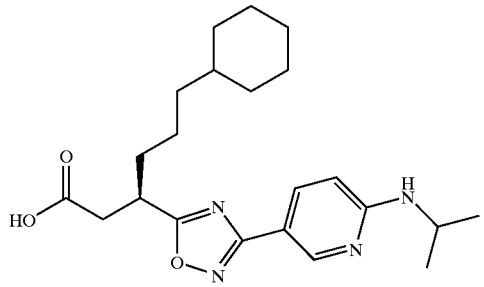

The title compound was obtained as a colorless oil (0.04 g) from the title compound of Preparation 70 (0.27 g) and isopropylamine, using a similar method to that described in Preparation 71 apart from copper sulphate (0.27 g, 1.1 mmol) was added to speed up the reaction.

$^1$H NMR (300 MHz, CDCl$_3$) δ 0.79–0.92 (m, 2H), 1.10–1.40 (m, 14H), 1.58–1.81 (m, 7H), 2.79 (dd, 1H), 2.92 (dd, 1H), 3.56–3.65 (m, 1H), 4.02–4.11 (m, 1H), 6.65 (d, 1H), 7.98 (dd, 1H), 8.57 (d, 1H).

LRMS (TSP) 401 (M+H).

Preparation 74

(3R)-6-Cyclohexyl-3-(3-{6-[(2-methoxyethyl)amino]-3-pyridinyl)-1,2,4-oxadiazol-5-yl}hexanoic acid

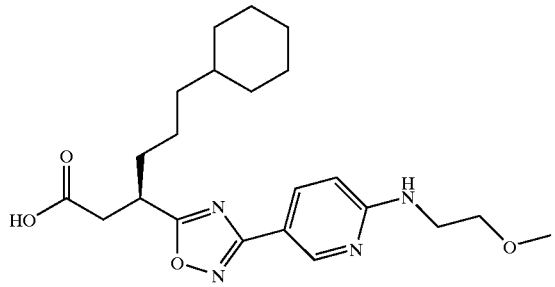

The title compound was obtained as a colorless oil from the title compound of Preparation 70 and 2-methoxyethylamine, using a similar method to that described in Preparation 71.

$^1$H NMR (400 MHz, CDCl$_3$) δ 0.79–0.90 (m, 2H), 1.08–1.42 (m, 8H), 1.57–1.70 (m, 5H), 1.70–1.91 (m, 2H), 2.79 (dd, 1H), 3.02 (dd, 1H), 3.37 (s, 3H), 3.50 (t, 2H), 3.56–3.65 (m, 1H), 3.58 (t, 2H), 6.52 (d, 1H), 8.07 (dd, 1H), 8.68 (d, 1H).

LRMS (TSP) 415 (M−H).

Preparation 75

(3R)-6-Cyclohexyl-3-{3-[6-(1-pyrrolidinyl)-3-pyridinyl]-1,2,4-oxadiazol-5-yl}hexanoic acid

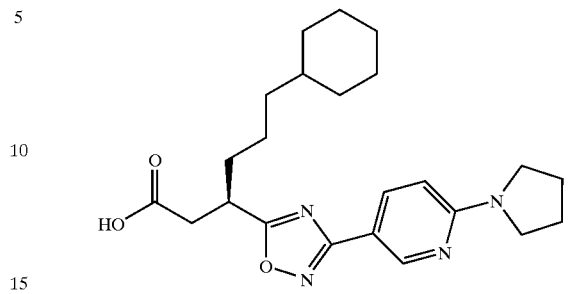

The title compound was obtained as a colorless oil from the title compound of Preparation 70 and pyrrolidine, using a similar method to that described in Preparation 71.

Preparation 76

(3R)-3-(3-{6-[4-(tert-Butoxycarbonyl)-1-piperazinyl]-3-pyridinyl}-1,2,4-oxadiazol-5-yl)-6-cyclohexylhexanoic acid

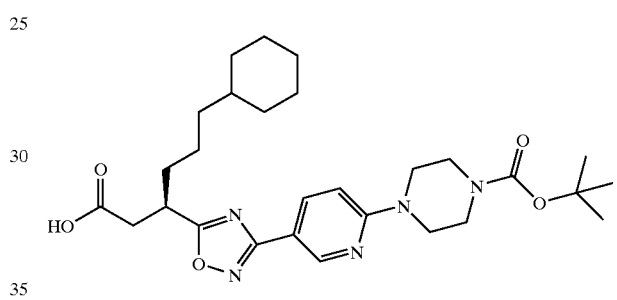

The title compound was obtained as a viscous oil from the title compound of Preparation 70 and BOC-piperazine, using a similar method to that described in Preparation 71.

$^1$H NMR (400 MHz, CDCl$_3$) δ 0.78–0.92 (m, 2H), 1.03–1.39 (m, 8H), 1.47 (s, 9H), 1.55–1.70 (m, 5H), 1.70–1.89 (m, 2H), 2.77 (dd, 1H), 2.99 (dd, 1H), 3.48–3.55 (m, 9H), 6.62 (d, 1H), 8.08 (d, 1H), 8.81(s, 1H).

LRMS (ES) 528 (M+H).

Preparation 77

(3R)-3-[3-(6-{6-[(tert-Butoxycarbonyl)amino]-3-azabicyclo[3.1.0]hex-3-yl}-3-pyridinyl)-1,2,4-oxadiazol-5-yl]-6-cyclohexylhexanoic acid

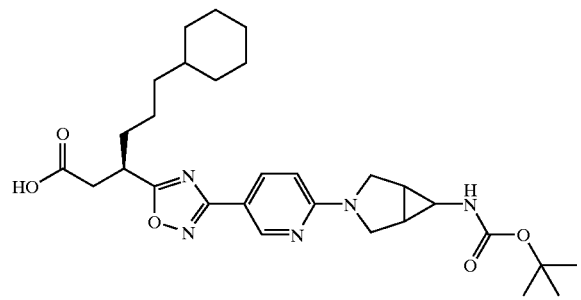

The title compound was obtained as a viscous oil from the title compound of Preparation 70 and tert-butyl 3-azabicyclo[3.1.0]hex-6-ylcarbamate (J. Chem. Soc. Perkin Trans. I 2000, 1615), using a similar method to that described in Preparation 71.

¹H NMR (300 MHz, CDCl₃) δ 0.77–0.90 (m, 2H), 1.07–1.52 (m, 17H), 1.52–1.90 (m, 9H), 2.77 (dd, 1H), 2.98 (dd, 1H), 3.40–3.60 (m, 3H), 3.60–3.81 (m, 2H), 4.80–5.40 (br, 1H), 7.31 (d, 1H), 8.02 (d, 1H), 8.20–8.80 (br s, 1H), 8.78 (s, 1H).

LRMS (TSP) 540 (M+H).

Preparation 78
tert-Butyl (3R)-6-Cyclohexyl-3-{3-[6-(4-methyl-1-piperazinyl)-3-pyridinyl]-1,2,4-oxadiazol-5-yl}hexanoate

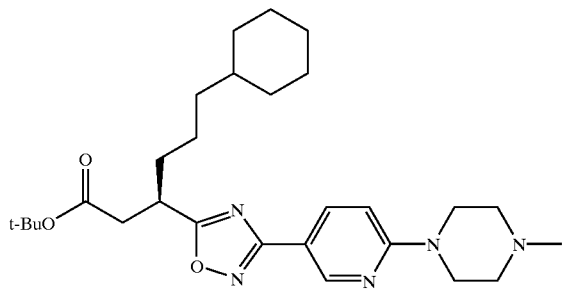

A mixture of the title compound from Preparation 69 (0.4 g, 0.9 mmol) and N-methylpiperazine (4.1 mL, 37 mmol) were heated in a sealed reaction vessel at 90° C. for 1.5 hours. The reaction was cooled to room temperature, the residue was dissolved in ethyl acetate (50 mL) and washed with 10% aqueous citric acid solution (30 mL) followed by saturated aqueous sodium bicarbonate solution (30 mL). The organic layer was dried (MgSO₄) and the solvent was removed in vacuo to give the title compound as a viscous oil (0.41 g).

¹H NMR (400 MHz, CDCl₃) δ 0.76–0.90 (m, 2H), 1.04–1.40 (m, 17H), 1.58–1.84 (m, 7H), 2.35 (s, 3H), 2.47–2.55 (m, 4H), 2.67 (dd, 1H), 2.86 (dd, 1H), 3.44–3.54 (m, 1H), 3.65–3.72 (m, 4H), 6.68 (d, 1H), 8.08 (dd, 1H), 8.86 (d, 1H).

LRMS (ES) 498 (M+H).

Preparation 79
(3R)-6-Cyclohexyl-3-{3-[6-(4-methyl-1-piperazinyl)-3-pyridinyl]-1,2,4-oxadiazol-5-yl}hexanoic acid

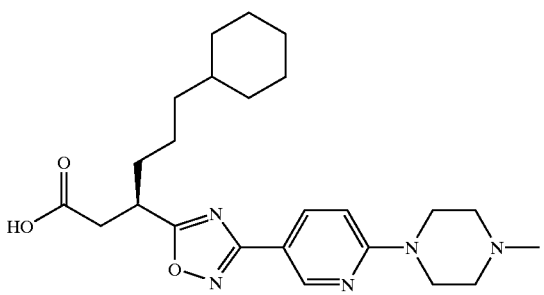

The title compound of Preparation 78 (0.41 g, 0.8 mmol) was dissolved in trifluoroacetic acid (5 mL) and the reaction was stirred at room temperature for 2.5 hours. The solvent was removed in vacuo, and the residue was azeotroped with toluene and then dichloromethane. The residue was dissolved in ethyl acetate (50 mL) and then washed with saturated aqueous sodium bicarbonate solution (30 mL). The organic layer was dried (MgSO₄) and the solvent was removed in vacuo to give the title compound as a yellow oil (0.26 g).

¹H NMR (300 MHz, CDCl₃) δ 0.76–0.90 (m, 2H), 1.00–1.40 (m, 8H), 1.56–1.86 (m, 7H), 2.42 (s, 3H), 2.54–2.80 (m, 5H), 2.90 (dd, 1H), 3.41–3.58 (m, 5H), 6.20 (d, 1H), 7.87 (dd, 1H), 8.66 (d, 1H).

LRMS (ES) 442 (M+H).

Preparation 80
tert-Butyl (3R)-6-Cyclohexyl-3-(3-{6-[3-(dimethylamino)-1-azetidinyl]-3-pyridinyl}-1,2,4-oxadiazol-5-yl)hexanoate

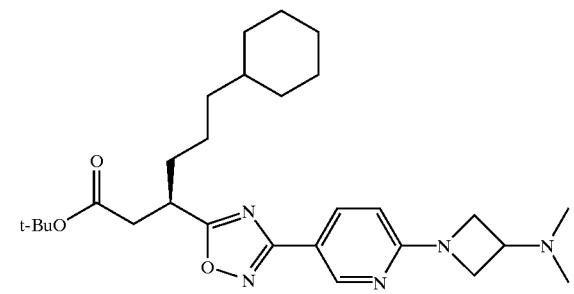

To a solution of 3-dimethylamino azetidine bis-trifluoroacetic acid salt (0.76 g, 2.3 mmol) in ethanol (5 mL) was added triethylamine (0.64 mL, 4.6 mmol) and the mixture was stirred at room temperature for 20 minutes. The title compound from Preparation 69 (0.5 g, 1.15 mmol) was added and the mixture was heated in a sealed reaction vessel at 100° C. for 48 hours. The reaction was cooled to room temperature, then purified by flash chromatography on silica gel (ethyl acetate/hexane/diethylamine 70:30:1 as eluant) to give the title compound as a viscous oil (0.41 g).

¹H NMR (400 MHz, CDCl₃) δ 0.73–0.90 (m, 2H), 1.07–1.42 (m, 17H), 1.57–1.88 (m, 7H), 2.22 (s, 6H), 2.66 (dd, 1H), 2.85 (dd, 1H), 3.21–3.30 (m, 1H), 3.42–3.52 (m, 1H), 3.88–3.97 (m, 2H), 4.09–4.18 (m, 2H), 6.32 (d, 1H), 8.05 (dd, 1H), 8.81 (d, 1H).

LRMS (ES) 498 (M+H).

Preparation 81
(3R)-6-Cyclohexyl-3-(3-{6-[3-(dimethylamino)-1-azetidinyl]-3-pyridinyl}-1,2,4-oxadiazol-5-yl)hexanoic acid

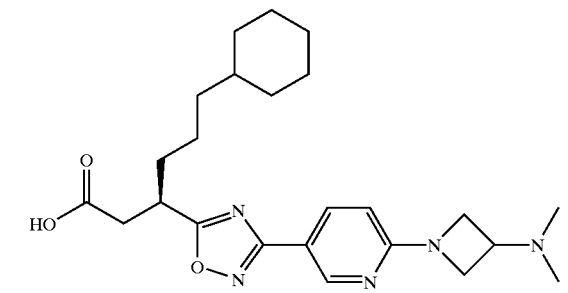

The title compound was obtained as a white solid from the title compound of Preparation 80, using a similar method to that described in Preparation 79.

¹H NMR (400 MHz, CDCl₃) δ 0.79–0.91 (m, 2H), 1.06–1.41 (m, 8H), 1.55–1.86 (m, 7H), 2.26 (s, 6H), 2.68 (dd, 1H), 2.87 (dd, 1H), 3.32–3.40 (m, 1H), 3.43–3.52 (m, 1H), 3.94–4.00 (m, 2H), 4.07–4.14 (m, 2H), 6.25 (d, 1H), 8.02 (dd, 1H), 8.78 (d, 1H).

LRMS (ES) 442 (M+H).

Preparation 82 tert-Butyl (3R)-6-Cyclohexyl-3-(3-{6-[3-(4-morpholinyl)-1-azetidinyl]-3-pyridinyl}-1,2,4-oxadiazol-5-yl)hexanoate

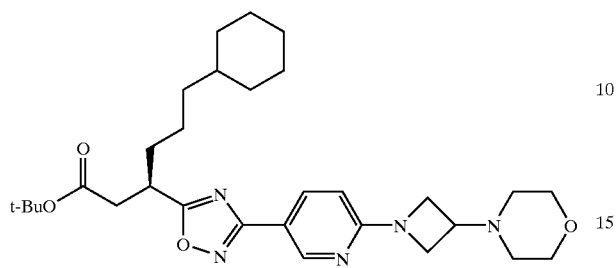

The title compound was obtained as a viscous oil from the title compound of Preparation 69 and 3-N-morpholinoazetidine, using a similar method to that described in Preparation 78.

$^1$H NMR (400 MHz, CDCl$_3$) δ 0.73–0.88 (m, 2H), 1.00–1.45 (m, 17H), 1.53–1.88 (m, 7H), 2.38–2.48 (m, 4H), 2.63 (dd, 1H), 2.82 (dd, 1H), 3.49–3.60 (m, 1H), 3.60–3.71 (m, 1H), 3.66–3.77 (m, 4H), 3.92–3.99 (m, 2H), 4.05–4.18 (m, 2H), 6.32 (d, 1H), 8.04 (dd, 1H), 8.80 (d, 1H).

LRMS (TSP) 540 (M+H).

Preparation 83

(3R)-6-Cyclohexyl-3-(3-{6-[3-(4-morpholinyl)-1-azetidinyl]-3-pyridinyl)-1,2,4-oxadiazol-5-yl)hexanoic acid

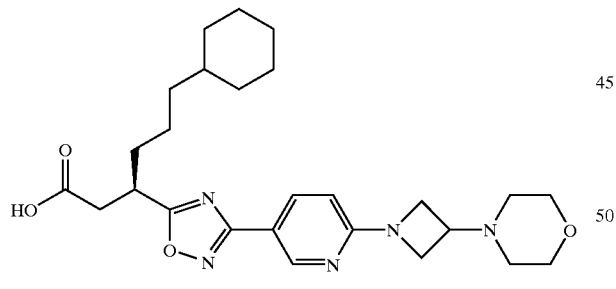

The title compound was obtained as a white solid from the title compound of Preparation 82, using a similar method to that described in Preparation 79.

$^1$H NMR (300 MHz, CDCl$_3$) δ 0.77–0.91 (m, 2H), 1.02–1.40 (m, 8H), 1.53–1.87 (m, 7H), 2.42–2.52 (m, 4H), 2.72 (dd, 1H), 2.94 (dd, 1H), 3.30–3.40 (m, 1H), 3.44–3.55 (m, 1H), 3.71–3.79 (m, 4H), 3.96–4.03 (m, 2H), 4.08–4.19 (m, 2H), 6.30 (d, 1H), 8.06 (dd, 1H), 8.79 (d, 1H).

LRMS (TSP) 483 (M).

Preparation 84 tert-Butyl (3R)-6-Cyclohexyl-3-{3-[6-(dimethylamino)-3-pyridiny]-1,2,4-oxadiazol-5-yl}hexanoate

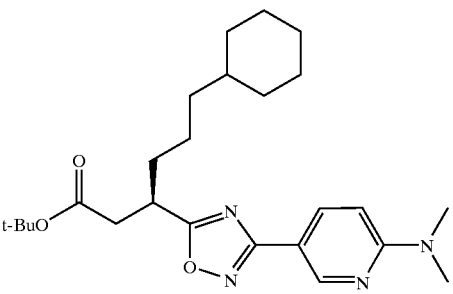

To a solution of the title compound from Preparation 69 (0.41 g, 0.9 mmol) in ethanol (10 RL) was added dimethylamine (1.7 mL of 5 6M solution in ethanol, 9.3 mmol) and the reaction was heated to 70° C. for 9 hours. The reaction was cooled to room temperature, the solvent was removed in vacuo and the residue was purified by flash chromatography on silica gel (hexane/diethyl ether 1:1 as eluant) to give the title compound as a clear oil (0.42 g).

$^1$H NMR (400 MHz, CDCl$_3$) δ 0.78–0.89 (m, 2H), 1.08–1.22 (m, 6H), 1.28–1.40 (m, 1H), 1.56–1.87 (m, 7H), 2.66 (dd, 1H), 2.85 (dd, 1H), 3.15 (s, 6H), 3.45–3.63 (m, 1H), 6.53 (d, 1H), 8.06 (dd, 1H), 8.84 (d, 1H).

LRMS (TSP) 443 (M+H).

Preparation 85

(3R)-6-Cyclohexyl-3-[3-[6-(dimethylamino)-3-pyridinyl]-1,2, 4-oxadiazol-5-yl}hexanoic acid

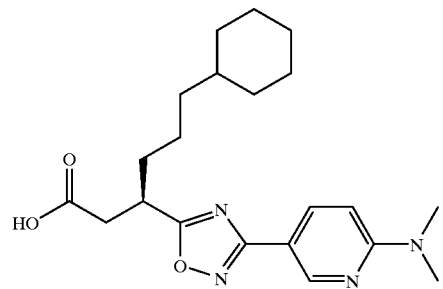

The title compound was obtained as a yellow oil from the title compound of Preparation 84, using a similar method to that described in Preparation 31.

$^1$H NMR (400 MHz, CDCl$_3$) δ 0.75–0.90 (m, 2H), 1.06–1.38 (m, 8H), 1.56–1.83 (m, 7H), 2.78 (dd, 1H), 2.99 (dd, 1H), 3.38 (s, 6H), 3.45–3.55 (m, 1H), 6.92 (d, 1H), 8.30 (dd, 1H), 8.74 (d, 1H).

LRMS (TSP) 387 (M+H).

Preparation 86
Ethyl 5-{5-[(1R)-]-(2-tert-Butoxy-2-oxoethyl)-4-cyclohexylbutyl]-1,2,4-oxadiazol-3yl}-2-pyridinecarboxylate

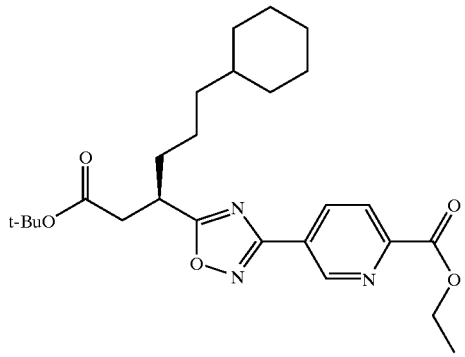

To a solution of the title compound from Preparation 69 (0.5 g, 1.15 mmol) in ethanol (6.5 mL) was added triethylamine (0.64 mL, 4.6 mmol), palladium(II) acetate (0.03 g, 10 mol %) and triphenylphosphine (0.06 g, 20 mol %) and the reaction was heated under 100 psi of carbon monoxide at 50° C. for 24 hours. Further catalyst (10 mol % of palladium(II) acetate and 20 mol % of triphenylphosphine) was added and the carbonylation was continued at 50° C./100 psi for a further 72 hours. The reaction was cooled to room temperature, the solvent was evaporated and the residue was purified by flash chromatography on silica gel (ethyl acetate/hexane 10:90 as eluant) to give the title compound as a colorless oil (0.24 g).

$^1$H NMR (300 MHz, CDCl$_3$) δ 0.77–0.93 (m, 2H), 1.02–1.51 (m, 20H), 1.55–1.94 (m, 7H), 2.70 (dd, 1H), 2.89 (dd, 1H), 3.50–3.60 (m, 1H), 4.52 (q, 2H), 8.25 (d, 1H), 8.50 (dd, 1H), 9.42 (d, 1H).

LRMS (TSP) 472 (M+H).

Preparation 87
(3R)-6-Cyclohexyl-3-{3-[6-(ethoxycarbonyl)-3-pyridinyl]-1,2,4-oxadiazol-5-yl}hexanoic acid

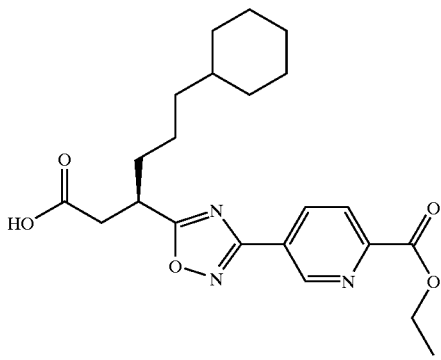

The title compound was obtained as a colorless oil from the title compound of Preparation 86, using a similar method to that described in Preparation 31.

$^1$H NMR (300 MHz, CDCl$_3$) δ 0.76–0.92 (m, 2H), 1.00–1.39 (m, 8H), 1.46 (t, 3H), 1.55–1.72 (m, 5H), 1.72–1.91 (m, 2H), 2.83 (dd, 1H), 3.06 (dd, 1H), 3.55–3.64 (m, 1H), 4.50 (q, 2H), 8.25 (d, 1H), 8.52 (dd, 1H), 9.42 (d, 1H).

LRMS (ES) 438 (M+Na), 416 (M+H).

Preparation 88
2-Chloro-N'-hydroxy-3-pyridinecarboximidamide

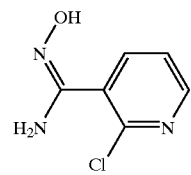

Sodium methoxide (150 ml of 0.25M solution in methanol, 37.5 mmol) was added to a solution of hydroxylamine hydrochloride (2.8 g, 39.7 mmol) in methanol (150 mL), and the reaction was stirred at room temperature for 30 minutes. The mixture was filtered, then 2-chloro-3-cyanopyridine (5.0 g, 36.1 mmol) was added, the reaction was stirred at room temperature for 16 hours and then heated to reflux for 2 hours. The reaction was cooled to room temperature, concentrated in vacuo to approximately 50 mL and filtered. The filtrate was concentrated to dryness in vacuo, the residue was triturated with dichloromethane and filtered to give the title compound as a white solid (6.2 g).

$^1$H NMR (400 MHz, D$_6$-DMSO) δ 5.92 (s, 2H), 7.40–7.47 (m, 1H), (d, 1H), 8.43 (dd, 1H), 9.58 (s, 1H).

LRMS (ES) 172 (M+H).

Preparation 89
(3R)-3-[3-(2-Chloro-3-pyridinyl)-1,2,4-oxadiazol-5-yl]-6-cyclohexylhexanoic acid

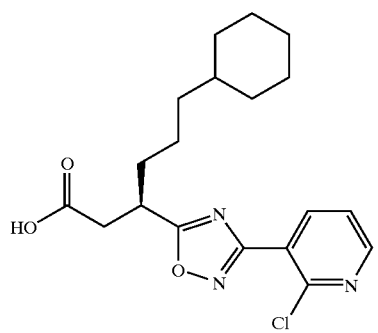

The title compound was obtained as an off-white solid from the title compounds of Preparation 175 and Preparation 88, using a similar method to that described in Preparation 47. Ester cleavage occurred upon flash chromatography on silica gel (graded elution of 2:1 to 1:1 hexane/ethyl acetate).

Preparation 90
(3R)-6-Cyclohexyl-3-{3-[2-(4-methyl-1-piperazinyl)-3-pyridinyl]-1,2,4-oxadiazol-5-yl}hexanoic acid

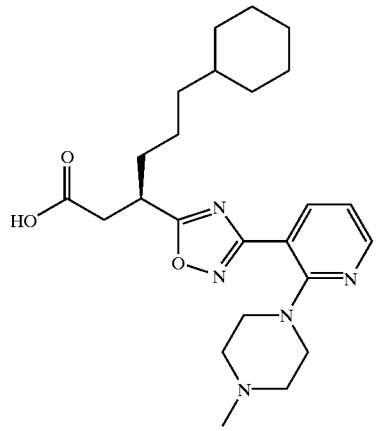

The title compound from Preparation 89 (0.4 g, 1.06 mmol) and N-methylpiperazine (4.0 mL, 36 mmol) were heated in a sealed reaction vessel at 100° C. for 8 hours. The reaction mixture was cooled to room temperature, dissolved in ethyl acetate (50 mL) then washed with 10% aqueous citric acid solution (20 mL), saturated aqueous sodium bicarbonate solution (20 mL) and water (20 mL). The aqueous citric acid washings were basified to pH 7 with saturated aqueous sodium bicarbonate solution and then extracted with ethyl acetate (2×50 mL). The combined organic layers were dried (MgSO$_4$) and the solvent was removed in vacuo to give the title compound as a brown oil (0.34 g).

$^1$H NMR (300 MHz, CDCl$_3$) δ 0.73–0.89 (m, 2H), 1.00–1.44 (m, 8H), 1.53–1.82 (m, 7H), 2.47 (s, 3H), 2.70 (dd, 1H), 2.77–2.97 (m, 5H), 3.13–3.38 (m, 4H), 3.38–3.52 (m, 1H), 6.86 (dd, 1H), 7.94 (d, 1H), 8.26 (dd, 1H), 9.80 (br s, 1H).

LRMS (TSP) 442 (M+H).

Preparation 91
(3R)-6-Cyclohexyl-3-{3-[2-(methylamino)-3-pyridinyl]-1,2,4-oxadiazol-5-yl}hexanoic acid

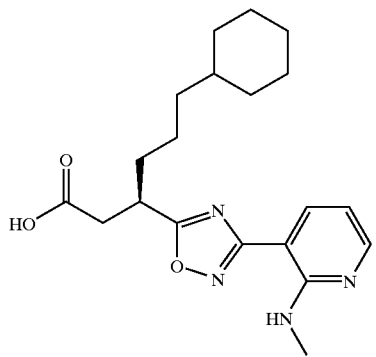

The title compound from Preparation 89 (0.5 g, 1.3 mmol) and methylamine (5.0 mL of 33% solution in ethanol, 50 mmol) were heated in a sealed reaction vessel at 100° C. for 3 hours. The reaction mixture was cooled to room temperature and the solvent was removed in vacuo. The residue was stirred in 10% aqueous citric acid solution (20 mL) for 30 minutes the mixture was extracted with ethyl acetate (2×20 mL). The combined organic layers were dried (MgSO$_4$), the solvent was removed in vacuo and the residue was purified by flash chromatography on silica gel (graded elution of dichloromethane/methanol 99:1 to 96:4) to give the title compound as a yellow oil (0.30 g).

$^1$H NMR (400 MHz, CDCl$_3$) δ 0.78–0.90 (m, 2H), 1.06–1.37 (m, 8H), 1.56–1.70 (m, 5H), 1.70–1.86 (m, 2H), 2.78 (dd, 1H), 2.99 (dd, 1H), 3.10 (s, 3H), 3.50–3.59 (m, 1H), 6.62 (dd, 1H), 7.15 (br s, 1H), 8.60 (br s, 1H).

LRMS (ES) 371 (M–H).

Preparation 92
tert-Butyl (3R)-6-Cyclohexyl-3-[3-(2-pyrazinyl]-1,2,4-oxadiazol-5-yl}hexanoate

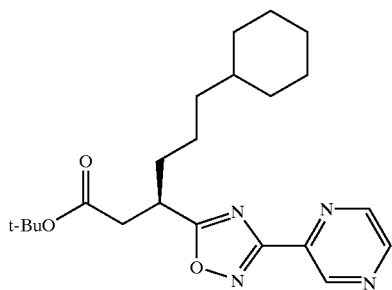

The title compound was obtained as a yellow oil from the title compound from Preparation 175 and Al-hydroxy-2-pyrazinecarboximidamide using a similar method to that described in Preparation 47, apart from the reaction solvent used was dichloromethane/dimethylformamide.

$^1$H NMR (400 MHz, CDCl$_3$) δ 0.77–0.87 (m, 2H), 1.03–1.47 (m, 17H), 1.57–1.69 (m, 5H), 1.69–1.93 (m, 2H), 2.71 (dd, 1H), 2.94 (dd, 1H), 3.54–3.61 (m, 1H), 8.62 (d, 1H), 8.66 (d, 1H), 9.38 (s, 1H).

LRMS (TSP) 401 (M+H).

Preparation 93
(3R)-6-Cyclohexyl-3-[3-(2-pyrazinyl)-1,2,4-oxadiazol-5-yl]hexanoic acid

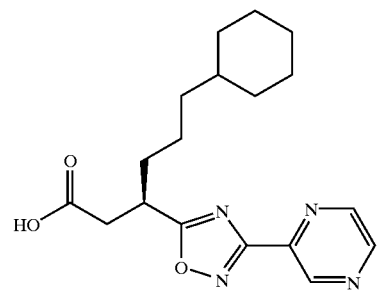

The title compound was obtained as a yellow oil from the title compound of Preparation 92, using a similar method to that described in Preparation 31.

$^1$H NMR (400 MHz, CDCl$_3$) δ 0.78–0.90 (m, 2H), 1.05–1.40 (m, 8H), 1.56–1.72 (m, 5H), 1.72–1.94 (m, 2H), 2.87 (dd, 1H), 3.12 (dd, 1H), 3.58–3.66 (m, 1H), 8.75 (d, 1H), 8.83 (d, 1H), 9.38 (s, 1H), 9.60 (br s, 1H).

LRMS (TSP) 345 (M+H).

Preparation 94
tert-Butyl (3R)-6-Cyclohexyl-3-{3-[6-(1-pyrrolidinyl)-2-pyrazinyl]-1,2,4-oxadiazol-5-yl}hexanoate

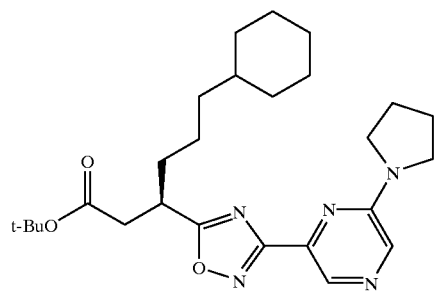

The title compound was obtained as a yellow oil from the title compound from Preparation 175 and N-hydroxy-6-(1-pyrrolidinyl)-2-pyrazinecarboximidamide (Pol. J. Pharmacol. 1977, 29, 61–68), using a similar method to that described in Preparation 47.

$^1$H NMR (400 MHz, CDCl$_3$) δ 0.78–0.90 (m, 2H), 1.08–1.37 (m, 8H), 1.40 (s, 9H), 1.58–1.70 (m, 5H), 1.70–1.90 (m, 2H), 2.02–2.10 (m, 4H), 2.68 (dd, 1H), 2.89 (dd, 1H), 3.51–3.64 (m, 5H), 8.00 (s, 1H), 8.50 (s, 1H).

LRMS (ES) 492 (M+Na), 401 (M+H).

Preparation 95

(3R)-6-Cyclohexyl-3-{3-[6-(1-pyrrolidinyl)-2-pyrazinyl]-1,2,4-oxadiazol-5-yl}hexanoic acid

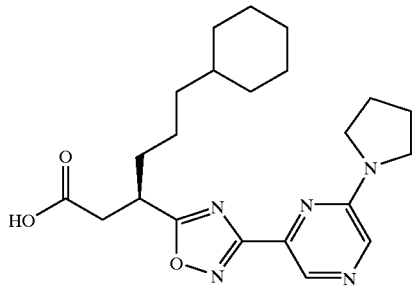

The title compound was obtained as a yellow oil from the title compound of Preparation 94, using a similar method to that described in Preparation 31.

$^1$H NMR (400 MHz, CDCl$_3$) δ 0.79–0.90 (m, 2H), 1.06–1.38 (m, 8H), 1.57–1.72 (m, 5H), 1.72–1.92 (m, 2H), 2.02–2.10 (m, 4H), 2.83 (dd, 1H), 3.07 (dd, 1H), 3.55–3.65 (m, 5H), 8.00 (s, 1H), 8.47 (s, 1H).

LRMS (ES) 436 (M+Na), 414 (M+H).

Preparation 96 tert-Butyl (3R)-3-[3-(6-chloro-2-pyrazinyl)-11,2,4-oxadiazol-5-yl]-6-cyclohexyl hexanoate

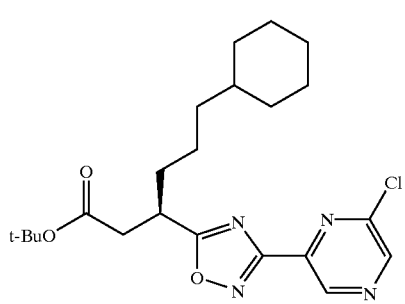

The title compound was obtained as a yellow oil from the title compound from Preparation 175 and 6-chloro-1hydroxy-2-pyrazinecarboximidamide (Pol. J. Pharmacol. 1977, 29, 61–68), using a similar method to that described in Preparation 47.

$^1$H NMR (400 MHz, CDCl$_3$) δ 0.78–0.93 (m, 2H), 1.03–1.47 (m, 17H), 1.50–1.73 (m, 5H), 1.73–1.95 (m, 2H), 2.71 (dd, 1H), 2.93 (dd, 1H), 3.55–3.63 (m, 1H), 8.73 (d, 1H), 9.25 (s, 1H).

LRMS (ES) 891 (2M+Na), 457 (M+Na), 435 (M+H).

Preparation 97

(3R)-3-[3-(6-Chloro-2-pyrazinyl)-1,2,4-oxadiazol-5-yl]-6-cyclohexyl hexanoic acid

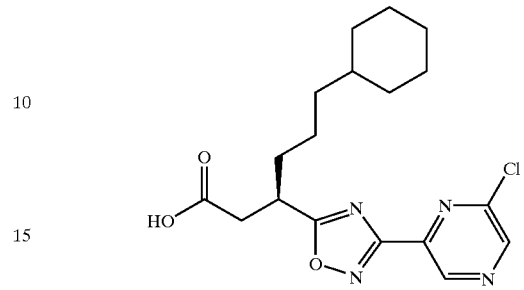

The title compound was obtained as a yellow oil from the title compound of Preparation 96, using a similar method to that described in Preparation 31.

$^1$H NMR (400 MHz, CDCl$_3$) δ 0.79–0.90 (m, 2H), 1.05–1.40 (m, 8H), 1.56–1.72 (m, 5H), 1.72–1.94 (m, 2H), 2.84 (dd, 1H), 3.08 (dd, 1H), 3.57–3.64 (m, 1H), 8.73 (s, 1H), 9.23 (s, 1H).

LRMS (ES) 401 (M+Na).

Preparation 98

(3R)-6-Cyclohexyl-3-{3-[6-(4-methyl-1-piperazinyl)-2-pyrazinyl]-1,2,4-oxadiazol-5-yl}hexanoic acid

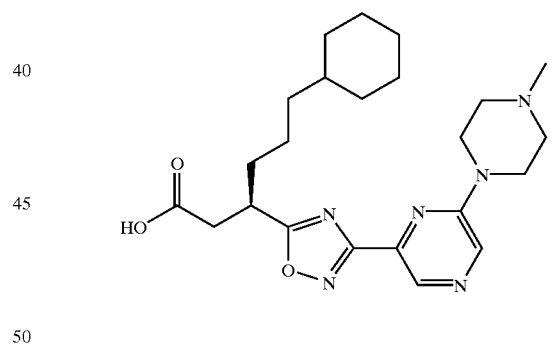

To a solution of the title compound from Preparation 97 (0.53 g, 1.4 mmol) in ethanol (5 mL) was added N-methylpiperazine (0.6 mL, 5.5 mmol) and the reaction was heated to 70° C. overnight. The solution was cooled to room temperature, the solvent was removed in vacuo and the residue was partitioned between ethyl acetate (50 mL) and water (50 mL). The organic layer was dried (MgSO$_4$) and the solvent was removed in vacuo to give the title compound as a yellow foam (0.66 g).

$^1$H NMR (400 MHz, CDCl$_3$) δ 0.78–0.90 (m, 2H), 1.04–1.43 (m, 8H), 1.56–1.86 (m, 7H), 2.47 (s, 3H), 2.65–2.90 (m, 5H), 2.96 (dd, 1H), 3.32–3.80 (m, 5H), 7.90 (s, 1H), 8.52 (s, 1H).

LRMS (ES) 465 (M+Na), 443 (M+H).

Preparation 99
tert-Butyl (3R)-6-Cyclohexyl-3-{3-[6-(1H-imidazol-1-yl)-2-pyrazinyl]-1,2,4-oxadiazol-5-yl}hexanoate

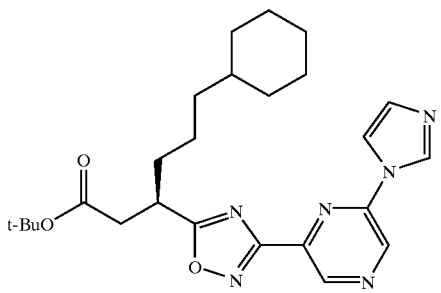

The title compound was obtained as a colorless oil as side-product during the formation of the title compound from Preparation 96.

$^1$H NMR (400 MHz, CDCl$_3$) δ 0.79–0.90 (m, 2H), 1.05–1.46 (m, 17H), 1.53–1.71 (m, 5H), 1.71–1.92 (m, 2H), 2.74 (dd, 1H), 2.92 (dd, 1H), 3.56–3.63 (m, 1H), 7.30 (s, 1H), 7.79 (s, 1H), 8.49 (s, 1if), 8.92 (s, 1H), 9.27 (s, 1H).

LRMS (ES) 489 (M+Na), 467 (M+H).

Preparation 100
(3R)-6-Cyclohexyl-3-{3-[6-(1H-imidazol-1-yl)-2-pyrazinyl]-1,2,4-oxadiazol-5-yl}hexanoic acid

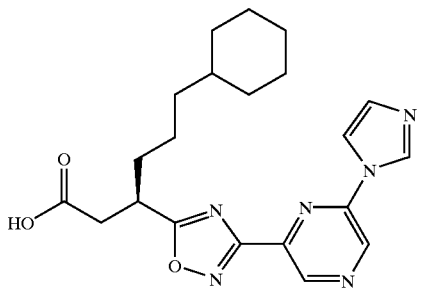

The title compound was obtained as its trifluoroacetic acid salt, as an orange foam from the title compound of Preparation 99, using a similar method to that described in Preparation 31.

$^1$H NMR (400 MHz, CDCl$_3$) δ 0.79–0.91 (m, 2H), 1.04–1.44 (m, 8H), 1.57–1.74 (m, 5H), 1.74–1.95 (m, 2H), 2.90 (dd, 1H), 3.10 (dd, 1H), 3.60–3.69 (m, 1H), 7.58 (s, 1H), 8.07 (s, 1H), 9.21 (s, 1H), 9.44 (s, 1H), 9.63 (s, 1H).

LRMS (ES) 411 (M+H).

Preparation 101
3-(4-Methyl-1-piperazinyl)-2-pyrazinecarbonitrile

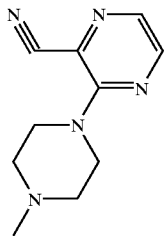

To a solution of 3-cyano-2-chloropyrazine (0.45 g, 3.2 mmol) in methanol (10 mL) was added N-methylpiperazine (0.75 mL, 6.4 mmol) and the reaction was stirred at room temperature overnight. The solvent was removed in vacuo, then the residue was dissolved in ethyl acetate. The precipitate was filtered off and the filtrate was concentrated under reduce pressure. The residue was then purified by flash chromatography on silica gel (dichloromethane/methanol 95:5) to give the title compound as a yellow oil (0.59 g).

$^1$H NMR (300 MHz, CD$_3$OD) δ 2.34 (s, 3H), 2.50–2.57 (m, 4H), 3.80–3.86 (m, 4H), 7.98 (d, 1H), 8.23 (dd, 1H).

LRMS (ES) 204 (M+H).

Preparation 102
N'-Hydroxy-3-(4-methyl-1-piperazinyl)-2-pyrazinecarboxyimidamide

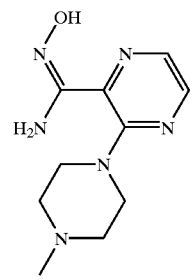

The title compound was obtained as a pale yellow solid from the title compound from Preparation 101, using a similar method to that described in Preparation 7.

$^1$H NMR (300 MHz, CD$_3$OD) δ 2.18 (s, 3H), 2.32–2.39 (m, 4H), 3.35–3.41 (m, 4H), 5.75 (s, 2H), 7.91 (d, 1H), 8.10 (d, 1H), 9.56 (s, 1H).

LRMS (TSP) 237 (M+H).

Preparation 103
tert-Butyl (3R)-6-Cyclohexyl-3-{3-[3-(4-methyl-1-piperazinyl)-2-pyrazinyl]-1,2,4-oxadiazol-5-yl}hexanoate

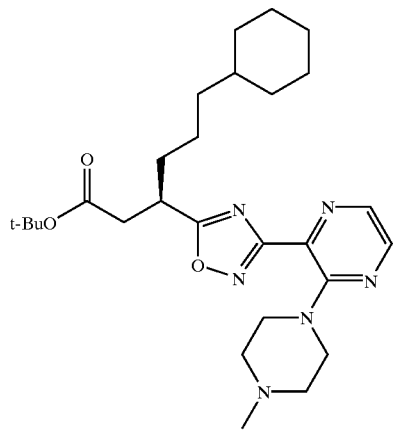

The title compound was obtained as a yellow oil from the title compound from Preparation 175 and the amidoxime from Preparation 102, using a similar method to that described in Preparation 47.

$^1$H NMR (400 MHz, CDCl$_3$) δ 0.78–0.90 (m, 2H), 1.03–1.44 (m, 17H), 1.55–1.71 (m, 5H), 1.71–1.90 (m, 2H), 2.33 (s, 3H), 2.46–2.54 (m, 4H), 2.70 (dd, 1H), 2.91 (dd, 1H), 3.31–3.40 (m, 4H), 3.51–3.60 (m, 1H), 8.16 (d, 1H), 8.21 (d, 1H).

LRMS (ES) 499 (M+Na).

Preparation 104

(3R)-6-Cyclohexyl-3-{3-[3-(4-methyl-1-piperazinyl)-2-pyrazinyl]-1,2,4-oxadiazol-5-yl}hexanoic acid

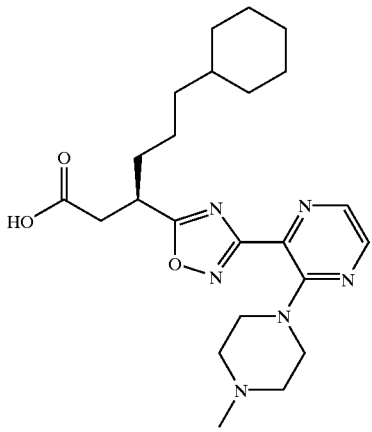

The title compound was obtained as its trifluoroacetic acid salt, as a yellow foam from the title compound of Preparation 103, using a similar method to that described in Preparation 31.

¹H NMR (400 MHz, CDCl₃) δ 0.78–0.89 (m, 2H), 1.05–1.40 (m, 8H), 1.58–1.90 (m, 7H), 2.78–2.92 (m, 7H), 2.92–3.09 (m, 2H), 3.41–3.70 (m, 5H), 8.26 (s, 2H), 11.80 (br s, 1H).

LRMS (ES) 443 (M+H).

Preparation 105

3-(4-Morpholinyl)-2-pyrazinecarbonitrile

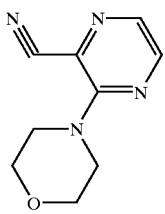

To a solution of 3-cyano-2-chloropyrazine (0.7 g, 5.0 mmol) in methanol (20 mL) was added morpholine (1.0 mL, 11.0 mmol) and the reaction was stirred at room temperature overnight. The solvent was removed in vacuo, then the residue was dissolved in diethyl ether. The precipitate was filtered off and the filtrate was concentrated under reduce pressure to give the title compound as an orange solid (0.95 g).

¹H NMR (400 MHz, CDCl₃) δ 3.78–3.87 (m, 8H), 8.06 (d, 1H), 8.27 (d, 1H).

LRMS (TSP) 208 (M+Na), 191 (M+H).

Preparation 106

N'-Hydroxy-3-(4-morpholinyl)-2-pyrazinecarboximidamide

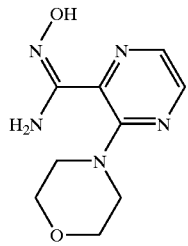

The title compound was obtained as a pale yellow solid from the title compound from Preparation 105, using a similar method to that described in Preparation 7. The product was purified by flash chromatography on silica gel (dichloromethane/methanol 95:5 as eluant).

¹H NMR (400 MHz, D₆-DMSO) δ 3.34–3.39 (m, 4H), 3.60–3.67 (m, 4H), 5.82 (s, 2H), 7.96 (d, 1H), 8.15 (d, 1H), 9.62 (s, 1H).

LRMS (TSP) 224 (M+H).

Preparation 107 tert-Butyl (3R)-6-Cyclohexyl-3-{3-[3-(4-morpholinyl)-2-pyrazinyl]-1,2,4-oxadiazol-5-yl}hexanoate

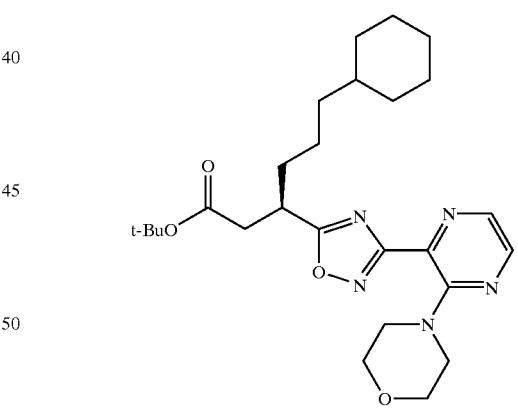

The title compound was obtained as an orange oil from the title compound from Preparation 175 and the amidoxime from Preparation 106, using a similar method to that described in Preparation 47.

¹H NMR (400 MHz, CDCl₃) δ 0.78–0.90 (m, 2H), 1.05–1.42 (m, 17H), 1.58–1.93 (m, 7H), 2.70 (dd, 1H), 2.91 (dd, 1H), 3.30–3.39 (m, 4H), 3.52–3.60 (m, 1H), 3.77–3.84 (m, 4H), 8.21 (d, 1H), 8.25 (d, 1H).

LRMS (ES) 508 (M+Na), 486 (M+H).

Preparation 108
(3R)-6-Cyclohexyl-3-{3-[3-(4-morpholinyl)-2-pyrazinyl]-1,2,4-oxadiazol-5-yl}hexanoic acid

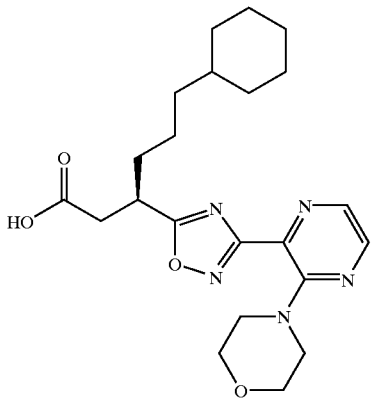

The title compound was obtained as a yellow foam from the title compound of Preparation 107, using a similar method to that described in Preparation 31. The product was washed with saturated aqueous sodium bicarbonate solution to remove trifluoroacetic acid.

$^1$H NMR (300 MHz, CDCl$_3$) δ 0.77–0.91 (m, 2H), 1.03–1.39 (m, 8H), 1.56–1.73 (m, 5H), 1.73–1.93 (m, 2H), 2.83 (dd, 1H), 3.09 (dd, 1H), 3.26–3.38 (m, 4H), 3.56–3.64 (m, 1H), 3.76–3.84 (m, 4H), 8.21 (d, 1H), 8.25 (d, 1H).
LRMS (ES) 430 (M+H).

Preparation 109
3-(1-Pyrrolidinyl)-2-pyrazinecarbonitrile

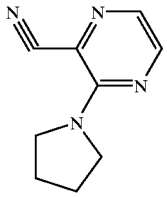

To the title compound was obtained as a yellow solid from 2-chloro-3-cyanopyrazine and pyrrolidine, using a similar method to that described in Preparation 105.

$^1$H NMR (400 MHz, CDCl$_3$) δ 2.01–2.09 (m, 4H), 3.74–3.82 (m, 4H), 7.96 (d, 1H), 8.28 (d, 1H).
LRMS (ES) 197 (M+Na), 175 (M+H).

Preparation 110
N'-Hydroxy-3-(1-pyrrolidinyl)-2-pyrazinecarboximidamide

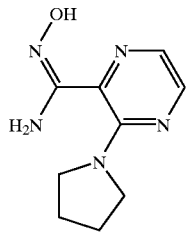

To a solution of hydroxylamine hydrochloride (0.24 g, 3.5 mmol) in methanol (30 mL) was added sodium metal (0.08 g, 3.5 mmol) portionwise. A solution of the title compound of Preparation 109 (0.60 g, 3.5 mmol) in methanol (10 mL) was added and the reaction was heated to reflux for 6 hours. The reaction was cooled to room temperature, the residue was dissolved in ethyl acetate (100 mL) and washed with water (50 mL). The organic layer was dried (MgSO$_4$) and the solvent was removed in vacuo. The residue was recrystallised from ethyl acetate to give the title compound as a yellow solid (0.32 g).

$^1$H NMR (400 MHz, D$_6$-DMSO) δ 1.81–1.87 (m, 4H), 3.39–3.65 (m, 4H), 5.80 (s, 2H), 7.77 (d, 1H), 8.05 (d, 1H), 9.43 (s, 1H).
LRMS (ES) 230 (M+Na), 208 (M+H).

Preparation 111
tert-Butyl (3R)-6-Cyclohexyl-3-{3-[3-(1-pyrrolidinyl)-2-pyrazinyl]-1,2,4-oxadiazol-5-yl}hexanoate

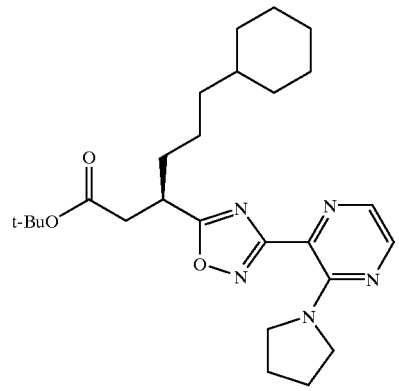

The title compound was obtained as a yellow oil from the title compound from Preparation 175 and the amidoxime from Preparation 110, using a similar method to that described in Preparation 47.

$^1$H NMR (400 MHz, CDCl$_3$) δ 0.78–0.90 (m, 2H), 1.07–1.47 (m, 17H), 1.58–1.93 (m, 1H), 2.69 (dd, 1H), 2.92 (dd, 1H), 3.23–3.34 (m, 4H), 3.51–3.59 (m, 1H), 7.99 (s, 1H), 8.17 (s, 1H).
LRMS (TSP) 471 (M+H).

Preparation 112
(3R)-6-Cyclohexyl-3-{3-[3-(1-pyrrolidinyl)-2-pyrazinyl]-1,2,4-oxadiazol-5-yl}hexanoic acid

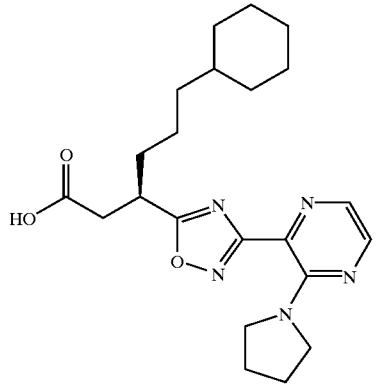

The title compound was obtained as a yellow foam from the title compound of Preparation 111, using a similar method to that described in Preparation 31.

$^1$H NMR (400 MHz, CDCl$_3$) δ 0.78–0.91 (m, 2H), 1.06–1.40 (m, 8H), 1.57–1.95 (m, 11H), 2.82 (dd, 1H), 3.08

(dd, 1H), 3.22–3.33 (m, 4H), 3.56–3.63 (m, 1H), 8.00 (d, 1H), 8.17 (d, 1H).

LRMS (ES) 436 (M+Na), 414 (M+H).

Preparation 113
3-(Dimethylamino)-2-pyrazinecarbonitrile

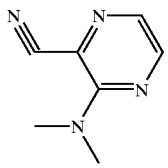

The title compound was obtained as a yellow solid from 2-chloro-3-cyanopyrazine and dimethylamine (33% in ethanol), using a similar method to that described in Preparation 105.

$^1$H NMR (400 MHz, CDCl$_3$) δ 3.34 (s, 6H), 7.93 (d, 1H), 8.21 (d, 1H).

LRMS (ES) 149 (M+H).

Preparation 114
3-(Dimethylamino)-N'-hydroxy-2-pyrazinecarboximidamide

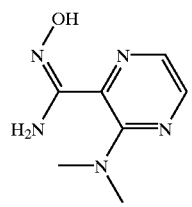

The title compound was obtained as a pale yellow solid from the title compound of Preparation 113, using a similar method to that described in Preparation 110.

$^1$H NMR (400 MHz, D$_6$-DMSO) δ 2.97 (s, 6H), 5.78 (s, 2H), 7.82 (d, 1H), 8.06 (d, 1H), 9.49 (s, 1H).

LRMS (ES) 204 (M+Na), 182 (M+H).

Preparation 115
tert-Butyl (3R)-6-Cyclohexyl-3-{3-[3-(dimethylamino)-2-pyrazinyl]-1,2,4-oxadiazol-5-yl}hexanoate

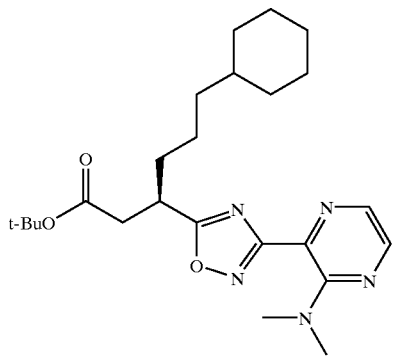

The title compound was obtained as a yellow oil from the title compound from Preparation 175 and the amidoxime from Preparation 114, using a similar method to that described in Preparation 47.

$^1$H NMR (400 MHz, CDCl$_3$) δ 0.78–0.90 (m, 2H), 1.08–1.37 (m, 8H), 1.39 (s, 9H), 1.58–1.90 (m, 7H), 2.69 (dd, 1H), 2.87–2.98 (m, 7H), 3.51–3.59 (m, 1H), 8.07 (d, 1H), 8.17 (d, 1H).

LRMS (ES) 466 (M+Na), 444 (M+H).

Preparation 116
(3R)-6-Cyclohexyl-3-{3-[3-(dimethylamino)-2-pyrazinyl]-1,2,4-oxadiazol-5-yl}hexanoic acid

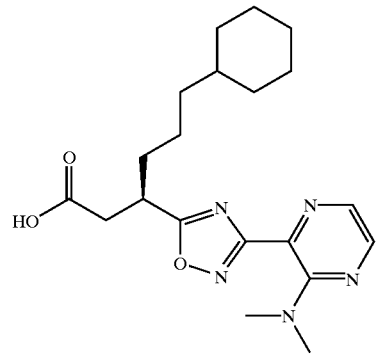

The title compound was obtained as a yellow oil from the title compound of Preparation 115, using a similar method to that described in Preparation 31.

$^1$H NMR (400 MHz, CDCl$_3$) δ 0.77–0.89 (m, 2H), 1.05–1.40 (m, 8H), 1.55–1.70 (m, 5H), 1.70–1.93 (m, 2H), 2.82 (dd, 1H), 2.90 (s, 6H), 3.09 (dd, 1H), 3.53–3.61 (m, 1H), 8.06 (d, 1H), 8.17 (d, 1H).

LRMS (ES) 410 (M+Na), 388 (M+H).

Preparation 117
N'-Hydroxy-3-(methylamino)-2-pyrazinecarboximidamide

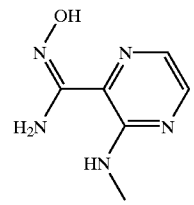

To a solution of 2-methylamino-3-cyanopyrazine (J. Heterocycl. Chem. 1992, 29, 1689–92) (0.37 g, 2.8 mmol) in methanol (10 mL) was added triethylamine (0.4 mL, 2.8 mmol) followed by hydroxylamine hydrochloride (0.19 g, 2.8 mmol) and the reaction was stirred at room temperature for 4 hours. The mixture was filtered, the filtrate was then evaporated to dryness. The residue was dissolved in ethyl acetate (50 mL) and washed with water (50 mL). The organic layer was dried (MgSO$_4$) and the solvent was removed in vacuo to give the title compound was a white solid (0.45 g).

$^1$H NMR (400 MHz, D$_6$-DMSO) δ 2.93 (d, 3H), 5.95 (s, 2H), 7.77 (d, 1H), 8.06 (d, 1H), 8.34 (br, 1H), 10.20 (s, 1H).

LRMS (ES) 167 (M+H).

Preparation 118 tert-Butyl (3R)-6-Cyclohexyl-3-{3-[3-(methylamino)-2-pyrazinyl]-1,2,4-oxadiazol-5-yl}hexanoate

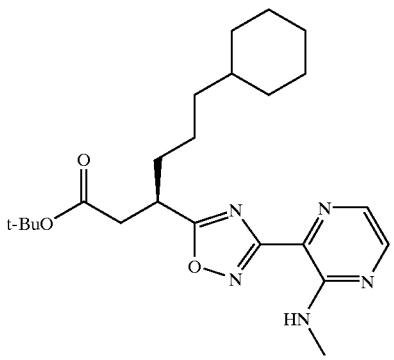

The title compound was obtained as a yellow oil from the title compound from Preparation 175 and the amidoxime from Preparation 117, using a similar method to that described in Preparation 47.

$^1$H NMR (400 MHz, CDCl$_3$) δ 0.78–0.92 (m, 2H), 1.04–1.40 (m, 17H), 1.56–1.80 (m, 6H), 1.80–1.93 (m, 1H), 2.70 (dd, 1H), 2.97 (dd, 1H), 3.15 (d, 3H), 3.54–3.61 (m, 1H), 8.03 (d, 1H), 8.20 (d, 1H).

LRMS (ES) 452 (M+Na), 430 (M+H).

Preparation 119

(3R)-6-Cyclohexyl-3-{3-[3-(methylamino)-2-pyrazinyl]-1,2,4-oxadiazol-5-yl}hexanoic acid

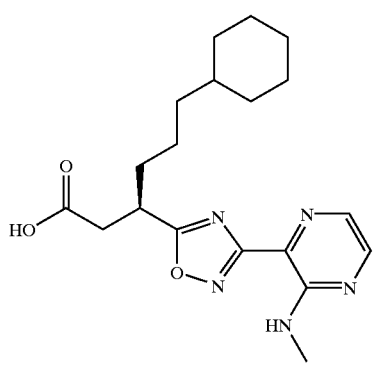

The title compound was obtained as a yellow oil from the title compound of Preparation 118, using a similar method to that described in Preparation 31.

$^1$H NMR (400 MHz, CDCl$_3$) δ 0.77–0.89 (m, 2H), 1.02–1.38 (m, 8H), 1.55–1.71 (m, 5H), 1.71–1.92 (m, 2H), 2.83 (dd, 1H), 3.05 (dd, 1H), 3.13 (d, 3H), 3.54–3.63 (m, 1H), 8.01 (d, 1H), 8.20 (d, 1H).

LRMS (ES) 396 (M+Na), 374 (M+H).

Preparation 120 tert-Butyl (3R)-6-Cyclohexyl-3-(3-phenyl-1,2,4-oxadiazol-5-yl)hexanoate

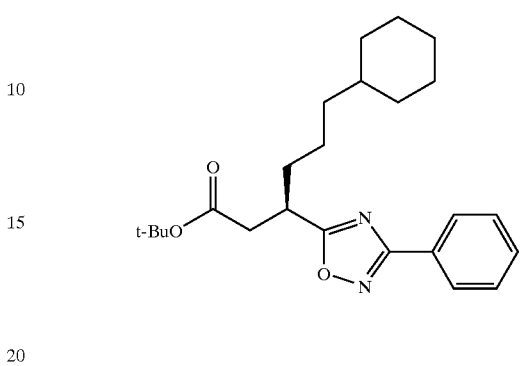

The title compound was obtained as a yellow oil from the title compound from Preparation 175 and N'-hydroxybenzenecarboximidamide, using a similar method to that described in Preparation 47.

$^1$H NMR (300 MHz, CDCl$_3$) δ 0.78–0.92 (m, 2H), 1.06–1.45 (m, 17H), 1.58–1.88 (m, 7H), 2.68 (dd, 1H), 2.88 (dd, 1H), 3.46–3.58 (m, 1$), 7.43–7.53 (m, 3H), 8.05–8.12 (m, 2H).

LRMS (TSP) 399 (M+H).

Preparation 121

(3R)-6-Cyclohexyl-3-(3-phenyl-1,2,4-oxadiazol-5-yl)hexanoic acid

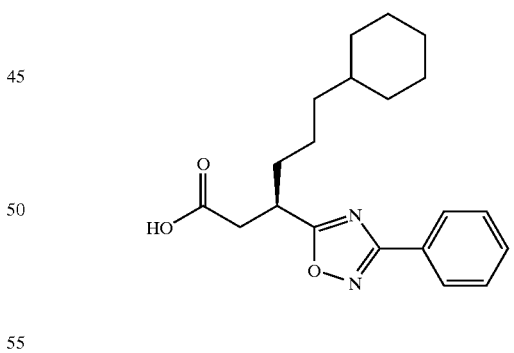

The title compound was obtained as a colorless oil from the title compound of Preparation 120, using a similar method to that described in Preparation 31.

$^1$H NMR (300 MHz, CDCl$_3$) δ 0.78–0.92 (m, 2H), 1.05–1.38 (m, 8H), 1.59–1.89 (m, 7H), 2.80 (dd, 1H), 3.05 (dd, 1H), 3.46–3.60 (m, 1H), 7.41–7.52 (m, 3H), 8.04–8.11 (m, 2H).

LRMS (TSP) 343 (M+H).

Preparation 122 tert-Butyl (3R)-6-Cyclohexyl-3-[3-(4-methoxyphenyl)-1,2,4-oxadiazol-5-yl]hexanoate

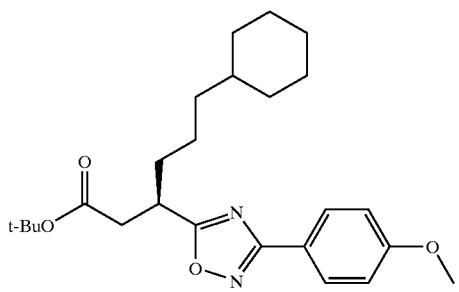

The title compound was obtained as a colorless oil from the title compound from Preparation 175 and N'-hydroxy-4-methoxybenzenecarboximidamide, using a similar method to that described in Preparation 49.

$^1$H NMR (400 MHz, CDCl$_3$) δ 0.79–0.91(m, 2H), 1.08–1.47 (m, 17H), 1.57–1.90 (m, 7H), 2.66 (dd, 1H), 2.86 (dd, 1H), 3.46–3.58 (m, 1H), 3.85 (s, 3H), 6.97 (d, 2H), 8.00 (d, 2H).

LRMS (TSP) 428 (M).

Preparation 123

(3R)-6-Cyclohexyl-3-[3-(4-methoxyphenyl)-1,2,4-oxadiazol-5-yl]hexanoic acid

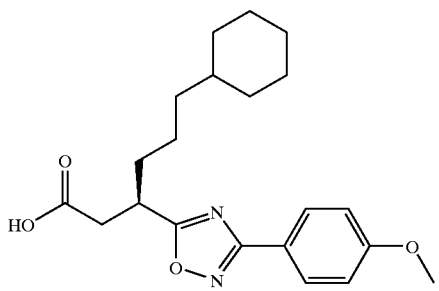

The title compound was obtained as a pale yellow oil from the title compound of Preparation 122, using a similar method to that described in Preparation 9.

$^1$H NMR (400 MHz, CDCl$_3$) δ 0.78–0.90 (m, 2H), 1.07–1.26 (m, 6H), 1.26–1.38 (m, 2H), 1.57–1.71 (m, 5H), 1.71–1.89 (m, 2H), 2.79 (dd, 1H), 3.02 (dd, 1H), 3.50–3.58 (m, 1H), 3.87 (s, 3H), 6.98 (d, 2H), 8.00 (d, 2H).

LRMS (ES) 373 (M+H).

Preparation 124 tert-Butyl (3R)-3-[3-(1,3-benzodioxol-5-yl)-1,2,4-oxadiazol-5-yl]-6-cyclohexyl hexanoate

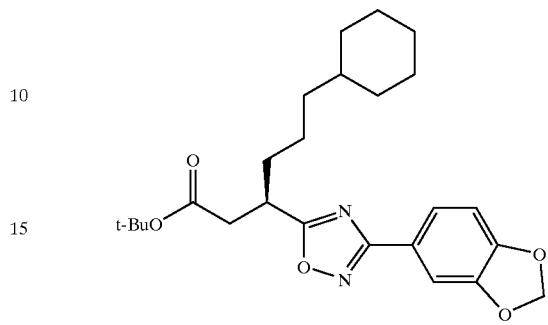

The title compound was obtained as a colorless oil from the title compound from Preparation 175 and N'-hydroxy-1,3-benzodioxole-5-carboximidamide, using a similar method to that described in Preparation 47.

$^1$H NMR (300 MHz, CDCl$_3$) δ 0.77–0.91 (m, 2H), 1.03–1.46 (m, 17H), 1.58–1.90 (m, 7H), 2.66 (dd, 1H), 2.86 (dd, 1H), 3.44–3.53 (m, 1H), 6.05 (s, 2H), 6.90 (d, 1H), 7.52 (s, 1H), 7.65 (d, 1H).

LRMS (TSP) 443 (M+H).

Preparation 125

(3R)-3-[3-(1,3-Benzodioxol-5-yl)-1,2,4-oxadiazol-5-yl]-6-cyclohexylhexanoic acid

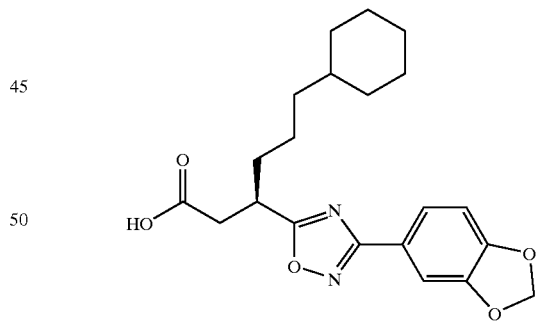

The title compound was obtained as a pale yellow oil from the title compound of Preparation 124, using a similar method to that described in Preparation 31.

$^1$H NMR (300 MHz, CDCl$_3$) δ 0.77–0.92 (m, 2H), 1.04–1.40 (m, 8H), 1.56–1.92 (m, 7H), 2.80 (dd, 1H), 3.03 (dd, 1H), 3.48–3.59 (m, 1H), 6.03 (s, 2H), 6.89 (d, 1H), 7.52 (s, 1H), 7.63 (d, 1H).

LRMS (TSP) 387 (M+H).

Preparation 126

Ethyl 4-{5-[(1R)-1-(2-tert-butoxy-2-oxoethyl)-4-cyclohexylbutyl]-1,2,4-oxadiazol-3-yl}benzoate

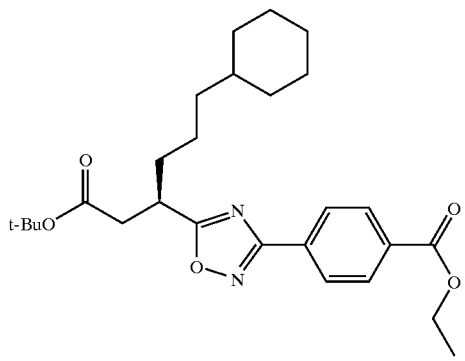

The title compound was obtained as a yellow oil from the title compound from Preparation 175 and ethyl 4-[amino(hydroxyimino)methyl]benzoate (J. Med. Chem. 1972, 15, 1194), using a similar method to that described in Preparation 49.

$^1$H NMR (400 MHz, CDCl$_3$) δ 0.79–0.90 (m, 2H), 1.04–1.27 (m, 6H), 1.27–1.47 (m, 14H), 1.57–1.90 (m, 7H), 2.70 (dd, 1H), 2.88 (dd, 1H), 3.49–3.58 (m, 1H), 4.42 (q, 2H), 8.14 (s, 4H).

LRMS (ES) 472 (M+H).

Preparation 127

(3R)-6-Cyclohexyl-3-{3-[4-(ethoxycarbonyl)phenyl]-1,2,4-oxadiazol-5-yl}hexanoic acid

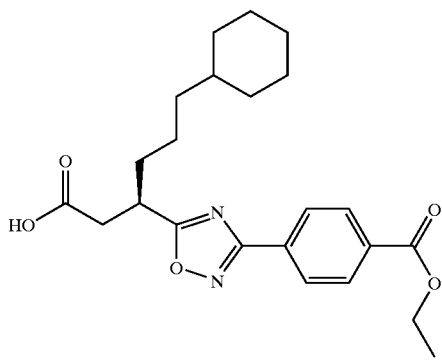

The title compound was obtained as a yellow oil from the title compound of Preparation 126, using a similar method to that described in Preparation 70. The reaction was carried out using dichloromethane as a co-solvent.

$^1$H NMR (400 MHz, CDCl$_3$) δ 0.78–0.88 (m, 2H), 1.05–1.37 (m, 8H), 1.41 (t, 3H), 1.57–1.70 (m, 5H), 1.70–1.90 (m, 2H), 2.81 (dd, 1H), 3.03 (dd, JH), 3.54–3.60 (m, 1H), 4.40 (q, 2H), 8.14 (s, 4H).

LRMS (ES) 415 (M+H).

Preparation 128 tert-Butyl (3R)-6-Cyclohexyl-3-[3-(4-nitrophenyl)-1,2,4-oxadiazol-5-yl]hexanoate

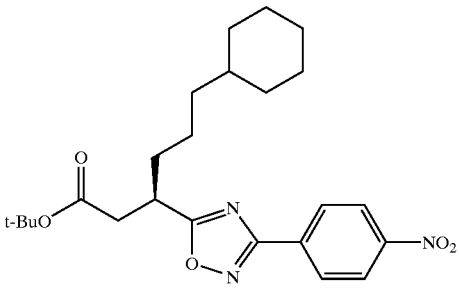

The title compound was obtained as a yellow oil from the title compound from Preparation 175 and N'-hydroxy-4-nitrobenzenecarboximidamide, using a similar method to that described in Preparation 49. The cyclisation was carried out in toluene at 110° C.

$^1$H NMR (400 MHz, CDCl$_3$) δ 0.80–0.94 (m, 2H), 1.00–1.47 (m, 17H), 1.57–1.94 (m, 7H), 2.70 (dd, 1H), 2.88 (dd, 1H), 3.50–3.59 (m, 1H), 8.08 (d, 2H), 8.14 (d, 2H),

LRMS (TSP) 444 (M+H).

Preparation 129 tert-Butyl (3R)-3-[3-(4-aminophenyl)-1,2,4-oxadiazol-5-yl]-6-cyclohexylhexanoate

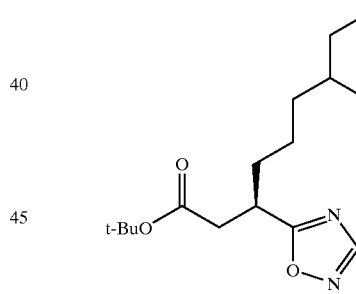

To a solution of the title compound from Preparation 128 (0.41 g, 0.9 mmol) in ethanol (20 mL) was added tin(II) chloride dihydrate (1.04 g, 4.6 mmol) and the reaction was heated to 70° C. for 3 hours. The mixture was cooled to room temperature, poured into saturated brine solution (30 mL) and then extracted with ethyl acetate (100 mL). The organic layer was washed with saturated brine solution (50 mL), dried (Na$_2$SO$_4$) and the solvent was removed in vacuo. The residue was purified by flash chromatography on silica gel (graded elution of hexane/ethyl acetate 90:10 to 50:50) to give the title compound as a pale yellow oil (0.28 g).

$^1$H NMR (300 MHz, CDCl$_3$) δ 0.78–0.93 (m, 2H), 1.03–1.47 (m, 17H), 1.56–1.90 (m, 7H), 2.72 (dd, 1H), 2.81 (dd, 1H), 3.40–3.51 (m, 1H), 6.74 (d, 2H), 7.76 (d, 2H).

LRMS (TSP) 414 (M+H).

Preparation 130
(3R)-3-[3-(4-Aminophenyl)-1,2,4-oxadiazol-5-yl]-6-cyclohexylhexanoic acid

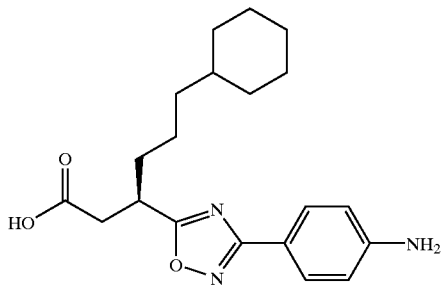

The title compound of Preparation 129 (0.63 g, 1.6 mmol) was dissolved in dichloromethane (15 mL) and trifluoroacetic acid (5 mL) and the reaction was stirred at room temperature overnight. The solvent was removed in vacuo, and the residue was azeotroped with toluene and then dichloromethane. The residue was dissolved in ethyl acetate (100 mL) and then washed with saturated aqueous sodium dihydrogen citrate solution (100 mL) and saturated brine solution (100 ml). The organic layer was dried (MgSO$_4$) and the solvent was removed in vacuo, then the residue was purified by flash chromatography on silica gel (dichloromethane as eluant) to give the title compound as a white solid (0.07 g).

$^1$H NMR (300 MHz, CDCl$_3$) δ 0.77–0.91 (m, 2H), 1.07–1.40 (m, 8H), 1.58–1.70 (m, 5H), 1.70–1.90 (m, 2H), 2.81 (dd, 1H), 3.03 (dd, 1H), 3.48–3.57 (m, 1H), 6.72 (d, 2H), 7.85 (d, 2H).

LRMS (TSP) 358 (M+H).

Preparation 131
(3R)-6-Cyclohexyl-3-(3-{4-[(dimethylamino)sulfonyl]phenyl}-1,2,4-oxadiazol-5-yl)hexanoic acid

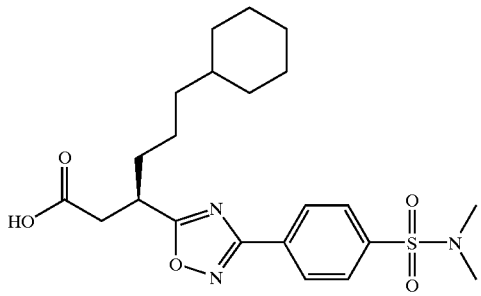

To a suspension of the title compound of Preparation 130 (0.13 g, 0.36 mmol) in glacial acetic acid (2.5 mL) and concentrated hydrochloric acid (2.5 mL) at −10 to −15° C. (ice-salt bath) was added sodium nitrite (0.04 g, 0.54 mmol) and the reaction was stirred at 0° C. for 1 hour. The mixture was then re-cooled to −10 to −15° C. and liquid sulfur dioxide was added (3–4 mL) followed by a solution of copper(II) chloride (0.14 g, 1.1 mmol) in water (approx 0.5 mL). The reaction was warmed to room temperature and stirred for 1 hour, then extracted with dichloromethane (20 mL). The aqueous layer was extracted with dichloromethane (3×20 mL), the combined organic extracts were dried (Na$_2$SO$_4$) and the solvent was removed in vacuo. The residue was azeotroped with toluene to remove acetic acid, then dissolved in dichloromethane (15 mL), cooled to 0° C. and dimethylamine (0.3 mL, 1.7 mmol) was added. The reaction was stirred at room temperature overnight, then the solvent was removed in vacuo and the residue was partitioned between dichloromethane (20 mL) and saturated sodium bicarbonate solution (20 mL). The organic layer was washed with saturated sodium bicarbonate solution (2×20 mL), saturated brine solution (20 mL) then dried (Na2SO4) and the solvent was removed in vacuo. The residue was purified by flash chromatography on silica gel (graded elution of dichloromethane/methanol 100:0 to 99:1 to 98:2) to give the title compound as a yellow oil (0.07 g).

$^1$H NMR (300 MHz, CDCl$_3$) δ 0.77–0.90 (m, 2H), 1.03–1.39 (m, 8H), 1.58–1.73 (m, 5H), 1.73–1.92 (m, 2H), 2.72 (s, 6H), 2.81 (dd, 1H), 3.04 (dd, 1H), 3.54–3.61 (m, 1H), 7.89 (d, 2H), 8.25 (d, 2H).

LRMS (TSP) 450 (M+H).

Preparation 132
tert-Butyl (3R)-6-Cyclohexyl-3-(3-{4-[(methylsulfonyl)amino]phenyl}-1,2,4-oxadiazol-5-yl)hexanoate

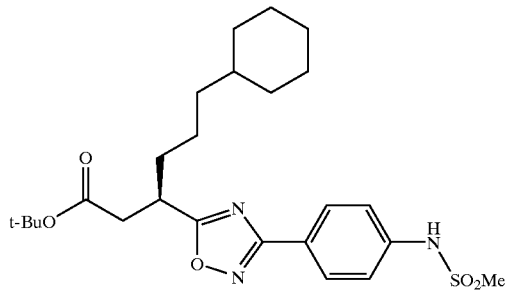

To a solution of the title compound from Preparation 129 (0.06 g, 0.14 mmol) in dichloromethane (10 mL) was added pyridine (0.013 mL, 0.16 mmol) and methanesulfonyl chloride (0.012 mL, 0.16 mmol). The reaction was heated to 40° C. then a solution of 4-dimethylaminopyridine (0.004 g, 0.03 mmol) in dichloromethane (5 mL) was added and the reaction was heated at reflux overnight. The mixture was cooled to room temperature, 1M aqueous hydrochloric acid (20 mL) was added, and the aqueous layer was extracted with dichloromethane (2×20 mL). The combined organic extracts were washed with saturated aqueous sodium bicarbonate solution (20 mL), saturated aqueous brine solution (20 mL) then dried (Na$_2$SO$_4$). The solvent was removed in vacuo, and the residue was purified by flash chromatography on silica gel (graded elution of hexane/ethyl acetate 90:10 to 70:30) to give the title compound as a colorless oil (0.06 g).

$^1$H NMR (300 MHz, CDCl$_3$) δ 0.78–0.92 (m, 2H), 1.07–1.44 (m, 17H), 1.60–1.90 (m, 7H), 2.68 (dd, 1H), 2.86 (dd, 1H), 3.08 (s, 3H), 3.46–3.58 (m, 1H), 7.07 (s, 1H), 7.32 (d, 2H), 8.07 (d, 2H).

LRMS (ES) 514 (M+Na), 492 (M+H).

Preparation 133
(3R)-6-Cyclohexyl-3-(3-{4-[(methylsulfonyl)amino]phenyl}-1,2,4-oxadiazol-5-yl)hexanoic acid

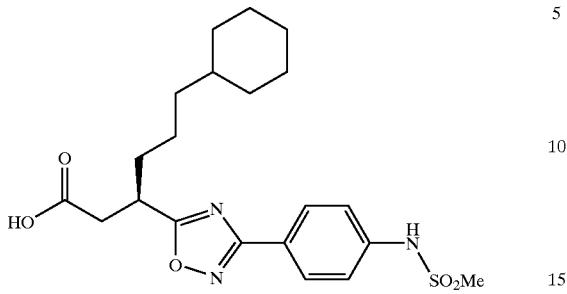

The title compound was obtained as a white foam from the title compound of Preparation 132, using a similar method to that described in Preparation 130.

$^1$H NMR (300 MHz, CDCl$_3$) δ 0.77–0.90 (m, 2H), 1.00–1.38 (m, 8H), 1.58–1.86 (m, 7H), 2.74–2.82 (m, 1H), 2.92–3.08 (m, 4H), 3.46–3.58 (m, 1H), 7.20 (d, 2H), 7.65 (br s, 1H), 7.94 (d, 2H).

LRMS (TSP) 436 (M+H).

Preparation 134
Ethyl 3-[Amino(hydroxyimino)methyl]benzoate

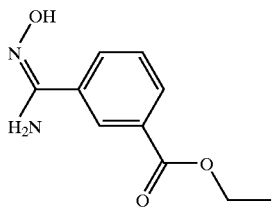

The title compound was obtained as a white solid from ethyl-(3-cyanophenyl)-carboxylate, using a similar method to that described in Preparation 117.

$^1$H NMR (400 MHz, CD$_3$OD) δ 1.40 (t, 3H), 4.38 (q, 2H), 7.50 (dd, 1H), 7.85 (d, 1H), 8.06 (d, 1H), 8.32 (s, 1H).

LRMS (ES) 209 (M+H).

Preparation 135
Ethyl 3-{5-[(1R)-1-(2-tert-butoxy-2-oxoethyl)-4-cyclohexylbutyl]-1,2,4-oxadiazol-3-yl}benzoate

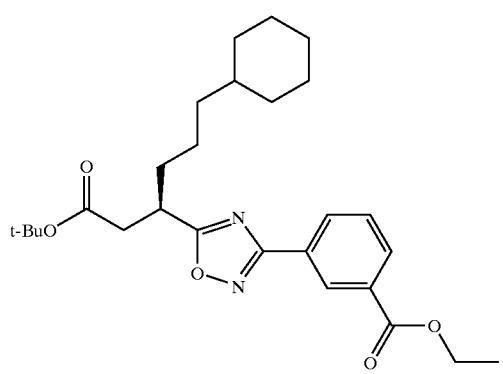

The title compound was obtained as a yellow oil from the title compound from Preparation 175 and the amidoxime from Preparation 134, using a similar method to that described in Preparation 47.

$^1$H NMR (300 MHz, CDCl$_3$) δ 0.78–0.91 (m, 2H), 1.04–1.45 (m, 20H), 1.55–1.93 (m, 7H), 2.69 (dd, 1H), 2.88 (dd, 1H), 3.48–3.59 (m, 1H), 4.42 (q, 2H), 7.57 (dd, 1H), 8.18 (d, 1H), 8.26 (d, 1H), 8.74 (s, 1H).

LRMS (ES) 452 (M+Na), 430 (M+H).

Preparation 136
(3R)-6-Cyclohexyl-3-{3-[3-(ethoxycarbonyl)phenyl]-1,2,4-oxadiazol-5-yl}hexanoic acid

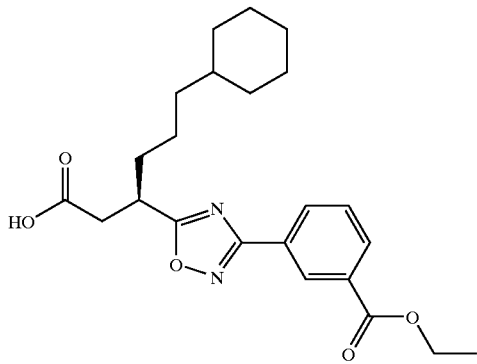

The title compound was obtained as a yellow oil from the title compound of Preparation 135, using a similar method to that described in Preparation 70. The reaction was carried out using dichloromethane as a co-solvent.

$^1$H NMR (300 MHz, CDCl$_3$) δ 0.77–0.91 (m, 2H), 1.04–1.45 (m, 1H), 1.55–1.70 (m, 5H), 1.70–1.93 (m, 2H), 2.81 (dd, 1H), 3.06 (dd, 1H), 3.52–3.62 (m, 1H), 4.42 (q, 2H), 7.57 (dd, 1H), 8.18 (d, 1H), 8.24 (d, 1H), 8.74 (s, 1H).

LRMS (TSP) 414 (M).

Preparation 137
tert-Butyl (3R)-6-Cyclohexyl-3-[3-(3,5-dimethoxyphenyl)-1,2,4-oxadiazol-5-yl]hexanoate

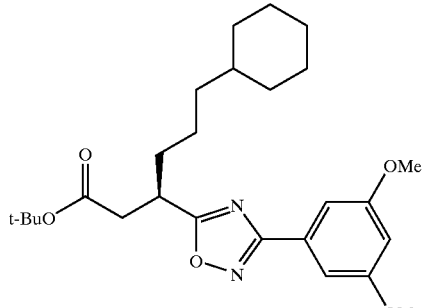

The title compound was obtained as a colorless oil from the title compound from Preparation 175 and N-hydroxy-3,5-dimethoxybenzenecarboximidamide, using a similar method to that described in Preparation 47.

$^1$H NMR (400 MHz, CDCl$_3$) δ 0.78–0.90 (m, 2H), 1.04–1.25 (m, 6H), 1.27–1.36 (m, 2H), 1.39 (s, 9H), 1.58–1.89 (m, 7H), 2.69 (dd, 1H), 2.88 (dd, 1H), 3.48–3.57 (m, 1H), 3.85 (s, 6H), 6.59 (s, 1H), 7.24 (s, 2H).

LRMS (TSP) 459 (M+H).

Preparation 138
(3R)-6-Cyclohexyl-3-[3-(3,5-dimethoxyphenyl)-1,2,4-oxadiazol-5-yl]hexanoic acid

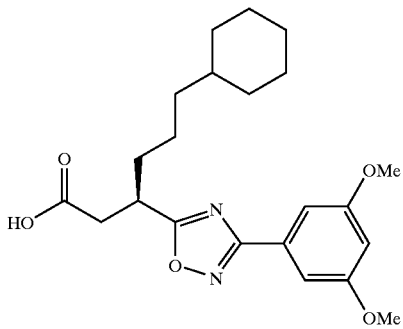

The title compound was obtained as a white solid from the title compound of Preparation 137, using a similar method to that described in Preparation 31.

$^1$H NMR (400 MHz, CDCl$_3$) δ 0.78–0.91 (m, 2H), 1.02–1.26 (m, 6H), 1.26–1.40 (m, 2H), 1.58–1.70 (m, 5H), 1.70–1.90 (m, 2H), 2.80 (dd, 1H), 3.05 (dd, 1H), 3.50–3.59 (m, 1H), 3.85 (s, 6H), 6.59 (s, 1H), 7.24 (s, 2H).

LRMS (TSP) 403 (M+H).

Preparation 139
N'-Hydroxy-1H-pyrazole-4-carboximidamide

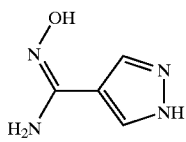

The title compound was obtained as a white solid from 4-cyanopyrazole using a similar method to that described in Preparation 110.

$^1$H NMR (400 MHz, CD$_3$OD) δ 5.60 (br s, 2H), 7.67 (br s, 1H), 7.93 (br s, 1H), 9.07 (br s, 1H), 12.85 (br s, 1H).

Preparation 140
tert-Butyl (3R)-6-Cyclohexyl-3-[3-(1H-pyrazol-4-yl)-1,2,4-oxadiazol-5-yl]hexanoate

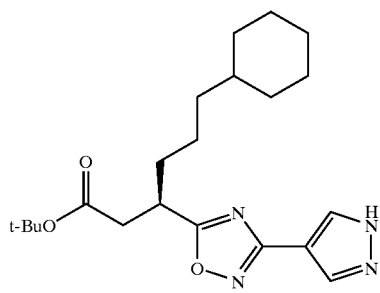

The title compound was obtained as a yellow oil from the title compound from Preparation 175 and the amidoxime from Preparation 139, using a similar method to that described in Preparation 47.

$^1$H NMR (400 MHz, CDCl$_3$) δ 0.78–0.91 (m, 2H), 1.05–1.47 (m, 17H), 1.58–1.87 (m, 7H), 2.67 (dd, 1H), 2.85 (dd, 1H), 3.46–3.54 (m, 1H), 7.98 (s, 1H), 8.15 (s, 2H), LRMS (TSP) 389 (M+H).

Preparation 141
(3R)-6-Cyclohexyl-3-[3-(1H-pyrazol-4-yl)-1,2,4-oxadiazol-5-yl]hexanoic acid

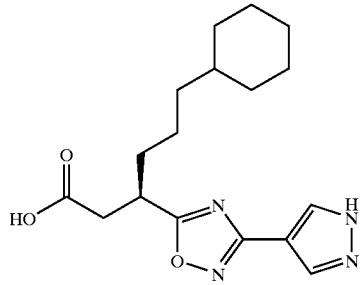

The title compound was obtained as a white solid from the title compound of Preparation 140, using a similar method to that described in Preparation 31. The product was purified by flash chromatography on silica gel (dichloromethane/methanol 92.5:7.5 as eluant).

$^1$H NMR (300 MHz, CDCl$_3$) δ 0.77–0.93 (m, 2H), 1.02–1.43 (m, 8H), 1.51–1.92 (m, 7H), 2.82 (dd, 1H), 3.02 (dd, 1H), 3.47–3.59 (m, 1H), 8.09 (s, 2H).

LRMS (TSP) 332 (M).

Preparation 142
tert-Butyl (3R)-6-Cyclohexyl-3-[3-(1H-pyrazol-3-yl)-1,2,4-oxadiazol-5-yl]hexanoate

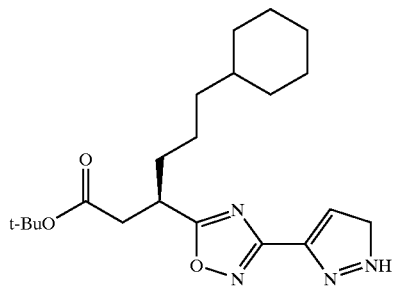

The title compound was obtained as a colorless oil from the title compound from Preparation 175 and 17-hydroxy-1H-pyrazole-3-carboximidamide, using a similar method to that described in Preparation 47.

$^1$H NMR (300 MHz, CDCl$_3$) δ 0.78–0.95 (m, 2H), 1.02–1.48 (m, 17H), 1.57–1.91 (m, 7H), 2.69 (dd, 1H), 2.90 (dd, 1H), 3.48–3.60 (m, 1H), 6.94 (s, 1H), 7.13 (s, 1H), 7.77 (s, 1H).

LRMS (ES) 389 (M+H).

Preparation 143
(3R)-6-Cyclohexyl-3-[3-(1H-pyrazol-3-yl)-1,2,4-oxadiazol-5-yl]hexanoic acid

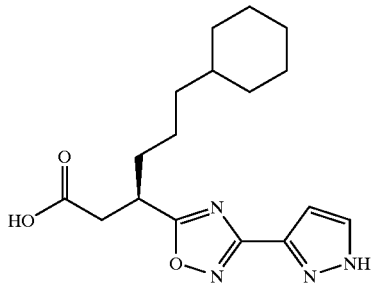

The title compound was obtained as a colorless oil from the title compound of Preparation 142, using a similar method to that described in Preparation 31.

¹H NMR (300 MHz, CDCl₃) δ 0.75–0.93 (m, 2H), 1.00–1.40 (m, 8H), 1.51–1.90 (m, 7H), 2.81 (dd, 1H), 3.01 (dd, 1H), 3.48–3.65 (m, 1H), 6.80–7.00 (br s, 1H), 7.60–7.80 (br s, 1H).

LRMS (TSP) 333 (M+H).

Preparation 144 tert-Butyl (3R)-6-Cyclohexyl-3-[3-(2-furyl)-1,2,4-oxadiazol-5-yl]hexanoate

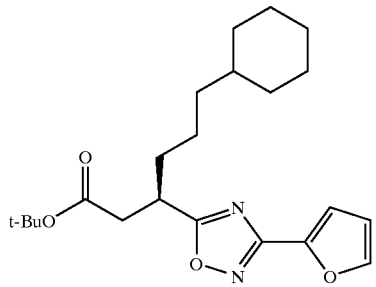

The title compound was obtained as a colorless oil from the title compound from Preparation 175 and N'-hydroxy-2-furancarboximidamide (U.S. Pat. No. 3,767,646), using a similar method to that described in Preparation 47.

¹H NMR (400 MHz, CDCl₃) δ 0.78–0.89 (m, 2H), 1.05–1.44 (m, 17H), 1.57–1.88 (m, 7H), 2.66 (dd, 1H), 2.85 (dd, 1H), 3.47–3.56 (m, 1H), 6.56 (d, 1H), 7.12 (d, 1H), 7.60 (s, 1H).

LRMS (ES) 389 (M+H).

Preparation 145

(3R)-6-Cyclohexyl-3-[3-(2-furyl)-1,2,4-oxadiazol-5-yl]hexanoic acid

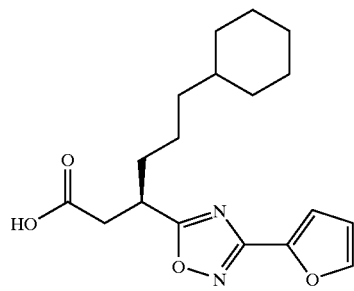

The title compound was obtained as a colorless oil from the title compound of Preparation 144, using a similar method to that described in Preparation 31.

¹H NMR (400 MHz, CDCl₃) δ 0.78–0.93 (m, 2H), 1.05–1.39 (m, 8H), 1.58–1.89 (m, 7H), 2.81 (dd, 1H), 3.03 (dd, 1H), 3.52–3.61 (m, 1H), 6.57 (d, 1H), 7.14 (d, 1H), 7.62 (s, 1H).

LRMS (TSP) 333 (M+H).

Preparation 146

N'-Hydroxy-3-quinolinecarboximidamide

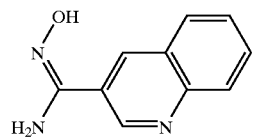

The title compound was obtained as a white solid from 3-cyanoquinoline using a similar method to that described in Preparation 110.

¹H NMR (300 MHz, D₆-DMSO) δ 6.08 (s, 2H), 7.62 (dd, 1H), 7.76 (dd, 1H), 7.76 (dd, 1H), 7.96 (d, 1H), 8.02(d, 1H), 8.56 (d, 1H), 9.12 (d, 1H), 9.97 (s, 1H).

Preparation 147 tert-Butyl (3R)-6-Cyclohexyl-3-[3-(3-quinolinyl)-1,2,4-oxadiazol-5-yl]hexanoate

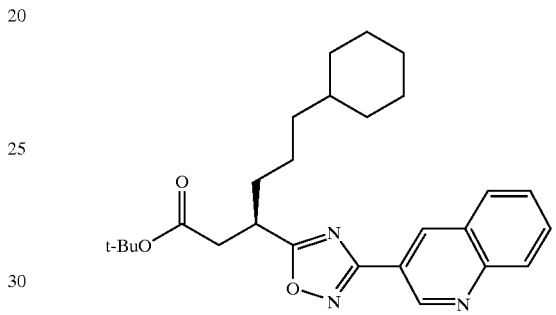

The title compound was obtained as a clear oil from the title compound from Preparation 175 and the amidoxime from Preparation 146, using a similar method to that described in Preparation 49.

¹H NMR (400 MHz, CDCl₃) δ 0.80–0.92 (m, 2H), 1.09–1.26 (m, 6H), 1.31–1.44 (m, 11H), 1.58–1.71 (m, 5H), 1.71–1.92 (m, 2H), 2.73 (dd, 1H), 2.92 (dd, 1H), 3.54–3.62 (m, 1H), 7.63 (dd, 1H), 7.80 (dd, 1H), 7.94 (d, 1H), 8.17 (d, 1H), 8.86 (d, 1H), 9.55 (d, 1H).

LRMS (TSP) 450 (M).

Preparation 148

(3R)-6-Cyclohexyl-3-[3-(3-quinolinyl)-1,2,4-oxadiazol-5-yl]hexanoic acid

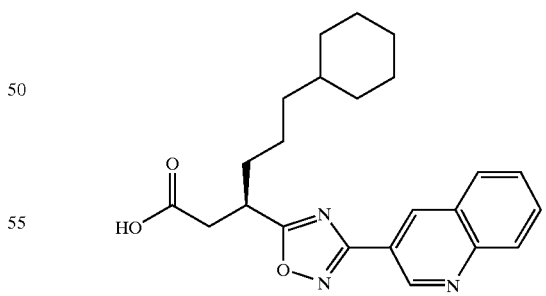

The title compound was obtained as a colorless oil from the title compound of Preparation 147, using a similar method to that described in Preparation 31.

¹H NMR (300 MHz, CDCl₃) δ 0.75–0.96 (m, 2H), 1.04–1.42 (m, 8H), 1.54–1.74 (m, 5H), 1.74–1.95 (m, 2H), 2.86 (dd, 1H), 3.07 (dd, 1H), 3.55–3.67 (m, 1H), 7.78 (dd, 1H), 7.97 (dd, 1H), 8.07 (d, 1H), 8.40 (d, 1H), 9.17 (d, 1H), 9.68 (d, 1H).

LRMS (ES) 394 (M+H).

Preparation 149
N'-Hydroxy-1-isoquinolinecarboximidamide

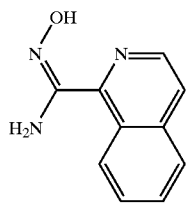

The title compound was obtained as a white solid from 1-cyanoisoquinoline using a similar method to that described in Preparation 110.

$^1$H NMR (300 MHz, D$_6$-DMSO) δ 5.94 (s, 2H), 7.67 (dd, 1H), 7.78 (dd, 1H), 7.86 (d, 1H), 7.99 (d, 1H), 8.52 (d, 1H), 9.07 (d, 1H), 10.11 (s, 1H).

Preparation 150
tert-Butyl (3R)-6-Cyclohexyl-3-[3-(1-isoquinolinyl)-1,2,4-oxadiazol-5-yl]hexanoate

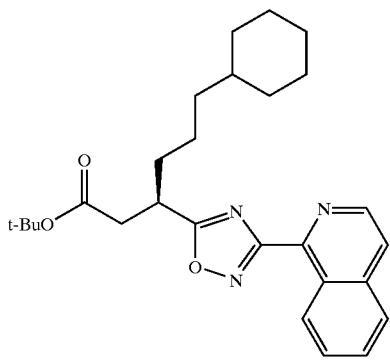

The title compound was obtained as a colorless oil from the title compound from Preparation 175 and the amidoxime from Preparation 149, using a similar method to that described in Preparation 49.

$^1$H NMR (300 MHz, CDCl$_3$) δ 0.78–0.95 (m, 2H), 1.04–1.48 (m, 17H), 1.50–1.74 (m, 5H), 1.74–2.00 (m, 2H), 2.75 (dd, 1H), 3.00 (dd, 1H), 3.60–3.71 (m, 1H), 7.65–7.85 (m, 3H), 7.92 (d, 1H), 8.77 (d, 1H), 8.98 (d, 1H).

LRMS (TSP) 451 (M+H).

Preparation 151
(3R)-6-Cyclohexyl-3-[3-(1-isoquinolinyl)-1,2,4-oxadiazol-5-yl]hexanoic acid

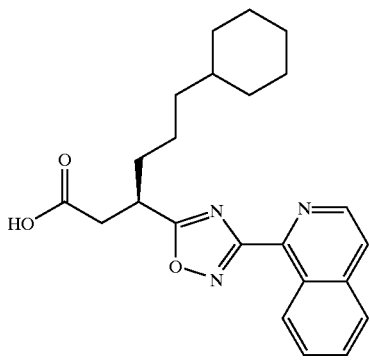

The title compound was obtained as a colorless oil from the title compound of Preparation 150, using a similar method to that described in Preparation 31.

$^1$H NMR (300 MHz, CDCl$_3$) δ 0.78–0.95 (m, 2H), 1.03–1.49 (m, 8H), 1.55–1.74 (m, 5H), 1.74–2.00 (m, 2H), 2.89 (dd, 1H), 3.20 (dd, 1H), 3.64–3.74 (m, 1H), 7.80 (dd, 1H), 7.89 (dd, 1H), 7.95–8.06 (m, 2H), 8.80 (d, 1H), 9.09 (d, 1H).

LRMS (ES) 394 (M+H).

Preparation 152
N'-Hydroxy-3-isoquinolinecarboximidamide

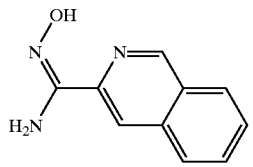

The title compound was obtained as a white solid from 3-cyanoisoquinoline using a similar method to that described in Preparation 110.

$^1$H NMR (400 MHz, D$_6$-DMSO) δ 5.93 (s, 2H), 7.67 (dd, 1H), 7.78 (dd, 1H), 8.03 (d, 1H), 8.14 (d, 1H), 8.29 (s, 1H), 9.33 (s, 1H), 9.78 (s, 1H).

Preparation 153
tert-Butyl (3R)-6-Cyclohexyl-3-[3-(3-isoquinolinyl)-1,2,4-oxadiazol-5-yl]hexanoate

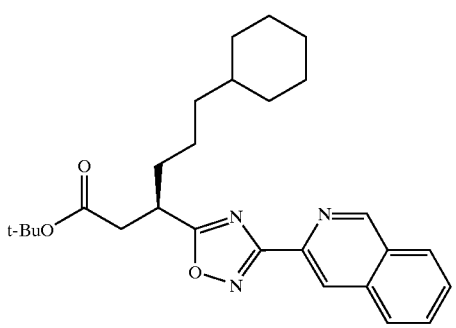

The title compound was obtained as a colorless oil from the title compound from Preparation 175 and the amidoxime from Preparation 152, using a similar method to that described in Preparation 49.

$^1$H NMR (300 MHz, CDCl$_3$) δ 0.78–0.93 (m, 2H), 1.04–1.47 (m, 17H), 1.52–1.71 (m, 5H), 1.71–1.97 (m, 2H), 2.72 (dd, 1H), 2.94 (dd, 1H), 3.56–3.64 (m, 1H), 7.71 (dd, 1H), 7.78 (dd, 1H), 7.94 (d, 1H), 8.07 (d, 1H), 8.75 (s, 1H), 9.40 (s, 1H).

LRMS (TSP) 450 (M+H).

Preparation 154

(3R)-6-Cyclohexyl-3-[3-(3-isoquinolinyl)-1,2,4-oxadiazol-5-yl]hexanoic acid

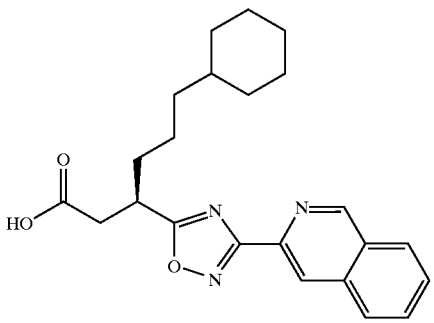

The title compound was obtained as a white solid from the title compound of Preparation 153, using a similar method to that described in Preparation 31. The product was purified by flash chromatography on silica gel (dichloromethane/methanol 96:4 as eluant).

$^1$H NMR (300 MHz, CDCl$_3$) δ 0.76–0.93 (m, 2H), 1.00–1.44 (m, 8H), 1.50–1.72 (m, 5H), 1.72–1.98 (m, 2H), 2.97 (dd, 1H), 3.18 (dd, 1H), 3.60–3.70 (m, 1H), 7.70 (dd, 1H), 7.78 (dd, 1H), 7.94 (d, 1H), 8.05 (d, 1H), 8.52 (s, 1H), 9.40 (s, 1H).

LRMS (ES) 809 (2M+Na, 30%), 416 (M+Na), 394 (M+H).

Preparation 155 tert-Butyl (3R)-3-(3-{6-[bis(methylsulfonyl)amino]-3-pyridinyl}-1,2,4-oxadiazol-5-yl)-6-cyclohexylhexanoate

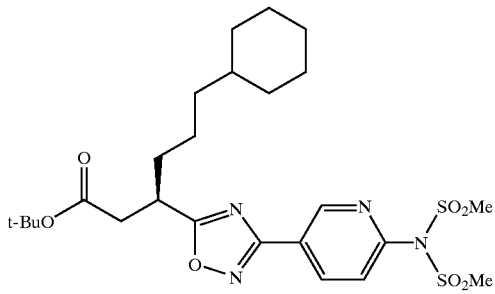

To a solution of the title compound from Preparation 58 (0.16 g, 0.4 mmol) and triethylamine (0.22 mL, 1.5 mmol) in 1,1,1-trichloroethane (10 mL) was added methanesulfonyl chloride (0.12 mL, 1.5 mmol) and the reaction was heated to 70° C. overnight. The reaction was cooled to room temperature and the solvent was removed in vacuo. The residue was dissolved in dichloromethane (10 mL) and washed with 1M hydrochloric acid solution (10 mL). The aqueous layer was basified to pH 10 and then extracted with dichloromethane (10 mL). The combined organic extracts were dried (MgSO$_4$) and the solvent was removed in vacuo. The residue was purified by flash chromatography on silica gel (hexane/ethyl acetate 3:1 as eluant) to give the title compound as a yellow solid (0.14 g).

$^1$H NMR (400 MHz, CDCl$_3$) δ 0.78–0.90 (m, 2H), 1.07–1.38 (m, 8H), 1.39 (s, 9H), 1.53–1.87 (m, 7H), 2.68 (dd, 1H), 2.86 (dd, 1H), 3.48–3.62 (m, 7H), 7.43 (d, 1H), 8.50 (d, 1H), 9.24 (s, 1H).

LRMS (ES) 593 (M+Na), 571 (M+H).

Preparation 156

(3R)-6-Cyclohexyl-3-(3-{6-[(methylsulfonyl)amino]-3-pyridinyl}-1,2,4-oxadiazol-5-yl)hexanoic acid

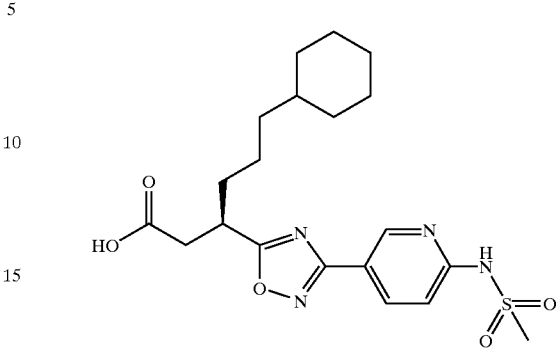

The title compound Preparation 155 (0.14 g, 0.25 mmol) was heated in a mixture of dioxane (5 mL) and 1M aqueous sodium hydroxide solution (5 mL) for 2 hours. The reaction was cooled to room temperature and washed with 2M hydrochloric acid solution (5 mL) and water (5 mL). The organic layer was dried (MgSO$_4$) and the solvent was removed in vacuo to give the title compound as a white solid (0.08 g).

$^1$H NMR (400 MHz, CD$_3$OD) δ 0.78–0.93 (m, 2H), 1.07–1.38 (m, 8H), 1.56–1.70 (m, 5H), 1.70–1.84 (m, 2H), 2.78 (dd, 1H), 2.92 (dd, 1H), 3.28 (s, 3H), 3.48–3.58 (m, 1H), 7.14 (d, 1H), 8.26 (d, 1H), 8.83 (s, 1H).

LRMS (ES) 459 (M+Na), 437 (M+H).

Preparation 157 tert-Butyl(3R)-6-Cyclohexyl-3-[3-(6-ethoxy-2-pyrazinyl)-1,2,4-oxadiazol-5-yl]hexanoate

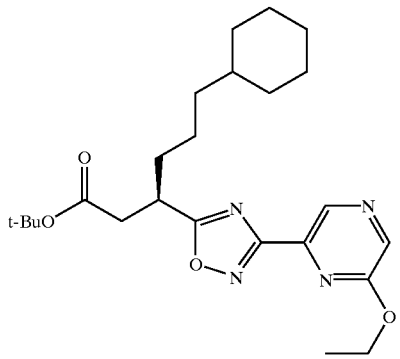

The title compound was obtained as a colorless oil from the compound of Preparation 175 and 3toyNyrxyrzncroiiaie using a similar method to that described in Preparation 47.

$^1$H NMR (400 MHz, CDCl$_3$) δ 0.78–0.88 (m, 2H, 1.07–1.24 (m, 6H), 1.24–1.34 (m, 2H), 1.40 (s, 9H), 1.44 (t, 3H), 1.58–1.70 (m, 5H), 1.71–1.92 (m, 2H), 2.72 (dd, 1H), 2.92 (dd, 1H), 3.58 (m, 1H), 4.53 (q, 2H), 8.35 (s, 1H), 8.86 (s, 1H).

LRMS (TSP) 455 (M+H).

Preparation 158

(3R)-6-Cyclohexyl-3-[3-(6-ethoxy-2-pyrazinyl)-1,2,4-oxadiazol-5-yl]hexanoic acid

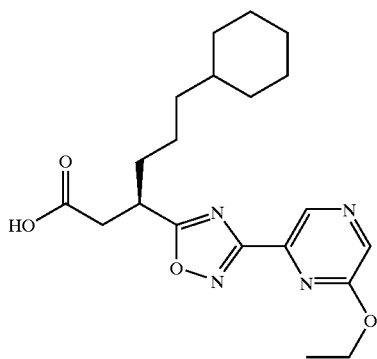

The title compound was obtained as a colorless gum from the compound of Preparation 157; using a similar method to that described in Preparation 31.

$^1$H NMR (400 MHz, CDCl$_3$) δ 0.78–0.88 (m, 2H), 1.07–1.24 (m, 6H), 1.24–1.34 (m, 2H), 1.44 (t, 3H), 1.58–1.70 (m, 5H), 1.71–1.92 (m, 2H), 2.82 (dd, 1H), 3.05 (dd, 1H), 3.58 (m, 1H), 4.53 (q, 2H), 8.35 (s, 1H), 8.86 (s, 1H).

LRMS (ES) 389 (M+H), 411 (M+Na).

Preparation 159

Tert-Butyl(3R)-3-(3-cyano-1,2,4-oxadiazol-5-yl)-6-cyclohexylhexanoate

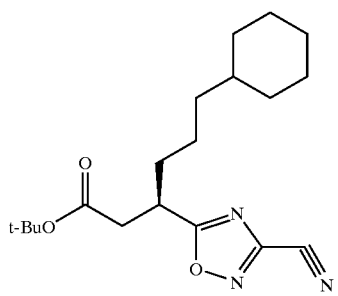

Trifluoroacetic anhydride (0.4 mL, 2.88 mmol) was added dropwise to a cooled solution of the title compound from Preparation 179 (1.0 g, 2.74 mmol) in dichloromethane (20 mL): pyridine (0.44 mL, 5.48 mmol). The reaction flask was stirred at 0° C. for 1 hour. The reaction was diluted with dichloromethane (10 mL) and washed with 5% citric acid (3×20 mL). The combined organic layers were dried (MgSO$_4$), the solvent was removed in vacuo to give the title compound as a colorless oil (0.863 g).

$^1$H NMR (400 MHz, CDCl$_3$) δ 0.79–0.94 (m, 2H), 1.08–1.39 (m, 8H), 1.41 (s, 9H), 1.60–1.85 (m, 7H), 2.70 (dd, 1H), 2.90 (dd, 1H), 3.53 (m, 1H).

LRMS (ES) 370 (M+Na).

Preparation 160

(3R)-3-[3-(1-tert-Butyl-1H-tetraazol-5-yl)-1,2,4-oxadiazol-5-yl]-6-cyclohexylhexanoic acid and (3R)-3-[3-(2-tert-Butyl-2H-tetraazol-5-yl)-1,2,4-oxadiazol-5-yl]-6-cyclohexylhexanoic acid

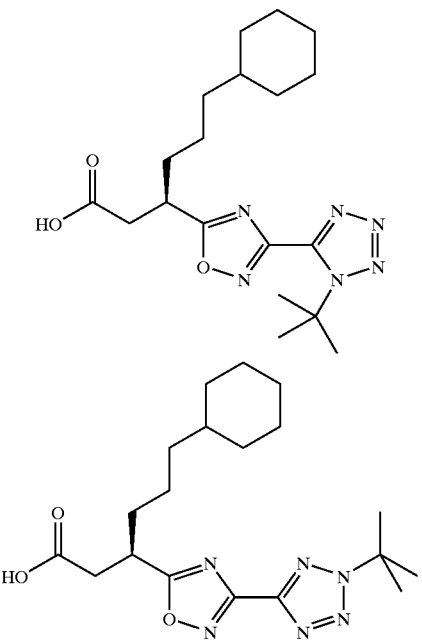

To a solution of the title compound from Preparation 159 (0.85 g, 2.45 mmol) in toluene (8 mL) was added trimethylsilyl azide (0.65 mL, 4.90 mmol) and dibutyltinoxide (0.1 g, 0.245 mmol). The reaction was heated at 100° C. for 24 hours under nitrogen, then the solvent was removed in vacuo. The residue was acidified with 2N hydrochloric acid (pH 1), diluted with water (2 mL) and extracted with ethyl acetate (2×20 mL). The combined organic layers were dried (MgSO$_4$), the solvent was removed in vacuo and the residue was purified by flash chromatography on silica gel (graded elution of dichloromethane to dichloromethane/methanol 98:2) to give the title compounds, a 1:1 mixture of tautomers, as a yellow oil (0.520 g).

$^1$H NMR (400 MHz, CDCl$_3$) δ 0.80–0.92 (m, 4H), 1.05–1.40 (m, 18H), 1.52–1.73 (m, 22H), 1.75–1.94 (m, 8H), 2.84 (m, 2H), 3.05 (m, 2H), 3.62 (m, 2H).

LRMS (ES) 389 (M–H).

Preparation 161 tert-Butyl(3R)-6-Cyclohexyl-3-{[(2-hydroxy2-Phenylethyl)amino]carbonyl}hexanoate

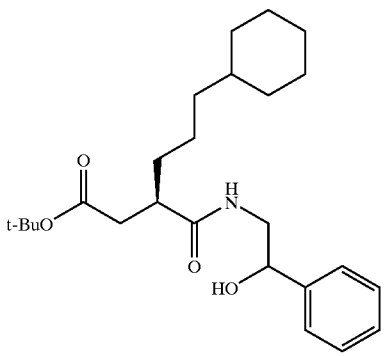

To a solution of the title compound from Preparation 175 (0.50 g, 1.86 mmol) in dichloromethane (15 mL) was added 1-hydroxybenzotriazole (0.294 g, 2.18 mmol), 1-(3-dimethylaminopropyl)-3-ethylcarbodiimide hydrochloride (0.418 g, 2.18 mmol) and 2-amino-1-phenylethanol (0.3 g, 2.18 mmol). The reaction was stirred at room temperature for 24 hours and then the solvent was remove in vacuo. The residue diluted in ethyl acetate (150 mL) and washed with 10% citric acid (100 mL), water (100 mL), saturated sodium bicarbonate solution (100 mL) and brine (100 mL). The organic layer was dried (MgSO$_4$) and concentrated in vacuo. The residue was then purified by flash chromatography on silica gel (graded elution of ethyl acetate/hexane 10:90 to 50:50) to give the title compound as an oil (0.668 g).

$^1$H NMR (300 MHz, CDCl$_3$) δ 0.78–0.88 (m, 2H), 1.06–1.50 (m, 8H), 1.42 (s, 9H), 1.45–1.77 (m, 7H), 2.31–2.58 (m, 2H), 2.58–2.78 (m, 1H), 3.18 (m, 0.5H), 3.40 (m, 0.5H), 3.60–3.84 (m, 2H), 4.88 (m, 1H), 6.13 (m, 1H), 7.25–7.42 (m, 5H).

LRMS (TSP) 418 (M+H).

Preparation 162 tert-Butyl(3R)-6-Cyclohexyl-3-{[(2-oxo-2-phenylethyl) amino]carbonyl}hexanoate

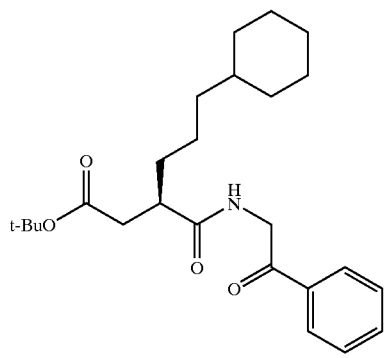

To a solution of the title compound from Preparation 161 (0.3 g, 0.72 mmol) in anhydrous dichloromethane (10 mL) was added 'Dess-Martin periodinane' (0.366 g, 0.86 mmol). The reaction was stirred at room temperature for 1.5 hours, then diluted with dichloromethane (25 mL). The reaction was treated with 20% sodium thiosulphate solution (6 mL) and saturated aqueous sodium bicarbonate solution (10 mL) and stirred for 10 mins. The layers were separated and aqueous layer extracted with dichloromethane (25 mL). The combined organic layers were washed with water, brine, dried (MgSO$_4$) and concentrated in vacuo. The residue was then purified by flash chromatography on silica gel (graded elution of ethyl acetate/hexane 5:95 to 20:80) to give the title compound as an oil (0.205 g).

$^1$H NMR (300 MHz, CDCl$_3$) δ 0.76–0.95 (m, 2H), 1.05–1.51 (m, 8H), 1.40 (s, 9H), 1.54–1.80 (m, 7H), 2.31–2.42 (m, 1H), 2.60–2.78 (m, 2H), 4.68–4.88 (m, 2H), 6.70 (m, 1H), 7.50 (m, 2H), 7.60 (t, 1H), 7.97 (d, 2H).

LRMS (TSP) 416 (M+H).

Preparation 163
tert-Butyl (3R)-6-Cyclohexyl-3-(5-Phenyl-1,3-oxazol-2-yl)hexanoate

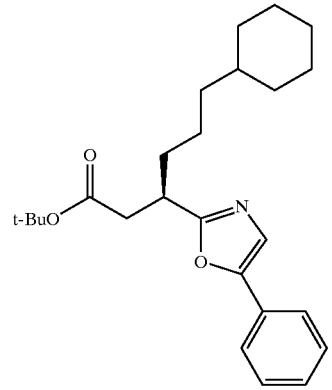

Trifluoromethanesulphonic anhydride (0.182 mL, 1.08 mmol) was added to a solution of triphenylphosphine oxide (0.603 g, 2.17 mmol) in dichloromethane (9 mL) at 0° C. under nitrogen. The reaction was stirred for 15 mins at 0° C. until a white precipitate was formed. A solution of the title compound from Preparation 162 (0.150 g, 0.36 mmol) in anhydrous dichloromethane (3 mL) was then added to the reaction, followed by triethylamine (0.2 mL, 1.44 mmol). After stirring for 10 mins the reaction was diluted with ethyl acetate (100 mL) and washed with 10% aqueous citric acid solution (50 mL), saturated aqueous sodium bicarbonate solution (50 mL) and brine. The organic layer was dried (Na$_2$SO$_4$), and concentrated in vacuo. The residue was then purified by flash chromatography on silica gel (hexane/ diethyl ether 2:1 as eluant) to give the title compound as colorless oil (0.104 g).

$^1$H NMR (300 MHz, CDCl$_3$) δ 0.76–0.95 (m, 2H), 1.05–1.48 (m, 8H), 1.40 (s, 9H), 1.60–1.88 (m, 7H), 2.60 (dd, 1H), 2.80 (dd, 1H), 3.40 (m, 1H), 7.20–7.37 (m, 2H), 7.40 (t, 2H), 7.62 (d, 2H).

LRMS (TSP) 398 (M+H).

Preparation 164
(3R)-6-Cyclohexyl-3-(5-phenyl-1,3-oxazol-2-yl)hexanoic acid

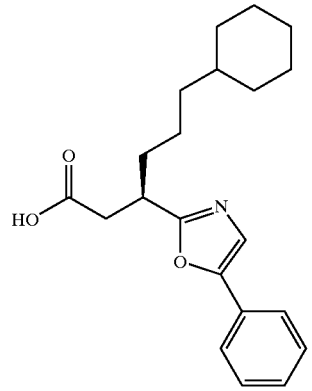

The title compound was obtained as a colorless oil (0.172 g) from the compound of Preparation 163 using a similar method to that described in Preparation 19. The residue was dissolved in ethyl acetate (100 mL) and washed with saturated aqueous sodium bicarbonate (50 mL) then water (2×50 mL). The organic solution was dried (MgSO$_4$) and then concentrated in vacuo.

$^1$H NMR (300 MHz, CDCl$_3$) δ 0.76–0.95 (m, 2H), 1.02–1.48 (m, 8H), 1.57–1.84 (m, 7H), 2.57 (dd, 1H), 2.96 (dd, 1H), 3.45 (m, 1H), 7.22–7.34 (d, 2H), 7.42 (t, 2H), 7.62 (d, 2H).

LRMS (TSP) 342 (M+H).

Preparation 165
tert-Butyl(3R)-6-Cyclohexyl-3-({[hydroxy(4-pyridinyl)methyl]amino}carbonyl)hexanoate

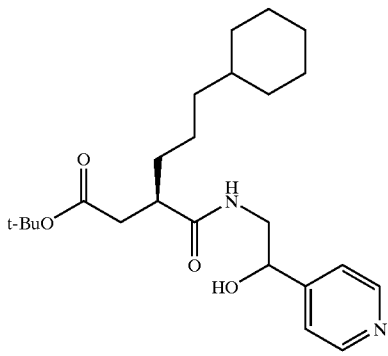

The title compound was obtained as a colorless oil (0.856 g) from the compound of Preparation 175 and 2-amino-1-(4-pyridinyl)ethanol (Ref. Burus; Powell; J. Amer. Chem. Soc.;67;1945;1468,1472;); using a similar method to that described in Preparation 161'. N,N-Dimethylformamide was added to the reaction and heated to 40° C. for 16 hours.

$^1$H NMR (300 MHz, CDCl$_3$) δ 0.78–0.98 (m, 2H), 1.04–1.50 (m, 8H), 1.41 (s, 9H), 1.52–1.84 (m, 6H), 2.28–2.78 (m, 3H), 3.06 (m, 1H), 3.38–3.48 (m, 1H), 3.65 (m, 0.5H), 3.82 (m, 0.5H), 4.30–4.65 (br d, 1H), 4.90 (m, 1H), 6.28 (m, 1H), 7.31 (m, 2H), 8.56 (m, 2H).

LRMS (TSP) 418 (M+).

Preparation 166
tert-butyl(3R)-6-Cyclohexyl-3-[(isonicotinoylamino)carbonyl]hexanoate

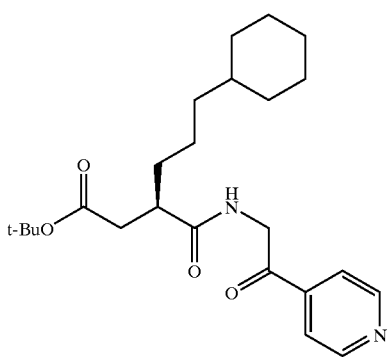

The title compound was obtained as a colorless oil from the title compound of Preparation 165; using a similar method to that described in Preparation 162. The residue was purified by flash chromatography on silica gel (ethyl acetate/methanol 98:2 as eluant).

$^1$H NMR (300 MHz, CDCl$_3$) δ 0.70–0.96 (m, 2H), 0.98–1.51 (m, 8H), 1.40 (s, 9H), 1.50–1.74 (m, 6H), 2.30–2.41 (m, 1H), 2.57–2.78 (m, 2H), 4.62–4.88 (m, 2H), 6.70 (m, 1H), 7.70 (m, 2H), 8.82 (m, 2H).

LRMS (TSP) 416 (M+).

Preparation 167
tert-butyl (3R)-6-Cyclohexyl-3-[5-(4-pyridinyl)-1,3-oxazol-2-yl]hexanoate

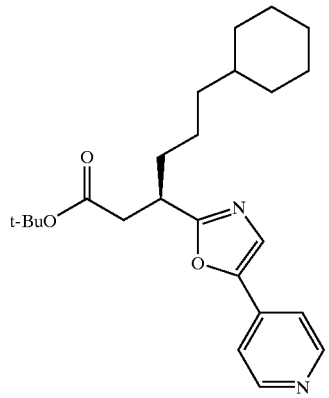

The title compound was obtained as a colorless oil from the compound of Preparation 166; using a similar method to that described in Preparation 163. The reaction was stiffed for 2 hours after the addition of triethylamine and was purified by flash chromatography (eluting with ethyl acetate-:hexane 1:1).

$^1$H NMR (300 MHz, CDCl$_3$) δ 0.74–0.96 (m, 2H), 1.00–1.48 (m, 8H), 1.34 (s, 9H), 1.55–1.90 (m, 7H), 2.60 (dd, 1H), 2.80 (dd, 1H), 3.40 (m, 1H), 7.44 (m, 3H), 7.62 (d, 2H).

LRMS (TSP) 399 (M+H).

Preparation 168
(3R)-6-Cyclohexyl-3-[5-(4-pyridinyl)-1,3-oxazol-2-yl]hexanoic acid

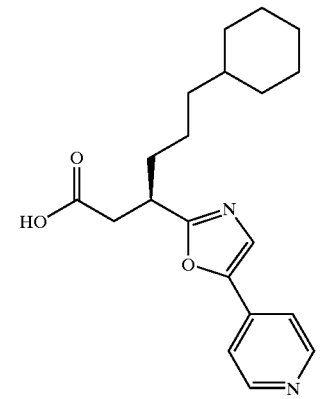

The title compound was obtained as a colorless oil (0.14 g) from the compound of Preparation 167 (0.17 g) using a similar method to that described in Preparation 19. The residue was recystallised from hexane/ethyl acetate. The yellow solid was then dissolved in saturated aqueous sodium bicarbonate (50 mL) and acidified to pH 4.0 with 10% citric acid solution. The aqueous layer was extracted with ethyl acetate (2×50 mL), dried (MgSO$_4$) and then concentrated in vacuo.

$^1$H NMR (400 MHz, CDCl$_3$) δ 0.78–0.94 (m, 2H), 1.04–1.46 (m, 8H), 1.58–1.90 (m, 7H), 2.80 (dd, 1H), 2.98 (dd, 1H), 3.45 (m, 1H), 7.74 (s, 1H), 7.80 (d, 2H), 8.80 (d, 2H).

LRMS (TSP) 342 (M+).

Preparation 169 tert-butyl(3R)-3-(aminocarbonyl)-6-cyclohexylhexanoate

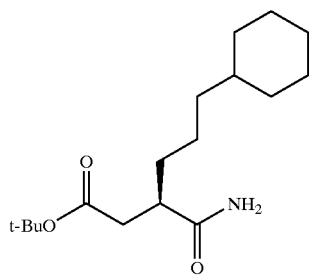

To a solution of the title compound from Preparation 175 (0.60 g, 0.2 mmol) in dichloromethane (20 mL) was added N-methylmorpholine (0.22 mL, 0.201 mmol). The reaction was cooled to 0° C. in an ice bath, then iso-butylchloroformate (0.27 mL, 0.207 mmol). The mixture was stirred for 1 hour, then ammonia gas was bubbled through the reaction until saturated. The reaction was warmed to room temperature and stirred for 45 mins. The reaction was diluted with dichloromethane (50 mL) and washed with 5% aqueous citric acid solution (25 mL). The aqueous layer was extracted with dichloromethane (2×50 mL). The combined organic extracts were washed with saturated aqueous ammonium chloride (30 mL), brine and dried (MgSO$_4$). The solvent was removed in vacuo and the residue was purified by flash chromatography on silica gel (graded elution of ethyl acetate/hexane 1:9 to 1:1) to give the title compound as a white solid (0.495 g).

$^1$H NMR (300 MHz, CDCl$_3$) δ 0.78–0.95 (m, 2H), 1.04–1.48 (m, 9H), 1.40 (s, 9H), 1.52–1.77 (m, 6H), 2.32 (m, 1H), 2.60 (m, 2H), 5.53 (br s, 1H), 5.78 (br s, 1H).

LRMS (ES) 3420 (M+Na).

Preparation 170 tert-butyl (3R)-3-cyano-6-cyclohexylhexanoate

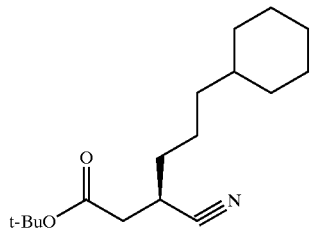

The title compound was obtained as a colorless oil from the compound of Preparation 169; using a similar method to that described in Preparation 159. The residue was purified by flash chromatography (graded elution of dichloromethane:hexane 1:4 to 1:0).

$^1$H NMR (300 MHz, CDCl$_3$) δ 0.78–1.00 (m, 2H), 1.04–1.36 (m, 6H), 1.36–1.80 (m, 9H), 1.47 (s, 9H), 2.47 (dd, 1H), 2.60 (dd, 1H), 2.98 (m, 1H).

LRMS (TSP) 297 (M+Na).

[α]$^{25}_D$=+12.6° (c=1, MeOH)

Preparation 171 tert-butyl(3R)-3-[(E)-amino(hydroxyimino)methyl]-6-cyclohexylhexanoate

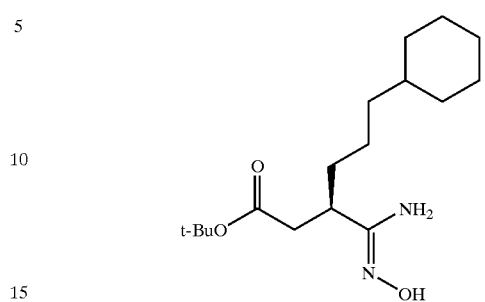

To a solution of the title compound from Preparation 170 (1.65 g, 5.9 mmol) in ethanol (60 mL) was added N-methylmorpholine (1.95 mL, 7.17 mmol), and hydroxylamine hydrochloride (1.23 g, 17.7 mmol). The reaction was stirred at reflux for 12 hours and then the solvent was remove in vacuo. The residue was diluted in ethyl acetate (150 mL) and washed with water (100 mL). The aqueous layer was extracted with ethyl acetate, the combined organic layers were washed with brine, dried (MgSO$_4$) and concentrated in vacuo. The residue was then purified by flash chromatography on silica gel (graded elution of dichloromethane/ethyl acetate 4:1 to 2:1) to give the title compound as an oil (0.41 g).

$^1$H NMR (300 MHz, CDCl$_3$) δ 0.78–0.98 (m, 2H), 1.03–1.96 (m, 17H), 1.42 (s, 9H), 2.32–2.73 (m, 3H), 4.72 (s, 1H).

LRMS (ES) 313 (M+H).

Preparation 172 tert-butyl (3R)-6-cyclohexyl-3-[5-(3-pyridinyl)-1,2,4-oxadiazol-3-yl]hexanoate

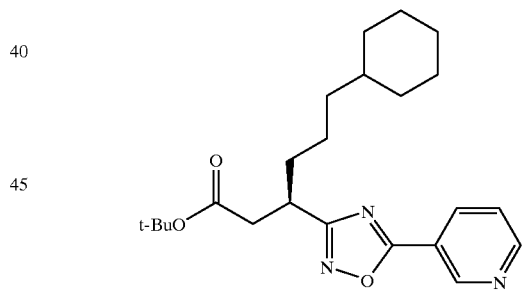

To a solution of the title compound from Preparation 170 (0.410 g, 1.3 mmol) in dichloromethane (15 mL) was added 1-(3-dimethylaminopropyl)-3-ethylcarbodiimide hydrochloride (0.265 g, 1.38 mmol), 4-dimethylamino pyridine (0.016 g, 0.13 mmol), and nicotinic acid (0.170 g, 1.38 mmol) and the reaction was stirred at room temperature overnight. The solvent was removed in vacuo and the residue was partitioned between ethyl acetate (30 mL) and water (30 mL). The layers were separated and aqueous layer extracted with ethyl acetate (2×30 mL). The combined organic layers were dried (MgSO$_4$) and concentrated under reduced pressure. The residue was then purified by flash chromatography on silica gel (gradient elution of dichloromethane/methanol 99:1 to 96:4), then dissolved in dichloromethane (5 mL) and heated at 140° C. for 1.5 hours. The solvent was removed in vacuo and residue purified by flash chromatography on silica gel (gradient elution of hexane/ethyl acetate 4:1 to 2:1), to give the title compound as a yellow oil (0.24 g).

¹H NMR (300 MHz, CDCl₃) δ 0.76–0.98 (m, 2H), 1.00–1.46 (m, 9H), 1.42 (s, 9H), 1.46–1.88 (m, 6H), 2.64 (m, 1H), 2.80 (m, 1H), 3.43 (m, 1H), 7.48 (m, 1H), 8.40 (m, 1H), 8.81 (1H), 9.37 (s, 1H).

LRMS (ES) 419 (M+NH4).

Preparation 173 tert-Butyl(3R)-6-Cyclohexyl-3-[5-(2-pyrazinyl)-1,2,4-oxadiazol-3-yl]hexanoate

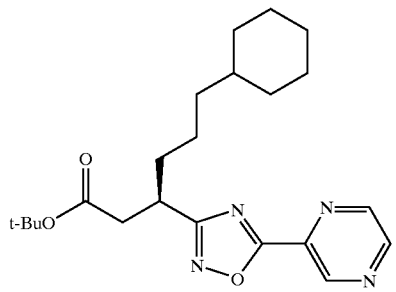

The title compound was obtained as a colorless oil from the compound of Preparation 171 and 2-pyrazinecarboxylic acid; using a similar method to that described in Preparation 172. The residue was heated at 130° C. for 3 hours.

¹H NMR (400 MHz, CDCl₃) δ 0.78–0.90 (m, 2H), 1.05–1.38 (m, 8H), 1.40 (s, 9H), 1.52–1.92 (m, 7H), 2.64 (dd, 1H), 2.80 (dd, 1H), 3.48 (m, 1H), 8.80 (s, 2H), 9.43 (s, 1H).

LRMS (TSP) 401 (M+H).

Preparation 174 tert-butyl(3R)-6-Cyclohexyl-3-[5-(5-pyrimidinyl)-1,2,4-oxadiazol-3-yl]hexanoate

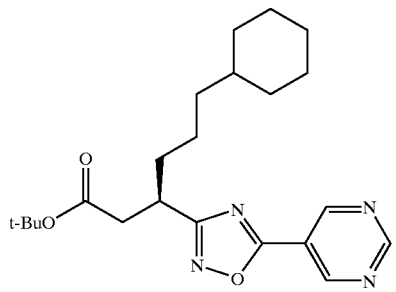

The title compound was obtained as a colorless oil from the compound of Preparation 171 and 5-pyrimidinecarboxylic acid; using a similar method to that described in Preparation 172. The residue was heated at 145° C. for 2.5 hours.

¹H NMR (300 MHz, CDCl₃) δ 0.76–0.92 (m, 2H), 1.05–1.46 (m, 8H), 1.41 (s, 9H), 1.53–1.86 (m, 7H), 2.64 (dd, 1H), 2.80 (dd, 1H), 3.45 (m, 1H), 9.42 (m, 3H).

LRMS (ES) 423 (M+Na).

Preparation 175

(2R)-2-[2-(tert-Butoxy)-2-oxoethyl]-5-cyclohexylpentanoic acid
Route A:
(2R)-2-[2-(tert-Butoxy)-2-oxoethyl]-5-cyclohexylpentanoic acid

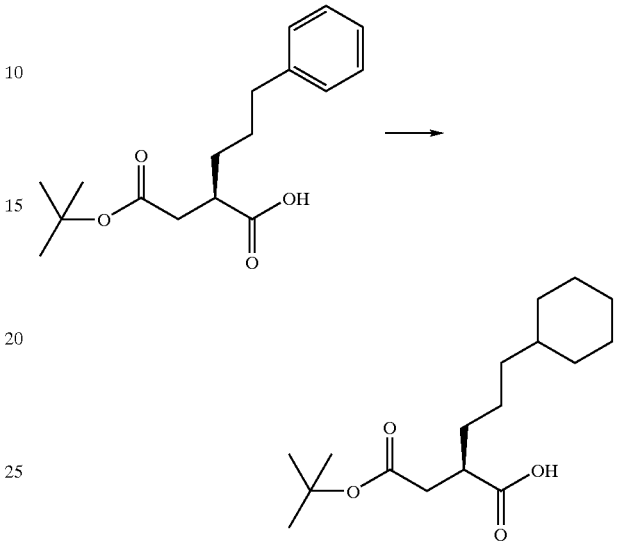

A solution of (2R)-2-[2-(tert-Butoxy)-2-oxoethyl]-5-phenylpentanoic acid (Syn. Lett.; 1998; 637–639) (10.00 g, 34.2 mmol) in acetic acid (120 ml) was treated with 5% Rhodium on alumina catalyst, pressurised to 60 psi with hydrogen in a sealed vessel and stirred at room temperature for 17 hours. The mixture was filtered through a pad of Arbocel® and the solvent was removed from the filtrate under reduced pressure. The residue was azeotroped from toluene to afford the title compound (7.53 g).

MS: 299 (MH⁺)
¹H-NMR (CDCl₃) δ:2.80 (1H, m), 2.61 (1H, m), 2.38 (1H, m), 1.75–1.56 (7H, m), 1.55–1.04 (17H, m), 0.84 (2H, m).

Route B:
(4S)-4-Benzyl-3-(5-cyclohexylpentanoyl)-1,3-oxazolidin-2-one

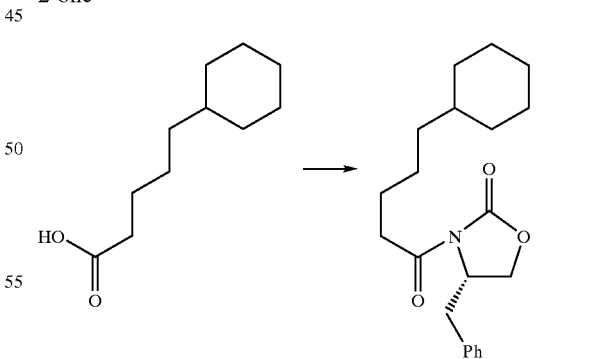

A solution of 5-cyclohexylpentanoic acid (63.50 g, 345 mmol) in N,N-dimethylformamide (0.5 ml) and dichloromethane (350 ml) was cooled to 5° C. and treated dropwise with oxalyl chloride (31.6 ml, 362 mmol) over 30 minutes. The mixture was stirred at 0° C. for 3 hours then the solvent was removed under reduced pressure to afford 5-cyclohexylpentanoyl chloride as a pale yellow solid (70.0 g).

A solution of n-butyllithium (100 ml, 250 mmol, 2.5M in hexanes) was added via a cannula to a solution of (4S)-4-benzyl-1,3-oxazolidin-2-one (44.300 g, 250 mmol) in anhydrous tetrahydrofuran (400 ml) at −78° C. The yellow solution was then stirred for 45 minutes. A solution of 5-cyclohexylpentanoyl chloride (55.5 g, 275 mmol) in tetrahydrofuran (100ml) was then added over 1 hour. The mixture was stirred at −78° C. for 30 minutes then warmed to room temperature over 1 hour. The mixture was quenched with an aqueous solution of ammonium chloride (20% w/v, 400 ml) and extracted with ethyl acetate. The layers were separated and the organic layer was washed with brine, dried over anhydrous sodium sulphate and the solvent removed under reduced pressure. The solid was recrystallised from hexane (500 ml) to afford the title compound as a white solid (81.0 g).

MS: 344 (MH$^+$)

$^1$H-NMR (CDCl$_3$) δ:7.41–7.13 (5H, m), 4.68 (1H, m), 4.27–4.02 (2H, m), 3.31 (1H, dd, J=16, 4 Hz), 3.06–2.70 (3H, m), 1.81–1.53 (7H, m), 1.49–1.04 (8H, m), 0.88 (2H, m)

tert-Butyl 3-{[(4S)-4-benzyl-2-oxo-1,3-oxazolidin-3-yl]carbonyl}-6-cyclohexylhexanoate

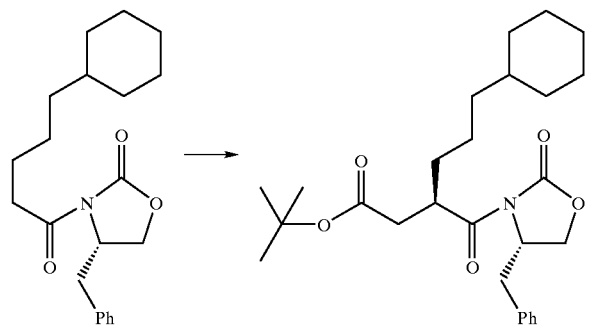

A solution of (4S)-4-benzyl-3-(5-cyclohexylpentanoyl)-1,3-oxazolidin-2-one (70.0 g, 204 mmol) in anhydrous tetrahydrofuran (650 ml) was cooled to −70° C. and treated dropwise with sodium hexamethyldisilazide (1M in tetrahydrofuran, 224 ml, 224 mmol) over 45 minutes. The mixture was stirred for a further 45 minutes before being treated with t-butylbromoacetate (31.6 ml, 214 mmol). This mixture was stirred at −70° C. for 30 minutes then warmed to −30° C. and quenched with an aqueous solution of ammonium chloride (20%w/v, 400 ml) and warmed to room temperature. The mixture was extracted with ethyl acetate and the combined organic extracts were washed with brine, dried over anhydrous sodium sulphate and the solvent removed under reduced pressure. The solid was recrystallised from hexane to afford the title compound as a white solid (71.4 g).

MS: 458(MH$^+$)

$^1$H-NMR (CDCl$_3$) δ:7.41–7.13 (5H, m), 4.66 (1H, m), 4.23–4.03 (3H, m), 3.35 (1H, dd, J=16, 4 Hz), 2.95–2.68 (3H, m), 2.47 (1H, m), 1.80–1.07 (24H, m), 0.85 (2H, m)

2-[2-(tert-Butoxy)-2-oxoethyl]-5-cyclohexylpentanoic acid

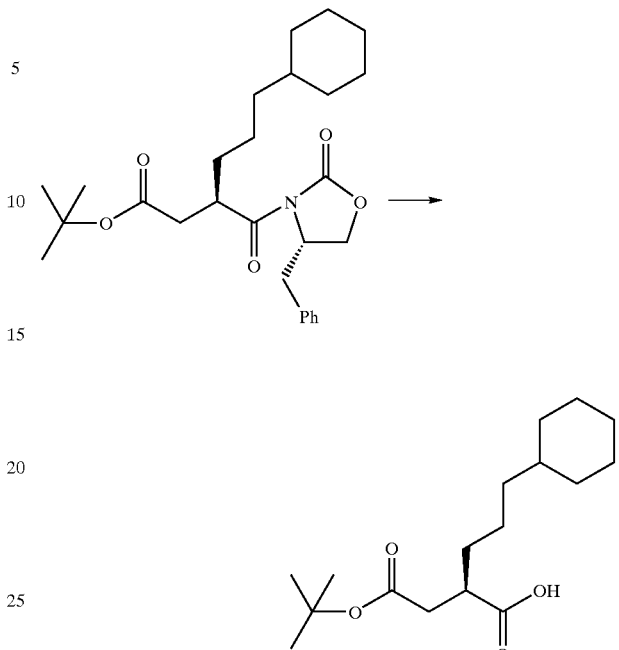

A solution of tert-Butyl 3-{[(4S)-4-benzyl-2-oxo-1,3-oxazolidin-3-yl]carbonyl}-6-cyclohexylhexanoate (64.0 g, 139.9 mmol) in tetrahydrofuran: water (3:1, 800 ml) was cooled to 5° C. then treated sequentially with hydrogen peroxide (30% w/v water, 87 ml, 769 mmol) then lithium hydroxide hydrate (10.0 g, 238 mmol). The reaction was stirred for 1 hour then quenched by dropwise addition of an aqueous solution of sodium thiosulphate (500 ml) keeping the temperature below 20° C. The mixture was extracted with ethyl acetate (discarded) and the aqueous phase was acidified to pH 2 with solid citric acid and extracted with ethyl acetate. The combined organic phases were washed with brine, dried over anhydrous sodium sulphate and the solvent removed under reduced pressure. The residue was purified by column chromatography on silica gel eluting with a gradient system of hexane:ethyl acetate (2:1) gradually changing to hexane:ethyl acetate (1:1) to afford the title compound (40.7 g).

Route C:

3-(Diethoxyphosphoryl)succinic acid 1-tert-butyl ester

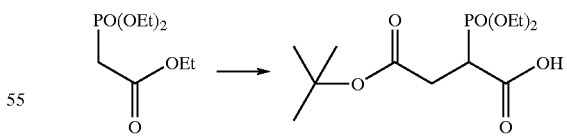

Triethylphosphonoacetate (102 g, 0.45 mol) was added dropwise over 11 min to a stirred solution of potassium tert-butoxide (60 g, 0.54 mol) in THF (500 ml), at 0° C., under nitrogen. The mixture was stirred for 1 hour at 0° C. and then dichloromethane (300 ml) was added and the reaction mixture was warmed to 25–30° C. The mixture was stirred at 25–30° C. for 1 hour and then added dropwise over 33 minutes to a solution of tert-butyl bromoacetate (96 g, 0.49 mol) in THF(500 ml), at 0° C., under nitrogen. The mixture was stirred at 0–5° C. for 2 hours and then a solution of citric acid (174 g, 0.91 mol) in demineralised water (250 ml) was added. The mixture was concentrated in vacuo to remove most of the THF and then toluene (750 ml) was added. The organic phase was separated, washed with brine (2×150 ml) and concentrated in vacuo to leave a colorless oil. The oil was taken up in ethanol and a solution of potassium hydroxide (36. g, 0.64 mol) in demineralised water (150 ml) was added dropwise over 15 mins. The mixture was stirred at 0° C. for 4 hours and then a solution of citric acid (158 g, 0.82 mol) in demineralised water (600 ml), and toluene (600 ml), were added. The organic phase was separated and the aqueous phase was re-extracted with toluene (600 ml). The combined organic phases were washed with demineralised water (2×150 ml) and concentrated in vacuo to leave a white solid. Toluene (150 ml) was added and the slurry was re-concentrated in vacuo to leave a white solid. The product was purified by crystallisation from tert-butylmethyl ether (300 ml) and cyclohexane (600 ml) to give the title compound as a solid (79 g).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

Alternative Preparation:

Triethylphosphonoacetate (12.0 Kg, 53.5 mol) was added over 30 minutes to a stirred solution of potassium tert-butoxide (7.20 Kg, 64.2 mol) in THF (118 liters), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 liters), between 0 and 5° C., under nitrogen. The mixture was stirred at 0–5° C. for 1 hour and then demineralised water (6.1 liters) and ethanol (30 liters) were added. A solution of potassium hydroxide (4.2 Kg, 75.0 mol) in demineralised water (84 liters) was then added over 2 hours, between −5 and 0° C. The mixture was stirred at −10° C. for 16 hours and then a solution of citric acid (16.5 Kg, 85.8 mol) in demineralised water (32 liters) was added. The mixture was concentrated in vacuo to a volume of 180 liters and then ethyl acetate (90 liters) was added. The organic phase was separated and the aqueous phase was re-extracted with ethyl acetate (30 liters). The combined organic phases were washed with water (30 liters) and then stripped and replaced with cyclohexane by distillation at atmospheric pressure, at a constant volume of 72 liters. tert-Butylmethyl ether (18 liters) was added and the mixture was stirred at ambient temperature for 12 hours and then filtered. The residue was washed with a mixture of cyclohexane (16 liters) and tert-butylmethyl ether (3.6 liters) then dried in vacuo for 16 hours to give the title compound as a colorless solid (10.0 Kg, 60%).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

(E)-2-[2-(tert-Butoxy)-2-oxoethyl]-5-phenyl-2-pentenoic acid

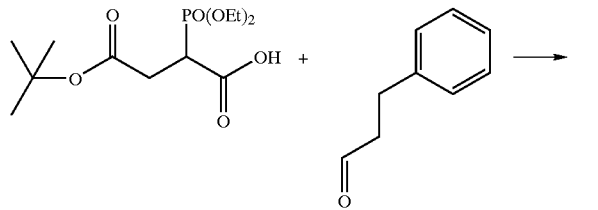

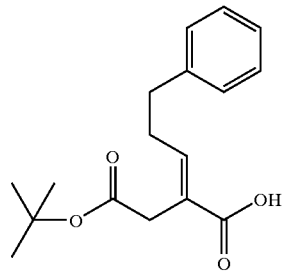

A solution of 3-(diethoxyphosphoryl)succinic acid 1-tert-butyl ester (100 g, 0.32 mol) in THF (300 ml) was added dropwise over 15 min to a stirred solution of potassium tert-butoxide (110 g, 0.98 mol) in THF (300 ml), between −10 and −5° C., under nitrogen. The mixture was stirred at −10° C. for 15 min and then a solution of hydrocinnamaldehyde (46.8 g, 0.35 mmol) in THF (100 ml) was added dropwise over 15 min, between −13 and −8° C. The mixture was stirred at −10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colorless solid (76 g, 81%).

MS: 289 [(M−H)]$^-$ $^1$H-NMR (CDCl$_3$) δ: 7.33–7.16 (5H, m), 7.05 (1H, br t), 3.20 (2H, s), 2.89 (2H, br t), 2.50 (2H, br dd), 1.41 (9H, s)

(R)-2-[2-(tert-Butoxy)-2-oxoethyl]-5-phenylpentanoic acid

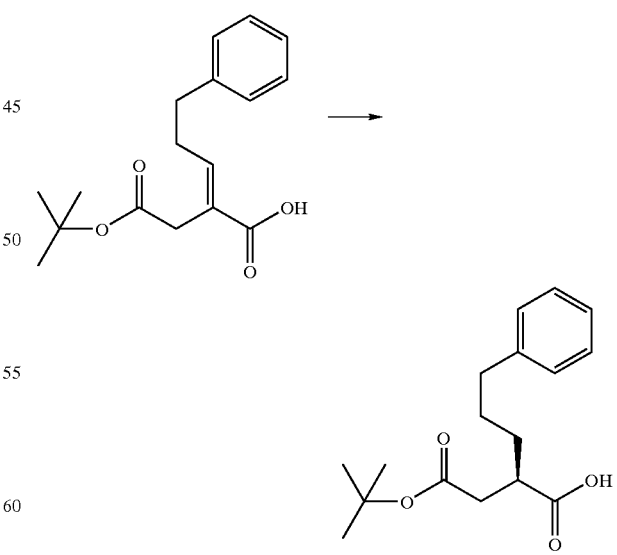

A stirred solution of (E)-2-[2-(tert-Butoxy)-2-oxoethyl]-5-phenyl-2-pentenoic acid (100 g, 0.34 mol), cyclohexylamine (39 ml, 0.34 mol) and [(S)-2,2'-bis(diphenylphosphino-1,1'-binaphthyl]chloro(p-cymene)

ruthenium chloride (0.64 g, 0.69 mmol) in methanol (1000 ml) was heated to 60° C., under hydrogen (60 p.s.i.), for 42 hours and then allowed to cool to room temperature. The mixture was filtered through celite and then concentrated in vacuo to a yellow solid which was purified by re-crystallisation from acetone (850 ml). The resulting solid was partitioned between ethyl acetate (1200 ml) and citric acid solution (10%, 1200 ml) and the organic phase was separated, washed with demineralised water (1200 ml) and concentrated in vacuo to leave the title compound as an oil (80 g).

$^1$H-NMR (CDCl$_3$) δ: 7.30–7.17 (5H, m), 2.85–2.78 (1H, m), 2.66–2.58 (3H, m), 2.37 (1H, br dd), 1.75–1.51 (4H, m), 1.40 (9H, s)

Preparation of Cyclohexylamine Salt:

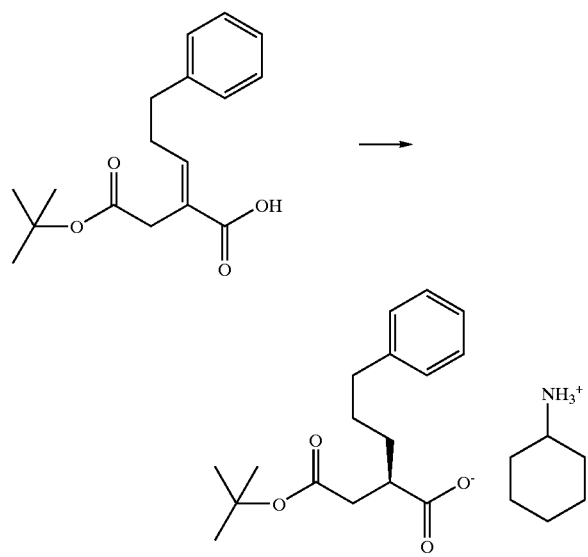

A stirred solution of cyclohexylamine (266 ml, 2.32 mol), (E)-2-[2-(tert-Butoxy)-2-oxoethyl]-5-phenyl-2-pentenoic acid (688 g, 2.37 mol) and [(S)-2,2'-bis(diphenylphosphino-1,1'-binaphthyl]chloro(p-cymene)ruthenium chloride (4.4 g, 4.7 mmol) in methanol (6.9 liters) was heated to 60° C., under hydrogen (60p.s.i.), for 47 hours and then allowed to cool to room temperature (enantiomeric excess=88%). The mixture was filtered through celite and then the solvent was stripped and replaced with acetone by distillation at atmospheric pressure, at a constant volume of 4.2 liters. The resulting suspension was cooled to room temperature where it was stirred for 4 hours and then filtered. The residue was washed with acetone (2×1 liter) and then dried in vacuo at 45° C. for 16 hours to leave the title compound as a colorless solid (590 g, 64%, enantiomeric excess=98.9%).

$^1$H-NMR (CD$_3$OD) δ: 7.23–7.09 (5H, m), 3.05–2.98 (1H, m), 2.64–2.56 (3H, m), 2.53 (1H, dd, J=15.2, 7.2 Hz), 2.23 (1fH, dd, J=15.2, 7.2 Hz), 2.00–1.97, (2H, m), 1.85–1.81 (2H, m), 1.72–1.20 (10H, m), 1.40 (9H, s)

(R)-2-[2-(tert-Butoxy)-2-oxoethyl]-5-cyclohexylpentanoic acid cyclohexylamine salt

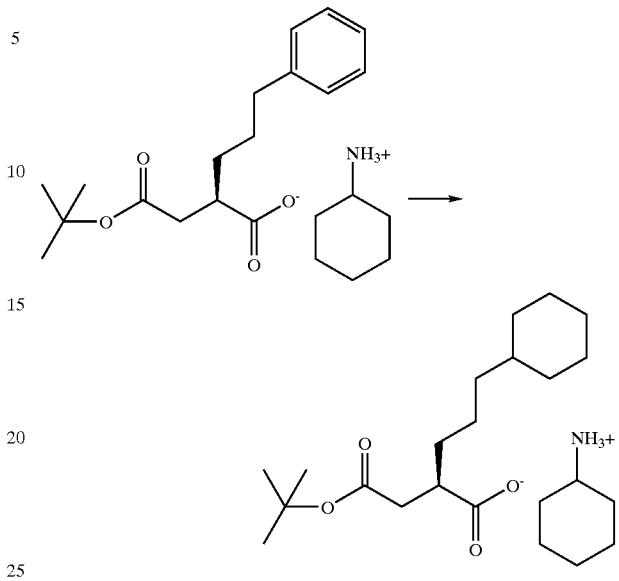

(R)-2-[2-(tert-Butoxy)-2-oxoethyl]-5-phenylpentanoic acid cyclohexylamine salt (691 g, 1.77 mol) and ethyl acetate (7.0 liters) were added to an aqueous solution of citric acid (10%, 6.3 liters) and the organic phase was separated, washed with water (7.0 liters) and concentrated in vacuo to a yellow oil. A solution of the oil and 5% rhodium on carbon (51.6 g) in methanol (7.0 liters) was stirred at ambient temperature, under hydrogen (150 p.s.i.) for 48 hours and then filtered through celite. To the filtrate was added cyclohexylamine (202 ml, 1.77 mol) and the methanol solution was stripped and replaced with methylethyl ketone by distillation at atmospheric pressure, to a volume of 5.5 liters. The mixture was allowed to cool to ambient temperature where it was stirred for 48 hours and then filtered. The residue was washed with methylethyl ketone (2×500 ml) and then dried in vacuo at 45° C. for 4 hours to leave the title compound as a colorless solid (495 g, 71%).

$^1$H-NMR (CD$_3$OD) δ: 3.06–2.99 (1H, m), 2.63–2.56 (1H, m), 2.53 (1H, dd, J 15.2, 7.2 Hz), 2.23 (1H, dd, J=15.2, 7.2 Hz), 2.02–1.97 (2H, m), 1.77–1.15 (21H, m), 1.43 (9H, s), 0.93–0.82 (2H, m)

(R)-2-[2-(tert-Butoxy)-2-oxoethyl]-5-cyclohexylpentanoic acid

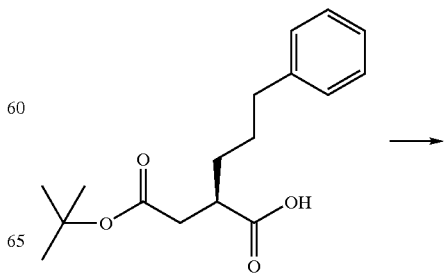

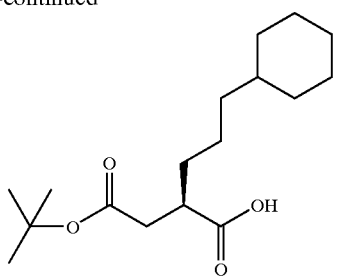

A solution of (R)-2-[2-(tert-Butoxy)-2-oxoethyl]-5-phenylpentanoic acid (2.2 g, 7.5 mmol) and 5%Rh/C (0.22 g) in methanol (220 ml) was stirred at room temperature, under hydrogen (150p.s.i.) for 24 hours and then filtered through celite. The filtrate was concentrated in vacuo to leave the title compound as an oil (2.0 g).

$^1$H-NMR (CDCl$_3$) δ: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

Preparation 176
tert-Butyl (3R)-3-[({[(Z)-1-amino-2-ethoxy-2-oxoethylidene]amino}oxy)carbonyl]-6-cyclohexylhexanoate

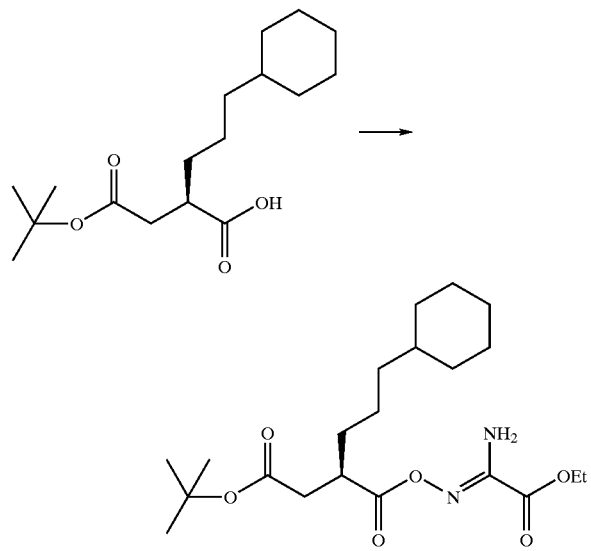

A solution of (2R)-2-[2-(tert-Butoxy)-2-oxoethyl]-5-cyclohexylpentanoic acid (Preparation 175) (7.53 g, 25.2 mmol) in 1,4-dioxane (175 ml) was treated with 1-hydroxybenzotriazole hydrate (3.75 g, 27.8 mmol) and the mixture cooled to 0° C. N,N'-Dicyclohexylcarbodiimide (5.47 g, 26.5 mmol) was then added and the mixture was stirred for 3 hours being allowed to warm to room temperature over this time. The mixture was then filtered and washed with 1,4-dioxane (2×50 ml). The filtrate was then treated with sodium carbonate (4.01 g, 37.8 mmol) and ethyl 2-amino-2-(hydroxyimino)acetate (J. Org. Chem.;23; 1958; 1794) (3.33 g, 25.2 mmol). The resulting mixture was stirred at room temperature for 17 hours. The solvent was removed under reduced pressure and the residue was partitioned between ethyl acetate and water. The layers were separated and the aqueous phase was extracted with ethyl acetate (×2). The combined organic layers were dried over anhydrous magnesium sulphate, filtered and the solvent removed under reduced pressure. The residue was purified by column chromatography on silica gel eluting with a gradient system of ethyl acetate:pentane (30:70) gradually changing to ethyl acetate:pentane (50:50) to afford the title compound as a white solid (6.50 g).

MS: 413 (MH$^+$)

$^1$H-NMR (CDCl$_3$) δ: 5.71 (2H, br s), 4.39 (2H, q), 2.92 (1H, m), 2.67 (1H, dd), 2.44 (1H, dd), 1.75–1.32 (22H, m), 1.26–1.04 (5H, m), 0.84 (2H, m).

Preparation 177
Ethyl 5-{(1R)-1-[2-(tert-Butoxy)-2-oxoethyl]-4-cyclohexylbutyl}-1,2,4-oxadiazole-3-carboxylate

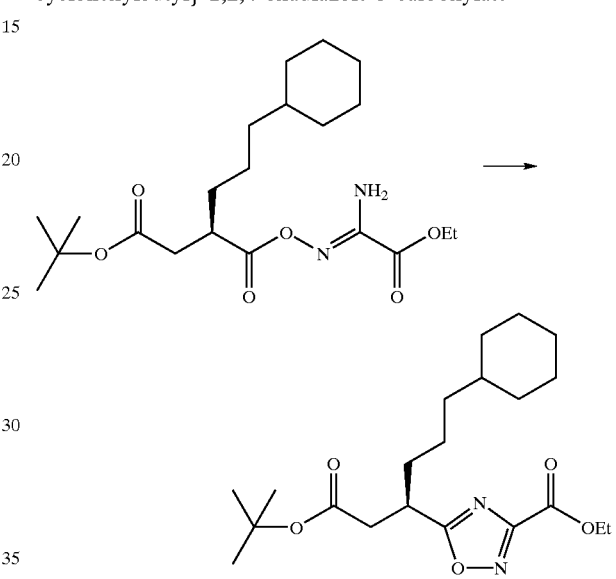

A solution of tert-Butyl (3R)-3-[({[(Z)-1-amino-2-ethoxy-2-oxoethylidene]amino}oxy)carbonyl]-6-cyclohexylhexanoate (Preparation 176) (21.0 g, 50.82 mmol) in xylene (400 ml) was heated at 130° C. for 17 hours, then allowed to cool to room temperature. The residue was purified by column chromatography on silica gel eluting with a gradient system of ethyl acetate:pentane (5:95) gradually changing to ethyl acetate:pentane (20:80) to afford the title compound as a colorless oil (20.0 g).

MS: 395 (MH$^+$), 412 (MNH$_4^+$)

$^1$H-NMR (CDCl$_3$) δ: 4.51 (2H, m), 3.54 (1H, m), 2.86 (1H, dd), 2.65 (1H, dd), 1.86–1.57 (7H, m), 1.50–1.33 (12H, m), 1.30–1.03 (8H, m), 0.82 (2H, m).

Preparation 178
(3R)-6-Cyclohexyl-3-[3-(ethoxycarbonyl)-1,2,4-oxadiazol-5-yl]hexanoic acid

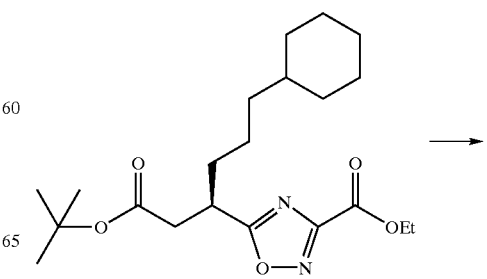

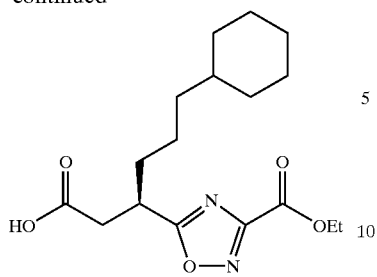

A solution of ethyl 5-{(1R)-1-[2-(tert-Butoxy)-2-oxoethyl]-4-cyclohexylbutyl}-1,2,4-oxadiazole-3-carboxylate (Preparation 177) (820 mg, 2.08 mmol) in dichloromethane (10 ml) was cooled to 0° C. and treated with trifluoroacetic acid (5 ml). The mixture was stirred for 2.5 hours being allowed to warm to room temperature over this time. The solvent was removed under reduced pressure and the residue azeotroped with toluene (×2). The residue was then dissolved in ethyl acetate, washed sequentially with an aqueous solution of sodium dihydrogen citrate and brine, dried over anhydrous sodium sulphate, filtered and the solvent removed under reduced pressure to afford the title compound as an oil (740 mg).

MS: 339(MH+)

$^1$H-NMR (CDCl$_3$) δ: 4.49 (2H, q J=7 Hz), 3.57 (1H, m), 3.05 (1H, dd J=17, 8Hz), 2.81 (1H, dd J=17, 4 Hz), 1.92–1.55 (7H, m), 1.45 (3H, t J=7 Hz), 1.35–1.02 (8H, m), 0.84 (2H, m)

Preparation 179
tert-Butyl (3R)-3-[3-(aminocarbonyl)-1,2,4-oxadiazol-5-yl]-6-phenylhexanoate

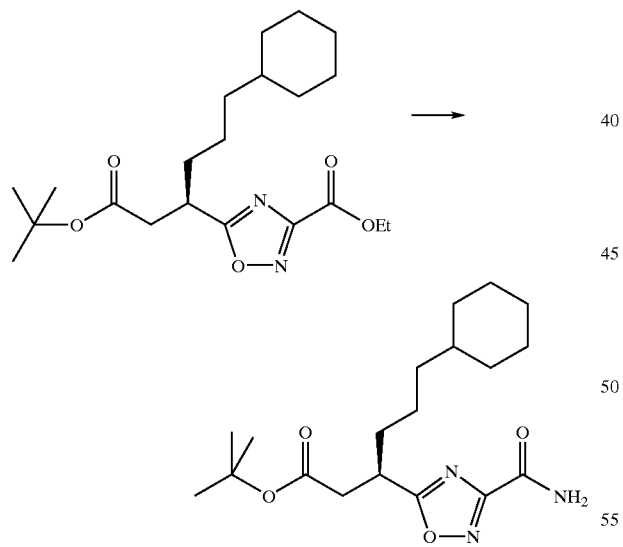

A solution of ethyl 5-{(1R)-1-[2-(tert-Butoxy)-2-oxoethyl]-4-cyclohexylbutyl}-1,2,4-oxadiazole-3-carboxylate (Preparation 178) (400 mg, 1.01 mmol) in ethanol saturated with ammonia gas (20 ml) was stirred at room temperature for 18 hours. The solvent was removed under reduced pressure and the residue was purified by column chromatography on silica gel eluting with a gradient system of hexane:ethyl acetate (90:10) gradually changing to hexane:ethyl acetate (60:40) to afford the title compound as a white solid (260 mg).

MPt: 77–79° C.
MS: 366 (MH+), 383 (MNa+)
Analysis: Found C, 62.42; H, 8.59; N, 11.48%; C$_{19}$H$_{31}$N$_3$O$_4$ requires C, 62.44; H, 8.55; N, 11.50%

$^1$H-NMR (CDCl$_3$) δ: 6.80 (1H, br s), 5.90 (1H, br s), 3.53 (1H, m), 2.87 (1H, m), 2.87 (1H, dd, J=17, 9 Hz), 2.66 (1H, dd, J=17, 5 Hz), 1.90–1.50 (7H, m), 1.46–1.02 (17H, m), 0.83 (2H, m).

What is claimed is:

1. A compound of formula (I):

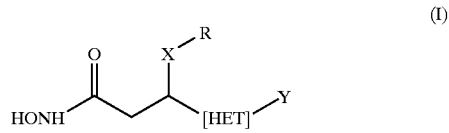

or a pharmaceutically acceptable salt, solvate, or hydrate thereof, in which,

X is $C_{1-6}$ alkylene or $C_{2-6}$ alkenylene, each of which is unsubstituted or substituted by one or more fluorine atoms;

R is aryl, $C_{5-8}$ cycloalkenyl or $C_{3-8}$ cycloalkyl unsubstituted or substituted by one or more fluorine atoms;
wherein aryl comprises phenyl unsubstituted or substituted by one or more substituents independently selected from the group consisting of R$^1$, OH, SO$_2$(C$_{1-4}$ alkyl) and C(O)$_p$(C$_{1-4}$ alkyl) groups;
wherein p=0, 1 or 2;

[HET] is a divalent heterocyclic moiety selected from:

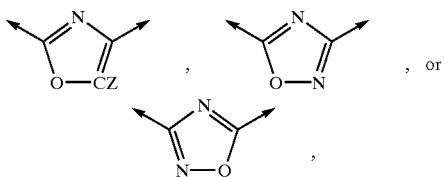

wherein Z is H or $C_{1-4}$ alkyl;

Y is a mono- or bicyclic unsaturated ring system containing from 5 to 10 ring atoms, of which up to 4 of said ring atoms are hetero-atoms independently selected from the group consisting of N, O and S, and said ring system is unsubstituted or substituted by one or more substituents independently selected from the group consisting of =O, C$_{1-4}$ alkyl, C$_{1-4}$ alkoxy, NR$^1$R$^2$, SO$_2$NR$^1$R$^2$, CO$_2$R$^1$, CONR$^1$R$^2$, CH$_2$CO$_2$R$^1$, NR$^1$CO$_2$R$^2$, NR$^1$SO$_2$R$^2$ and het$^1$;

wherein R$^1$ and R$^2$ are each independently selected from H or C$_{1-4}$ alkyl unsubstituted or substituted by C$_{1-4}$ alkoxy;

wherein het$^1$ is a N-linked 4- to 6-membered mono- or bicyclic heterocycle unsubstituted or containing 1 or 2 further hetero ring atoms independently selected from the group consisting of N and O, which heterocycle is unsubstituted or substituted by one or more substituents independently selected from the group consisting of =O, C$_{1-4}$ alkyl, C$_{1-4}$ alkoxy, NR$^1$R$^2$, SO$_2$NR$^1$R$^2$, CO$_2$R$^1$, CONR$^1$R$^2$, CH$_2$CO$_2$R$^1$, NR$^1$CO$_2$R$^2$, NR$^1$SO$_2$R$^2$ and het$^2$;

wherein het$^2$ is a N-linked 4- to 6-membered mono- or bicyclic heterocycle unsubstituted or containing 1 or 2 further hetero ring atoms independently selected from the group consisting of N and O.

2. A compound according to claim 1 having the

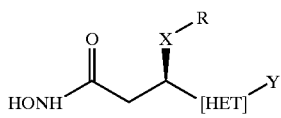

stereochemistry of formula (IA).

3. A compound according to claim 2 wherein X is a linear $C_{2-6}$ alkylene moiety unsubstituted or substituted by one or more fluorine atoms.

4. A compound according to claim 3 wherein X is propylene.

5. A compound according to claim 3 wherein R is $C_{3-8}$ cycloalkyl unsubstituted or substituted by one or more fluorine atom.

6. A compound according to claim 5 wherein R is cyclobutyl, cyclopentyl or cyclohexyl unsubstituted or substituted by one or more fluorine atoms.

7. A compound according to claim 6 wherein R is cyclohexyl.

8. A compound according to claim 5 wherein Y is a 5- or 6-membered unsaturated ring containing 0, 1 or 2 ring hetero-atoms independently selected from the group consisting of N and O, and said ring is unsubstituted or substituted by one or more substituents independently selected from the group consisting of =O, $C_{1-4}$ alkyl, $C_{1-4}$ alkoxy, $NR^1R^2$, $SO_2NR^1R^2$, $CO_2R^1$, $CONR^1R^2$, $CH_2CO_2R^1$, $NR^1CO_2R^2$, $NR^1SO_2R^2$ and $het^1$.

9. A compound according to claim 8 wherein Y is a 5- or 6-membered unsaturated ring containing 0, 1 or 2 ring hetero-atoms independently selected from the group consisting of N and O, and said ring is unsubstituted or substituted by one or more substituents independently selected from the group consisting of =O, $CONH_2$, $CONHCH_3$, $CON(CH_3)_2$, $CH_3$, $NH_2CO_2C_2H_5$, $CO_2H$, $CH_2CO_2CH_3$, $NHCH_3$, $NHC_2H_5$, $N(CH_3)_2$, morpholino, imidazol-1-yl, methoxy, ethoxy and $NHSO_2CH_3$.

10. A compound according to claim 9 wherein Y is 5-carbamoylpyridin-3-yl, uracil-5-yl, pyridin-4yl, 6-methylpyridin-3-yl, 5-carboxypyridin-3-yl, 6-methoxycarbonylpyridin-3-yl, 6-(4-methylpiperazino)pyridin-3yl, 4-carboxypridin-2-yl, 6-dimethylaminopyridin-3yl, 6-(imidazol-1-yl)pyrazin-2-yl, 3-morpholinopyrazin-2-yl, 3-pyrrolidinopyrazin-2yl, 3-dimethylaminopyrazin-2-yl, 3-methylaminopyrazin-2-yl, 3-methylsulphonamidophenyl, 3-carboxyphenyl or 6-ethoxypyrazin-2-yl.

11. A compound according to claim 10 wherein Y is uracil-5-yl or 4-carboxpyridin-2-yl.

12. A compound according to claim 2 wherein [HET] is 1,2,4-oxadiazol-3,5-ylene.

13. A compound according to claim 1, which is selected from the group consisting of:

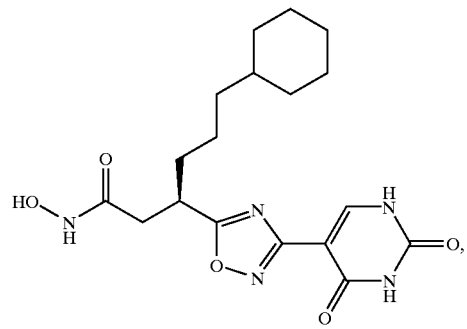

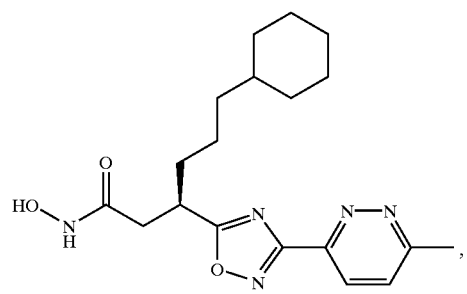

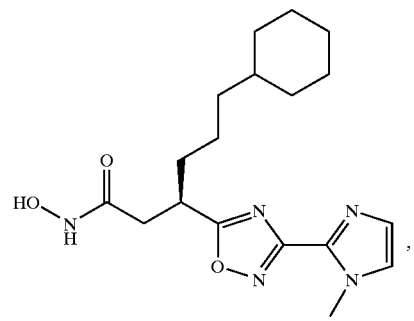

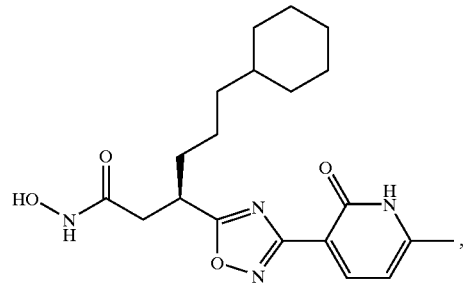

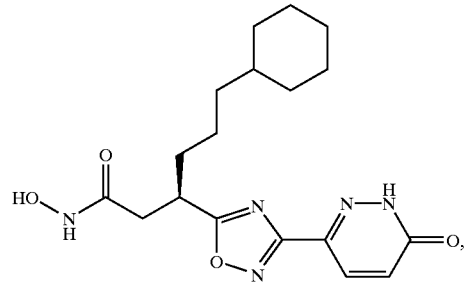

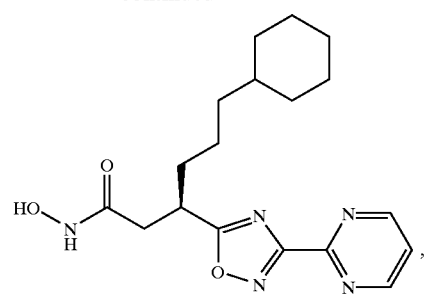
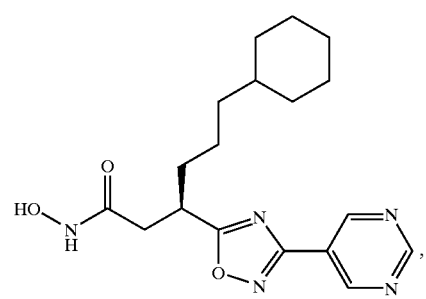
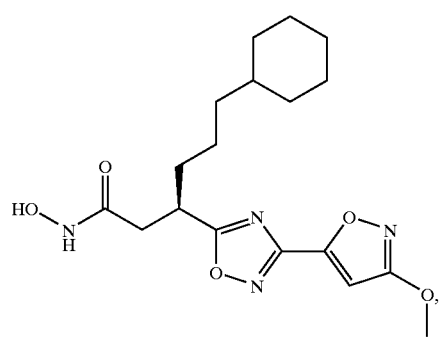
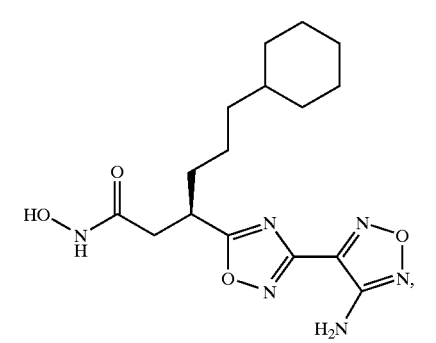
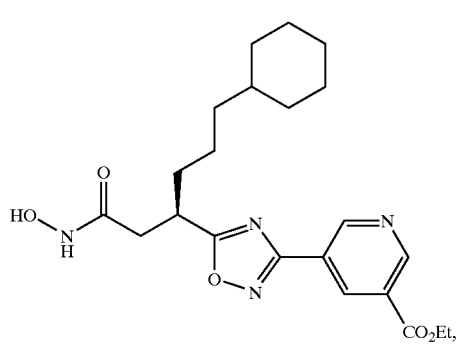
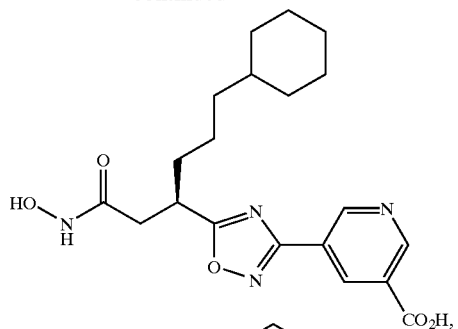
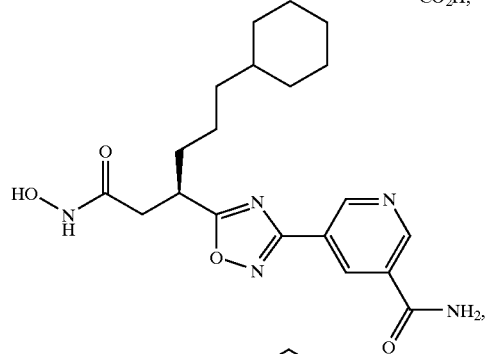
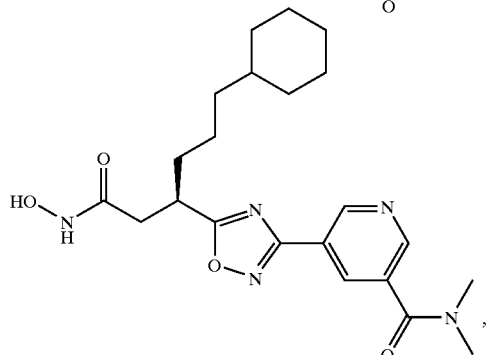
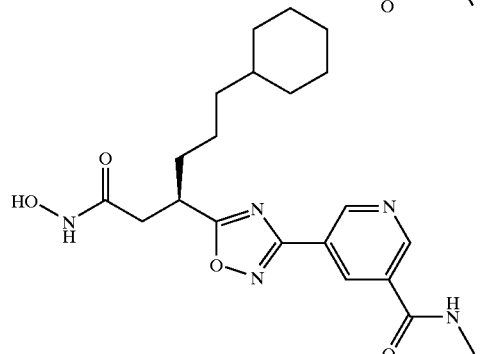
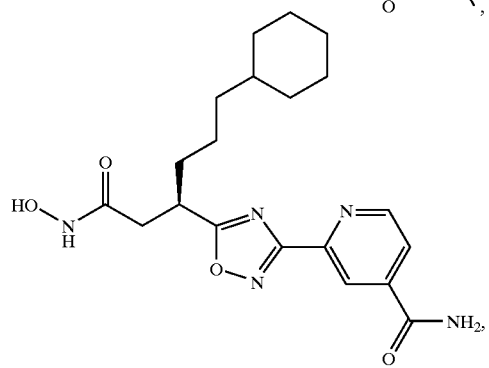

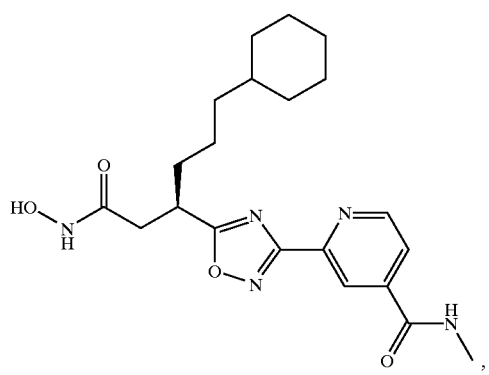
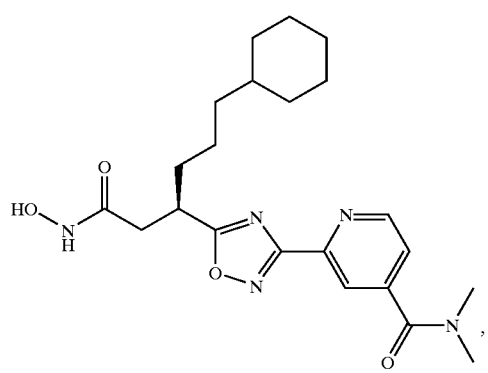
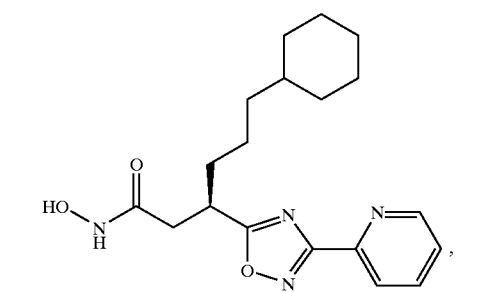
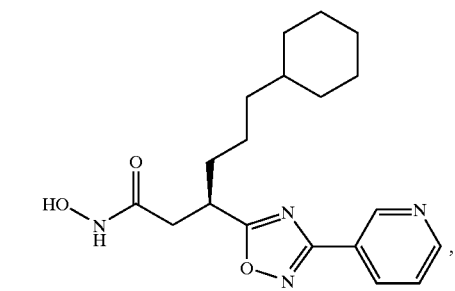
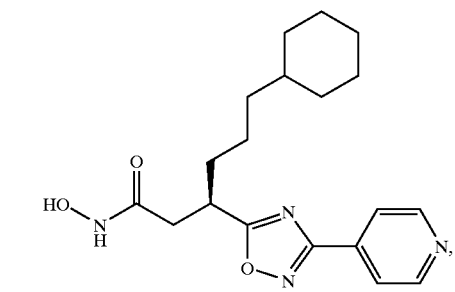
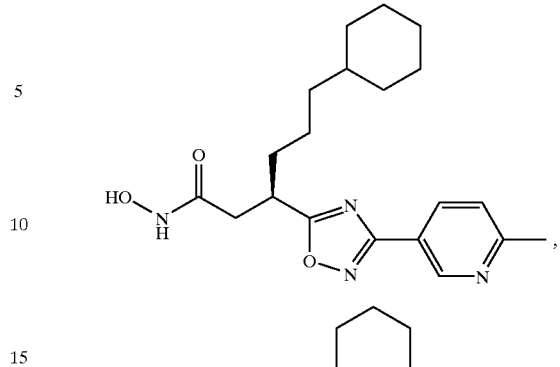
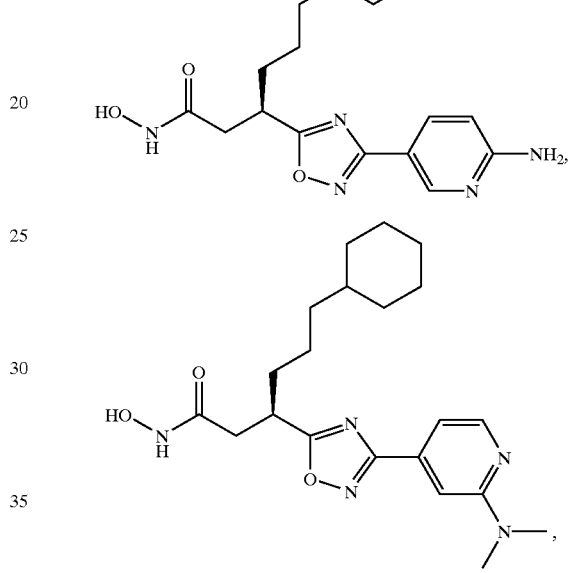
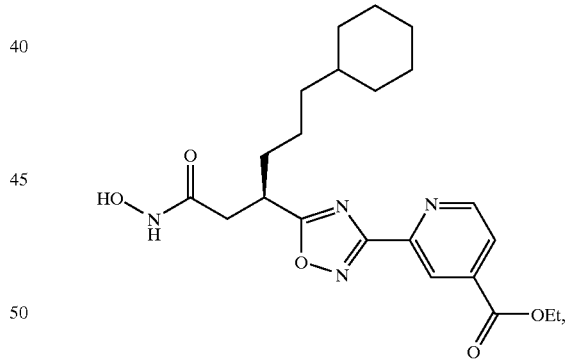
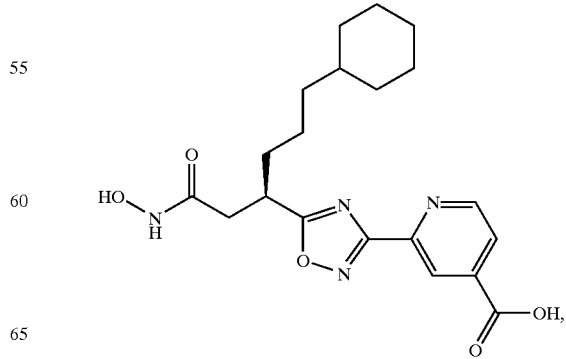

163
-continued
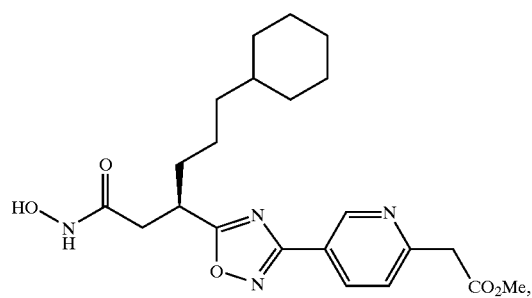
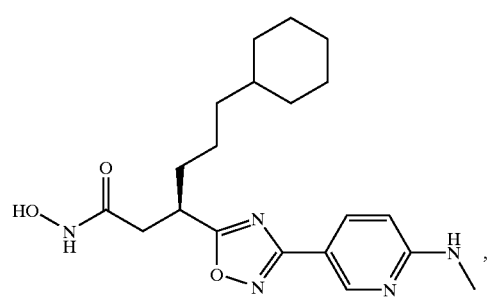
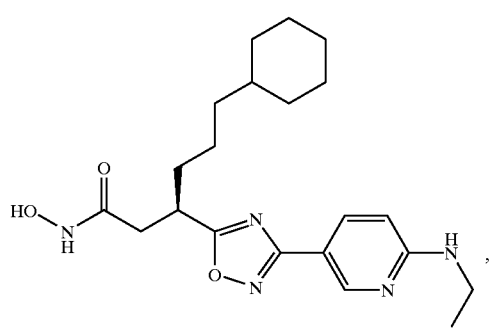
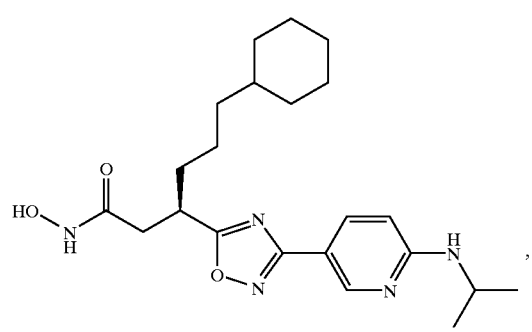
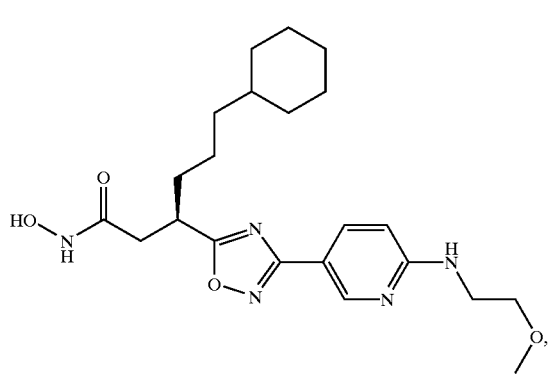
164
-continued
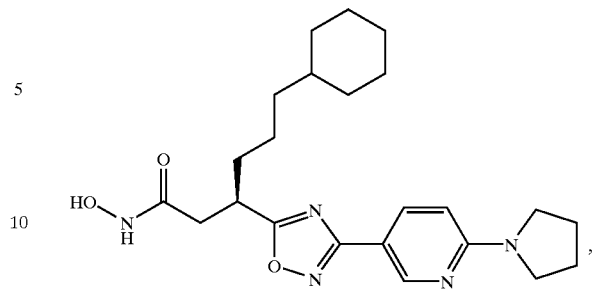
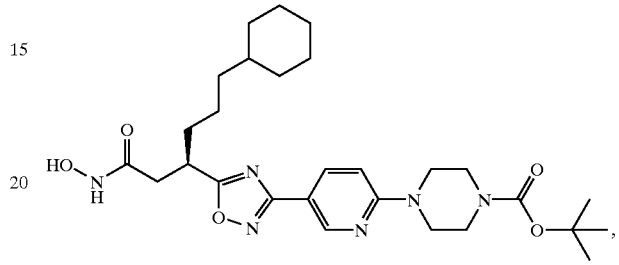
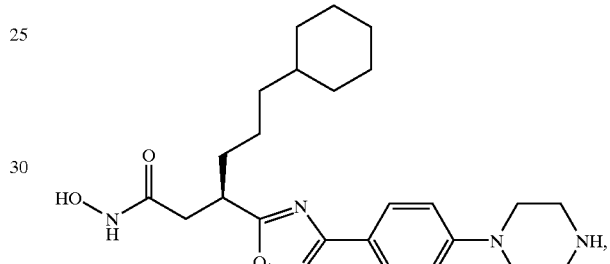
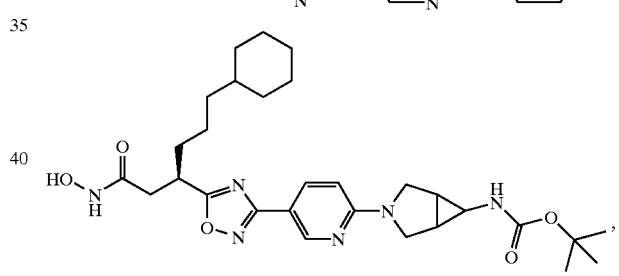
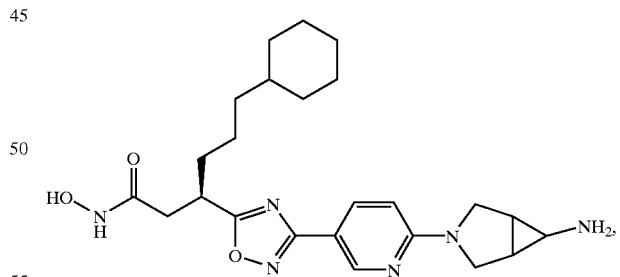
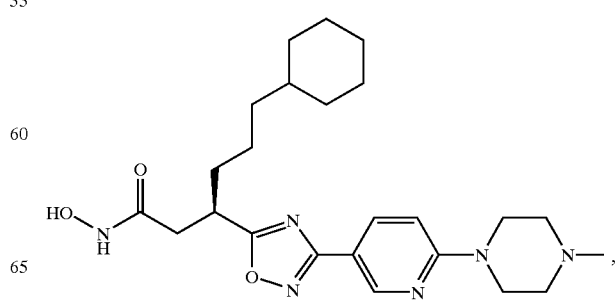

165
-continued
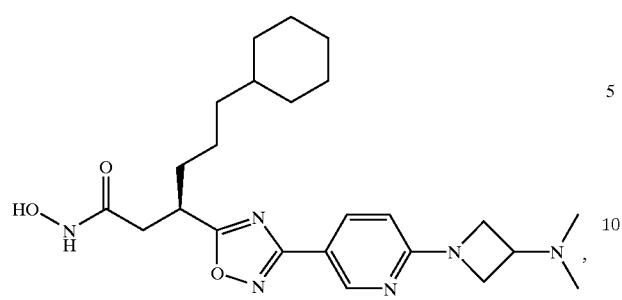
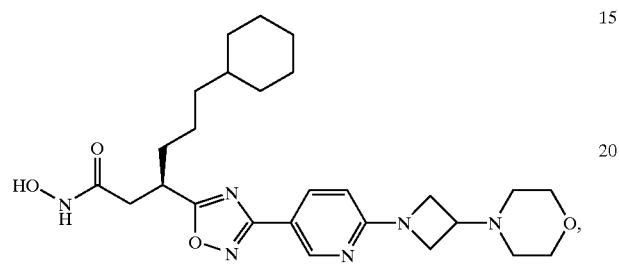
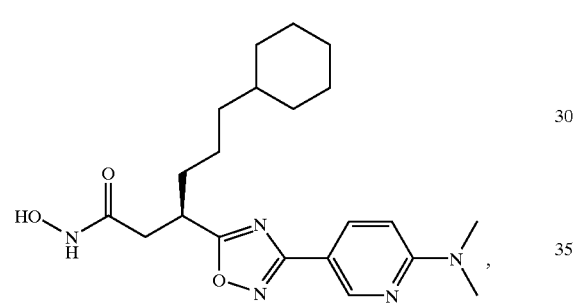
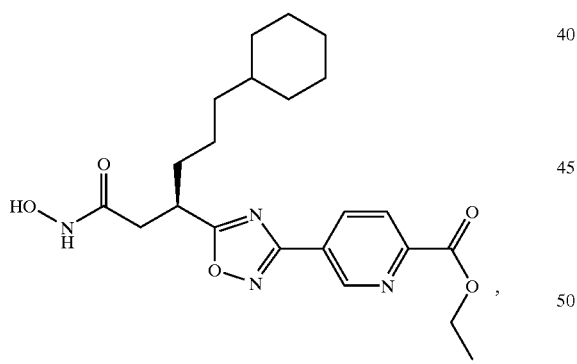
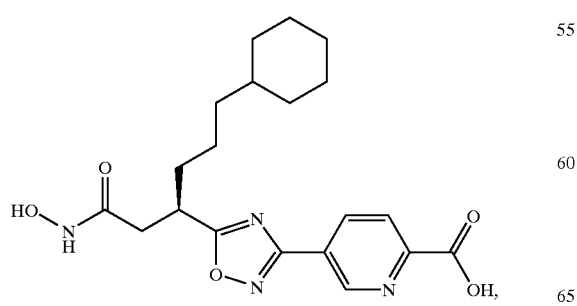
166
-continued
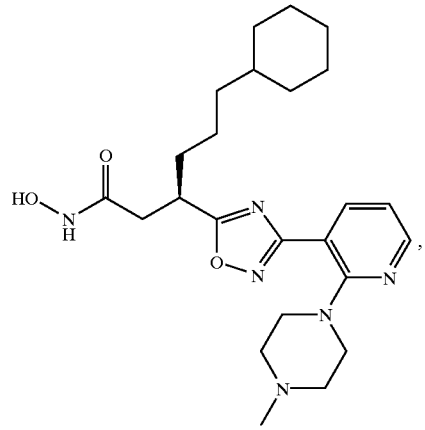
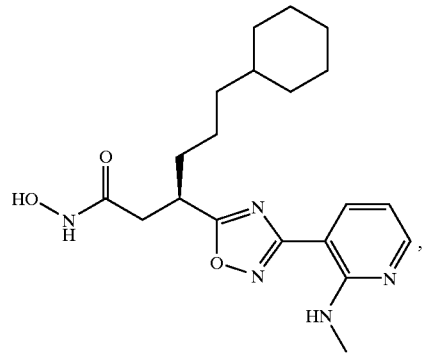
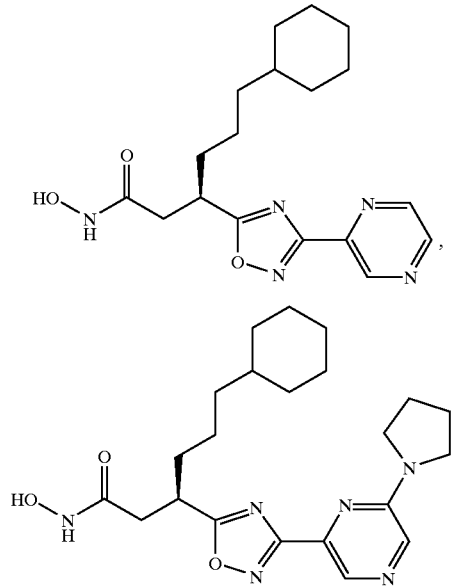
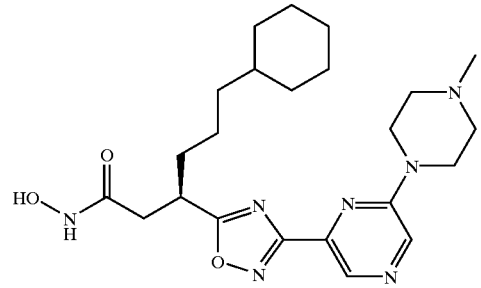

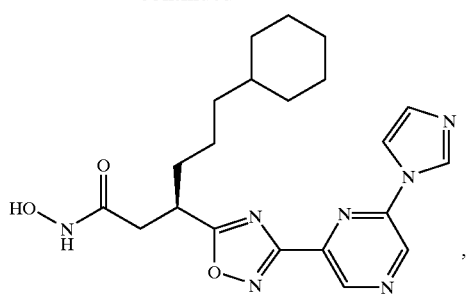
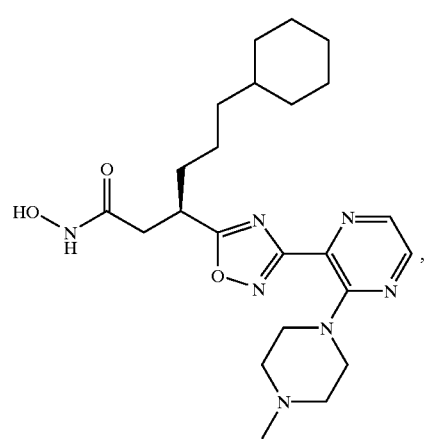
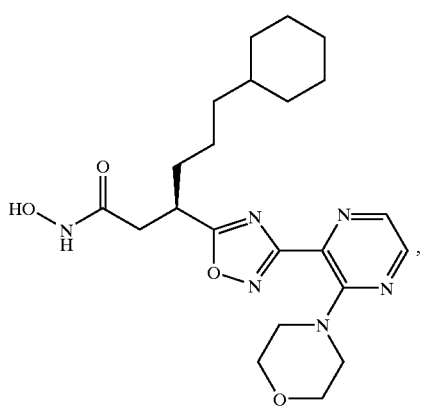
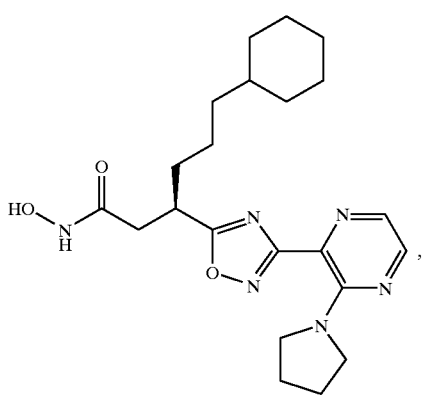
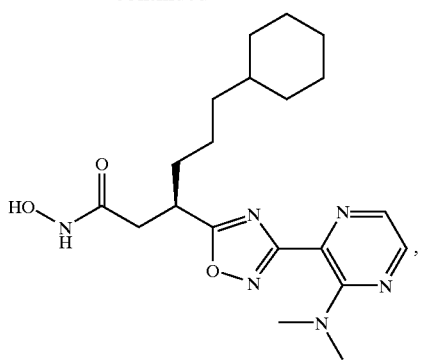
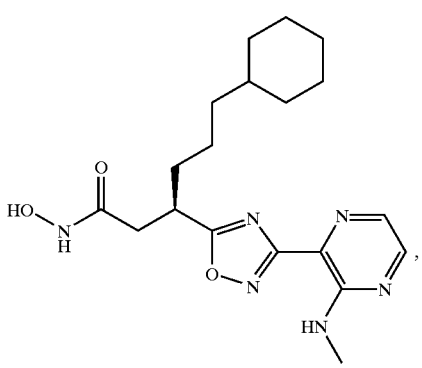
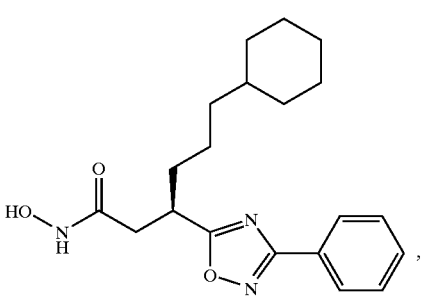
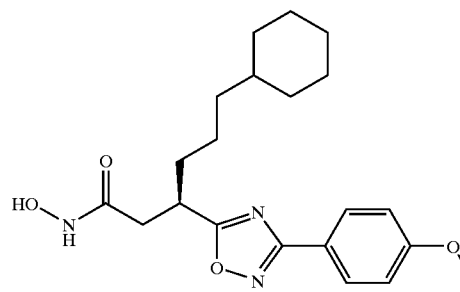
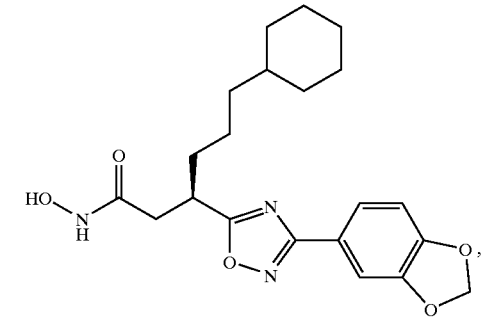

169
-continued
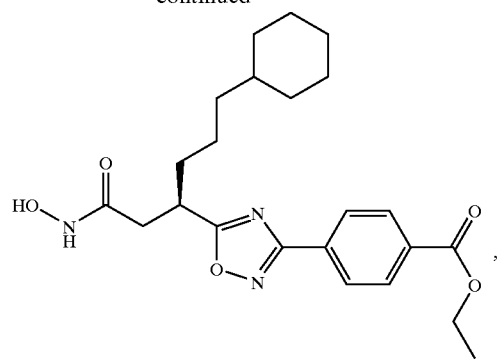
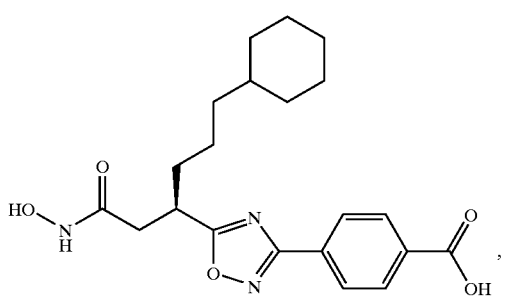
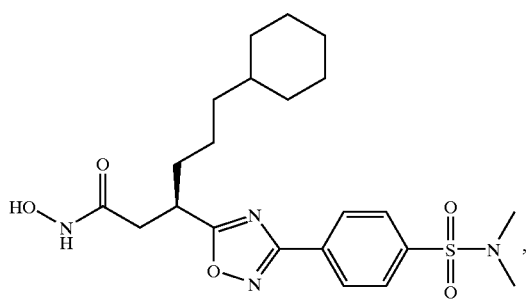
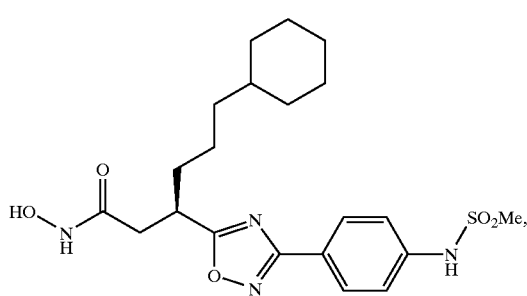
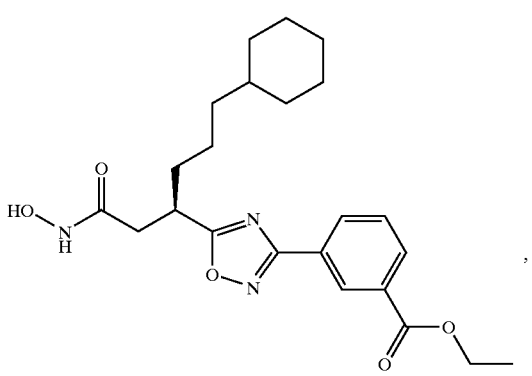
170
-continued
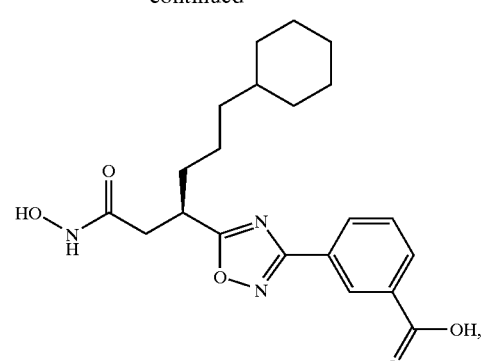
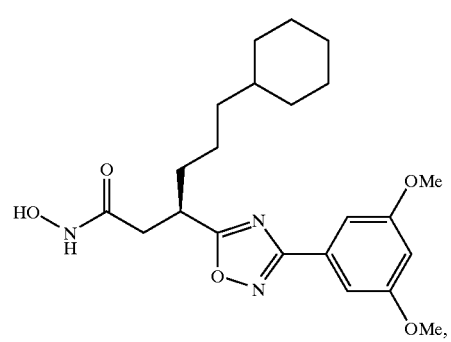
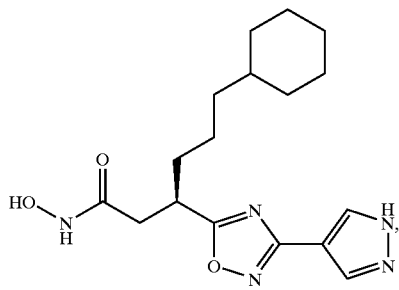
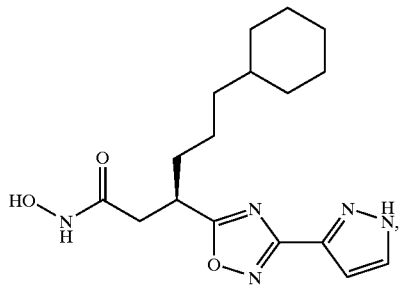
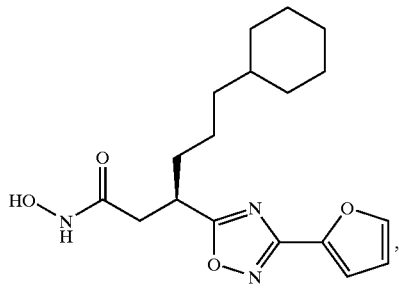

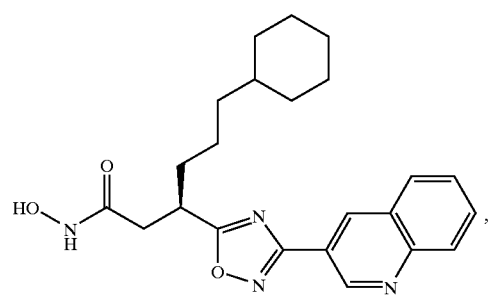
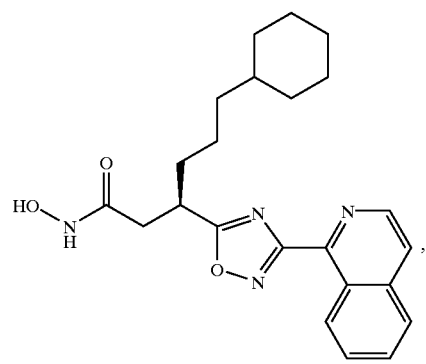
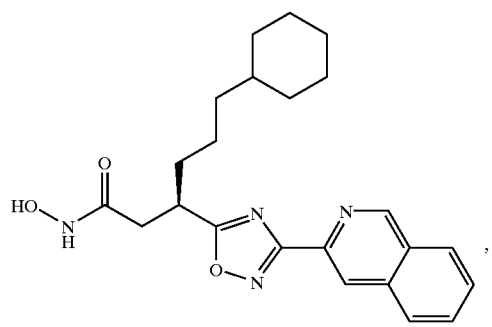
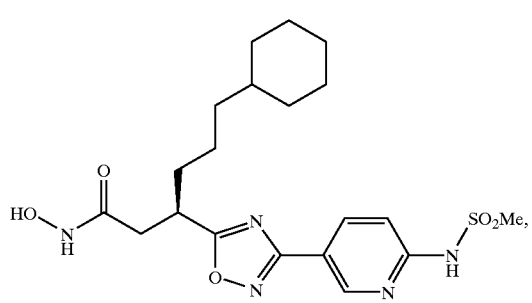
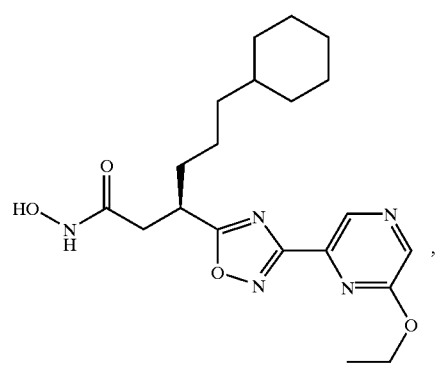
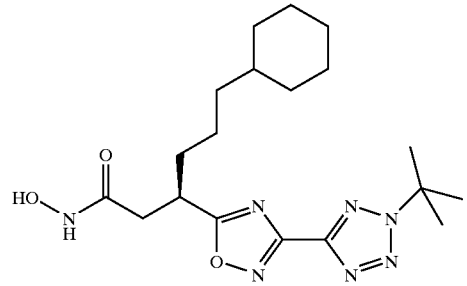
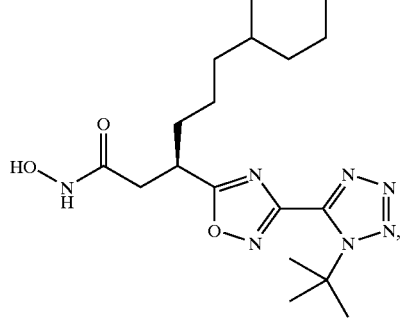
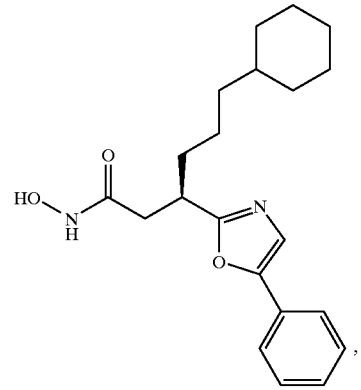
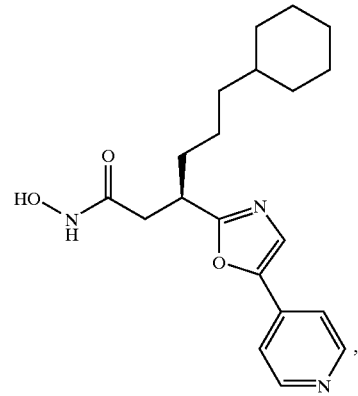
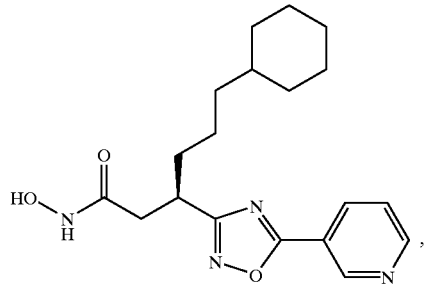

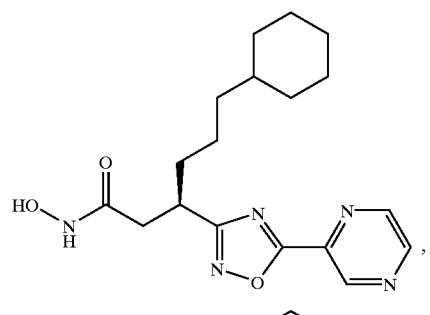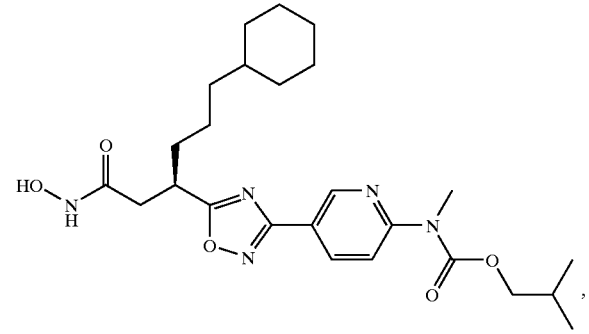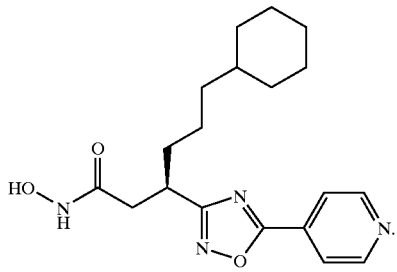
14. A pharmaceutical composition comprising a compound according to claim 1 and a pharmaceutically acceptable adjuvant, diluent or excipient.
* * * * *

UNITED STATES PATENT AND TRADEMARK OFFICE
CERTIFICATE OF CORRECTION

PATENT NO. : 6,821,972 B2
DATED : November 23, 2004
INVENTOR(S) : Simon Bailey et al.

It is certified that error appears in the above-identified patent and that said Letters Patent is hereby corrected as shown below:

Title page,
Item [30], Foreign Application Priority Data, "Mar. 30, 2001 (GB) 0108102" should read -- Mar. 30, 2001 (GB) 0108102.5 --.

Column 157,
Line 51, "5-carbamoylpyridin-3-yl, uracil-5-yl, pyridin-4yl," should read
-- 5-carbamoylpyridin-3-yl, uracil-5-yl, pyridin-4-yl, --.
Line 53, "6-methoxycarbonylpyridin-3-yl, 6-(4-methylpiperazino)" should read
-- 6-methoxycarbonylmethylpyridin-3-yl, 6-(4-methylpiperazino) --.
Line 54, "pyridin-3yl, 4-carboxypridin-2-yl, 6-dimethylaminopyridin-" should read
-- pyridin-3-yl, 6-(3-dimethylaminoazetidino)pyridin-3-yl, 6-(3-morpholinoazetidino) pyridin-3-yl, 4-carboxypridin-2-yl, 6-dimethylaminopyridin- --.
Line 55, "3yl, 6-(imidazol-1-yl)pyrazin-2-yl, 3-morpholinopyrazin-2-" should read
-- 3-yl, 6-(imidazol-1-yl)pyrazin-2-yl, 3-morpholinopyrazin-2- --.
Line 56, "yl, 3-pyrrolidinopyrazin-2yl, 3-dimethylaminopyrazin-2-yl," should read
-- yl, 3-pyrrolidinopyrazin-2-yl, 3-dimethylaminopyrazin-2-yl, --.

Signed and Sealed this

Thirtieth Day of August, 2005

JON W. DUDAS
*Director of the United States Patent and Trademark Office*